US012672655B2

(12) United States Patent
Sun et al.

(10) Patent No.: US 12,672,655 B2
(45) Date of Patent: Jul. 7, 2026

(54) ALKENE-CONTAINING CARBOXYLATE COMPOUND AND USE THEREOF

(71) Applicants: SHENYANG SINOCHEM AGROCHEMICALS R&D CO., LTD, Shenyang (CN); JIANGSU YANGNONG CHEMICAL CO., LTD., Yangzhou (CN)

(72) Inventors: Bing Sun, Shenyang (CN); Huibin Yang, Shenyang (CN); Hongjuan Ma, Shenyang (CN); Junwu Ying, Shenyang (CN); Dongliang Cui, Shenyang (CN); Bo Qin, Shenyang (CN); Shuang Liang, Shenyang (CN); Gang Wang, Shenyang (CN); Lu Shang, Shenyang (CN); Fan Zhang, Shenyang (CN); Lin Chen, Shenyang (CN); Heying Pei, Shenyang (CN); Zheng Wang, Shenyang (CN); Mingxin Wang, Shenyang (CN); Bin Li, Shenyang (CN)

(73) Assignees: SHENYANG SINOCHEM AGROCHEMICALS R&D CO., LTD, Shenyang (CN); JIANGSU YANGNONG CHEMICAL CO., LTD., Yangzhou (CN)

( * ) Notice: Subject to any disclaimer, the term of this patent is extended or adjusted under 35 U.S.C. 154(b) by 1075 days.

(21) Appl. No.: 17/754,670

(22) PCT Filed: Sep. 30, 2020

(86) PCT No.: PCT/CN2020/119168
§ 371 (c)(1),
(2) Date: Apr. 8, 2022

(87) PCT Pub. No.: WO2021/068820
PCT Pub. Date: Apr. 15, 2021

(65) Prior Publication Data

US 2023/0157290 A1 May 25, 2023

(30) Foreign Application Priority Data

Oct. 8, 2019 (CN) ......................... 201910950256.1
Mar. 13, 2020 (CN) ......................... 202010174549.8

(51) Int. Cl.

| | |
|---|---|
| *A01N 43/56* | (2006.01) |
| *A01N 43/80* | (2006.01) |
| *A01N 47/06* | (2006.01) |
| *A01N 47/12* | (2006.01) |
| *A01N 47/30* | (2006.01) |
| *A01P 13/00* | (2006.01) |

(Continued)

(52) U.S. Cl.
CPC ............. *A01N 43/56* (2013.01); *A01N 43/80* (2013.01); *A01N 47/06* (2013.01); *A01N 47/12* (2013.01); *A01N 47/30* (2013.01); *A01P 13/00* (2021.08); *C07D 231/20* (2013.01); *C07D 231/24* (2013.01); *C07D 401/06* (2013.01); *C07D 401/10* (2013.01); *C07D 401/12* (2013.01); *C07D 403/10* (2013.01); *C07D 405/12* (2013.01); *C07D 405/14* (2013.01); *C07D 413/10* (2013.01); *C07D 413/14* (2013.01)

(58) Field of Classification Search
CPC ........ A01N 43/56; A01N 43/80; A01N 47/06; A01N 47/12; A01N 47/30; A01N 43/50; A01N 43/653; A01P 13/00; C07D 231/20; C07D 231/24; C07D 401/06; C07D 401/10; C07D 401/12; C07D 403/10; C07D 405/12; C07D 405/14; C07D 413/10; C07D 413/14; C07D 231/18
See application file for complete search history.

(56) References Cited

U.S. PATENT DOCUMENTS 4,063,925 A * 12/1977 Konotsune ........ C07F 9/650905 548/369.4
4,261,729 A 4/1981 Konotsune et al.
(Continued)

FOREIGN PATENT DOCUMENTS

CN 1250447 A 4/2000
CN 1436184 A 8/2003
(Continued)

OTHER PUBLICATIONS

Ma, Haijun et al.; "Synthesis and Insecticidal Activity of 3-[2,6-Dichloro-4-(3,3-dichloroallyloxy) phenoxy] Propyl Pyrazole-5-carboxamide Derivatives"; Modern Agrochemicals; vol. 10, No. 5; Oct. 2011; pp. 16-20 and 23.

*Primary Examiner* — Monica A Shin
(74) *Attorney, Agent, or Firm* — NKL Law; Allen Xue

(57) ABSTRACT

An alkene-containing carboxylic ester compound of formula (I) and its agriculturally acceptable salt can be used as a herbicide.

I

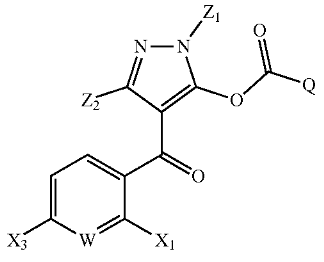

6 Claims, No Drawings

(51) Int. Cl.

| | |
|---|---|
| *C07D 231/20* | (2006.01) |
| *C07D 231/24* | (2006.01) |
| *C07D 401/06* | (2006.01) |
| *C07D 401/10* | (2006.01) |
| *C07D 401/12* | (2006.01) |
| *C07D 403/10* | (2006.01) |
| *C07D 405/12* | (2006.01) |
| *C07D 405/14* | (2006.01) |
| *C07D 413/10* | (2006.01) |
| *C07D 413/14* | (2006.01) |

(56) References Cited

U.S. PATENT DOCUMENTS

| | | | | |
|---|---|---|---|---|
| 4,301,293 | A | 11/1981 | Konotsune et al. | |
| 4,414,392 | A | 11/1983 | Konotsune et al. | |
| 4,508,910 | A | 4/1985 | Konotsune et al. | |
| 4,643,757 | A * | 2/1987 | Baba ...................... | A01N 47/18<br>548/369.4 |
| 4,687,858 | A | 8/1987 | Konotsune et al. | |
| 6,541,423 | B1 | 4/2003 | Mayer et al. | |

FOREIGN PATENT DOCUMENTS

| | | | |
|---|---|---|---|
| DE | 2513750 | A1 | 10/1975 |
| EP | 0240001 | A1 | 10/1987 |
| WO | 199959991 | A1 | 11/1999 |
| WO | 200003993 | A1 | 1/2000 |

* cited by examiner

ALKENE-CONTAINING CARBOXYLATE COMPOUND AND USE THEREOF

TECHNICAL FIELD

The present invention belongs to the field of herbicides, and particularly relates to an alkene-containing carboxylic ester compound and an application thereof.

BACKGROUND

Due to the succession and change of weed populations and the emergence and rapid development of resistance to chemical pesticides, people have continuously strengthened awareness on ecological environmental protection, and have paid more attention to the knowledge of chemical pesticide pollution and the influence of pesticides on non-target organisms and the end-result problem in the pesticide ecological environment. With the gradual decrease of the arable land area in the world, the continuous increase of the population and the increase of the demands for food, people are forced to rapidly develop agricultural production technologies, enhance and improve the farming system, and continuously invent novel and improved herbicidal compounds and compositions.

DE 2513750A1 has reported that some benzoyl pyrazole compounds have herbicidal activity, such as compound 79 ($KC_1$):

$KC_1$

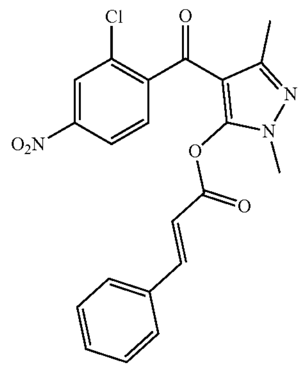

WO 0003993A1 has reported that some benzoyl pyrazole compounds have herbicidal activity, such as compound 357 ($KC_2$):

$KC_2$

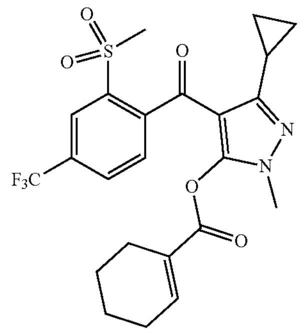

The alkene-containing carboxylic ester compound shown in the present invention is not disclosed.

SUMMARY

The purpose of the present invention is to provide an alkene-containing carboxylic ester compound with novel structure and safety for crops and an application thereof as a herbicide.

To achieve the above purpose, the present invention adopts the following technical solution: An alkene-containing carboxylic ester compound is shown in formula I:

I

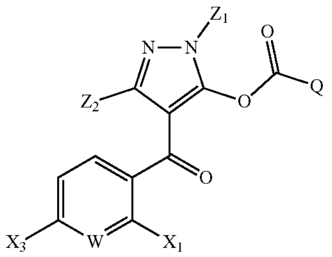

in the formula:

$X_1$ is selected from hydrogen, cyano, nitro, halogen, $C_1$-$C_6$ alkylsulfonyl, $C_1$-$C_6$ haloalkylsulfonyl, $C_1$-$C_6$ alkylsulfinyl, $C_1$-$C_6$ haloalkylsulfinyl, $C_1$-$C_6$ alkylthio, $C_1$-$C_6$ haloalkylthio, $C_1$-$C_6$ alkyl, $C_1$-$C_6$ haloalkyl, $C_1$-$C_6$ alkoxy, $C_1$-$C_6$ haloalkoxy, $C_1$-$C_6$ alkoxy $C_1$-$C_3$ alkyl, $C_1$-$C_6$ alkoxy $C_1$-$C_3$ alkoxy, $C_1$-$C_6$ alkoxy $C_1$-$C_3$ alkoxy $C_1$-$C_3$ alkyl, $C_3$-$C_6$ cycloalkyl, $C_3$-$C_6$ cycloalkyl $C_1$-$C_3$ alkyl, $C_3$-$C_6$ cycloalkyl $C_1$-$C_3$ alkoxy, $C_3$-$C_6$ cycloalkyloxy, $C_2$-$C_6$ alkenyl, $C_2$-$C_6$ alkynyl, phenyl, $C_2$-$C_6$ alkenylsulfonyl, $C_2$-$C_6$ alkynylsulfonyl, phenylsulfonyl, $C_2$-$C_6$ alkenyloxy, $C_2$-$C_6$ alkynyloxy, phenyloxy, $C_2$-$C_6$ alkenylthio, $C_2$-$C_6$ alkynylthio, phenylthio, 5-7 membered aliphatic heterocycle containing 1-4 heteroatoms, 5-7 membered aromatic heterocycle containing 1-4 heteroatoms, 5-7 membered aliphatic heterocyclic $C_1$-$C_6$ alkyl containing 1-4 heteroatoms or 5-7 membered aromatic heterocyclic $C_1$-$C_6$ alkyl containing 1-4 heteroatoms; hydrogen on the phenyl, the aliphatic heterocycle and the aromatic heterocycle mentioned above may be substituted by one or more of the following substituents which are selected from nitro, halogen, $C_1$-$C_6$ alkyl, $C_1$-$C_6$ haloalkyl, $C_1$-$C_6$ alkoxy, $C_1$-$C_6$ haloalkoxy or $C_3$-$C_6$ cycloalkyl;

W is selected from N or $CX_2$;

$X_2$ is selected from hydrogen, cyano, nitro, halogen, $C_1$-$C_6$ alkyl, $C_1$-$C_6$ haloalkyl, $C_3$-$C_6$ cycloalkyl, $C_3$-$C_6$ cycloalkyl $C_1$-$C_6$ alkyl, $C_3$-$C_6$ halocycloalkyl $C_1$-$C_6$ alkyl, $Y_1$ oxy, $Y_1$ thio, $Y_1Y_2$ amino, $Y_1$ sulfinyl, $Y_1$ sulfonyl, $Y_1$ oxy $C_1$-$C_6$ alkyl, $Y_1$ thio $C_1$-$C_6$ alkyl, YjY2 amino $C_1$-$C_6$ alkyl, $Y_1$ sulfinyl $C_1$-$C_6$ alkyl, $Y_1$ sulfonyl $C_1$-$C_6$ alkyl, $C(O)Y_1$, $C(O)OY_1$, $OC(O)OY_1$, $N(Y_1)C(O)OY_2$, $C(O)N(Y_1)Y_2$, $N(Y_1)C(O)N(Y_1)Y_2$, $OC(O)N(Y_1)Y_2$, $C(O)N(Y_1)OY_2$, $N(Y_1)S(O)_2Y_2$, $N(Y_1)C(O)Y_2$, $OS(O)_2Y_1$, $CH{=}NOY_1$, $C_1$-$C_6$ alkyl-$CH{=}NOY_1$, $C_1$-$C_6$ alkyl-O—$N{=}C(Y_1)Y_2$, phenyl, 5-7 membered alicyclic heterocycle containing 1-4 heteroatoms, 5-7 membered aromatic heterocycle containing 1-4 heteroatoms, 5-7 membered aliphatic heterocyclic $C_1$-$C_6$ alkyl containing 1-4 heteroatoms or 5-7 membered aromatic heterocyclic $C_1$-$C_6$ alkyl containing 1-4 heteroatoms; the hydrogen on the phenyl, the aliphatic heterocycle and the aromatic heterocycle mentioned above may be substituted by one or more of the following substituents which are selected from nitro, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, $C_3$-$C_6$ cycloalkoxy, $C_2$-$C_6$ alkenyl, $C_2$-$C_6$ alkynyl, phenyl or halophenyl;

$Y_1$ and $Y_2$ are independently selected from $C_1$-$C_6$ alkyl, $C_1$-$C_6$ haloalkyl, $C_3$-$C_6$ cycloalkyl, $C_3$-$C_6$ cycloalkyl $C_1$-$C_6$ alkyl, $C_1$-$C_6$ alkoxy $C_1$-$C_6$ alkyl, $C_2$-$C_6$ alkenyl, $C_2$-$C_6$ alkynyl, phenyl, 5-7 membered aliphatic heterocycle containing 1-4 heteroatoms, 5-7 membered aromatic heterocycle containing 1-4 heteroatoms, 5-7 membered aliphatic heterocyclic $C_1$-$C_6$ alkyl containing 1-4 heteroatoms or 5-7 membered aromatic heterocyclic $C_1$-$C_6$ alkyl containing 1-4 heteroatoms; the hydrogen on the phenyl, the aliphatic heterocycle and the aromatic heterocycle mentioned above may be substituted by one or more of the following substituents which are selected from nitro, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, $C_3$-$C_6$ cycloalkoxy, $C_2$-$C_6$ alkenyl, $C_2$-$C_6$ alkynyl, phenyl or halophenyl;

$X_3$ is selected from hydrogen, cyano, nitro, halogen, $C_1$-$C_6$ alkylsulfonyl, $C_1$-$C_6$ haloalkylsulfonyl, $C_1$-$C_6$ alkylsulfinyl, $C_1$-$C_6$ haloalkylsulfinyl, $C_1$-$C_6$ alkylthio, $C_1$-$C_6$ haloalkylthio, $C_1$-$C_6$ alkyl, $C_1$-$C_6$ haloalkyl, $C_1$-$C_6$ alkoxy, $C_1$-$C_6$ haloalkoxy, $C_1$-$C_6$ alkoxy $C_1$-$C_3$ alkyl, $C_1$-$C_6$ alkoxy $C_1$-$C_3$ alkoxy, $C_1$-$C_6$ alkoxy $C_1$-$C_3$ alkoxy $C_1$-$C_3$ alkyl, $C_3$-$C_6$ cycloalkyl, $C_3$-$C_6$ cycloalkyl $C_1$-$C_3$ alkyl, $C_3$-$C_6$ cycloalkyl $C_1$-$C_3$ alkoxy, $C_3$-$C_6$ cycloalkyloxy, $C_2$-$C_6$ alkenyl, $C_2$-$C_6$ alkynyl, $C_2$-$C_6$ alkenylsulfonyl, $C_2$-$C_6$ alkynylsulfonyl, $C_2$-$C_6$ alkenyloxy, $C_2$-$C_6$ alkynyloxy, $C_2$-$C_6$ alkenylthio, $C_2$-$C_6$ alkynylthio, phenyl, phenyloxy, phenylthio, phenylsulfonyl, 5-7 membered alicyclic heterocycle containing 1-4 heteroatoms, 5-7 membered aromatic heterocycle containing 1-4 heteroatoms, 5-7 membered alicyclic heterocyclic $C_1$-$C_6$ alkyl containing 1-4 heteroatoms or 5-7 membered aromatic heterocyclic $C_1$-$C_6$ alkyl containing 1-4 heteroatoms; hydrogen on the phenyl, aliphatic heterocycle and aromatic heterocycle mentioned above may be substituted with one or more of the following substituents selected from nitro, halogen, $C_1$-$C_6$ alkyl, $C_1$-$C_6$ haloalkyl, $C_1$-$C_6$ alkoxy, $C_1$-$C_6$ haloalkoxy or $C_3$-$C_6$ cycloalkyl;

when $X_1$ is selected from chlorine and $X_3$ is selected from methylsulfonyl, $X_2$ is not 2-thiazolyl;

$Z_1$ is selected from $C_1$-$C_6$ alkyl, $C_3$-$C_6$ cycloalkyl, $C_3$-$C_6$ cycloalkyl $C_1$-$C_6$ alkyl, $C_3$-$C_6$ alkenyl, $C_3$-$C_6$ alkynyl, $C_1$-$C_6$ alkylsulfonyl $C_1$-$C_6$ alkyl or phenyl;

$Z_2$ is selected from H, $C_1$-$C_6$ alkyl, $C_3$-$C_6$ cycloalkyl, $C_1$-$C_6$ haloalkyl or phenyl; hydrogen on the phenyl mentioned above can be substituted by one or more of the following substituents; and the substituents are selected from halogen, cyano, nitro, $C_1$-$C_6$ alkyl, $C_3$-$C_6$ cycloalkyl or $C_1$-$C_6$ haloalkyl;

Q is selected from $Q_1$ or $Q_2$ group;

$Q_1$

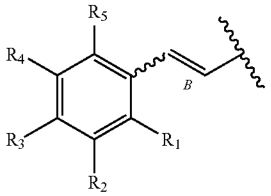

$Q_2$ is selected from $C_3$-$C_8$ cycloalkenyl; the hydrogen on the ring can be substituted by the following substituents; the following substituents are selected from nitro, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl or $C_3$-$C_6$ cycloalkyl;

when Q is selected from $Q_2$, $Z_2$ is not cyclopropyl;

$R_1$ to $R_5$ are independently selected from hydrogen, cyano, nitro, halogen, phenyl, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_1$-$C_6$ alkylthio or benzyloxy;

wherein $R_1$ and $R_2$ form a benzene ring, a 5-7 membered aliphatic heterocycle containing 1-3 heteroatoms or a 5-7 membered aromatic heterocycle containing 1-3 heteroatoms together with the carbon atoms on the connected benzene ring;

$R_2$ and $R_3$ can form a benzene ring, a 5-7 membered aliphatic heterocycle containing 1-3 heteroatoms or a 5-7 membered aromatic heterocycle containing 1-3 heteroatoms together with the carbon atoms on the connected benzene ring;

a stereoisomer of the compound of the above formula I; or, the compound of the formula I and agriculturally acceptable salt of the isomer.

A preferred compound is: in the formula I:

$X_1$ is selected from hydrogen, cyano, nitro, halogen, $C_1$-$C_6$ alkylsulfonyl, $C_1$-$C_6$ alkylsulfinyl, $C_1$-$C_6$ alkylthio, $C_1$-$C_6$ haloalkylthio, $C_1$-$C_6$ alkyl, $C_1$-$C_6$ haloalkyl, $C_1$-$C_6$ alkoxy, $C_1$-$C_6$ alkoxy $C_1$-$C_3$ alkyl, $C_1$-$C_6$ alkoxy $C_1$-$C_3$ alkoxy, $C_1$-$C_6$ alkoxy $C_1$-$C_3$ alkoxy $C_1$-$C_3$ alkyl, $C_3$-$C_6$ cycloalkyl, $C_3$-$C_6$ cycloalkyl $C_1$-$C_3$ alkyl, $C_3$-$C_6$ cycloalkyl, $C_1$-$C_3$ alkoxy, $C_3$-$C_6$ cycloalkyloxy, $C_2$-$C_6$ alkenyloxy, $C_2$-$C_6$ alkenyl, $C_2$-$C_6$ alkynyl, phenyl, phenylsulfonyl, phenyloxy, a 5-7 membered aliphatic heterocycle containing 1-4 heteroatoms and a 5-7 membered aromatic heterocycle containing 1-4 heteroatoms; the hydrogen on the phenyl, the aliphatic heterocycle and the aromatic heterocycle mentioned above may be substituted by one or more of the following substituents which are selected from nitro, halogen, $C_1$-$C_6$ alkyl, $C_1$-$C_6$ haloalkyl, $C_1$-$C_6$ alkoxy, $C_1$-$C_6$ haloalkoxy or $C_3$-$C_6$ cycloalkyl;

W is selected from N or $CX_2$;

$X_2$ is selected from hydrogen, cyano, nitro, halogen, $C_1$-$C_6$ alkyl, $C_1$-$C_6$ haloalkyl, $C_3$-$C_6$ cycloalkyl, $C_3$-$C_6$ cycloalkyl $C_1$-$C_6$ alkyl, $C_3$-$C_6$ halocycloalkyl $C_1$-$C_6$ alkyl, $Y_1$ oxy, $Y_1$ thio, $Y_1Y_2$ amino, $Y_1$ sulfinyl, $Y_1$ sulfonyl, $Y_1$ oxy $C_1$-$C_6$ alkyl, $Y_1$ thio $C_1$-$C_6$ alkyl, $Y_1Y_2$ amino $C_1$-$C_6$ alkyl, $Y_1$ sulfinyl $C_1$-$C_6$ alkyl, $Y_1$ sulfonyl $C_1$-$C_6$ alkyl, $C(O)Y_1$, $C(O)OY_1$, $OC(O)OY_1$, $N(Y_1)C(O)OY_2$, $C(O)N(Y_1)Y_2$, $N(Y_1)C(O)N(Y_1)Y_2$, $OC(O)N(Y_1)Y_2$, $C(O)N(Y_1)OY_2$, $N(Y_1)S(O)_2Y_2$, $N(Y_1)C(O)Y_2$, $OS(O)_2Y_1$, $CH{=}NOY_1$, $C_1$-$C_6$ alkyl-$CH{=}NOY_1$, $C_1$-$C_6$ alkyl-O—$N{=}C(Y_1)Y_2$, phenyl, 5-7 membered alicyclic heterocycle containing 1-4 heteroatoms, 5-7 membered aromatic heterocycle containing 1-4 heteroatoms, 5-7 membered aliphatic heterocyclic $C_1$-$C_6$ alkyl containing 1-4 heteroatoms or 5-7 membered aromatic heterocyclic $C_1$-$C_6$ alkyl containing 1-4 heteroatoms; the hydrogen on the phenyl, the aliphatic heterocycle and the aromatic heterocycle mentioned above may be substituted by one or more of the following substituents which are selected from nitro, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl or $C_3$-$C_6$ cycloalkoxy;

$Y_1$ and $Y_2$ are independently selected from $C_1$-$C_6$ alkyl, $C_1$-$C_6$ haloalkyl, $C_3$-$C_6$ cycloalkyl, $C_3$-$C_6$ cycloalkyl $C_1$-$C_6$ alkyl, $C_1$-$C_6$ alkoxy $C_1$-$C_6$ alkyl, phenyl, a 5-7 membered aliphatic heterocycle containing 1-4 heteroatoms, a 5-7 membered aromatic heterocycle containing 1-4 heteroatoms, a 5-7 membered aliphatic heterocyclic $C_1$-$C_6$ alkyl containing 1-4 heteroatoms or a 5-7 membered aromatic heterocyclic $C_1$-$C_6$ alkyl containing 1-4 heteroatoms; the hydrogen on the phenyl, the aliphatic heterocycle and the aromatic heterocycle mentioned above may be substituted by one or more of the following substituents which are selected from nitro, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl or $C_3$-$C_6$ cycloalkoxy;

$X_3$ is selected from hydrogen, cyano, halogen, $C_1$-$C_6$ alkylsulfonyl, $C_1$-$C_6$ alkylsulfinyl, $C_1$-$C_6$ alkylthio, $C_1$-$C_6$ haloalkylthio, $C_1$-$C_6$ alkyl, $C_1$-$C_6$ haloalkyl, $C_1$-$C_6$ alkoxy, $C_1$-$C_6$ alkoxy $C_1$-$C_3$ alkyl, $C_1$-$C_6$ alkoxy $C_1$-$C_3$ alkoxy, $C_1$-$C_6$ alkoxy $C_1$-$C_3$ alkoxy $C_1$-$C_3$ alkyl, $C_3$-$C_6$ cycloalkyl, $C_3$-$C_6$ cycloalkyl $C_1$-$C_3$ alkyl, $C_3$-$C_6$ cycloalkyl, $C_1$-$C_3$ alkoxy, $C_3$-$C_6$ cycloalkyloxy, $C_2$-$C_6$ alkenyloxy, $C_2$-$C_6$ alkenyl, $C_2$-$C_6$ alkynyl, phenyl, phenylsulfonyl, phenyloxy, a 5-7 membered aliphatic heterocycle containing 1-4 heteroatoms and a 5-7 membered aromatic heterocycle containing 1-4 heteroatoms; the hydrogen on the phenyl, the aliphatic heterocycle and the aromatic heterocycle mentioned above may be substituted by one or more of the following substituents which are selected from nitro, halogen, $C_1$-$C_6$ alkyl, $C_1$-$C_6$ haloalkyl, $C_1$-$C_6$ alkoxy, $C_1$-$C_6$ haloalkoxy or $C_3$-$C_6$ cycloalkyl;

when $X_1$ is selected from chlorine and $X_3$ is selected from methylsulfonyl, $X_2$ is not 2-thiazolyl;

$Z_1$ is selected from $C_1$-$C_6$ alkyl, $C_3$-$C_6$ cycloalkyl, $C_3$-$C_6$ cycloalkyl $C_1$-$C_6$ alkyl, $C_3$-$C_6$ alkenyl, $C_3$-$C_6$ alkynyl or phenyl;

$Z_2$ is selected from H, $C_1$-$C_6$ alkyl, $C_1$-$C_6$ haloalkyl or phenyl; hydrogen on the phenyl mentioned above can be substituted by one or more of the following substituents; and the substituents are selected from halogen, cyano, nitro, $C_1$-$C_6$ alkyl, $C_3$-$C_6$ cycloalkyl or $C_1$-$C_6$ haloalkyl;

Q is selected from $Q_1$ or $Q_2$ group;

$Q_1$

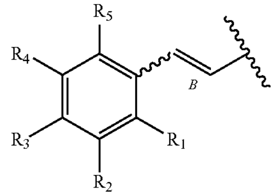

$Q_2$ is selected from $C_3$-$C_8$ cycloalkenyl; the hydrogen on the ring can be substituted by the following substituents; the following substituents are selected from nitro, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl or $C_3$-$C_6$ cycloalkyl; $R_1$ to $R_5$ are independently selected from hydrogen, cyano, nitro, halogen, phenyl, $C_1$-$C_6$ alkyl, $C_2$-$C_6$ alkenyl, $C_2$-$C_6$ alkynyl, $C_1$-$C_6$ alkoxy, $C_1$-$C_6$ alkylthio or benzyloxy;

wherein $R_1$ and $R_2$ form a benzene ring, a 5-7 membered aliphatic heterocycle containing 1-3 heteroatoms or a 5-7 membered aromatic heterocycle containing 1-3 heteroatoms together with the carbon atoms on the connected benzene ring;

$R_2$ and $R_3$ can form a benzene ring, a 5-7 membered aliphatic heterocycle containing 1-3 heteroatoms or a 5-7 membered aromatic heterocycle containing 1-3 heteroatoms together with the carbon atoms on the connected benzene ring;

the Q of the above formula I is selected from a stereoisomer of the compound shown by $Q_1$.

A further preferred compound is: in the formula I:

$X_1$ is selected from hydrogen, cyano, nitro, halogen, $C_1$-$C_3$ alkylsulfonyl, $C_1$-$C_3$ alkylsulfinyl, $C_1$-$C_3$ alkylthio, $C_1$-$C_3$ haloalkylthio, $C_1$-$C_3$ alkyl, $C_1$-$C_3$ haloalkyl, $C_1$-$C_3$ alkoxy, $C_1$-$C_3$ alkoxy $C_1$-$C_3$ alkyl, $C_1$-$C_3$ alkoxy $C_1$-$C_3$ alkoxy, $C_1$-$C_3$ alkoxy $C_1$-$C_3$ alkoxy $C_1$-$C_3$ alkyl, $C_3$-$C_6$ cycloalkyl or $C_3$-$C_6$ cycloalkyloxy;

W is selected from N or $CX_2$;

$X_2$ is selected from hydrogen, cyano, nitro, halogen, $C_1$-$C_3$ alkyl, $C_1$-$C_3$ haloalkyl, $C_3$-$C_6$ cycloalkyl, $C_3$-$C_6$ cycloalkyl $C_1$-$C_3$ alkyl, $C_3$-$C_6$ halocycloalkyl $C_1$-$C_3$ alkyl, $Y_1$ oxy, $Y_1$ thio, $Y_1Y_2$ amino, $Y_1$ sulfinyl, $Y_1$ sulfonyl, $Y_1$ oxy $C_1$-$C_3$ alkyl, $Y_1$ thio $C_1$-$C_3$ alkyl, $Y_1Y_2$ amino $C_1$-$C_3$ alkyl, $Y_1$ sulfinyl $C_1$-$C_3$ alkyl, $Y_1$ sulfonyl $C_1$-$C_3$ alkyl, $C(O)Y_1$, $C(O)OY_1$, $OC(O)OY_1$, $N(Y_1)C(O)OY_2$, $C(O)N(Y_1)Y_2$, $N(Y_1)C(O)N(Y_1)Y_2$, $OC(O)N(Y_1)Y_2$, $C(O)N(Y_1)OY_2$, $N(Y_1)S(O)_2Y_2$, $N(Y_1)C(O)Y_2$, $OS(O)_2Y_1$, $CH{=}NOY_1$, $C_1$-$C_6$ alkyl-$CH{=}NOY_1$, $C_1$-$C_6$ alkyl-O—$N{=}C(Y_1)Y_2$, phenyl, 5-7 membered alicyclic heterocycle containing 1-4 heteroatoms, 5-7 membered aromatic heterocycle containing 1-4 heteroatoms, 5-7 membered aliphatic heterocyclic $C_1$-$C_3$ alkyl containing 1-4 heteroatoms or 5-7 membered aromatic heterocyclic $C_1$-$C_3$ alkyl containing 1-4 heteroatoms; the hydrogen on the phenyl, the aliphatic heterocycle and the aromatic heterocycle mentioned above may be substituted by one or more of the following substituents which are selected from nitro, halogen, $C_1$-$C_3$ alkyl, $C_1$-$C_3$ haloalkyl, $C_1$-$C_3$ alkoxy, $C_3$-$C_6$ cycloalkyl or $C_3$-$C_6$ cycloalkoxy;

$Y_1$ and $Y_2$ are independently selected from $C_1$-$C_6$ alkyl, $C_1$-$C_6$ haloalkyl, $C_3$-$C_6$ cycloalkyl, $C_3$-$C_6$ cycloalkyl $C_1$-$C_6$ alkyl, $C_1$-$C_6$ alkoxy $C_1$-$C_6$ alkyl, phenyl, a 5-7 membered aliphatic heterocycle containing 1-4 heteroatoms, a 5-7 membered aromatic heterocycle containing 1-4 heteroatoms, a 5-7 membered aliphatic heterocyclic $C_1$-$C_6$ alkyl containing 1-4 heteroatoms or a 5-7 membered aromatic heterocyclic $C_1$-$C_6$ alkyl containing 1-4 heteroatoms; the hydrogen on the phenyl, the aliphatic heterocycle and the aromatic heterocycle mentioned above may be substituted by one or more of the following substituents which are selected from nitro, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl or $C_3$-$C_6$ cycloalkoxy;

$X_3$ is selected from hydrogen, cyano, halogen, $C_1$-$C_3$ alkylsulfonyl, $C_1$-$C_3$ alkylsulfinyl, $C_1$-$C_3$ alkylthio, $C_1$-$C_3$ haloalkylthio, $C_1$-$C_3$ alkyl, $C_1$-$C_3$ haloalkyl, $C_1$-$C_3$ alkoxy, $C_1$-$C_3$ alkoxy $C_1$-$C_3$ alkyl, $C_1$-$C_3$ alkoxy $C_1$-$C_3$ alkoxy, $C_1$-$C_3$ alkoxy $C_1$-$C_3$ alkoxy $C_1$-$C_3$ alkyl, $C_3$-$C_6$ cycloalkyl or $C_3$-$C_6$ cycloalkyloxy;

when $X_1$ is selected from chlorine and $X_3$ is selected from methylsulfonyl, $X_2$ is not 2-thiazolyl;

$Z_1$ is selected from $C_1$-$C_6$ alkyl, $C_3$-$C_6$ cycloalkyl, $C_3$-$C_6$ alkenyl, $C_3$-$C_6$ alkynyl or phenyl;

$Z_2$ is selected from H, $C_1$-$C_6$ alkyl, $C_1$-$C_6$ haloalkyl or phenyl; hydrogen on the phenyl mentioned above can be substituted by one or more of the following substituents; and the substituents are selected from halogen, cyano, nitro, $C_1$-$C_6$ alkyl, $C_3$-$C_6$ cycloalkyl or $C_1$-$C_6$ haloalkyl;

Q is selected from $Q_1$ or $Q_2$ group;

$Q_1$

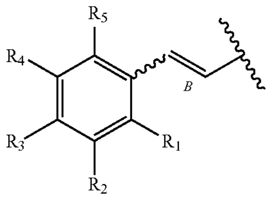

$Q_2$ is selected from cycloalkenyl; the hydrogen on the ring may be substituted by the following substituents which are selected from $C_1$-$C_6$ alkyl, $C_1$-$C_6$ alkoxy or $C_1$-$C_6$ alkenyl;

$R_1$ to $R_5$ are independently selected from hydrogen, hydroxyl, cyano, nitro, halogen, phenyl, $C_1$-$C_6$ alkyl, $C_2$-$C_6$ alkenyl, $C_2$-$C_6$ alkynyl, $C_1$-$C_6$ alkoxy or benzyloxy, wherein $R_1$ and $R_2$ form a benzene ring or a 5-7 membered aliphatic heterocycle containing 1-3 heteroatoms together with the carbon atoms on the connected benzene ring;

$R_2$ and $R_3$ can form a benzene ring or a 5-7 membered aliphatic heterocycle containing 1-3 heteroatoms together with the carbon atoms on the connected benzene ring;

the Q of the above formula I is selected from a stereoisomer of the compound shown by $Q_1$.

A further preferred compound is: in the formula I:

$X_1$ is selected from hydrogen, cyano, nitro, halogen, $C_1$-$C_3$ alkylsulfonyl, $C_1$-$C_3$ alkyl and $C_1$-$C_3$ haloalkyl;

W is selected from N or $CX_2$;

$X_2$ is selected from hydrogen, halogen, $C_1$-$C_3$ alkyl, $C_1$-$C_3$ haloalkyl, $C_3$-$C_6$ cycloalkyl, $C_3$-$C_6$ cycloalkyl $C_1$-$C_3$ alkyl, $C_3$-$C_6$ halocycloalkyl $C_1$-$C_3$ alkyl, $Y_1$ oxy, $Y_1$ thio, $Y_1Y_2$ amino, $Y_1$ sulfonyl, $Y_1$ oxy $C_1$-$C_3$ alkyl, $Y_1$ thio $C_1$-$C_3$ alkyl, $Y_1Y_2$ amino $C_1$-$C_3$ alkyl, $Y_1$ sulfonyl $C_1$-$C_3$ alkyl, $C(O)Y_1$, $C(O)OY_1$, $OC(O)OY_1$, $N(Y_1)C(O)OY_2$, $C(O)N(Y_1)Y_2$, $N(Y_1)C(O)N(Y_1)Y_2$, $OC(O)N(Y_1)Y_2$, $C(O)N(Y_1)OY_2$, $N(Y_1)S(O)_2Y_2$, $N(Y_1)C(O)Y_2$, $OS(O)_2Y_1$, $CH{=}NOY_1$, $C_1$-$C_6$ alkyl-$CH{=}NOY_1$, $C_1$-$C_6$ alkyl-$O{-}N{=}C(Y_1)Y_2$, phenyl, 5-7 membered alicyclic heterocycle containing 1-4 heteroatoms, 5-7 membered aromatic heterocycle containing 1-4 heteroatoms, 5-7 membered aliphatic heterocyclic $C_1$-$C_3$ alkyl containing 1-4 heteroatoms or 5-7 membered aromatic heterocyclic $C_1$-$C_3$ alkyl containing 1-4 heteroatoms; the hydrogen on the phenyl, the aliphatic heterocycle and the aromatic heterocycle mentioned above may be substituted by one or more of the following substituents which are selected from nitro, halogen, $C_1$-$C_3$ alkyl, $C_1$-$C_3$ haloalkyl, $C_1$-$C_3$ alkoxy, $C_3$-$C_6$ cycloalkyl or $C_3$-$C_6$ cycloalkoxy;

$Y_1$ and $Y_2$ are independently selected from $C_1$-$C_6$ alkyl, $C_1$-$C_6$ haloalkyl, $C_3$-$C_6$ cycloalkyl, $C_3$-$C_6$ cycloalkyl $C_1$-$C_6$ alkyl, $C_1$-$C_6$ alkoxy $C_1$-$C_6$ alkyl, phenyl, a 5-7 membered aliphatic heterocycle containing 1-4 heteroatoms, a 5-7 membered aromatic heterocycle containing 1-4 heteroatoms, a 5-7 membered aliphatic heterocyclic $C_1$-$C_6$ alkyl containing 1-4 heteroatoms or a 5-7 membered aromatic heterocyclic $C_1$-$C_6$ alkyl containing 1-4 heteroatoms; the hydrogen on the phenyl, the aliphatic heterocycle and the aromatic heterocycle mentioned above may be substituted by one or more of the following substituents which are selected from nitro, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl or $C_3$-$C_6$ cycloalkoxy;

$X_3$ is selected from hydrogen, cyano, halogen, $C_1$-$C_3$ alkylsulfonyl, $C_1$-$C_3$ alkyl and $C_1$-$C_3$ haloalkyl;

when $X_1$ is selected from chlorine and $X_3$ is selected from methylsulfonyl, $X_2$ is not 2-thiazolyl;

$Z_1$ is selected from $C_1$-$C_3$ alkyl or phenyl;

$Z_2$ is selected from H, $C_1$-$C_3$ alkyl and $C_1$-$C_3$ haloalkyl;

Q is selected from $Q_1$ or $Q_2$ group;

$Q_1$

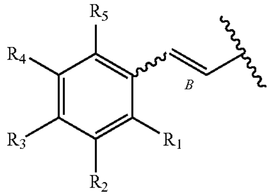

$Q_2$ is selected from G1, G2, G3, G4, G5 or G6 group;

$G_1$

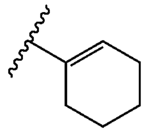

$G_2$

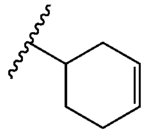

$G_3$

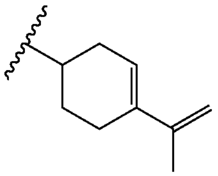

$G_4$

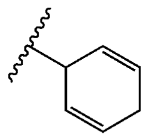

$G_5$

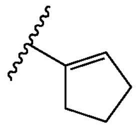

$G_6$

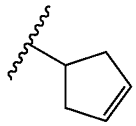

$R_1$ to $R_5$ are independently selected from hydrogen, hydroxyl, cyano, nitro, halogen, phenyl, methyl, ethyl, propyl, vinyl, propenyl, ethynyl, propynyl, methoxy, ethoxyl, benzyloxy, trifluoromethyl or trifluoromethoxy;

$R_1$ and $R_2$ are selected from a benzene ring formed together with the carbon atoms on the connected benzene ring;

$R_2$ and $R_3$ are selected from a benzene ring, 1,3-dioxane ring or 1,4-dioxane ring formed together with the carbon atoms on the connected benzene ring;

the Q of the above formula I is selected from a trans-stereoisomer of the compound shown by $Q_1$.

In the definitions of the compounds of the formula I provided above, the terms used in the collection are defined as follows:

Alkyl refers to linear or branched groups such as methyl, ethyl, n-propyl, isopropyl, n-butyl, isobutyl, sec-butyl, tert-butyl, n-pentyl, isopentyl and n-hexyl and so on. Cycloalkyl refers to groups in the form of cyclic chain, such as cyclopropyl, methylcyclopropyl, cyclopropylcyclopropyl, cyclobutyl, cyclopentyl and cyclohexyl and so on. Alkenyl refers to linear or branched alkenyl, such as vinyl, 1-propenyl, 2-propenyl, butenyl, pentenyl and hexenyl and so on. Alkynyl refers to linear or branched chain alkynyl, such as 1-propynyl, 2-propynyl, butynyl, pentynyl and hexynyl and so on. Alkoxy refers to a group having an oxygen atom at the end of the alkyl, such as methoxy, ethoxy, n-propoxy, isopropoxy and tert-butoxy and so on. The 5-7-membered heterocycle containing 1-4 heteroatoms refers to a 5-7-membered heterocyclic compound containing 1-4 heteroatoms without aromatic characteristics, such as ethylene oxide, tetrahydrofuran, imidazolinone, caprolactam, 1,3-dioxane ring and 1,4-dioxane ring and so on. The 5-7-membered aromatic heterocycle containing 1-4 heteroatoms refers to a 5-7-membered heterocyclic compound containing 1-4 heteroatoms having aromatic characteristics, such as furan, thiophene, pyrazole and pyridine and so on. Stereoisomers mean that hydrogen atoms on the carbon-carbon double bond B in the formula I are on the same side (cis) or on both sides (trans) of the bond B.

The compound of the formula I in the present invention can be prepared by the following method:

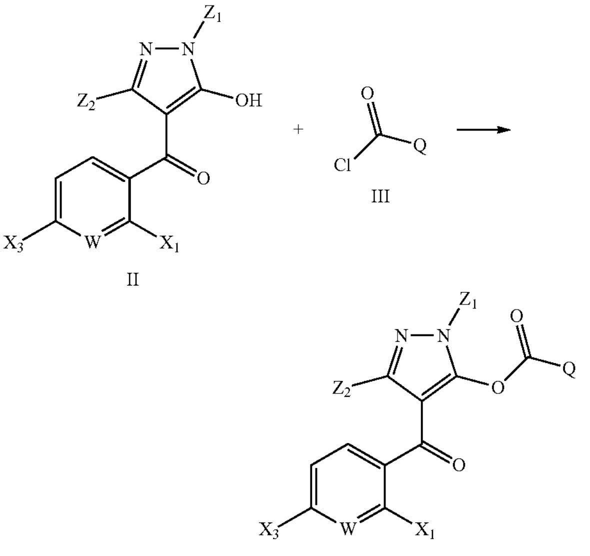

II III I

The compound of the formula II and the compound of the formula III react in a suitable solvent at temperature of −10° C. to a boiling point of the suitable solvent for 0.5-48 hours to obtain a target compound I. The suitable solvent is selected from dichloromethane, 1,2-dichloroethane, chloroform, carbon tetrachloride, hexane, benzene, toluene, ethyl acetate, acetonitrile, acetic acid, tetrahydrofuran, dioxane, N,N-dimethylformamide or dimethylsulfoxide and so on.

Addition of a suitable alkali substance can be beneficial to the reaction. The suitable alkali is selected from organic alkali such as triethylamine, N, N-dimethylaniline or pyridine and so on, or inorganic alkali such as sodium hydroxide, potassium hydroxide, sodium carbonate, sodium bicarbonate, potassium carbonate, sodium methoxide, sodium tert-butoxide or potassium tert-butoxide and so on.

The compound of the formula III can be prepared from the corresponding acid (commercially available) by reference to Modern Agrochemicals 10(5), 16-20, 23; 2011.

The preparation method of the compound of the formula II is as follows:

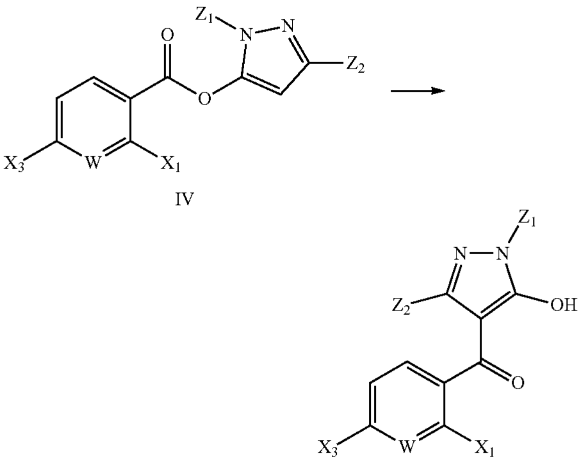

IV II

The compound of the formula IV reacts under the action of alkali and catalyst in a suitable solvent at temperature of −10° C. to a boiling point of the suitable solvent for 0.5-48 hours to obtain a compound of formula II. The suitable solvent is selected from dichloromethane, 1,2-dichloroethane, chloroform, carbon tetrachloride, hexane, benzene, toluene, ethyl acetate, acetonitrile, acetic acid, tetrahydrofuran, dioxane, N,N-dimethylformamide or dimethylsulfoxide and so on. Proper alkali is selected from sodium carbonate, potassium carbonate or triethylamine and so on. A proper catalyst is selected from sodium carbonate, potassium carbonate, acetone cyanohydrin, azide, azide quaternary ammonium salt, metal cyanide or DMAP and so on.

The preparation method of the compound of the formula IV is as follows:

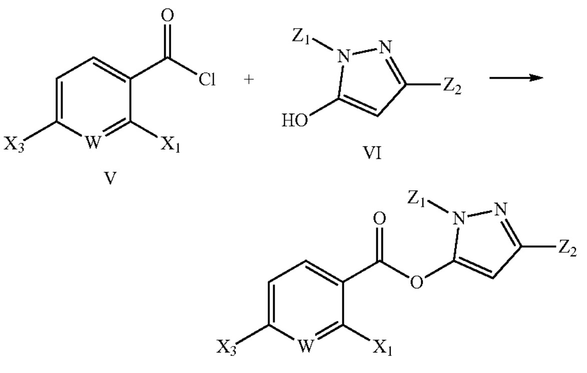

V VI IV

The compound of the formula V and the compound of the formula VI (commercially available or prepared by the method described in reference EP0240001) react in a suitable solvent at temperature of −10° C. to a boiling point of the suitable solvent for 0.5-24 hours to obtain the compound of the formula IV. The suitable solvent is selected from dichloromethane, 1,2-dichloroethane, chloroform, carbon tetrachloride, hexane, benzene, toluene, ethyl acetate, acetonitrile, acetic acid, tetrahydrofuran, dioxane, N,N-dimethylformamide or dimethylsulfoxide and so on.

Addition of a suitable alkali substance can be beneficial to the reaction. The suitable alkali is selected from organic alkali such as triethylamine, N, N-dimethylaniline or pyridine and so on, or inorganic alkali such as sodium hydroxide, potassium hydroxide, sodium carbonate, sodium bicarbonate, potassium carbonate, sodium methoxide, sodium tert-butoxide or potassium tert-butoxide and so on.

The corresponding raw material carboxylic acid (commercially available) of the compound of the formula V and an acyl halide reagent react in a suitable solvent at temperature of −10° C. to a boiling point of the suitable solvent for 0.5-48 hours to obtain the compound of the formula V. The acyl halide reagent is selected from oxalyl chloride, thionyl chloride, phosphorous oxychloride, phosphorus trichloride or phosphorus pentachloride and so on. The suitable solvent is selected from dichloromethane, 1,2-dichloroethane, hexane, benzene, toluene, acetonitrile, acetic acid, dioxane or liquid acyl halide reagent and so on.

The compound of the formula I of the present invention and the stereoisomer thereof or the compound of the formula I and the agriculturally acceptable salt of the isomer have herbicidal activity and can be used for agriculturally controlling various weeds.

The present invention also comprises a herbicidal composition using the compound of the formula I and the stereoisomer thereof or the compound of the formula I and the agriculturally acceptable salt of the isomer as active ingredients. The weight percentage of the active ingredient in the herbicidal composition is 1-99%. The herbicidal composition also comprises an agriculturally acceptable carrier.

The herbicidal composition of the present invention can be applied in the forms of various formulations. The compound of the present invention is generally dissolved or dispersed in the carrier and prepared into the formulation for easier dispersion when used as a herbicide. For example, the chemical formulations can be prepared into wettable powder or missible oil. Therefore, in the compositions, at least one liquid or solid carrier is added, and generally a suitable surfactant needs to be added.

The present invention also provides an implementing method for controlling weeds. The method comprises applying an effective dose of the herbicidal composition of the present invention to the weed or a weed growing place or a surface of a growth medium thereof. A suitable effective dose is 1 to 1000 grams per hectare, and a preferred effective dose is 10 to 500 grams per hectare. For some applications, one or more other herbicides can be added to the herbicidal composition of the present invention, thereby generating additional advantages and effects.

The compound of the present invention can be used alone or in combination with other known pesticides, bactericides, plant growth regulators or fertilizers.

Compared with the prior art, the alkene-containing carboxylate compound of the present invention not only has excellent herbicidal activity, but also is safe for crops.

It should be clear that various changes and modifications can be made within the scope defined by the claims of the present invention.

DETAILED DESCRIPTION

The following examples and biometric test results can be used to further illustrate the present invention, but are not intended to limit the present invention.

SYNTHESIS EXAMPLE

Embodiment 1 Synthesis of Compound 1-1

(1) Synthesis of 2-methanesulfonyl-4-trifluoromethyl benzoyl chloride

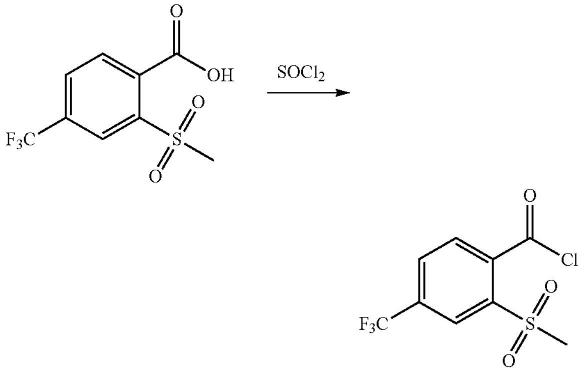

2-methanesulfonyl-4-trifluoromethylbenzoic acid (30 g, 112 mmol) and toluene (200 ml) were added to a reaction flask; thionyl chloride (53 g, 447 mmol) was slowly added; the mixture was heated and refluxed for 4 hours; and the solvent was evaporated under reduced pressure to obtain 32 g of yellow solid, which is directly used in the next step.

(2) Synthesis of 2-methanesulfonyl-4-trifluoromethyl benzoic acid (1,3-dimethylpyrazole-5-yl) ester

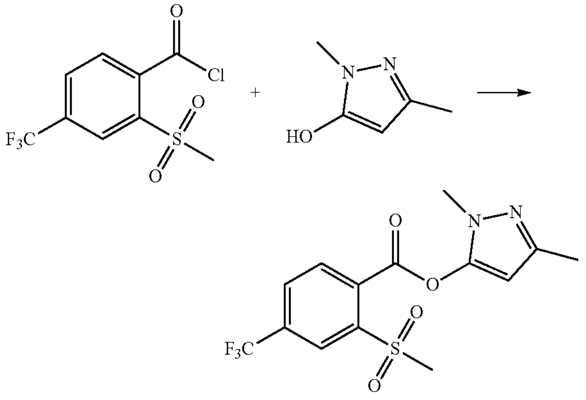

1,3-dimethyl-5-hydroxypyrazole (13 g, 112 mmol), 1,2-dichloroethane (200 ml) and triethylamine (34 g, 336 mmol) were added to the reaction flask, and the 1,2-dichloroethane solution (100 ml) of 2-methanesulfonyl-4-trifluoromethyl benzoyl chloride in the above step was added dropwise. The mixture was stirred at room temperature for 1 hour; the solvent was evaporated under reduced pressure; ethyl acetate (1000 ml) was added to the residue; water (500 ml) was used for separation and extraction; the organic phase was sequentially washed with saturated salt water (500 ml) and dried with anhydrous magnesium sulfate; the solvent was evaporated under reduced pressure; and the residue was separated by column chromatography to obtain 28 g of yellow solid, with a yield of 68%.

(3) Synthesis of 1,3-dimethyl-4-(2-methanesulfonyl-4-trifluoromethylbenzoyl)-5-hydroxypyrazole

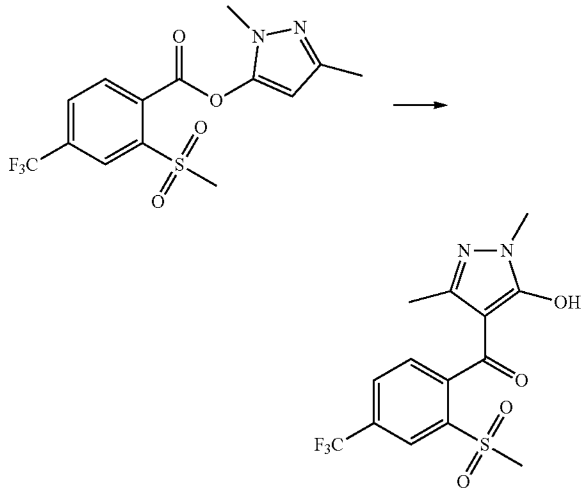

2-methanesulfonyl-4-trifluoromethyl benzoic acid (1,3-dimethylpyrazole-5-yl) ester (6 g, 16.6 mmol), 1,2-dichloroethane (50 ml), triethylamine (15 g, 148 mmol) and acetone cyanohydrin (1 ml) were added to the reaction flask; the mixture was kept at 60° C. to react for 6 hours and cooled to room temperature; water (100 ml) was added to the reaction solution, and shaken thoroughly and layered; the pH of the aqueous phase was adjusted to be 2-3 with 20% hydrochloric acid, and the aqueous phase was extracted twice with ethyl acetate (100 ml). The organic phase was washed with saturated salt water (50 ml) and dried with anhydrous magnesium sulfate; and the solvent was evaporated under reduced pressure to obtain 5.4 g of red oil with a yield of 90%.

(4) Synthesis of Cinnamyl Chloride

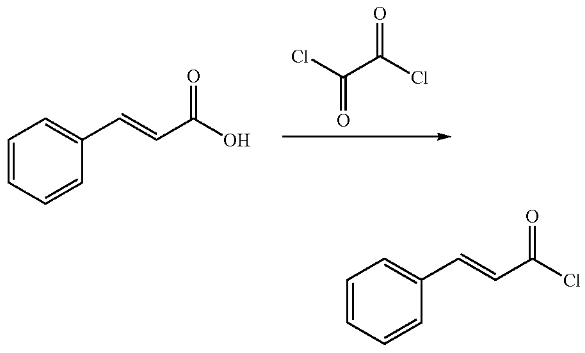

Cinnamic acid (0.17 g, 1.1 mmol), dichloromethane (30 ml) and DMF (1 drop) were added into the reaction flask; oxalyl chloride (0.7 g, 5.5 mmol) was slowly added; the mixture was stirred at room temperature for 1 hour; the solvent was evaporated under reduced pressure; toluene (15 ml) was added to the residue and stirred for 3 minutes; and then the solvent was evaporated under reduced pressure to obtain 0.18 g of pale yellow solid which was used directly in the next step.

(5) Synthesis of Compound 1-1

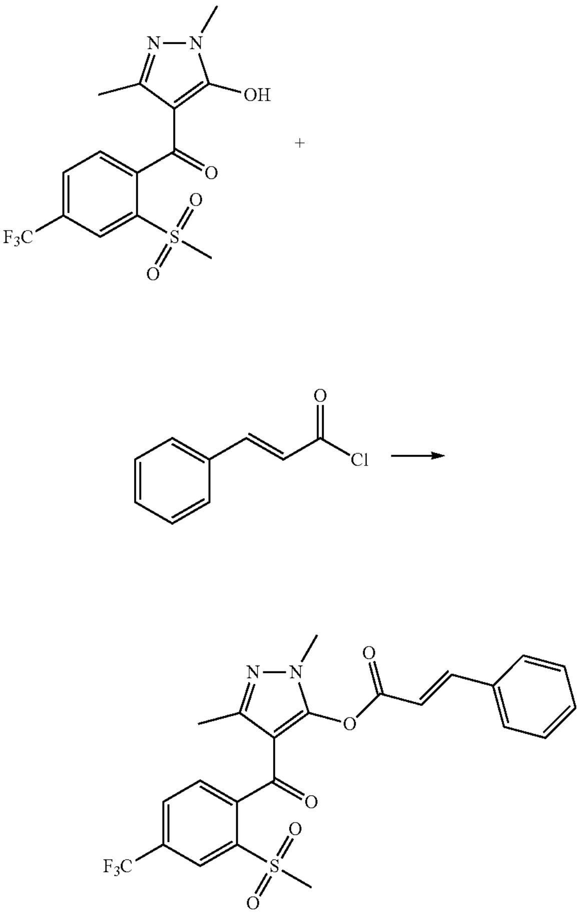

1,3-dimethyl-4-(2-methanesulfonyl-4-trifluoromethylbenzoyl)-5-hydroxypyrazole (0.4 g, 1.1 mmol), dichloromethane (20 ml) and triethylamine (0.22 g, 2.2 mmol) were added to the reaction flask, and the dichloromethane solution (15 ml) of cinnamyl chloride in the above step was added dropwise. The mixture was stirred at room temperature for 1 hour; the solvent was evaporated under reduced pressure; ethyl acetate (100 ml) was added to the residue; water (50 ml) was used for separation and extraction; the organic phase was sequentially washed with saturated salt water (50 ml) and dried with anhydrous magnesium sulfate; the solvent was evaporated under reduced pressure; and the residue was separated by column chromatography to obtain 0.35 g of white solid compound 1, with a purity of 99.3% and a yield of 64%.

Embodiment 2 Synthesis of Compound 1-7

(1) Synthesis of 3,4-(methylenedioxy) cinnamyl Chloride

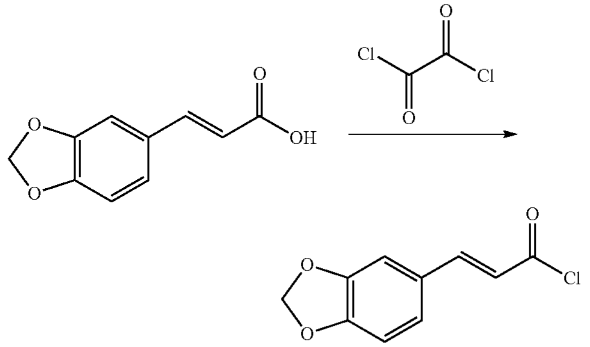

3,4-(methylenedioxy) cinnamic acid (0.21 g, 1.1 mmol), dichloromethane (30 ml) and DMF (1 drop) were added into the reaction flask; oxalyl chloride (0.7 g, 5.5 mmol) was slowly added; the mixture was stirred at room temperature for 1 hour; the solvent was evaporated under reduced pressure; toluene (15 ml) was added to the residue and stirred for 3 minutes; and then the solvent was evaporated under reduced pressure to obtain 0.23 g of pale yellow solid which was used directly in the next step.

(2) Synthesis of Compound 1-7

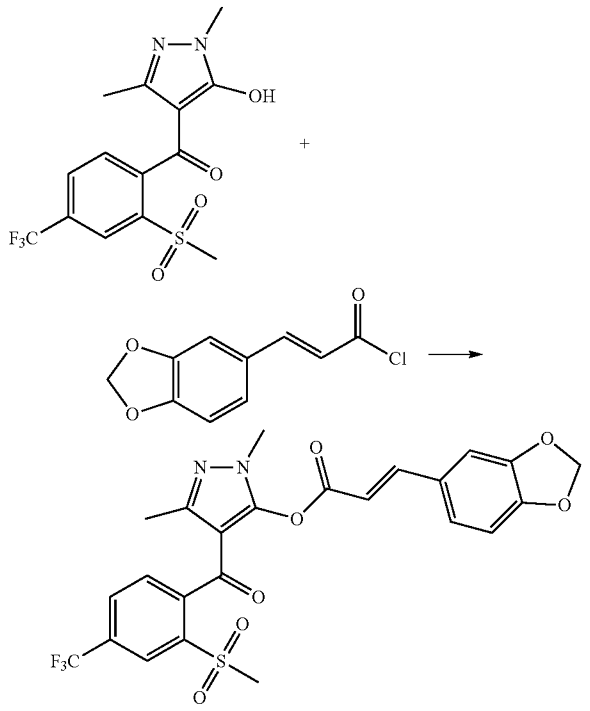

1,3-dimethyl-4-(2-methanesulfonyl-4-trifluoromethylbenzoyl)-5-hydroxypyrazole (0.4 g, 1.1 mmol, see step 3 of embodiment 1 for preparation), dichloromethane (20 ml)

and triethylamine (0.22 g, 2.2 mmol) were added to the reaction flask, and the dichloromethane solution (15 ml) of 3,4-(methylenedioxy) cinnamyl chloride in the above step was added dropwise. The mixture was stirred at room temperature for 1 hour; the solvent was evaporated under reduced pressure; ethyl acetate (100 ml) was added to the residue; water (50 ml) was used for separation and extraction; the organic phase was sequentially washed with saturated salt water (50 ml) and dried with anhydrous magnesium sulfate; the solvent was evaporated under reduced pressure; and the residue was separated by column chromatography to obtain 0.38 g of pale yellow solid compound 7, with a purity of 94.6% and a yield of 60.7%.

Embodiment 3 Synthesis of Compound 2-379

(1) Synthesis of 1-cyclohexenoyl Chloride

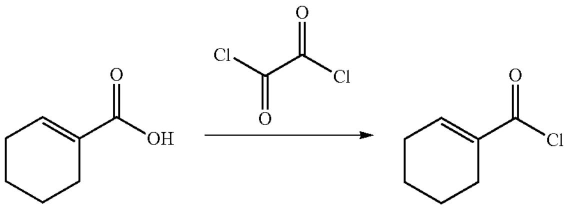 [SMILES: O=C(O)C1=CCCCC1 ; O=C(Cl)C(=O)Cl ; O=C(Cl)C1=CCCCC1]

1-cyclohexenoic acid (0.14 g, 1.1 mmol), dichloromethane (30 ml) and DMF (1 drop) were added into the reaction flask; oxalyl chloride (0.7 g, 5.5 mmol) was slowly added; the mixture was stirred at room temperature for 1 hour; the solvent was evaporated under reduced pressure; toluene (15 ml) was added to the residue and stirred for 3 minutes; and then the solvent was evaporated under reduced pressure to obtain 0.16 g of pale yellow solid which was used directly in the next step.

(2) Synthesis of Compound 2-379

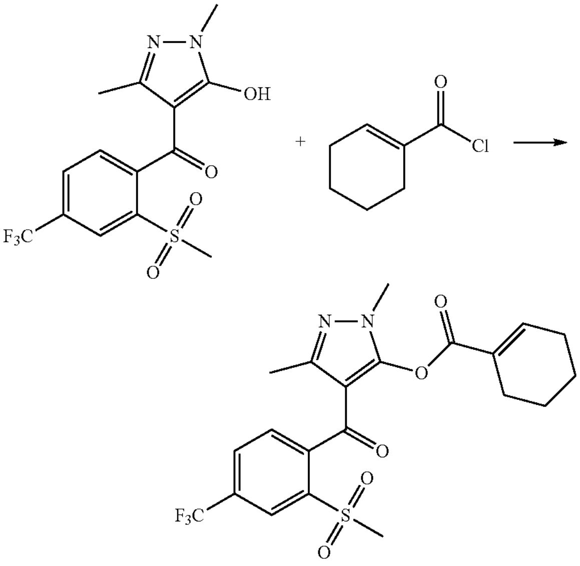

1,3-dimethyl-4-(2-methanesulfonyl-4-trifluoromethylbenzoyl)-5-hydroxypyrazole (0.4 g, 1.1 mmol, see step 3 of embodiment 1 for preparation), dichloromethane (20 ml) and triethylamine (0.22 g, 2.2 mmol) were added to the reaction flask, and the dichloromethane solution (15 ml) of 1-cyclohexenoyl chloride in the above step was added dropwise. The mixture was stirred at room temperature for 1 hour; the solvent is evaporated under reduced pressure; ethyl acetate (100 ml) was added to the residue; water (50 ml) was used for separation and extraction; the organic phase was sequentially washed with saturated salt water (50 ml) and dried with anhydrous magnesium sulfate; the solvent was evaporated under reduced pressure; and the residue was separated by column chromatography to obtain 0.4 g of off-white solid compound 2-379, with a purity of 99.4% and a yield of 77.1%.

Embodiment 4 Synthesis of Compound 1-16

(1) Synthesis of 2-chloro-3-methoxymethyl-4-methylsulfonyl benzoyl chloride

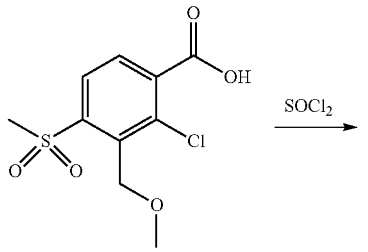

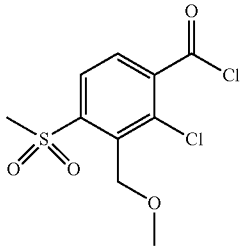

2-methanesulfonyl-4-trifluoromethylbenzoic acid (4 g, 14.35 mmol), dichloromethane (30 ml) and DMF (1 drop) were added into the reaction flask; oxalyl chloride (9.11 g, 71.8 mmol) was slowly added; the mixture was stirred at room temperature for 40 minutes; the solvent was evaporated under reduced pressure; toluene (15 ml) was added to the residue and stirred for 3 minutes; and then the solvent was evaporated under reduced pressure to obtain 4.26 g of yellow solid which was used directly in the next step.

(2) Synthesis of 2-chloro-3-methoxymethyl-4-methylsulfonyl benzoic acid (1,3-dimethylpyrazole-5-yl) ester

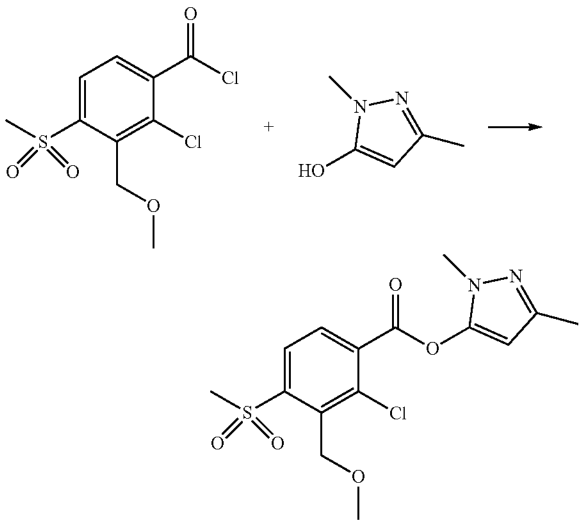

1,3-dimethyl-5-hydroxypyrazole (1.77 g, 15.79 mmol), dichloroethane (100 ml) and triethylamine (2.9 g, 28.7 mmol) were added to the reaction flask, and the dichloroethane solution (30 ml) of 2-chloro-3-methoxymethyl-4-methylsulfonyl benzoyl chloride in the above step was added dropwise. The mixture was stirred at room temperature for 1 hour; the solvent was evaporated under reduced pressure; ethyl acetate (100 ml) was added to the residue; water (1000 ml) was used for separation and extraction; the organic phase was sequentially washed with saturated salt water (100 ml) and dried with anhydrous magnesium sulfate; the solvent was evaporated under reduced pressure; and the residue was separated by column chromatography to obtain 3.4 g of off-white solid, with a yield of 63.5%.

(3) Synthesis of 1,3-dimethyl-4-(2-chloro-3-methoxymethyl-4-methylsulfonyl benzoyl)-5-hydroxypyrazole

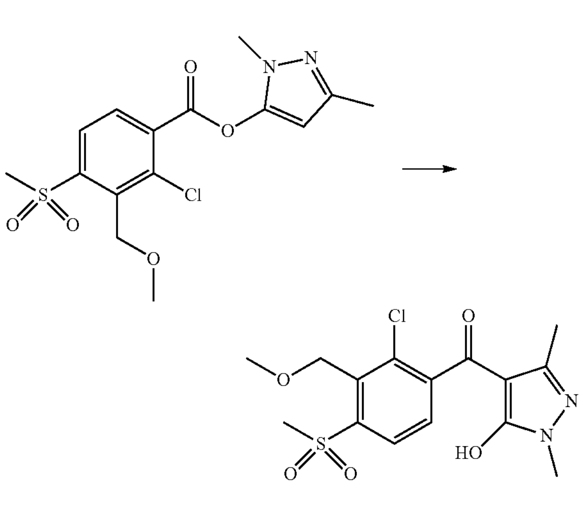

2-chloro-3-methoxymethyl-4-methylsulfonyl benzoic acid (1,3-dimethylpyrazole-5-yl) ester (3.4 g, 9.12 mmol), dichloromethane (100 ml), triethylamine (1.38 g, 13.68 mmol) and acetone cyanohydrin (1 ml) were added to the reaction flask to react at room temperature for 12 hours; and water extraction (50 ml (3)) was added to the reaction solution. After the aqueous phase was collected, the pH was adjusted to be 2-3 with 20% hydrochloric acid, and the aqueous phase was extracted twice with ethyl acetate (100 ml). The organic phase was washed with saturated salt water (50 ml) and dried with anhydrous magnesium sulfate; and the solvent was evaporated under reduced pressure to obtain 3.26 g of yellow solid with a yield of 96%.

(4) Synthesis of Compound 1-16

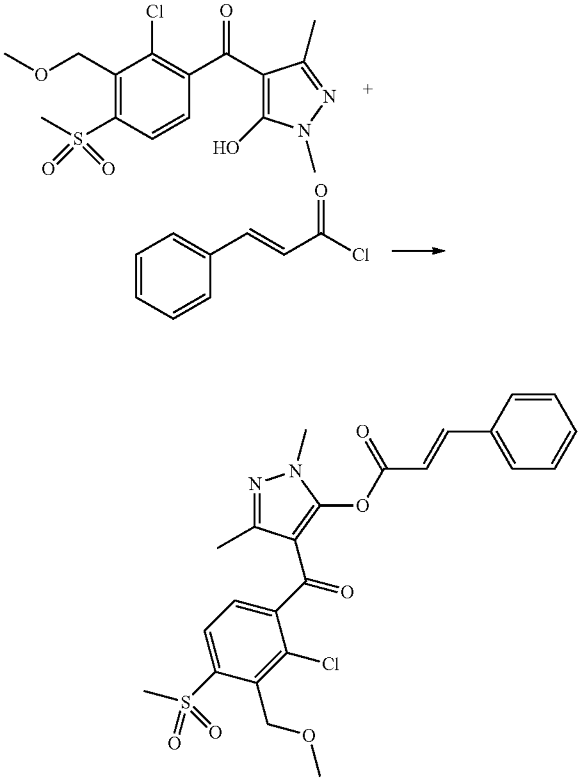

1,3-dimethyl-4-(2-chloro-3-methoxymethyl-4-methylsulfonyl benzoyl)-5-hydroxypyrazole (0.4 g, 1.07 mmol), dichloromethane (20 ml) and triethylamine (0.22 g, 2.15 mmol) were added to the reaction flask, and the dichloromethane solution (15 ml, see step 4 of embodiment 1 for preparation) of cinnamyl chloride in the above step was added dropwise. The mixture was stirred at room temperature for 1 hour; the solvent was evaporated under reduced pressure; ethyl acetate (100 ml) was added to the residue; water (50 ml) was used for separation and extraction; the organic phase was sequentially washed with saturated salt water (50 ml) and dried with anhydrous magnesium sulfate; the solvent was evaporated under reduced pressure; and the residue was separated by column chromatography to obtain 0.31 g of white solid compound 16, with a purity of 93.2% and a yield of 53.5%.

Embodiment 5 Synthesis of Compound 2-307

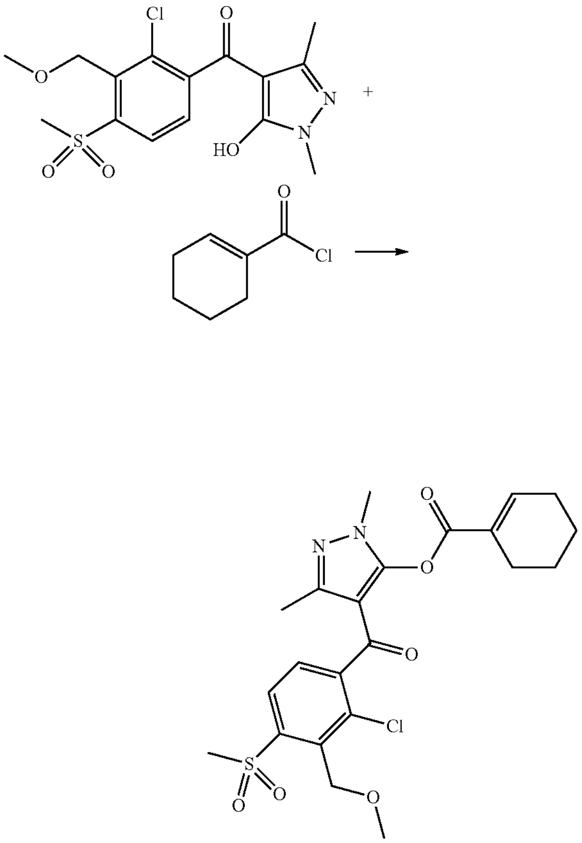

1,3-dimethyl-4-(2-chloro-3-methoxymethyl-4-methylsulfonyl benzoyl)-5-hydroxypyrazole (0.4 g, 1.1 mmol, see step 3 of embodiment 4 for preparation), dichloromethane (20 ml) and triethylamine (0.22 g, 2.2 mmol) were added to the reaction flask, and the dichloromethane solution of 1-cyclohexene-1-acyl chloride (0.2 g of 1.1 mmol 1-cyclohexene-1-acyl chloride was dissolved in 15 ml of dichloromethane, see step 1 of embodiment 3 for preparation) was added dropwise. The mixture was stirred at room temperature for 1 hour; the solvent was evaporated under reduced pressure; ethyl acetate (100 ml) was added to the residue; water (50 ml) was used for separation and extraction; the organic phase was sequentially washed with saturated salt water (50 ml) and dried with anhydrous magnesium sulfate; the solvent was evaporated under reduced pressure; and the residue was separated by column chromatography to obtain 0.45 g of white solid, with a purity of 99.6% and a yield of 87%.

The initial substances are replaced according to the above recorded method to obtain other compounds shown by the formula I. Part of the compounds of the formula I can be found in Table 1, Table 2, Table 3 and Table 4, wherein in Table 1 and Table 2, W is selected from $CX_2$ and the stereo configuration in Table 1 is trans; in Table 3 and Table 4, W is selected from N and the stereo configuration in Table 3 is trans.

In the compound of the formula I, W is $CX_2$ and the stereo configuration is trans.

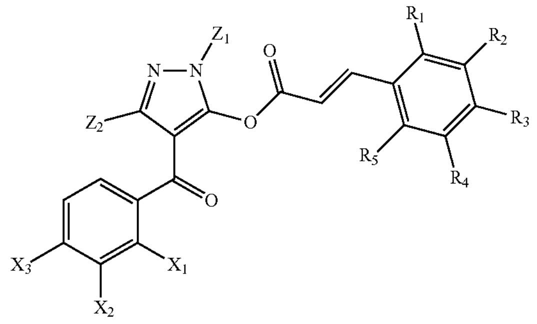

TABLE 1

| Structures and Physical Properties of Part of Compounds of Formula 1 | | | | | | | | | | | |
|---|---|---|---|---|---|---|---|---|---|---|---|
| Compound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
| 1-1 | $SO_2CH_3$ | H | $CF_3$ | $CH_3$ | $CH_3$ | H | H | H | H | H | white solid (144-146) |
| 1-2 | $SO_2CH_3$ | H | $CF_3$ | $CH_3$ | $CH_3$ | Cl | H | Cl | H | H | |
| 1-3 | $SO_2CH_3$ | H | $CF_3$ | $CH_3$ | $CH_3$ | H | H | $OCH_3$ | H | H | |
| 1-4 | $SO_2CH_3$ | H | $CF_3$ | $CH_3$ | $CH_3$ | H | H | $NO_2$ | H | H | |
| 1-5 | $SO_2CH_3$ | H | $CF_5$ | $CH_3$ | $CH_3$ | H | H | $CH_3$ | H | H | |
| 1-6 | $SO_2CH_3$ | H | $CF_3$ | $CH_3$ | $CH_3$ | H | H | 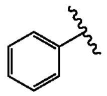 [SMILES: *c1ccccc1] | H | H | |
| 1-7 | $SO_2CH_3$ | H | $CF_3$ | $CH_3$ | $CH_3$ | H | 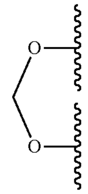 [SMILES: *OCO*] | | H | H | pale yellow solid (99-101) |
| 1-8 | $SO_2CH_3$ | H | $CF_3$ | $CH_3$ | $CH_3$ | H | 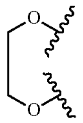 | | H | H | |
| 1-9 | $SO_2CH_3$ | H | $CF_5$ | $CH_3$ | $CH_3$ | H | 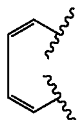 | | H | H | |
| 1-10 | $SO_2CH_3$ | H | $CF_3$ | $CH_3$ | $CH_3$ | 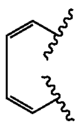 | | H | H | H | |
| 1-11 | $SO_2CH_3$ | H | $CF_3$ | $CH_3$ | $CF_3$ | H | H | H | H | H | |
| 1-12 | $SO_2CH_3$ | H | $CF_3$ | $CH_3$ | H | H | H | H | H | H | |
| 1-13 | $SO_2CH_3$ | H | $CF_3$ | $CH_3$ | $CH_2CH_3$ | H | H | H | H | H | |
| 1-14 | $SO_2CH_3$ | H | $CF_3$ | 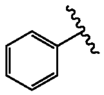 [SMILES: *c1ccccc1] | $CH_3$ | H | H | H | H | H | |

TABLE 1-continued

| Structures and Physical Properties of Part of Compounds of Formula 1 | | | | | | | | | | | |
|---|---|---|---|---|---|---|---|---|---|---|---|
| Compound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
| 1-15 | $SO_2CH_3$ | H | $CF_3$ | $CH_3$ | 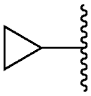 [SMILES: *C1CC1] | H | H | H | H | H | |
| 1-16 | Cl | 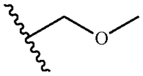 [SMILES: *COC] | $SO_2CH_3$ | $CH_3$ | $CH_3$ | H | H | H | H | H | white solid (139-141) |
| 1-17 | Cl | 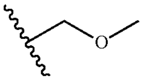 [SMILES: *COC] | $SO_2CH_3$ | $CH_3$ | $CH_3$ | Cl | H | Cl | H | H | |
| 1-18 | Cl | 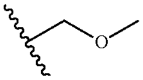 [SMILES: *COC] | $SO_2CH_3$ | $CH_3$ | $CH_3$ | H | H | $OCH_3$ | H | H | white solid (151-153) |
| 1-19 | Cl | 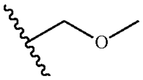 [SMILES: *COC] | $SO_2CH_3$ | $CH_3$ | $CH_3$ | H | H | $NO_2$ | H | H | |
| 1-20 | Cl | 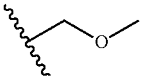 [SMILES: *COC] | $SO_2CH_3$ | $CH_3$ | $CH_3$ | H | H | $CF_3$ | H | H | white solid (139-141) |
| 1-21 | Cl | 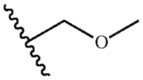 [SMILES: *COC] | $SO_2CH_3$ | $CH_3$ | $CH_3$ | H | H | 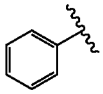 [SMILES: *c1ccccc1] | H | H | pale pink solid (195-197) |
| 1-22 | Cl | 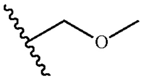 [SMILES: *COC] | $SO_2CH_3$ | $CH_3$ | $CH_3$ | H | | 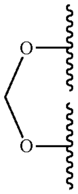 [SMILES: *OCO*] | H | H | pale yellow solid (160-162) |
| 1-23 | Cl | 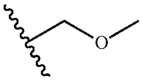 [SMILES: *COC] | $SO_2CH_3$ | $CH_3$ | $CH_3$ | H | | 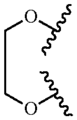 | H | H | |
| 1-24 | Cl | 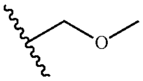 [SMILES: *COC] | $SO_2CH_3$ | $CH_3$ | $CH_3$ | H | | 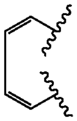 | H | H | |
| 1-25 | Cl | 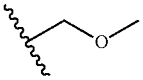 [SMILES: *COC] | $SO_2CH_3$ | $CH_3$ | $CH_3$ | 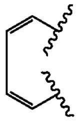 | | H | H | H | |
| 1-26 | Cl | 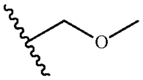 [SMILES: *COC] | SO2$CH_3$ | $CH_3$ | $CF_3$ | H | H | H | H | H | |

TABLE 1-continued

Structures and Physical Properties of Part of Compounds of Formula 1

| Compound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
|---|---|---|---|---|---|---|---|---|---|---|---|
| 1-27 | Cl | 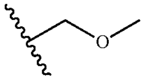 [SMILES: *COC] | $SO_2CH_3$ | $CH_3$ | H | H | H | H | H | H | |
| 1-28 | Cl | 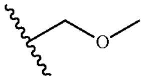 [SMILES: *COC] | $SO_2CH_3$ | $CH_3$ | $CH_2CH_3$ | H | H | H | H | H | |
| 1-29 | Cl | 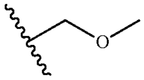 [SMILES: *COC] | $SO_2CH_3$ | 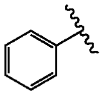 U | $CH_3$ | H | H | H | H | H | |
| 1-30 | Cl | 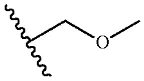 [SMILES: *COC] | $SO_2CH_3$ | $CH_3$ | 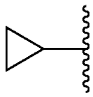 [SMILES: *C1CC1] | H | H | H | H | H | |
| 1-31 | Cl | $CH_3$ | $SO_2CH_3$ | $CH_3$ | $CH_3$ | H | H | H | H | H | pale yellow solid (199-201) |
| 1-32 | Cl | $CH_3$ | $SO_2CH_3$ | $CH_3$ | $CH_3$ | Cl | H | Cl | H | H | |
| 1-33 | Cl | $CH_3$ | $CO_2CH_3$ | $CH_3$ | $CH_3$ | H | H | $OCH_3$ | H | H | |
| 1-34 | Cl | $CH_3$ | $SO_2CH_3$ | $CH_3$ | $CH_3$ | H | H | $NO_3$ | H | H | |
| 1-35 | Cl | $CH_3$ | $SO_2CH_3$ | $CH_3$ | $CH_3$ | H | H | $CF_3$ | H | H | |
| 1-36 | Cl | $CH_3$ | $SO_2CH_3$ | $CH_3$ | $CH_3$ | H | H | 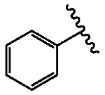 | H | H | |
| 1-37 | Cl | $CH_3$ | $SO_2CH_3$ | $CH_3$ | $CH_3$ | H | | 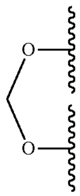 [SMILES: *OCO*] | H | H | white solid (227-229) |
| 1-38 | Cl | $CH_3$ | $SO_2CH_3$ | $CH_3$ | $CH_3$ | H | | 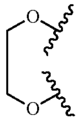 | H | H | |
| 1-39 | Cl | $CH_3$ | $SO_2CH_3$ | $CH_3$ | $CH_3$ | H | | 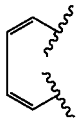 | H | H | |
| 1-40 | Cl | $CH_3$ | $SO_2CH_3$ | $CH_3$ | $CH_3$ | 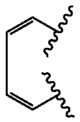 [SMILES: */C=C\C=C/*] | | H | H | H | |
| 1-41 | Cl | $CH_3$ | $SO_2CH_3$ | $CH_3$ | $CF_3$ | H | H | H | H | H | |

TABLE 1-continued

| Structures and Physical Properties of Part of Compounds of Formula 1 | | | | | | | | | | | |
|---|---|---|---|---|---|---|---|---|---|---|---|
| Compound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
| 1-42 | Cl | $CH_3$ | $SO_2CH_3$ | $CH_3$ | H | H | | 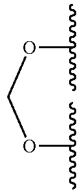 | H | H | yellow solid (151-152) |
| 1-43 | Cl | $CH_3$ | $SO_2CH_3$ | $CH_3$ | $CH_2CH_3$ | H | H | H | H | H | |
| 1-44 | Cl | $CH_3$ | $SO_2CH_3$ | 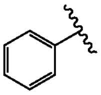 | $CH_3$ | H | H | H | H | H | |
| 1-45 | Cl | $CH_3$ | SO.CH, | $CH_3$ | 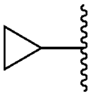 [SMILES: *C1CC1] | H | H | H | H | H | |
| 1-46 | Cl | 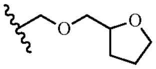 | $SO_2CH_3$ | $CH_3$ | $CH_3$ | H | H | H | H | H | |
| 1-47 | Cl | 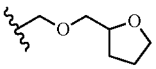 [SMILES: *COCC1CCCO1] | $SO_2CH_3$ | $CH_3$ | $CH_3$ | Cl | H | Cl | H | H | |
| 1-48 | Cl | 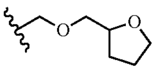 [SMILES: *COCC1CCCO1] | $SO_2CH_3$ | $CH_3$ | $CH_3$ | H | H | $OCH_3$ | H | H | |
| 1-49 | Cl | 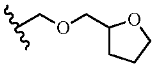 | $SO_2CH_3$ | $CH_3$ | $CH_3$ | H | H | $NO_2$ | H | H | |
| 1-50 | Cl | 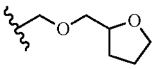 | $SO_2CH_3$ | $CH_3$ | $CH_3$ | H | H | $CF_3$ | H | H | |
| 1-51 | Cl | 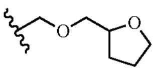 [SMILES: *COCC1CCCO1] | $SO_2CH_3$ | $CH_3$ | $CH_3$ | H | H | 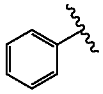 [SMILES: *c1ccccc1] | H | H | |
| 1-52 | Cl | 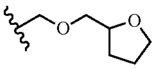 | $SO_2CH_3$ | $CH_3$ | $CH_3$ | H | | 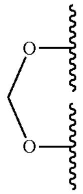 [SMILES: *OCO*] | H | H | |
| 1-53 | Cl | 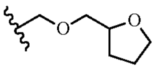 | $SO_2CH_3$ | $CH_3$ | $CH_3$ | H | | 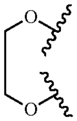 | H | H | |
| 1-54 | Cl | 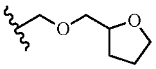 [SMILES: *COCC1CCCO1] | $SO_2CH_3$ | $CH_3$ | $CH_3$ | H | | 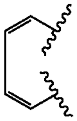 | H | H | |

TABLE 1-continued

Structures and Physical Properties of Part of Compounds of Formula 1

| Compound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
|---|---|---|---|---|---|---|---|---|---|---|---|
| 1-55 | Cl | 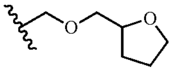 [SMILES: *COCC1CCCO1] | $SO_2CH_3$ | $CH_3$ | $CH_3$ | 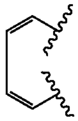 [SMILES: */C=C\C=C/*] | | H | H | H | |
| 1-56 | Cl | 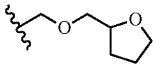 | $SO_2CH_3$ | $CH_3$ | $CF_3$ | H | H | H | H | H | |
| 1-57 | Cl | 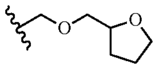 [SMILES: *COCC1CCCO1] | $SO_2CH_3$ | $CH_3$ | H | H | H | H | H | H | |
| 1-58 | Cl | 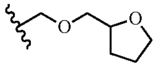 [SMILES: *COCC1CCCO1] | $SO_2CH_3$ | $CH_3$ | $CH_2CH_3$ | H | H | H | H | H | |
| 1-59 | Cl | 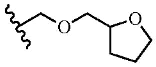 | $SO_2CH_3$ | 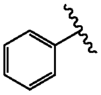 | $CH_3$ | H | H | H | H | H | |
| 1-60 | Cl | 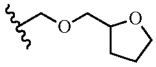 [SMILES: *COCC1CCCO1] | $SO_2CH_3$ | $CH_3$ | 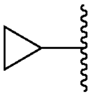 [SMILES: *C1CC1] | H | H | H | H | H | |
| 1-61 | Cl | 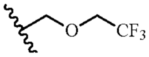 | $SO_2CH_3$ | $CH_3$ | $CH_3$ | H | H | H | H | H | |
| 1-62 | Cl | 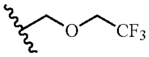 [SMILES: *COCC(F)(F)F] | $SO_2CH_3$ | $CH_3$ | $CH_3$ | Cl | H | Cl | H | H | |
| 1-63 | Cl | 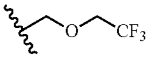 | $SO_2CH_3$ | $CH_3$ | $CH_3$ | H | H | $OCH_3$ | H | H | |
| 1-64 | Cl | 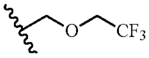 | $SO_2CH_3$ | $CH_3$ | $CH_3$ | H | H | $NO_2$ | H | H | |
| 1-65 | Cl | 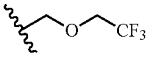 | $SO_2CH_3$ | $CH_3$ | $CH_3$ | H | H | $CF_3$ | H | H | |
| 1-66 | Cl | 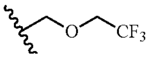 | $SO_2CH_3$ | $CH_3$ | $CH_3$ | H | H | 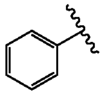 | H | H | |
| 1-67 | Cl | 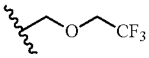 | $SO_2CH_3$ | $CH_3$ | $CH_3$ | H | 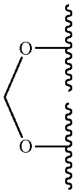 | | H | H | |
| 1-68 | Cl | 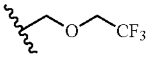 [SMILES: *COCC(F)(F)F] | $SO_2CH_3$ | $CH_3$ | $CH_3$ | H | 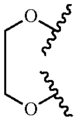 | | H | H | |

TABLE 1-continued

Structures and Physical Properties of Part of Compounds of Formula 1

| Compound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
|---|---|---|---|---|---|---|---|---|---|---|---|
| 1-69 | Cl | 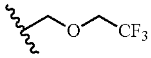 | $SO_2CH_3$ | $CH_3$ | $CH_3$ | H | | 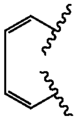 | H | H | |
| 1-70 | Cl | 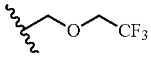 [SMILES: *COCC(F)(F)F] | $SO_2CH_3$ | $CH_3$ | $CH_3$ | 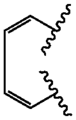 | | H | H | H | |
| 1-71 | Cl | 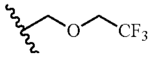 [SMILES: *COCC(F)(F)F] | $SO_2CH_3$ | $CH_3$ | $CF_3$ | H | H | H | H | H | |
| 1-72 | Cl | 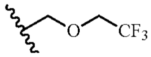 [SMILES: *COCC(F)(F)F] | $SO_2CH_3$ | $CH_3$ | H | H | H | H | H | H | |
| 1-73 | Cl | 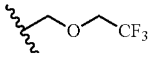 | $SO_2CH_3$ | $CH_3$ | $CH_2CH_3$ | H | H | H | H | H | |
| 1-74 | Cl | 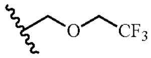 | $SO_2CH_3$ | 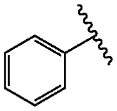 [SMILES: *c1ccccc1] | $CH_3$ | H | H | H | H | H | |
| 1-75 | Cl | 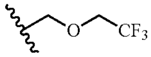 | $SO_2CH_3$ | $CH_3$ | 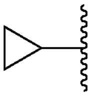 [SMILES: *C1CC1] | H | H | H | H | H | |
| 1-76 | Cl | 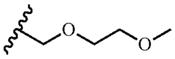 [SMILES: *COCCOC] | $SO_2CH_3$ | $CH_3$ | $CH_3$ | H | H | H | H | H | white solid (123-125) |
| 1-77 | Cl | 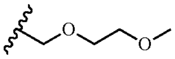 [SMILES: *COCCOC] | $SO_2CH_3$ | $CH_3$ | $CH_3$ | Cl | H | Cl | H | H | |
| 1-78 | Cl | 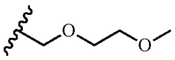 [SMILES: *COCCOC] | $SO_2CH_3$ | $CH_3$ | $CH_3$ | H | H | $OCH_3$ | H | H | |
| 1-79 | Cl | 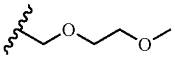 [SMILES: *COCCOC] | $SO_2CH_3$ | $CH_3$ | $CH_3$ | H | H | $NO_2$ | H | H | |
| 1-80 | Cl | 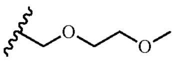 [SMILES: *COCCOC] | $SO_2CH_3$ | $CH_3$ | $CH_3$ | H | H | $CF_3$ | H | H | |
| 1-81 | Cl | 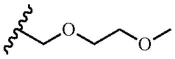 | $SO_2CH_3$ | $CH_3$ | $CH_3$ | H | H | 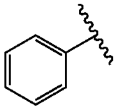 | H | H | yellow solid (135-136) |
| 1-82 | Cl | 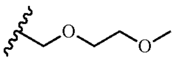 [SMILES: *COCCOC] | $SO_2CH_3$ | $CH_3$ | $CH_3$ | H | | 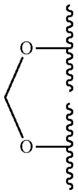 [SMILES: *OCO*] | H | H | yellow solid (87-88) |

TABLE 1-continued

Structures and Physical Properties of Part of Compounds of Formula 1

| Compound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
|---|---|---|---|---|---|---|---|---|---|---|---|
| 1-83 | Cl | 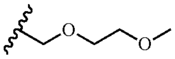 [SMILES: *COCCOC] | $SO_2CH_3$ | $CH_3$ | $CH_3$ | H | | 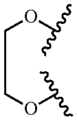 | H | H | |
| 1-84 | Cl | 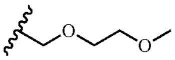 | $SO_2CH_3$ | $CH_3$ | $CH_3$ | H | | 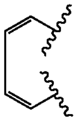 | H | H | |
| 1-85 | Cl | 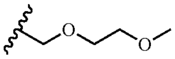 [SMILES: *COCCOC] | $SO_2CH_3$ | $CH_3$ | $CH_3$ | 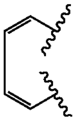 [SMILES: */C=C\C=C/*] | | H | H | H | |
| 1-86 | Cl | 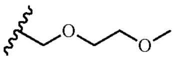 [SMILES: *COCCOC] | $SO_2CH_3$ | $CH_3$ | $CF_3$ | H | H | H | H | H | |
| 1-87 | Cl | 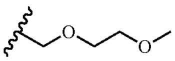 [SMILES: *COCCOC] | $SO_2CH_3$ | $CH_3$ | H | H | H | H | H | H | |
| 1-88 | Cl | 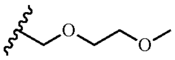 [SMILES: *COCCOC] | $SO_2CH_3$ | $CH_3$ | $CH_2CH_3$ | H | H | H | H | H | |
| 1-89 | Cl | 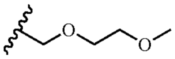 [SMILES: *COCCOC] | $SO_2CH_3$ | 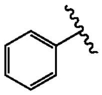 [SMILES: *c1ccccc1] | $CH_3$ | H | H | H | H | H | |
| 1-90 | Cl | 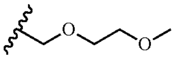 | $SO_2CH_3$ | $CH_3$ | 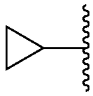 [SMILES: *C1CC1] | H | H | H | H | H | |
| 1-91 | Cl | $CH_2Br$ | $SO_2CH_3$ | $CH_3$ | $CH_3$ | H | H | H | H | H | |
| 1-92 | Cl | $CH_2Br$ | $SO_2CH_3$ | 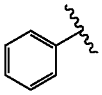 [SMILES: *c1ccccc1] | $CH_3$ | H | H | H | H | H | |
| 1-93 | Cl | $CH_2Br$ | $SO_2CH_3$ | $CH_3$ | 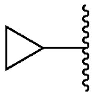 [SMILES: *C1CC1] | H | H | H | H | H | |
| 1-94 | Cl | 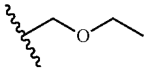 | $SO_2CH_3$ | $CH_3$ | $CH_3$ | H | H | H | H | H | |
| 1-95 | Cl | 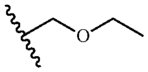 [SMILES: *COCC] | $SO_2CH_3$ | 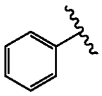 | $CH_3$ | H | H | H | H | H | |
| 1-96 | Cl | 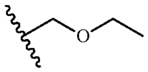 | $SO_2CH_3$ | $CH_3$ | 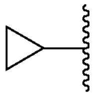 [SMILES: *C1CC1] | H | H | H | H | H | |
| 1-97 | Cl | 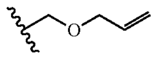 [SMILES: *COCC=C] | $SO_2CH_3$ | $CH_3$ | $CH_3$ | H | H | H | H | H | |

TABLE 1-continued

Structures and Physical Properties of Part of Compounds of Formula 1

| Compound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
|---|---|---|---|---|---|---|---|---|---|---|---|
| 1-98 | Cl | 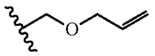 [SMILES: *COCC=C] | $SO_2CH_3$ | 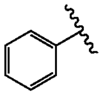 | $CH_3$ | H | H | H | H | H | |
| 1-99 | Cl | 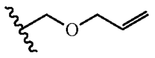 [SMILES: *COCC=C] | $SO_2CH_3$ | $CH_3$ | 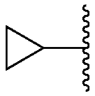 [SMILES: *C1CC1] | H | H | H | H | H | |
| 1-100 | Cl | 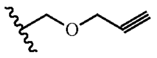 | $SO_2CH_3$ | $CH_3$ | $CH_3$ | H | H | H | H | H | |
| 1-101 | Cl | 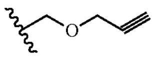 [SMILES: *COCC#C] | $SO_2CH_3$ | 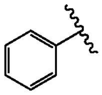 | $CH_3$ | H | H | H | H | H | |
| 1-102 | Cl | 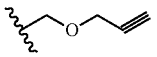 [SMILES: *COCC#C] | $SO_2CH_3$ | $CH_3$ | 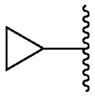 [SMILES: *C1CC1] | H | H | H | H | H | |
| 1-103 | Cl | 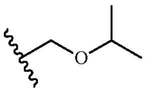 [SMILES: *COC(C)C] | $SO_2CH_3$ | $CH_3$ | $CH_3$ | H | H | H | H | H | |
| 1-104 | Cl | 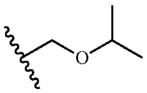 [SMILES: *COC(C)C] | $SO_2CH_3$ | 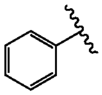 | $CH_3$ | H | H | H | H | H | |
| 1-105 | Cl | 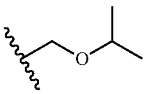 | $SO_2CH_3$ | $CH_3$ | 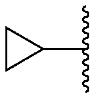 [SMILES: *C1CC1] | H | H | H | H | H | |
| 1-106 | Cl | 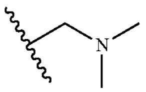 | $SO_2CH_3$ | $CH_3$ | $CH_3$ | H | H | H | H | H | |
| 1-107 | Cl | 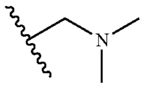 [SMILES: *CN(C)C] | $SO_2CH_3$ | 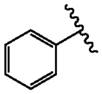 | $CH_3$ | H | H | H | H | H | |
| 1-108 | Cl | 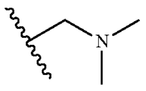 [SMILES: *CN(C)C] | $SO_2CH_3$ | $CH_3$ | 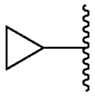 [SMILES: *C1CC1] | H | H | H | H | H | |
| 1-109 | Cl | 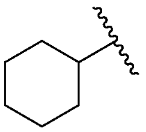 [SMILES: *C1CCCCC1] | $SO_2CH_3$ | $CH_3$ | $CH_3$ | H | H | H | H | H | |
| 1-110 | Cl | 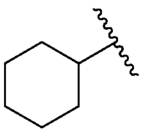 [SMILES: *C1CCCCC1] | $SO_2CH_3$ | 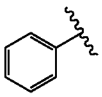 | $CH_3$ | H | H | H | H | H | |

TABLE 1-continued

Structures and Physical Properties of Part of Compounds of Formula 1

| Compound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
|---|---|---|---|---|---|---|---|---|---|---|---|
| 1-111 | Cl | 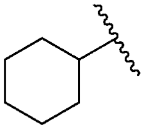 [SMILES: *C1CCCCC1] | $SO_2CH_3$ | $CH_3$ | 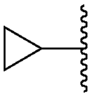 [SMILES: *C1CC1] | H | H | H | H | H | |
| 1-112 | Cl | 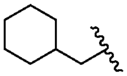 | $SO_2CH_3$ | $CH_3$ | $CH_3$ | H | H | H | H | H | |
| 1-113 | Cl | 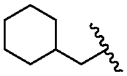 [SMILES: *CC1CCCCC1] | $SO_2CH_3$ | 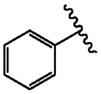 [SMILES: *c1ccccc1] | $CH_3$ | H | H | H | H | H | |
| 1-114 | Cl | 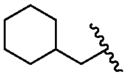 [SMILES: *CC1CCCCC1] | $SO_2CH_3$ | $CH_3$ | 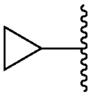 [SMILES: *C1CC1] | H | H | H | H | H | |
| 1-115 | Cl | 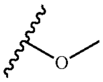 | $SO_2CH_3$ | $CH_3$ | $CH_3$ | H | H | H | H | H | pale yellow oil |
| 1-116 | Cl | 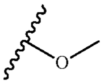 | $SO_2CH_3$ | 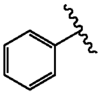 | $CH_3$ | H | H | H | H | H | |
| 1-117 | Cl | 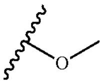 [SMILES: *OC] | $SO_2CH_3$ | $CH_3$ | 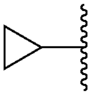 [SMILES: *C1CC1] | H | H | H | H | H | |
| 1-118 | Cl | 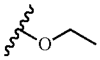 | $SO_2CH_3$ | $CH_3$ | $CH_3$ | H | H | H | H | H | |
| 1-119 | Cl | 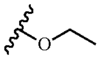 | $SO_2CH_3$ | 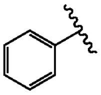 [SMILES: *c1ccccc1] | $CH_3$ | H | H | H | H | H | |
| 1-120 | Cl | 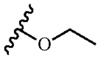 | $SO_2CH_3$ | $CH_3$ | 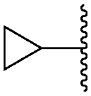 [SMILES: *C1CC1] | H | H | H | H | H | |
| 1-121 | Cl | 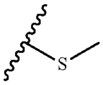 | $SO_2CH_3$ | $CH_3$ | $CH_3$ | H | H | H | H | H | |
| 1-122 | Cl | 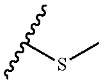 | $SO_2CH_3$ | 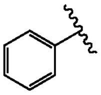 [SMILES: *c1ccccc1] | $CH_3$ | H | H | H | H | H | |
| 1-123 | Cl | 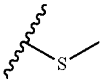 | $SO_2CH_3$ | $CH_3$ | 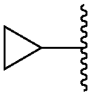 [SMILES: *C1CC1] | H | H | H | H | H | |
| 1-124 | Cl | 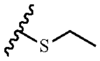 | $SO_2CH_3$ | $CH_3$ | $CH_3$ | H | H | H | H | H | |

TABLE 1-continued

| Structures and Physical Properties of Part of Compounds of Formula 1 | | | | | | | | | | | |
|---|---|---|---|---|---|---|---|---|---|---|---|
| Compound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
| 1-125 | Cl | 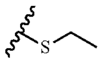 | $SO_2CH_3$ | 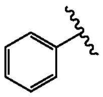 | $CH_3$ | H | H | H | H | H | |
| 1-126 | Cl | 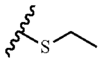 [SMILES: *SCC] | $SO_2CH_3$ | $CH_3$ | 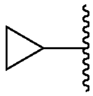 [SMILES: *C1CC1] | H | H | H | H | H | |
| 1-127 | Cl | 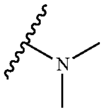 | $SO_2CH_3$ | $CH_3$ | $CH_3$ | H | H | H | H | H | |
| 1-128 | Cl | 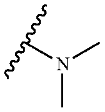 [SMILES: *N(C)C] | $SO_2CH_3$ | 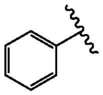 | $CH_3$ | H | H | H | H | H | |
| 1-129 | Cl | 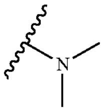 | $SO_2CH_3$ | $CH_3$ | 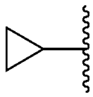 [SMILES: *C1CC1] | H | H | H | H | H | |
| 1-130 | Cl | $SO_2CH_3$ | $SO_2CH_3$ | $CH_3$ | $CH_3$ | H | H | H | H | H | |
| 1-131 | Cl | $SO_2CH_3$ | $SO_2CH_3$ | 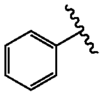 | $CH_3$ | H | H | H | H | H | |
| 1-132 | Cl | $SO_2CH_3$ | $SO_2CH_3$ | $CH_3$ | 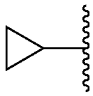 [SMILES: *C1CC1] | H | H | H | H | H | |
| 1-133 | Cl | $SO_2CH_3$ | $CF_3$ | $CH_3$ | $CH_3$ | H | H | H | H | H | |
| 1-134 | Cl | $SO_2CH_3$ | $CF_3$ | 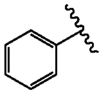 [SMILES: *c1ccccc1] | $CH_3$ | H | H | H | H | H | |
| 1-135 | Cl | $SO_2CH_3$ | $CF_3$ | $CH_3$ | 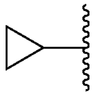 [SMILES: *C1CC1] | H | H | H | H | H | |
| 1-136 | Cl | 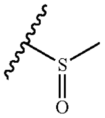 | $SO_2CH_3$ | $CH_3$ | $CH_3$ | H | H | H | H | H | |
| 1-137 | Cl | 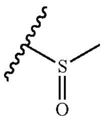 [SMILES: *S(C)=O] | $SO_2CH_3$ | 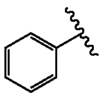 | $CH_3$ | H | H | H | H | H | |
| 1-138 | Cl | 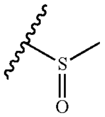 | $SO_2CH_3$ | $CH_3$ | 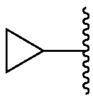 [SMILES: *C1CC1] | H | H | H | H | H | |

TABLE 1-continued

| Structures and Physical Properties of Part of Compounds of Formula 1 | | | | | | | | | | | |
|---|---|---|---|---|---|---|---|---|---|---|---|
| Com-pound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
| 1-139 | Cl | 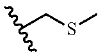 | $SO_2CH_3$ | $CH_3$ | $CH_3$ | H | H | H | H | H | |
| 1-140 | Cl | 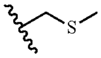 | $SO_2CH_3$ | 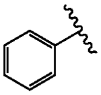 | $CH_3$ | H | H | H | H | H | |
| 1-141 | Cl | 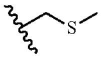 | $SO_2CH_3$ | $CH_3$ | 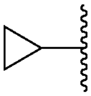 [SMILES: *C1CC1] | H | H | H | H | H | |
| 1-142 | Cl | 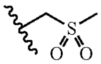 | $SO_2CH_3$ | $CH_3$ | $CH_3$ | H | H | H | H | H | |
| 1-143 | Cl | 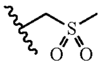 | $SO_2CH_3$ | 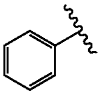 | $CH_3$ | H | H | H | H | H | |
| 1-144 | Cl | 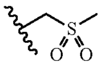 | $SO_2CH_3$ | $CH_3$ | 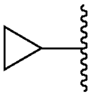 [SMILES: *C1CC1] | H | H | H | H | H | |
| 1-145 | Cl | 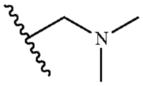 | $SO_2CH_3$ | $CH_3$ | $CH_3$ | H | H | H | H | H | |
| 1-146 | Cl | 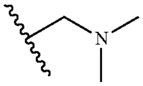 [SMILES: *CN(C)C] | $SO_2CH_3$ | 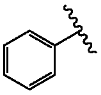 [SMILES: *c1ccccc1] | $CH_3$ | H | H | H | H | H | |
| 1-147 | Cl | 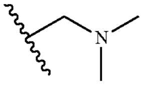 | $SO_2CH_3$ | $CH_3$ | 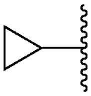 [SMILES: *C1CC1] | H | H | H | H | H | |
| 1-148 | Cl | 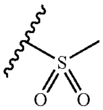 | $SO_2CH_3$ | $CH_3$ | $CH_3$ | H | H | H | H | H | |
| 1-149 | Cl | 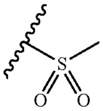 | $SO_2CH_3$ | 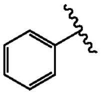 | $CH_3$ | H | H | H | H | H | |
| 1-150 | Cl | 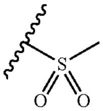 | $SO_2CH_3$ | $CH_3$ | 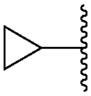 [SMILES: *C1CC1] | H | H | H | H | H | |
| 1-151 | Cl | 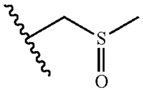 | $SO_2CH_3$ | $CH_3$ | $CH_3$ | H | H | H | H | H | |

TABLE 1-continued

Structures and Physical Properties of Part of Compounds of Formula 1

| Compound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
|---|---|---|---|---|---|---|---|---|---|---|---|
| 1-152 | Cl | 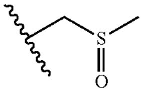 [SMILES: *CS(C)=O] | $SO_2CH_3$ | 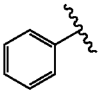 | $CH_3$ | H | H | H | H | H | |
| 1-153 | Cl | 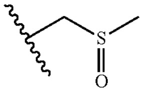 [SMILES: *CS(C)=O] | $SO_2CH_3$ | $CH_3$ | 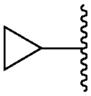 [SMILES: *C1CC1] | H | H | H | H | H | |
| 1-154 | Cl | 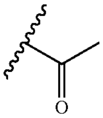 [SMILES: *C(C)=O] | $SO_2CH_3$ | $CH_3$ | $CH_3$ | H | H | H | H | H | |
| 1-155 | Cl | 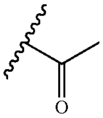 [SMILES: *C(C)=O] | $SO_2CH_3$ | 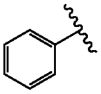 [SMILES: *c1ccccc1] | $CH_3$ | H | H | H | H | H | |
| 1-156 | Cl | 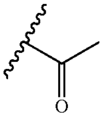 [SMILES: *C(C)=O] | $SO_2CH_3$ | $CH_3$ | 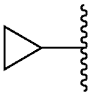 [SMILES: *C1CC1] | H | H | H | H | H | |
| 1-157 | Cl | 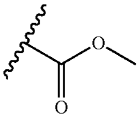 [SMILES: *C(=O)OC] | $SO_2CH_3$ | $CH_3$ | $CH_3$ | H | H | H | H | H | |
| 1-158 | Cl | 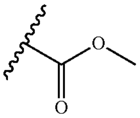 [SMILES: *C(=O)OC] | $SO_2CH_3$ | 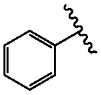 | $CH_3$ | H | H | H | H | H | |
| 1-159 | Cl | 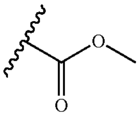 [SMILES: *C(=O)OC] | $SO_2CH_3$ | $CH_3$ | 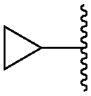 [SMILES: *C1CC1] | H | H | H | H | H | |
| 1-160 | Cl | 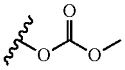 | $SO_2CH_3$ | $CH_3$ | $CH_3$ | H | H | H | H | H | |
| 1-161 | Cl | 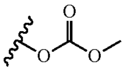 [SMILES: *OC(=O)OC] | $SO_2CH_3$ | 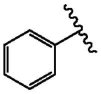 | $CH_3$ | H | H | H | H | H | |
| 1-162 | Cl | 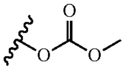 | $SO_2CH_3$ | $CH_3$ | 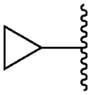 [SMILES: *C1CC1] | H | H | H | H | H | |
| 1-163 | Cl | 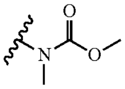 [SMILES: *N(C)C(=O)OC] | $SO_2CH_3$ | $CH_3$ | $CH_3$ | H | H | H | H | H | |

TABLE 1-continued

Structures and Physical Properties of Part of Compounds of Formula 1

| Compound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
|---|---|---|---|---|---|---|---|---|---|---|---|
| 1-164 | Cl | 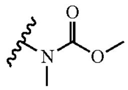 [SMILES: *N(C)C(=O)OC] | $SO_2CH_3$ | 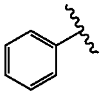 | $CH_3$ | H | H | H | H | H | |
| 1-165 | Cl | 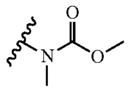 [SMILES: *N(C)C(=O)OC] | $SO_2CH_3$ | $CH_3$ | 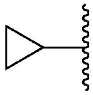 [SMILES: *C1CC1] | H | H | H | H | H | |
| 1-166 | Cl | 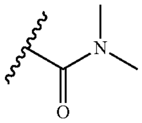 [SMILES: *C(=O)N(C)C] | $SO_2CH_3$ | $CH_3$ | $CH_3$ | H | H | H | H | H | |
| 1-167 | Cl | 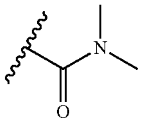 [SMILES: *C(=O)N(C)C] | $SO_2CH_3$ | 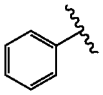 | $CH_3$ | H | H | H | H | H | |
| 1-168 | Cl | 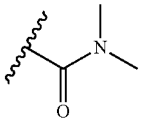 [SMILES: *C(=O)N(C)C] | $SO_2CH_3$ | $CH_3$ | 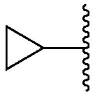 [SMILES: *C1CC1] | H | H | H | H | H | |
| 1-169 | Cl | 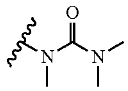 [SMILES: *N(C)C(=O)N(C)C] | $SO_2CH_3$ | $CH_3$ | $CH_3$ | H | H | H | H | H | |
| 1-170 | Cl | 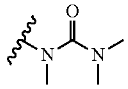 | $SO_2CH_3$ | 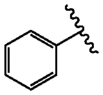 | $CH_3$ | H | H | H | H | H | |
| 1-171 | Cl | 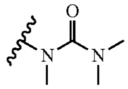 [SMILES: *N(C)C(=O)N(C)C] | $SO_2CH_3$ | $CH_3$ | 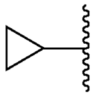 [SMILES: *C1CC1] | H | H | H | H | H | |
| 1-172 | Cl | 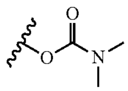 [SMILES: *OC(=O)N(C)C] | $SO_2CH_3$ | $CH_3$ | $CH_3$ | H | H | H | H | H | |
| 1-173 | Cl | 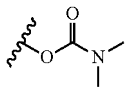 | $SO_2CH_3$ | 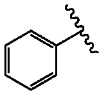 | $CH_3$ | H | H | H | H | H | |
| 1-174 | Cl | 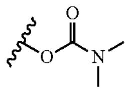 [SMILES: *OC(=O)N(C)C] | $SO_2CH_3$ | $CH_3$ | 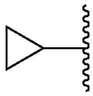 [SMILES: *C1CC1] | H | H | H | H | H | |
| 1-175 | Cl | 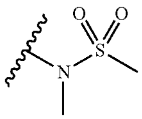 [SMILES: *N(C)S(C)(=O)=O] | $SO_2CH_3$ | $CH_3$ | $CH_3$ | H | H | H | H | H | |

TABLE 1-continued

Structures and Physical Properties of Part of Compounds of Formula 1

| Compound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
|---|---|---|---|---|---|---|---|---|---|---|---|
| 1-176 | Cl | 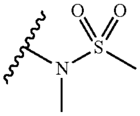 [SMILES: *N(C)S(C)(=O)=O] | $SO_2CH_3$ | 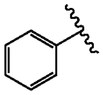 | $CH_3$ | H | H | H | H | H | |
| 1-177 | Cl | 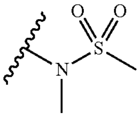 [SMILES: *N(C)S(C)(=O)=O] | $SO_2CH_3$ | $CH_3$ | 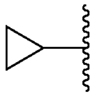 [SMILES: *C1CC1] | H | H | H | H | H | |
| 1-178 | Cl | 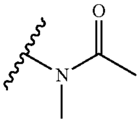 [SMILES: *N(C)C(C)=O] | $SO_2CH_3$ | $CH_3$ | $CH_3$ | H | H | H | H | H | |
| 1-179 | Cl | 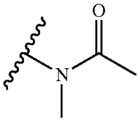 [SMILES: *N(C)C(C)=O] | $SO_2CH_3$ | 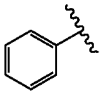 | $CH_3$ | H | H | H | H | H | |
| 1-180 | Cl | 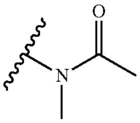 [SMILES: *N(C)C(C)=O] | $SO_2CH_3$ | $CH_3$ | 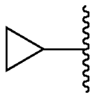 [SMILES: *C1CC1] | H | H | H | H | H | |
| 1-181 | Cl | 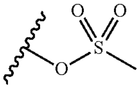 [SMILES: *OS(C)(=O)=O] | $SO_2CH_3$ | $CH_3$ | $CH_3$ | H | H | H | H | H | |
| 1-182 | Cl | 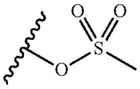 [SMILES: *OS(C)(=O)=O] | $SO_2CH_3$ | 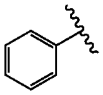 | $CH_3$ | H | H | H | H | H | |
| 1-183 | Cl | 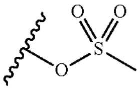 | $SO_2CH_3$ | $CH_3$ | 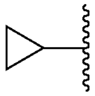 [SMILES: *C1CC1] | H | H | H | H | H | |
| 1-184 | Cl | 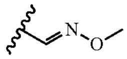 | $SO_2CH_3$ | $CH_3$ | $CH_3$ | H | H | H | H | H | |
| 1-185 | Cl | 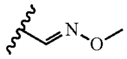 | $SO_2CH_3$ | 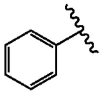 | $CH_3$ | H | H | H | H | H | |
| 1-186 | Cl | 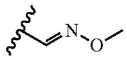 | $SO_2CH_3$ | $CH_3$ | 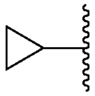 [SMILES: *C1CC1] | H | H | H | H | H | |
| 1-187 | Cl | 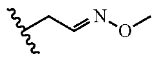 [SMILES: *C/C=N/OC] | $SO_2CH_3$ | $CH_3$ | $CH_3$ | H | H | H | H | H | |
| 1-188 | Cl | 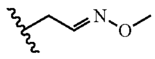 [SMILES: *C/C=N/OC] | $SO_2CH_3$ | 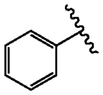 | $CH_3$ | H | H | H | H | H | |

TABLE 1-continued

Structures and Physical Properties of Part of Compounds of Formula 1

| Compound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
|---|---|---|---|---|---|---|---|---|---|---|---|
| 1-189 | Cl | 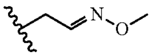 | $SO_2CH_3$ | $CH_3$ | 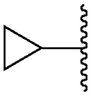 [SMILES: *C1CC1] | H | H | H | H | H | |
| 1-190 | Cl | 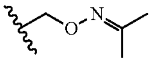 [SMILES: *CON=C(C)C] | $SO_2CH_3$ | $CH_3$ | $CH_3$ | H | H | H | H | H | |
| 1-191 | Cl | 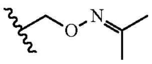 [SMILES: *CON=C(C)C] | $SO_2CH_3$ | 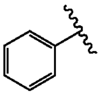 | $CH_3$ | H | H | H | H | H | |
| 1-192 | Cl | 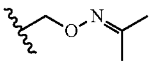 [SMILES: *CON=C(C)C] | $SO_2CH_3$ | $CH_3$ | 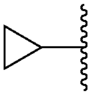 [SMILES: *C1CC1] | H | H | H | H | H | |
| 1-193 | Cl | 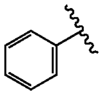 | $SO_2CH_3$ | $CH_3$ | $CH_3$ | H | H | H | H | H | |
| 1-194 | Cl | 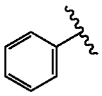 [SMILES: *c1ccccc1] | $SO_2CH_3$ | 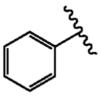 | $CH_3$ | H | H | H | H | H | |
| 1-195 | Cl | 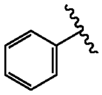 [SMILES: *c1ccccc1] | $SO_2CH_3$ | $CH_3$ | 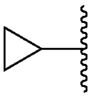 [SMILES: *C1CC1] | H | H | H | H | H | |
| 1-196 | Cl | CN | $SO_2CH_3$ | $CH_3$ | $CH_3$ | H | H | H | H | H | |
| 1-197 | Cl | CN | $SO_2CH_3$ | 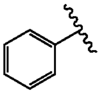 [SMILES: *c1ccccc1] | $CH_3$ | H | H | H | H | H | |
| 1-198 | Cl | CN | $SO_2CH_3$ | $CH_3$ | 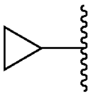 [SMILES: *C1CC1] | H | H | H | H | H | |
| 1-199 | Cl | $NO_2$ | $SO_2CH_3$ | $CH_3$ | $CH_3$ | H | H | H | H | H | |
| 1-200 | Cl | $NO_2$ | $SO_2CH_3$ | 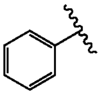 [SMILES: *c1ccccc1] | $CH_3$ | H | H | H | H | H | |
| 1-201 | Cl | $NO_2$ | $SO_2CH_3$ | $CH_3$ | 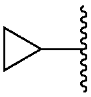 [SMILES: *C1CC1] | H | H | H | H | H | |
| 1-202 | Cl | 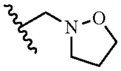 [SMILES: *CN1CCCO1] | $SO_2CH_3$ | $CH_3$ | $CH_3$ | H | H | H | H | H | |
| 1-203 | Cl | 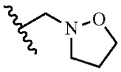 [SMILES: *CN1CCCO1] | $SO_2CH_3$ | 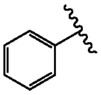 | $CH_3$ | H | H | H | H | H | |

TABLE 1-continued

Structures and Physical Properties of Part of Compounds of Formula 1

| Compound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
|---|---|---|---|---|---|---|---|---|---|---|---|
| 1-204 | Cl | 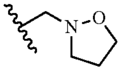 | $SO_2CH_3$ | $CH_3$ | 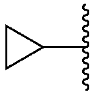 [SMILES: *C1CC1] | H | H | H | H | H | |
| 1-205 | Cl | 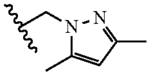 | $SO_2CH_3$ | $CH_3$ | $CH_3$ | H | H | H | H | H | |
| 1-206 | Cl | 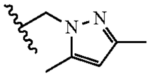 | $SO_2CH_3$ | 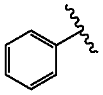 | $CH_3$ | H | H | H | H | H | |
| 1-207 | Cl | 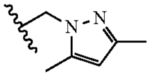 [SMILES: *Cn1nc(C)cc1C] | $SO_2CH_3$ | $CH_3$ | 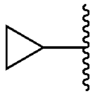 [SMILES: *C1CC1] | H | H | H | H | H | |
| 1-208 | Cl | 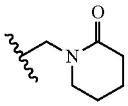 [SMILES: *CN1CCCCC1=O] | $SO_2CH_3$ | $CH_3$ | $CH_3$ | H | H | H | H | H | |
| 1-209 | Cl | 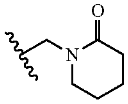 | $SO_2CH_3$ | 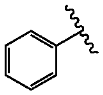 | $CH_3$ | H | H | H | H | H | |
| 1-210 | Cl | 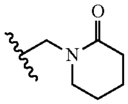 [SMILES: *CN1CCCCC1=O] | $SO_2CH_3$ | $CH_3$ | 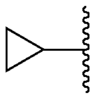 [SMILES: *C1CC1] | H | H | H | H | H | |
| 1-211 | Cl | 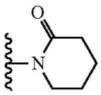 | $SO_2CH_3$ | $CH_3$ | $CH_3$ | H | H | H | H | H | |
| 1-212 | Cl | 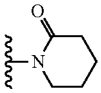 [SMILES: *N1CCCCC1=O] | $SO_2CH_3$ | 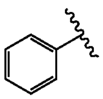 | $CH_3$ | H | H | H | H | H | |
| 1-213 | Cl | 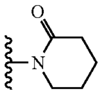 [SMILES: *N1CCCCC1=O] | $SO_2CH_3$ | $CH_3$ | 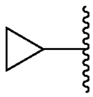 [SMILES: *C1CC1] | H | H | H | H | H | |
| 1-214 | Cl | 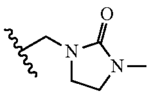 [SMILES: *CN1CCN(C)C1=O] | $SO_2CH_3$ | $CH_3$ | $CH_3$ | H | H | H | H | H | |
| 1-215 | Cl | 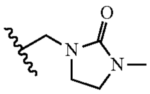 [SMILES: *CN1CCN(C)C1=O] | $SO_2CH_3$ | 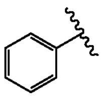 [SMILES: *c1ccccc1] | $CH_3$ | H | H | H | H | H | |
| 1-216 | Cl | 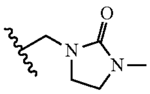 [SMILES: *CN1CCN(C)C1=O] | $SO_2CH_3$ | $CH_3$ | 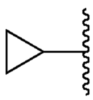 [SMILES: *C1CC1] | H | H | H | H | H | |

TABLE 1-continued

Structures and Physical Properties of Part of Compounds of Formula 1

| Compound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
|---|---|---|---|---|---|---|---|---|---|---|---|
| 1-217 | Cl | 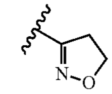 [SMILES: *C1=NOCC1] | $SO_2CH_3$ | $CH_3$ | $CH_3$ | H | H | H | H | H | |
| 1-218 | Cl | 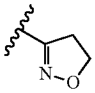 | $SO_2CH_3$ | 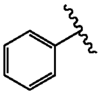 [SMILES: *c1ccccc1] | $CH_3$ | H | H | H | H | H | |
| 1-219 | Cl | 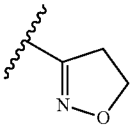 [SMILES: *C1=NOCC1] | $SO_2CH_3$ | $CH_3$ | 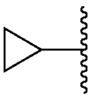 [SMILES: *C1CC1] | H | H | H | H | H | |
| 1-220 | Cl | 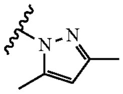 [SMILES: *n1nc(C)cc1C] | $SO_2CH_3$ | $CH_3$ | $CH_3$ | H | H | H | H | H | |
| 1-221 | Cl | 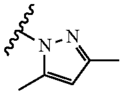 [SMILES: *n1nc(C)cc1C] | $SO_2CH_3$ | 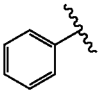 | $CH_3$ | H | H | H | H | H | |
| 1-222 | Cl | 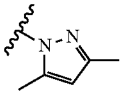 [SMILES: *n1nc(C)cc1C] | $SO_2CH_3$ | $CH_3$ | 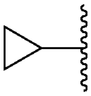 [SMILES: *C1CC1] | H | H | H | H | H | |
| 1-223 | Cl | H | $SO_2CH_3$ | $CH_3$ | $CH_3$ | H | H | H | H | H | white solid (150-152) |
| 1-224 | Cl | H | $SO_2CH_3$ | 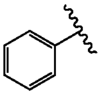 | $CH_3$ | H | H | H | H | H | |
| 1-225 | Cl | H | $SO_2CH_3$ | $CH_3$ | 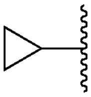 [SMILES: *C1CC1] | H | H | H | H | H | |
| 1-226 | Cl | H | $SO_2CH_3$ | $CH_3$ | $CH_3$ | H | | 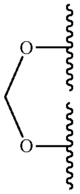 [SMILES: *OCO*] | H | H | pale yellow solid (185-187) |
| 1-227 | Cl | H | $SO_2CH_3$ | 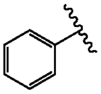 | $CH_3$ | H | | 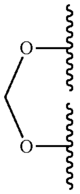 [SMILES: *OCO*] | H | H | |

TABLE 1-continued

Structures and Physical Properties of Part of Compounds of Formula 1

| Compound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
|---|---|---|---|---|---|---|---|---|---|---|---|
| 1-228 | Cl | H | $SO_2CH_3$ | $CH_3$ | 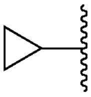 [SMILES: *C1CC1] | H | | 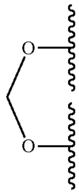 | H | H | |
| 1-229 | Cl | H | Cl | $CH_3$ | $CH_3$ | H | H | H | H | H | pale yellow solid (95-97) |
| 1-230 | Cl | H | Cl | 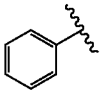 [SMILES: *c1ccccc1] | $CH_3$ | H | H | H | H | H | |
| 1-231 | Cl | H | Cl | $CH_3$ | 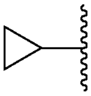 [SMILES: *C1CC1] | H | H | H | H | H | |
| 1-232 | Cl | H | Cl | $CH_3$ | $CH_3$ | H | | 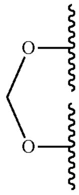 | H | H | pale yellow solid (114-116) |
| 1-233 | Cl | H | Cl | 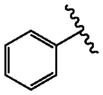 [SMILES: *c1ccccc1] | $CH_3$ | H | | 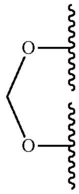 [SMILES: *OCO*] | H | H | |
| 1-234 | Cl | H | Cl | $CH_3$ | 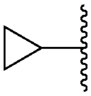 [SMILES: *C1CC1] | H | | 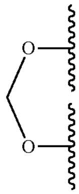 [SMILES: *OCO*] | H | H | |
| 1-235 | $NO_2$ | H | $SO_2CH_3$ | $CH_3$ | $CH_3$ | H | H | H | H | H | orange solid (196-198) |
| 1-236 | $NO_2$ | H | $SO_2CH_3$ | 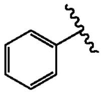 [SMILES: *c1ccccc1] | $CH_3$ | H | H | H | H | H | |
| 1-237 | $NO_2$ | H | $SO_2CH_3$ | $CH_3$ | 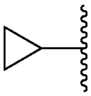 [SMILES: *C1CC1] | H | H | H | H | H | |

TABLE 1-continued

Structures and Physical Properties of Part of Compounds of Formula 1

| Compound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
|---|---|---|---|---|---|---|---|---|---|---|---|
| 1-238 | $NO_2$ | H | $SO_2CH_3$ | $CH_3$ | $CH_3$ | H | | 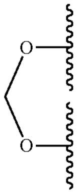 [SMILES: *OCO*] | H | H | yellow solid (173-175) |
| 1-239 | $NO_2$ | H | $SO_2CH_3$ | 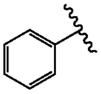 [SMILES: *c1ccccc1] | $CH_3$ | H | | 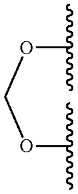 [SMILES: *OCO*] | H | H | |
| 1-240 | $NO_2$ | H | $SO_2CH_3$ | $CH_3$ | 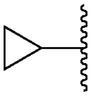 [SMILES: *C1CC1] | H | | 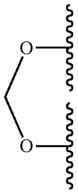 [SMILES: *OCO*] | H | H | |
| 1-241 | Cl | Cl | $SO_2CH_3$ | $CH_3$ | $CH_3$ | H | H | H | H | H | |
| 1-242 | Cl | Cl | $SO_2CH_3$ | 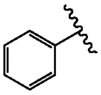 [SMILES: *c1ccccc1] | $CH_3$ | H | H | H | H | H | |
| 1-243 | Cl | Cl | $SO_2CH_3$ | $CH_3$ | 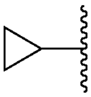 [SMILES: *C1CC1] | H | H | H | H | H | |
| 1-244 | Cl | Cl | $SO_2CH_3$ | $CH_3$ | $CH_3$ | H | | 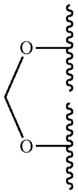 [SMILES: *OCO*] | H | H | |
| 1-245 | Cl | Cl | $SO_2CH_3$ | 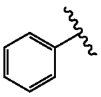 | $CH_3$ | H | | 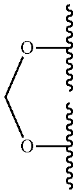 | H | H | |
| 1-246 | Cl | Cl | $SO_2CH_3$ | $CH_3$ | 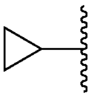 [SMILES: *C1CC1] | H | | 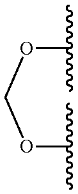 [SMILES: *OCO*] | H | H | |

TABLE 1-continued

Structures and Physical Properties of Part of Compounds of Formula 1

| Compound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
|---|---|---|---|---|---|---|---|---|---|---|---|
| 1-247 | Cl | 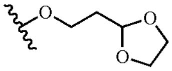 [SMILES: *OCCC1OCCO1] | $SO_2CH_3$ | $CH_3$ | $CH_3$ | H | H | H | H | H | |
| 1-248 | Cl | 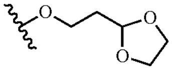 [SMILES: *OCCC1OCCO1] | $SO_2CH_3$ | 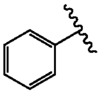 | $CH_3$ | H | H | H | H | H | |
| 1-249 | Cl | 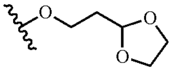 [SMILES: *OCCC1OCCO1] | $SO_2CH_3$ | $CH_3$ | 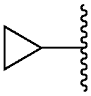 [SMILES: *C1CC1] | H | H | H | H | H | |
| 1-250 | Cl | 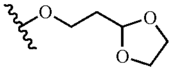 [SMILES: *OCCC1OCCO1] | $SO_2CH_3$ | $CH_3$ | $CH_3$ | H | | 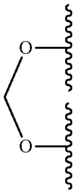 | H | H | |
| 1-251 | Cl | 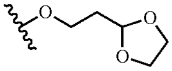 [SMILES: *OCCC1OCCO1] | $SO_2CH_3$ | 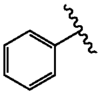 | $CH_3$ | H | | 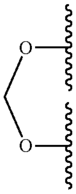 [SMILES: *OCO*] | H | H | |
| 1-252 | Cl | 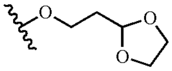 [SMILES: *OCCC1OCCO1] | $SO_2CH_3$ | $CH_3$ | 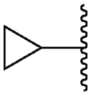 [SMILES: *C1CC1] | H | | 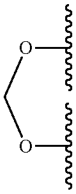 [SMILES: *OCO*] | H | H | |
| 1-253 | Cl | 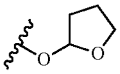 | $SO_2CH_3$ | $CH_3$ | $CH_3$ | H | | H | H | H | |
| 1-254 | Cl | 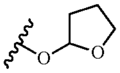 | $SO_2CH_3$ | 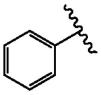 | $CH_3$ | H | | H | H | H | |
| 1-255 | Cl | 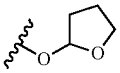 [SMILES: *OC1CCCO1] | $SO_2CH_3$ | $CH_3$ | 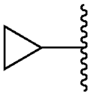 [SMILES: *C1CC1] | H | | H | H | H | |
| 1-256 | Cl | 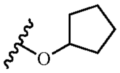 | $SO_2CH_3$ | $CH_3$ | $CH_3$ | H | | H | H | H | |
| 1-257 | Cl | 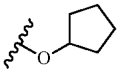 [SMILES: *OC1CCCC1] | $SO_2CH_3$ | 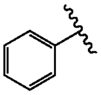 | $CH_3$ | H | | H | H | H | |

TABLE 1-continued

Structures and Physical Properties of Part of Compounds of Formula 1

| Compound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
|---|---|---|---|---|---|---|---|---|---|---|---|
| 1-258 | Cl | 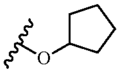 | $SO_2CH_3$ | $CH_3$ | 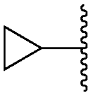 [SMILES: *C1CC1] | H | | H | H | H | |
| 1-259 | $CH_3$ | 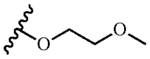 [SMILES: *OCCOC] | $SO_2CH_3$ | $CH_3$ | $CH_3$ | H | H | H | H | H | pale yellow solid (70-72) |
| 1-260 | $CH_3$ | 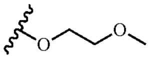 [SMILES: *OCCOC] | $SO_2CH_3$ | 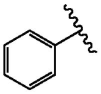 [SMILES: *c1ccccc1] | $CH_3$ | H | H | H | H | H | |
| 1-261 | $SO_2CH_3$ | 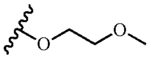 [SMILES: *OCCOC] | $SO_2CH_3$ | $CH_3$ | 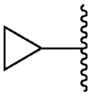 [SMILES: *C1CC1] | H | H | H | H | H | |
| 1-262 | $CH_3$ | 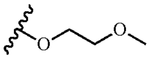 | $SO_2CH_3$ | $CH_3$ | $CH_3$ | H | | 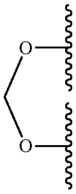 | H | H | pale yellow solid (134-136) |
| 1-263 | $CH_3$ | 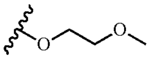 | $SO_2CH_3$ | 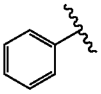 [SMILES: *c1ccccc1] | $CH_3$ | H | | 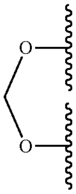 [SMILES: *OCO*] | H | H | |
| 1-264 | $CH_3$ | 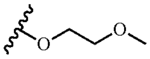 | $SO_2CH_3$ | $CH_3$ | 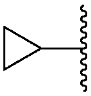 [SMILES: *C1CC1] | H | | 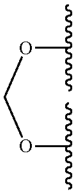 [SMILES: *OCO*] | H | H | |
| 1-265 | $CH_3$ | 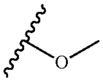 [SMILES: *OC] | $SO_2CH_3$ | $CH_3$ | $CH_3$ | H | H | H | H | H | white solid (187-188) |
| 1-266 | $CH_3$ | 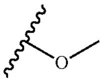 | $SO_2CH_3$ | 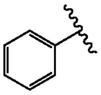 [SMILES: *c1ccccc1] | $CH_3$ | H | H | H | H | H | |
| 1-267 | $CH_3$ | 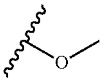 | $SO_2CH_3$ | $CH_3$ | 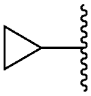 [SMILES: *C1CC1] | H | H | H | H | H | |
| 1-268 | $CH_3$ | $CH_3$ | $SO_2CH_3$ | $CH_3$ | $CH_3$ | H | H | H | H | H | white solid (191-193) |

TABLE 1-continued

Structures and Physical Properties of Part of Compounds of Formula 1

| Compound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
|---|---|---|---|---|---|---|---|---|---|---|---|
| 1-269 | $CH_3$ | $CH_3$ | $SO_2CH_3$ | 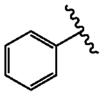 | $CH_3$ | H | H | H | H | H | |
| 1-270 | $CH_3$ | $CH_3$ | $SO_2CH_3$ | $CH_3$ | 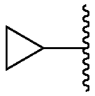 [SMILES: *C1CC1] | H | H | H | H | H | |
| 1-271 | $CH_3$ | $CH_2Br$ | $SO_2CH_3$ | $CH_3$ | $CH_3$ | H | H | H | H | H | |
| 1-272 | $CH_3$ | $CH_2Br$ | $SO_2CH_3$ | 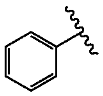 [SMILES: *c1ccccc1] | $CH_3$ | H | H | H | H | H | |
| 1-273 | $CH_3$ | $CH_2Br$ | $SO_2CH_3$ | $CH_3$ | 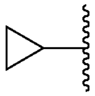 [SMILES: *C1CC1] | H | H | H | H | H | |
| 1-274 | $CH_3$ | F | $SO_2CH_3$ | $CH_3$ | $CH_3$ | H | H | H | H | H | |
| 1-275 | $CH_3$ | F | $SO_2CH_3$ | 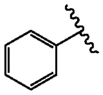 | $CH_3$ | H | H | H | H | H | |
| 1-276 | $CH_3$ | F | $SO_2CH_3$ | $CH_3$ | 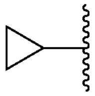 [SMILES: *C1CC1] | H | H | H | H | H | |
| 1-277 | $CH_3$ | Br | $SO_2CH_3$ | $CH_3$ | $CH_3$ | H | H | H | H | H | |
| 1-278 | $CH_3$ | Br | $SO_2CH_3$ | 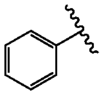 [SMILES: *c1ccccc1] | $CH_3$ | H | H | H | H | H | |
| 1-279 | $CH_3$ | Br | $SO_2CH_3$ | $CH_3$ | 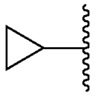 [SMILES: *C1CC1] | H | H | H | H | H | |
| 1-280 | $CH_3$ | 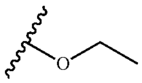 | $SO_2CH_3$ | $CH_3$ | $CH_3$ | H | H | H | H | H | pale yellow solid (152-154) |
| 1-281 | $CH_3$ | 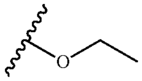 [SMILES: *OCC] | $SO_2CH_3$ | 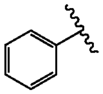 | $CH_3$ | H | H | H | H | H | |
| 1-282 | $CH_3$ | 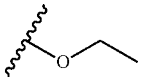 [SMILES: *OCC] | $SO_2CH_3$ | $CH_3$ | 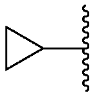 [SMILES: *C1CC1] | H | H | H | H | H | |
| 1-283 | $CH_3$ | 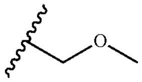 [SMILES: *COC] | $SO_2CH_3$ | $CH_3$ | $CH_3$ | H | H | H | H | H | |

TABLE 1-continued

Structures and Physical Properties of Part of Compounds of Formula 1

| Com-pound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
|---|---|---|---|---|---|---|---|---|---|---|---|
| 1-284 | $CH_3$ | 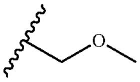 [SMILES: *COC] | $SO_2CH_3$ | 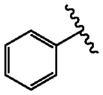 [SMILES: *c1ccccc1] | $CH_3$ | H | H | H | H | H | |
| 1-285 | $CH_3$ | 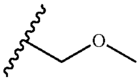 [SMILES: *COC] | $SO_2CH_3$ | $CH_3$ | 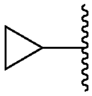 [SMILES: *C1CC1] | H | H | H | H | H | |
| 1-286 | $CH_3$ | 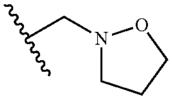 [SMILES: *CN1CCCO1] | $SO_2CH_3$ | $CH_3$ | $CH_3$ | H | H | H | H | H | |
| 1-287 | $CH_3$ | 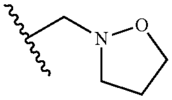 [SMILES: *CN1CCCO1] | $SO_2CH_3$ | 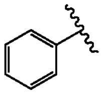 | $CH_3$ | H | H | H | H | H | |
| | | | | I | | | | | | | |
| 1-288 | $CH_3$ | 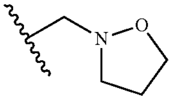 [SMILES: *CN1CCCO1] | $SO_2CH_3$ | $CH_3$ | 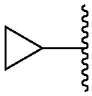 [SMILES: *C1CC1] | H | H | H | H | H | |
| 1-289 | $CH_3$ | 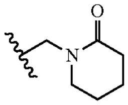 [SMILES: *CN1CCCCC1=O] | $SO_2CH_3$ | $CH_3$ | $CH_3$ | H | H | H | H | H | |
| 1-290 | $CH_3$ | 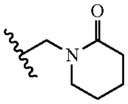 [SMILES: *CN1CCCCC1=O] | $SO_2CH_3$ | 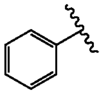 | $CH_3$ | H | H | H | H | H | |
| 1-291 | $CH_3$ | 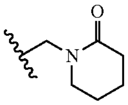 [SMILES: *CN1CCCCC1=O] | $SO_2CH_3$ | $CH_3$ | 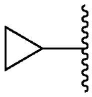 [SMILES: *C1CC1] | H | H | H | H | H | |
| 1-292 | $CH_3$ | 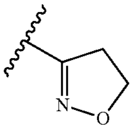 [SMILES: *C1=NOCC1] | $SO_2CH_3$ | $CH_3$ | H | H | H | H | H | H | off-white solid (118-120) |
| 1-293 | $CH_3$ | 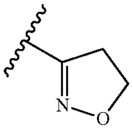 [SMILES: *C1=NOCC1] | $SO_2CH_3$ | 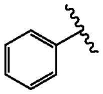 [SMILES: *c1ccccc1] | CH, | H | H | H | H | H | |
| 1-294 | $CH_3$ | 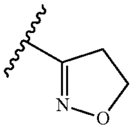 [SMILES: *C1=NOCC1] | $SO_2CH_3$ | $CH_3$ | 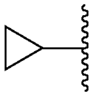 [SMILES: *C1CC1] | H | H | H | H | H | |
| 1-295 | CN | 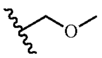 | $SO_2CH_3$ | $CH_3$ | $CH_3$ | H | H | H | H | H | |

TABLE 1-continued

Structures and Physical Properties of Part of Compounds of Formula 1

| Compound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
|---|---|---|---|---|---|---|---|---|---|---|---|
| 1-296 | CN | 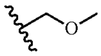 | $SO_2CH_3$ | 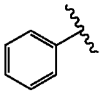 [SMILES: *c1ccccc1] | $CH_3$ | H | H | H | H | H | |
| 1-297 | CN | 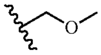 | $SO_2CH_3$ | $CH_3$ | 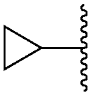 [SMILES: *C1CC1] | H | H | H | H | H | |
| 1-298 | $CF_3$ | 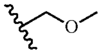 | $SO_2CH_3$ | $CH_3$ | $CH_3$ | H | H | H | H | H | |
| 1-299 | $CF_3$ | 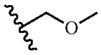 | $SO_2CH_3$ | 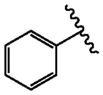 | $CH_3$ | H | H | H | H | H | |
| 1-300 | $CF_3$ | 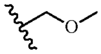 | $SO_2CH_3$ | $CH_3$ | 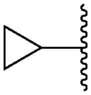 [SMILES: *C1CC1] | H | H | H | H | H | |
| 1-301 | 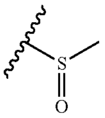 | 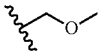 | $SO_2CH_3$ | $CH_3$ | $CH_3$ | H | H | H | H | H | |
| 1-302 | 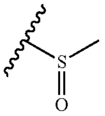 | 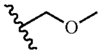 | $SO_2CH_3$ | 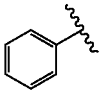 [SMILES: *c1ccccc1] | $CH_3$ | H | H | H | H | H | |
| 1-303 | 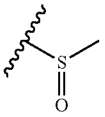 | 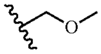 | $SO_2CH_3$ | $CH_3$ | 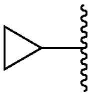 [SMILES: *C1CC1] | H | H | H | H | H | |
| 1-304 | 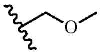 | 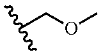 | $SO_2CH_3$ | $CH_3$ | $CH_3$ | H | H | H | H | H | |
| 1-305 | 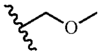 | 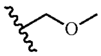 | $SO_2CH_3$ | 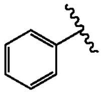 | $CH_3$ | H | H | H | H | H | |
| 1-306 | 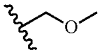 | 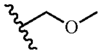 | $SO_2CH_3$ | $CH_3$ | 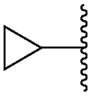 [SMILES: *C1CC1] | H | H | H | H | H | |
| 1-307 | 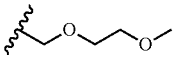 [SMILES: *COCCOC] | 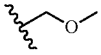 | $SO_2CH_3$ | $CH_3$ | $CH_3$ | H | H | H | H | H | |
| 1-308 | 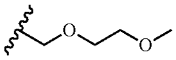 | 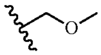 | $SO_2CH_3$ | 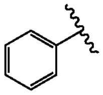 | $CH_3$ | H | H | H | H | H | |
| 1-309 | 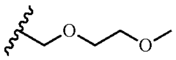 [SMILES: *COCCOC] | 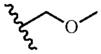 | $SO_2CH_3$ | $CH_3$ | 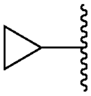 [SMILES: *C1CC1] | H | H | H | H | H | |

TABLE 1-continued

Structures and Physical Properties of Part of Compounds of Formula 1

| Compound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
|---|---|---|---|---|---|---|---|---|---|---|---|
| 1-310 | 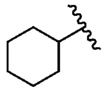 [SMILES: *C1CCCCC1] | 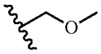 | $SO_2CH_3$ | $CH_3$ | $CH_3$ | H | H | H | H | H | |
| 1-311 | 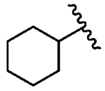 | 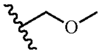 | $SO_2CH_3$ | 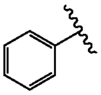 | $CH_3$ | H | H | H | H | H | |
| 1-312 | 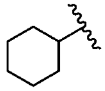 | 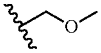 | $SO_2CH_3$ | $CH_3$ | 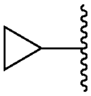 [SMILES: *C1CC1] | H | H | H | H | H | |
| 1-313 | 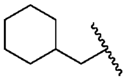 | 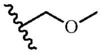 | $SO_2CH_3$ | $CH_3$ | $CH_3$ | H | H | H | H | H | |
| 1-314 | 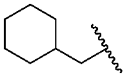 | 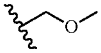 | $SO_2CH_3$ | 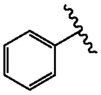 | $CH_3$ | H | H | H | H | H | |
| 1-315 | 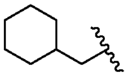 [SMILES: *CC1CCCCC1] | 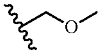 | $SO_2CH_3$ | $CH_3$ | 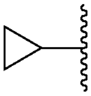 [SMILES: *C1CC1] | H | H | H | H | H | |
| 1-316 | 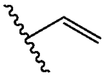 [SMILES: *C=C] | 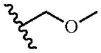 | $SO_2CH_3$ | $CH_3$ | $CH_3$ | H | H | H | H | H | |
| 1-317 | 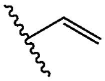 [SMILES: *C=C] | 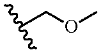 | $SO_2CH_3$ | 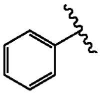 | $CH_3$ | H | H | H | H | H | |
| 1-318 | 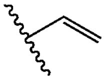 | 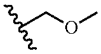 | $SO_2CH_3$ | $CH_3$ | 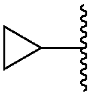 [SMILES: *C1CC1] | H | H | H | H | H | |
| 1-319 | 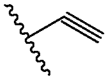 [SMILES: *C#C] | 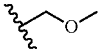 | $SO_2CH_3$ | $CH_3$ | $CH_3$ | H | H | H | H | H | |
| 1-320 | 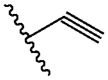 [SMILES: *C#C] | 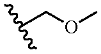 | $SO_2CH_3$ | 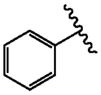 | $CH_3$ | H | H | H | H | H | |
| 1-321 | 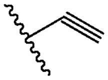 [SMILES: *C#C] | 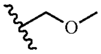 | $SO_2CH_3$ | $CH_3$ | 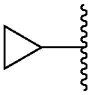 [SMILES: *C1CC1] | H | H | H | H | H | |
| 1-322 | $SO_2CH{=}CH$, | 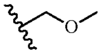 | $SO_2CH_3$ | $CH_3$ | $CH_3$ | H | H | H | H | H | |
| 1-323 | $SO_2CH{=}CH$, | 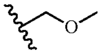 | $SO_2CH_3$ | 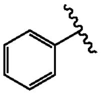 [SMILES: *c1ccccc1] | $CH_3$ | H | H | H | H | H | |

TABLE 1-continued

Structures and Physical Properties of Part of Compounds of Formula 1

| Compound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
|---|---|---|---|---|---|---|---|---|---|---|---|
| 1-324 | $SO_2CH{=}CH$ | 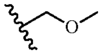 | $SO_2CH_3$ | $CH_3$ | 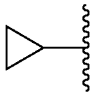 [SMILES: *C1CC1] | H | H | H | H | H | |
| 1-325 | 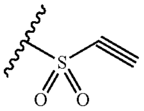 [SMILES: *S(=O)(=O)C#C] | 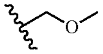 | $SO_2CH_3$ | $CH_3$ | $CH_3$ | H | H | H | H | H | |
| 1-326 | 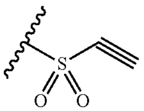 [SMILES: *S(=O)(=O)C#C] | 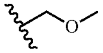 | $SO_2CH_3$ | 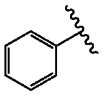 | $CH_3$ | H | H | H | H | H | |
| 1-327 | 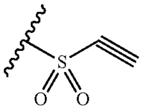 [SMILES: *S(=O)(=O)C#C] | 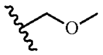 | $SO_2CH_3$ | $CH_3$ | 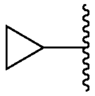 [SMILES: *C1CC1] | H | H | H | H | H | |
| 1-328 | 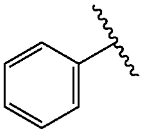 [SMILES: *c1ccccc1] | 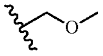 | $SO_2CH_3$ | $CH_3$ | $CH_3$ | H | H | H | H | H | |
| 1-329 | 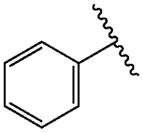 | 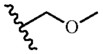 | $SO_2CH_3$ | 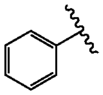 [SMILES: *c1ccccc1] | $CH_3$ | H | H | H | H | H | |
| 1-330 | 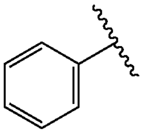 [SMILES: *c1ccccc1] | 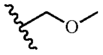 | $SO_2CH_3$ | $CH_3$ | 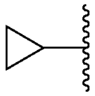 [SMILES: *C1CC1] | H | H | H | H | H | |
| 1-331 | 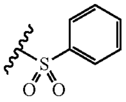 [SMILES: *S(=O)(=O)c1ccccc1] | 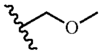 | $SO_2CH_3$ | $CH_3$ | $CH_3$ | H | H | H | H | H | |
| 1-332 | 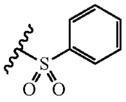 [SMILES: *S(=O)(=O)c1ccccc1] | 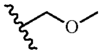 | $SO_2CH_3$ | 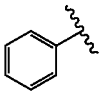 | $CH_3$ | H | H | H | H | H | |
| 1-333 | 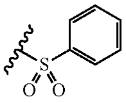 [SMILES: *S(=O)(=O)c1ccccc1] | 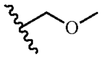 | $SO_2CH_3$ | $CH_3$ | 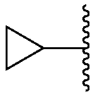 [SMILES: *C1CC1] | H | H | H | H | H | |
| 1-334 | 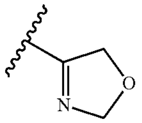 [SMILES: *C1=NCOC1] | 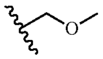 | $SO_2CH_3$ | $CH_3$ | $CH_3$ | H | H | H | H | H | |

TABLE 1-continued

Structures and Physical Properties of Part of Compounds of Formula 1

| Compound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
|---|---|---|---|---|---|---|---|---|---|---|---|
| 1-335 | 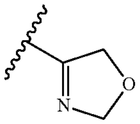 | 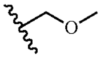 | $SO_2CH_3$ | 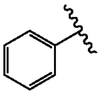 | $CH_3$ | H | H | H | H | H | |
| 1-336 | 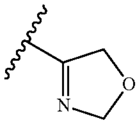 | 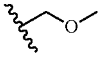 | $SO_2CH_3$ | $CH_3$ | 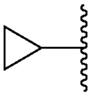 | H | H | H | H | H | |
| 1-337 | 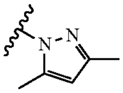 | 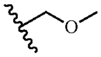 | $SO_2CH_3$ | $CH_3$ | $CH_3$ | H | H | H | H | H | |
| 1-338 | 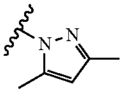 | 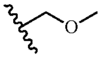 | $SO_2CH_3$ | 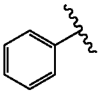 [SMILES: *c1ccccc1] | $CH_3$ | H | H | H | H | H | |
| 1-339 | 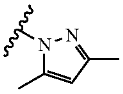 | 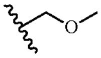 | $SO_2CH_3$ | $CH_3$ | 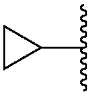 [SMILES: *C1CC1] | H | H | H | H | H | |
| 1-340 | 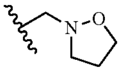 [SMILES: *CN1CCCO1] | 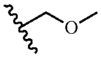 | $SO_2CH_3$ | $CH_3$ | $CH_3$ | H | H | H | H | H | |
| 1-341 | 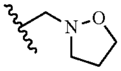 [SMILES: *CN1CCCO1] | 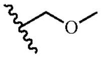 | $SO_2CH_3$ | 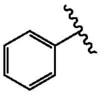 | $CH_3$ | H | H | H | H | H | |
| 1-342 | 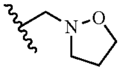 [SMILES: *CN1CCCO1] | 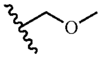 | $SO_2CH_3$ | $CH_3$ | 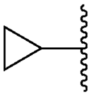 [SMILES: *C1CC1] | H | H | H | H | H | |
| 1-343 | 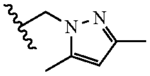 [SMILES: *Cn1nc(C)cc1C] | 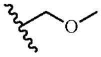 | $SO_2CH_3$ | $CH_3$ | $CH_3$ | H | H | H | H | H | |
| 1-344 | 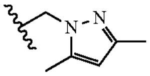 [SMILES: *Cn1nc(C)cc1C] | 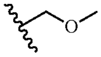 | $SO_2CH_3$ | 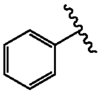 | $CH_3$ | H | H | H | H | H | |
| 1-345 | 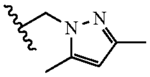 [SMILES: *Cn1nc(C)cc1C] | 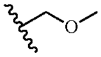 | $SO_2CH_3$ | $CH_3$ | 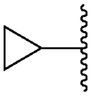 [SMILES: *C1CC1] | H | H | H | H | H | |
| 1-346 | $CH_3$ | 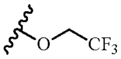 | $SO_2CH_3$ | $CH_3$ | $CH_3$ | H | H | H | H | H | white solid (135-137) |
| 1-347 | $CH_3$ | 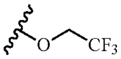 | $SO_2CH_3$ | 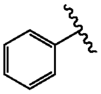 | $CH_3$ | H | H | H | H | H | |

TABLE 1-continued

| Structures and Physical Properties of Part of Compounds of Formula 1 | | | | | | | | | | | |
|---|---|---|---|---|---|---|---|---|---|---|---|
| Compound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
| 1-348 | $CH_3$ | 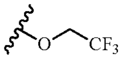 | $SO_2CH_3$ | $CH_3$ | 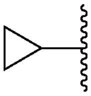 [SMILES: *C1CC1] | H | H | H | H | H | |
| 1-349 | $CH_3$ | 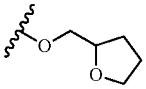 [SMILES: *OCC1CCCO1] | $SO_2CH_3$ | $CH_3$ | $CH_3$ | H | H | H | H | H | yellow oil |
| 1-350 | $CH_3$ | 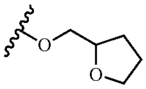 | $SO_2CH_3$ | 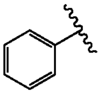 | $CH_3$ | H | H | H | H | H | |
| 1-351 | $CH_3$ | 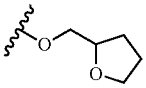 [SMILES: *OCC1CCCO1] | $SO_2CH_3$ | $CH_3$ | 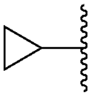 | H | H | H | H | H | |
| 1-352 | $CH_3$ | 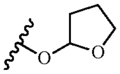 | $SO_2CH_3$ | $CH_3$ | $CH_3$ | H | H | H | H | H | |
| 1-353 | $CH_3$ | 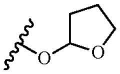 | $SO_2CH_3$ | 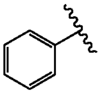 [SMILES: *c1ccccc1] | $CH_3$ | H | H | H | H | H | |
| 1-354 | $CH_3$ | 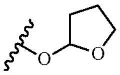 | $SO_2CH_3$ | $CH_3$ | 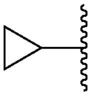 [SMILES: *C1CC1] | H | H | H | H | H | |
| 1-355 | $CH_3$ | 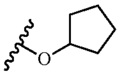 | $SO_2CH_3$ | $CH_3$ | $CH_3$ | H | H | H | H | H | |
| 1-356 | $CH_3$ | 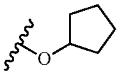 | $SO_2CH_3$ | 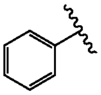 | $CH_3$ | H | H | H | H | H | |
| 1-357 | $CH_3$ | 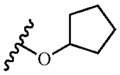 | $SO_2CH_3$ | $CH_3$ | 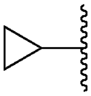 [SMILES: *C1CC1] | H | H | H | H | H | |
| 1-358 | $CH_3$ | 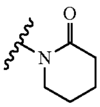 [SMILES: *N1CCCCC1=O] | $SO_2CH_3$ | $CH_3$ | $CH_3$ | H | H | H | H | H | |
| 1-359 | $CH_3$ | 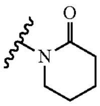 [SMILES: *N1CCCCC1=O] | $SO_2CH_3$ | 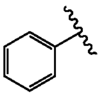 | $CH_3$ | H | H | H | H | H | |
| 1-360 | $CH_3$ | 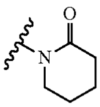 [SMILES: *N1CCCCC1=O] | $SO_2CH_3$ | $CH_3$ | 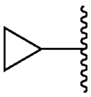 [SMILES: *C1CC1] | H | H | H | H | H | |
| 1-361 | $CH_3$ | $SO_2CH_3$ | $CF_3$ | $CH_3$ | $CH_3$ | H | H | H | H | H | |

TABLE 1-continued

| Structures and Physical Properties of Part of Compounds of Formula 1 | | | | | | | | | | | |
|---|---|---|---|---|---|---|---|---|---|---|---|
| Compound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
| 1-362 | $CH_3$ | $SO_2CH_3$ | $CF_3$ | 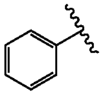 | $CH_3$ | H | H | H | H | H | |
| 1-363 | $CH_3$ | $SO_2CH_3$ | $CF_3$ | $CH_3$ | 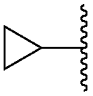 [SMILES: *C1CC1] | H | H | H | H | H | |
| 1-364 | $CH_3$ | 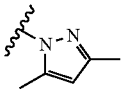 [SMILES: *n1nc(C)cc1C] | $SO_2CH_3$ | $CH_3$ | $CH_3$ | H | H | H | H | H | |
| 1-365 | $CH_3$ | 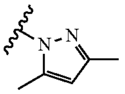 [SMILES: *n1nc(C)cc1C] | $SO_2CH_3$ | 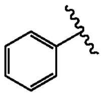 | $CH_3$ | H | H | H | H | H | |
| 1-366 | $CH_3$ | 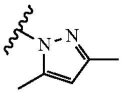 | $SO_2CH_3$ | $CH_3$ | 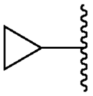 [SMILES: *C1CC1] | H | H | H | H | H | |
| 1-367 | $NO_2$ | H | Cl | $CH_3$ | $CH_3$ | H | H | H | H | H | orange solid (107-109) |
| 1-368 | $NO_2$ | H | Cl | 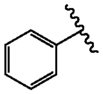 | $CH_3$ | H | H | H | H | H | |
| 1-369 | $NO_2$ | H | Cl | $CH_3$ | 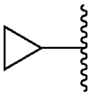 [SMILES: *C1CC1] | H | H | H | H | H | |
| 1-370 | $CH_3$ | 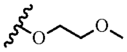 | $SO_2CH_3$ | $CH_3$ | $CH_3$ | H | H | $OCH_3$ | H | H | yellow oil |
| 1-371 | $SO_2CH_3$ | H | Cl | $CH_3$ | $CH_3$ | H | H | H | H | H | white solid (153-154) |
| 1-372 | $CH_3$ | 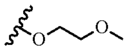 [SMILES: *OCCOC] | $SO_2CH_3$ | $CH_3CH_2$ | H | H | H | H | H | H | yellow oil |
| 1-373 | Cl | 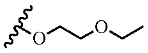 | $SO_2CH_3$ | $CH_3$ | $CH_3$ | H | H | H | H | H | yellow oil |
| 1-374 | Cl | 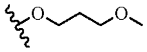 | $SO_2CH_3$ | $CH_3$ | $CH_3$ | H | H | H | H | H | yellow oil |
| 1-375 | Cl | 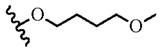 [SMILES: *OCCCCOC] | $SO_2CH_3$ | $CH_3$ | $CH_3$ | H | H | H | H | H | yellow oil |
| 1-376 | Cl | 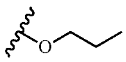 | $SO_2CH_3$ | $CH_3$ | $CH_3$ | H | H | H | H | H | pale yellow oil |

TABLE 1-continued

| Structures and Physical Properties of Part of Compounds of Formula 1 | | | | | | | | | | | |
|---|---|---|---|---|---|---|---|---|---|---|---|
| Compound | $X_1$ | $X_2$ | $X_3$ | $Z_1$ | $Z_2$ | $R_1$ | $R_2$ | $R_3$ | $R_4$ | $R_5$ | Appearance (Melting Point° C.) |
| 1-377 | Cl | 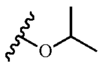 [SMILES: *OC(C)C] | $SO_2CH_3$ | $CH_3$ | $CH_3$ | H | H | H | H | H | pale yellow oil |

In the compound of the formula I, W is $CX_2$.

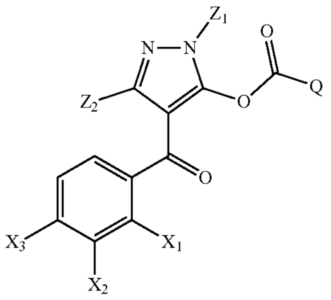

TABLE 2

| Structures and Physical Properties of Part of Compounds of Formula I | | | | | | | |
|---|---|---|---|---|---|---|---|
| Compound | $X_1$ | $X_2$ | $X_3$ | $Z_1$ | $Z_2$ | Q | Appearance (Melting Point ° C.) |
| 2-1 | $CH_3$ | 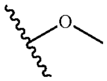 | $SO_2CH_3$ | $CH_3$ | $CH_3$ | 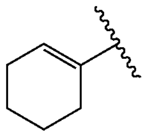 | white solid (170-171) |
| 2-2 | $CH_3$ | 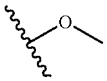 [SMILES: *OC] | $SO_2CH_3$ | $CH_3$ | $CH_3$ | 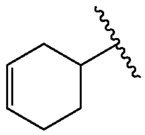 | |
| 2-3 | $CH_3$ | 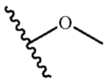 [SMILES: *OC] | $SO_2CH_3$ | $CH_3$ | $CH_3$ | 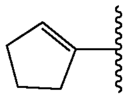 [SMILES: *C1=CCCC1] | |
| 2-4 | $CH_3$ | 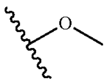 [SMILES: *OC] | $SO_2CH_3$ | $CH_3$ | $CH_3$ | 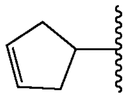 | |
| 2-5 | $CH_3$ | 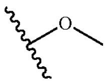 | $SO_2CH_3$ | $CH_3$ | $CH_3$ | 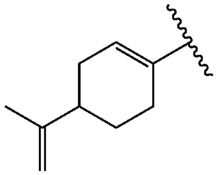 [SMILES: *C1=CCC(C(=C)C)CC1] | |

TABLE 2-continued

Structures and Physical Properties of Part of Compounds of Formula I

| Compound | $X_1$ | $X_2$ | $X_3$ | $Z_1$ | $Z_2$ | Q | Appearance (Melting Point ° C.) |
|---|---|---|---|---|---|---|---|
| 2-6 | $CH_3$ | 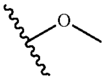 [SMILES: *OC] | $SO_2CH_3$ | $CH_3$ | $CH_3$ | 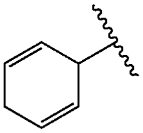 [SMILES: *C1C=CCC=C1] | |
| 2-7 | $CH_3$ | 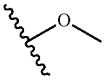 [SMILES: *OC] | $SO_2CH_3$ | $CH_3CH_2$ | H | 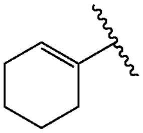 [SMILES: *C1=CCCCC1] | |
| 2-8 | $CH_3$ | 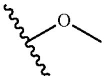 [SMILES: *OC] | $SO_2CH_3$ | $CH_3CH_2$ | H | 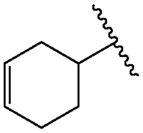 [SMILES: *C1CC=CCC1] | |
| 2-9 | $CH_3$ | 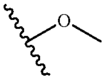 [SMILES: *OC] | $SO_2CH_3$ | $CH_3CH_2$ | H | 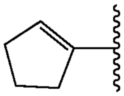 | |
| 2-10 | $CH_3$ | 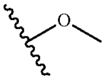 [SMILES: *OC] | $SO_2CH_3$ | $CH_3CH_2$ | H | 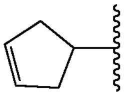 [SMILES: *C1CC=CC1] | |
| 2-11 | $CH_3$ | 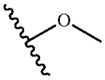 [SMILES: *OC] | $SO_2CH_3$ | $CH_3CH_2$ | H | 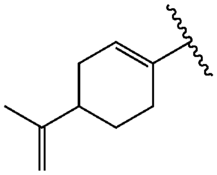 [SMILES: *C1=CCC(C(=C)C)CC1] | |
| 2-12 | $CH_3$ | 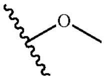 [SMILES: *OC] | $SO_2CH_3$ | $CH_3CH_2$ | H | 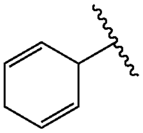 [SMILES: *C1C=CCC=C1] | |
| 2-13 | $CH_3$ | 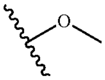 | $SO_2CH_3$ | $CH_3$ | H | 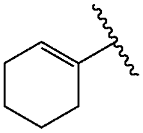 | |
| 2-14 | $CH_3$ | 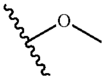 | $SO_2CH_3$ | $CH_3$ | H | 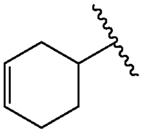 | |
| 2-15 | $CH_3$ | 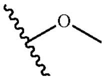 | $SO_2CH_3$ | $CH_3$ | H | 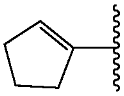 [SMILES: *C1=CCCC1] | |
| 2-16 | $CH_3$ | 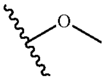 | $SO_2CH_3$ | $CH_3$ | H | 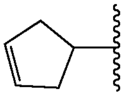 [SMILES: *C1CC=CC1] | |

TABLE 2-continued

Structures and Physical Properties of Part of Compounds of Formula I

| Compound | $X_1$ | $X_2$ | $X_3$ | $Z_1$ | $Z_2$ | Q | Appearance (Melting Point ° C.) |
|---|---|---|---|---|---|---|---|
| 2-17 | $CH_3$ | 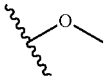 [SMILES: *OC] | $SO_2CH_3$ | $CH_3$ | H | 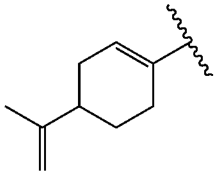 [SMILES: *C1=CCC(C(=C)C)CC1] | |
| 2-18 | $CH_3$ | 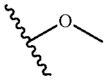 [SMILES: *OC] | $SO_2CH_3$ | $CH_3$ | H | 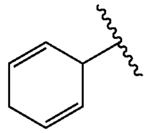 [SMILES: *C1C=CCC=C1] | |
| 2-19 | $CH_3$ | 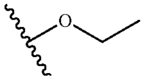 [SMILES: *OCC] | $SO_2CH_3$ | $CH_3$ | $CH_3$ | 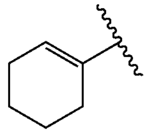 | white solid (164-165) |
| 2-20 | $CH_3$ | 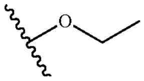 | $SO_2CH_3$ | $CH_3$ | $CH_3$ | 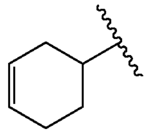 | |
| 2-21 | $CH_3$ | 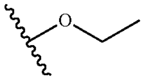 [SMILES: *OCC] | $SO_2CH_3$ | $CH_3$ | $CH_3$ | 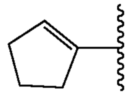 | |
| 2-22 | $CH_3$ | 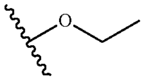 [SMILES: *OCC] | $SO_2CH_3$ | $CH_3$ | $CH_3$ | 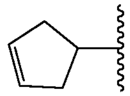 [SMILES: *C1CC=CC1] | |
| 2-23 | $CH_3$ | 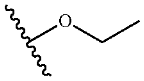 [SMILES: *OCC] | $SO_2CH_3$ | $CH_3$ | $CH_3$ | 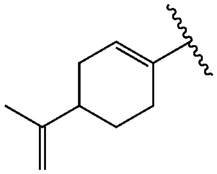 [SMILES: *C1=CCC(C(=C)C)CC1] | |
| 2-24 | $CH_3$ | 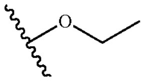 [SMILES: *OCC] | $SO_2CH_3$ | $CH_3$ | $CH_3$ | 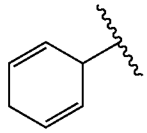 | |
| 2-25 | $CH_3$ | 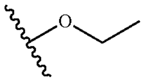 [SMILES: *OCC] | $SO_2CH_3$ | $CH_2CH_3$ | H | 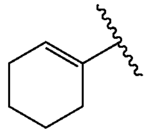 | |
| 2-26 | $CH_3$ | 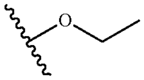 [SMILES: *OCC] | $SO_2CH_3$ | $CH_2CH_3$ | H | 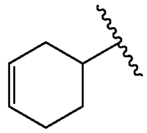 [SMILES: *C1CC=CCC1] | |

TABLE 2-continued
| Compound | $X_1$ | $X_2$ | $X_3$ | $Z_1$ | $Z_2$ | Q | Appearance (Melting Point ° C.) |
|---|---|---|---|---|---|---|---|
| Structures and Physical Properties of Part of Compounds of Formula I | | | | | | | |
| 2-27 | $CH_3$ | 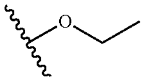 | $SO_2CH_3$ | $CH_2CH_3$ | H | 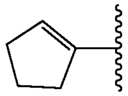 | |
| 2-28 | $CH_3$ | 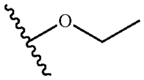 [SMILES: *OCC] | $SO_2CH_3$ | $CH_2CH_3$ | H | 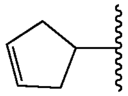 [SMILES: *C1CC=CC1] | |
| 2-29 | $CH_3$ | 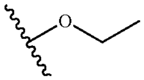 [SMILES: *OCC] | $SO_2CH_3$ | $CH_2CH_3$ | H | 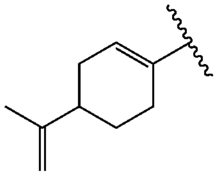 [SMILES: *C1=CCC(C(=C)C)CC1] | |
| 2-30 | $CH_3$ | 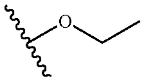 [SMILES: *OCC] | $SO_2CH_3$ | $CH_2CH_3$ | H | 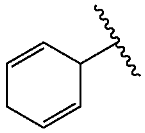 [SMILES: *C1C=CCC=C1] | |
| 2-31 | $CH_3$ | 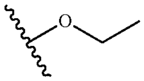 [SMILES: *OCC] | $SO_2CH_3$ | $CH_3$ | H | 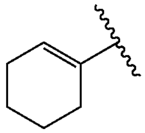 [SMILES: *C1=CCCCC1] | |
| 2-32 | $CH_3$ | 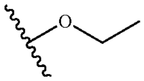 [SMILES: *OCC] | $SO_2CH_3$ | $CH_3$ | H | 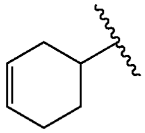 [SMILES: *C1CC=CCC1] | |
| 2-33 | $CH_3$ | 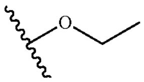 [SMILES: *OCC] | $SO_2CH_3$ | $CH_3$ | H | 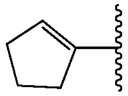 [SMILES: *C1=CCCC1] | |
| 2-34 | $CH_3$ | 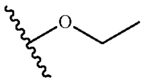 [SMILES: *OCC] | $SO_2CH_3$ | $CH_3$ | H | 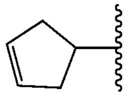 [SMILES: *C1CC=CC1] | |
| 2-35 | $CH_3$ | 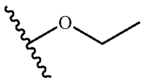 [SMILES: *OCC] | $SO_2CH_3$ | $CH_3$ | H | 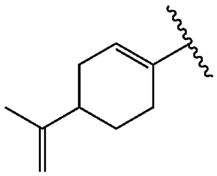 [SMILES: *C1=CCC(C(=C)C)CC1] | |
| 2-36 | $CH_3$ | 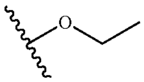 [SMILES: *OCC] | $SO_2CH_3$ | $CH_3$ | H | 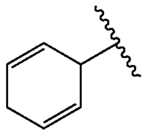 [SMILES: *C1C=CCC=C1] | |

TABLE 2-continued

Structures and Physical Properties of Part of Compounds of Formula I

| Compound | $X_1$ | $X_2$ | $X_3$ | $Z_1$ | $Z_2$ | Q | Appearance (Melting Point ° C.) |
|---|---|---|---|---|---|---|---|
| 2-37 | $CH_3$ | 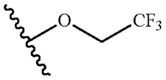 [SMILES: *OCC(F)(F)F] | $SO_2CH_3$ | $CH_3$ | $CH_3$ | 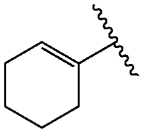 [SMILES: *C1=CCCCC1] | white solid (157-158) |
| 2-38 | $CH_3$ | 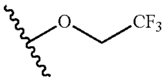 | $SO_2CH_3$ | $CH_3$ | $CH_3$ | 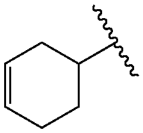 [SMILES: *C1CC=CCC1] | |
| 2-39 | $CH_3$ | 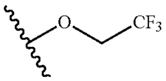 | $SO_2CH_3$ | $CH_3$ | $CH_3$ | 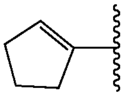 [SMILES: *C1=CCCC1] | |
| 2-40 | $CH_3$ | 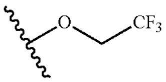 [SMILES: *OCC(F)(F)F] | $SO_2CH_3$ | $CH_3$ | $CH_3$ | 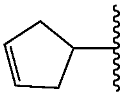 [SMILES: *C1CC=CC1] | |
| 2-41 | $CH_3$ | 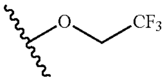 [SMILES: *OCC(F)(F)F] | $SO_2CH_3$ | $CH_3$ | $CH_3$ | 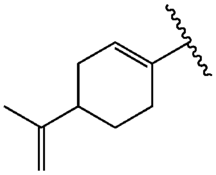 [SMILES: *C1=CCC(C(=C)C)CC1] | |
| 2-42 | $CH_3$ | 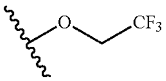 [SMILES: *OCC(F)(F)F] | $SO_2CH_3$ | $CH_3$ | $CH_3$ | 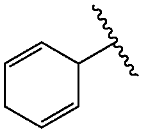 [SMILES: *C1C=CCC=C1] | |
| 2-43 | $CH_3$ | 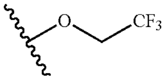 | $SO_2CH_3$ | $CH_3CH_2$ | H | 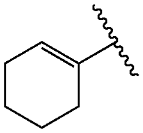 | |
| 2-44 | $CH_3$ | 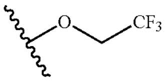 [SMILES: *OCC(F)(F)F] | $SO_2CH_3$ | $CH_3CH_2$ | H | 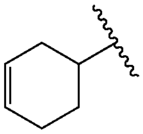 | |
| 2-45 | $CH_3$ | 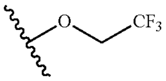 [SMILES: *OCC(F)(F)F] | $SO_2CH_3$ | $CH_3CH_2$ | H | 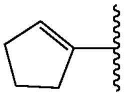 | |
| 2-46 | $CH_3$ | 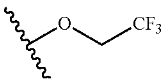 [SMILES: *OCC(F)(F)F] | $SO_2CH_3$ | $CH_3CH_2$ | H | 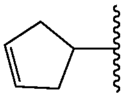 | |

TABLE 2-continued
Structures and Physical Properties of Part of Compounds of Formula I
| Compound | $X_1$ | $X_2$ | $X_3$ | $Z_1$ | $Z_2$ | Q | Appearance (Melting Point ° C.) |
|---|---|---|---|---|---|---|---|
| 2-47 | $CH_3$ | 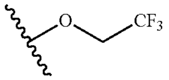 [SMILES: *OCC(F)(F)F] | $SO_2CH_3$ | $CH_3CH_2$ | H | 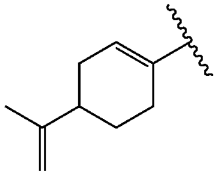 [SMILES: *C1=CCC(C(=C)C)CC1] | |
| 2-48 | $CH_3$ | 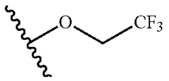 | $SO_2CH_3$ | $CH_3CH_2$ | H | 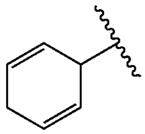 [SMILES: *C1C=CCC=C1] | |
| 2-49 | $CH_3$ | 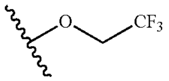 | $SO_2CH_3$ | $CH_3$ | H | 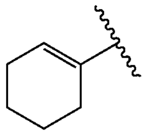 | |
| 2-50 | $CH_3$ | 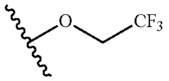 [SMILES: *OCC(F)(F)F] | $SO_2CH_3$ | $CH_3$ | H | 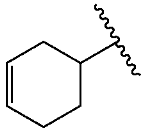 | |
| 2-51 | $CH_3$ | 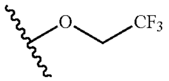 | $SO_2CH_3$ | $CH_3$ | H | 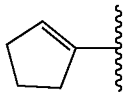 | |
| 2-52 | $CH_3$ | 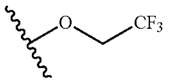 [SMILES: *OCC(F)(F)F] | $SO_2CH_3$ | $CH_3$ | H | 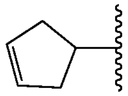 | |
| 2-53 | $CH_3$ | 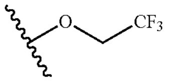 | $SO_2CH_3$ | $CH_3$ | H | 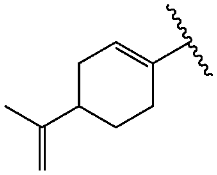 [SMILES: *C1=CCC(C(=C)C)CC1] | |
| 2-54 | $CH_3$ | 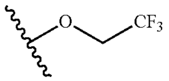 [SMILES: *OCC(F)(F)F] | $SO_2CH_3$ | $CH_3$ | H | 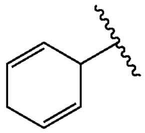 [SMILES: *C1C=CCC=C1] | |
| 2-55 | $CH_3$ | 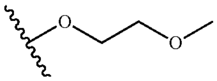 [SMILES: *OCCOC] | $SO_2CH_3$ | $CH_3$ | $CH_3$ | 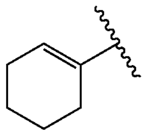 | yellow oil |
| 2-56 | $CH_3$ | 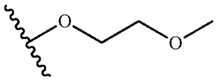 [SMILES: *OCCOC] | $SO_2CH_3$ | $CH_3$ | $CH_3$ | 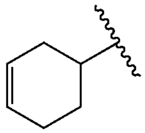 [SMILES: *C1CC=CCC1] | |

TABLE 2-continued

Structures and Physical Properties of Part of Compounds of Formula I

| Compound | $X_1$ | $X_2$ | $X_3$ | $Z_1$ | $Z_2$ | Q | Appearance (Melting Point ° C.) |
|---|---|---|---|---|---|---|---|
| 2-57 | $CH_3$ | 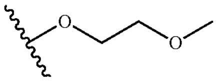 [SMILES: *OCCOC] | $SO_2CH_3$ | $CH_3$ | $CH_3$ | 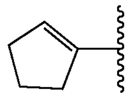 | pale yellow solid (134-136) |
| 2-58 | $CH_3$ | 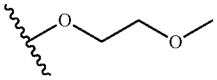 [SMILES: *OCCOC] | $SO_2CH_3$ | $CH_3$ | $CH_3$ | 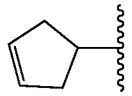 | |
| 2-59 | $CH_3$ | 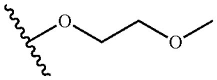 [SMILES: *OCCOC] | $SO_2CH_3$ | $CH_3$ | $CH_3$ | 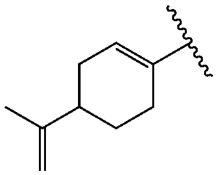 [SMILES: *C1=CCC(C(=C)C)CC1] | |
| 2-60 | $CH_3$ | 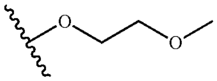 [SMILES: *OCCOC] | $SO_2CH_3$ | $CH_3$ | $CH_3$ | 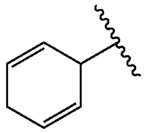 [SMILES: *C1C=CCC=C1] | |
| 2-61 | $CH_3$ | 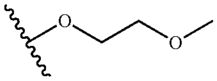 [SMILES: *OCCOC] | $SO_2CH_3$ | $CH_3CH_2$ | H | 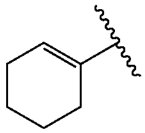 | yellow oil |
| 2-62 | $CH_3$ | 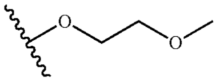 [SMILES: *OCCOC] | $SO_2CH_3$ | $CH_3CH_2$ | H | 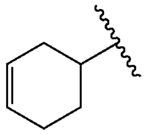 | |
| 2-63 | $CH_3$ | 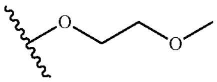 [SMILES: *OCCOC] | $SO_2CH_3$ | $CH_3CH_2$ | H | 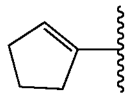 [SMILES: *C1=CCCC1] | yellow oil |
| 2-64 | $CH_3$ | 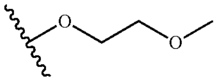 [SMILES: *OCCOC] | $SO_2CH_3$ | $CH_3CH_2$ | H | 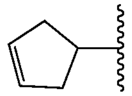 | |
| 2-65 | $CH_3$ | 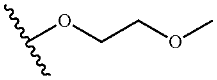 [SMILES: *OCCOC] | $SO_2CH_3$ | $CH_3CH_2$ | H | 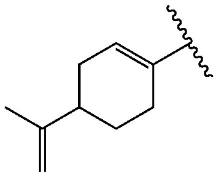 [SMILES: *C1=CCC(C(=C)C)CC1] | |
| 2-66 | $CH_3$ | 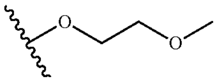 [SMILES: *OCCOC] | $SO_2CH_3$ | $CH_3CH_2$ | H | 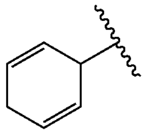 [SMILES: *C1C=CCC=C1] | |

TABLE 2-continued
Structures and Physical Properties of Part of Compounds of Formula I
| Compound | $X_1$ | $X_2$ | $X_3$ | $Z_1$ | $Z_2$ | Q | Appearance (Melting Point ° C.) |
|---|---|---|---|---|---|---|---|
| 2-67 | $CH_3$ | 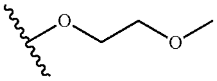 [SMILES: *OCCOC] | $SO_2CH_3$ | $CH_3$ | H | 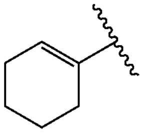 | yellow oil |
| 2-68 | $CH_3$ | 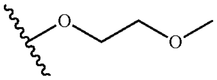 [SMILES: *OCCOC] | $SO_2CH_3$ | $CH_3$ | H | 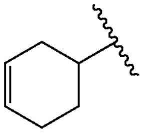 | |
| 2-69 | $CH_3$ | 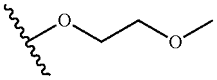 [SMILES: *OCCOC] | $SO_2CH_3$ | $CH_3$ | H | 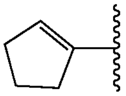 [SMILES: *C1=CCCC1] | |
| 2-70 | $CH_3$ | 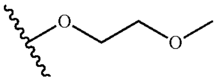 [SMILES: *OCCOC] | $SO_2CH_3$ | $CH_3$ | H | 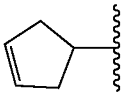 | |
| 2-71 | $CH_3$ | 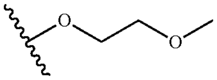 [SMILES: *OCCOC] | $SO_2CH_3$ | $CH_3$ | H | 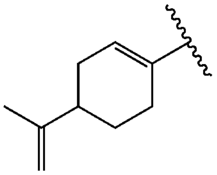 [SMILES: *C1=CCC(C(=C)C)CC1] | |
| 2-72 | $CH_3$ | 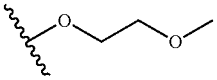 [SMILES: *OCCOC] | $SO_2CH_3$ | $CH_3$ | H | 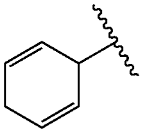 [SMILES: *C1C=CCC=C1] | |
| 2-73 | $CH_3$ | 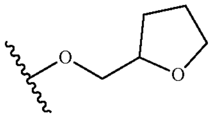 [SMILES: *OCC1CCCO1] | $SO_2CH_3$ | $CH_3$ | $CH_3$ | 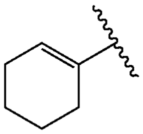 [SMILES: *C1=CCCCC1] | brown oil |
| 2-74 | $CH_3$ | 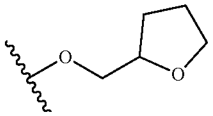 [SMILES: *OCC1CCCO1] | $SO_2CH_3$ | $CH_3$ | $CH_3$ | 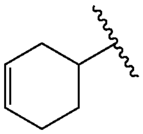 [SMILES: *C1CC=CCC1] | |
| 2-75 | $CH_3$ | 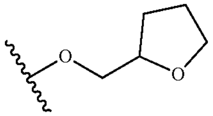 [SMILES: *OCC1CCCO1] | $SO_2CH_3$ | $CH_3$ | $CH_3$ | 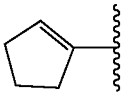 [SMILES: *C1=CCCC1] | |
| 2-76 | $CH_3$ | 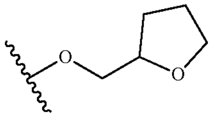 [SMILES: *OCC1CCCO1] | $SO_2CH_3$ | $CH_3$ | $CH_3$ | 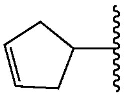 | |

TABLE 2-continued
Structures and Physical Properties of Part of Compounds of Formula I
| Compound | $X_1$ | $X_2$ | $X_3$ | $Z_1$ | $Z_2$ | Q | Appearance (Melting Point ° C.) |
|---|---|---|---|---|---|---|---|
| 2-77 | $CH_3$ | 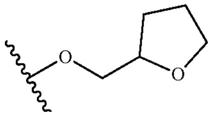 [SMILES: *OCC1CCCO1] | $SO_2CH_3$ | $CH_3$ | $CH_3$ | 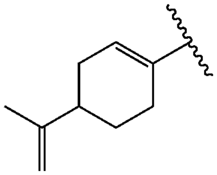 [SMILES: *C1=CCC(C(=C)C)CC1] | |
| 2-78 | $CH_3$ | 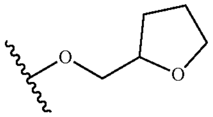 [SMILES: *OCC1CCCO1] | $SO_2CH_3$ | $CH_3$ | $CH_3$ | 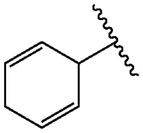 [SMILES: *C1C=CCC=C1] | |
| 2-79 | $CH_3$ | 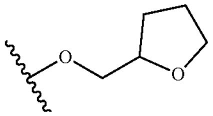 [SMILES: *OCC1CCCO1] | $SO_2CH_3$ | $CH_3CH_2$ | H | 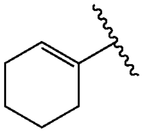 | |
| 2-80 | $CH_3$ | 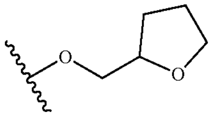 [SMILES: *OCC1CCCO1] | $SO_2CH_3$ | $CH_3CH_2$ | H | 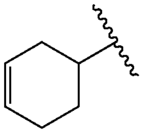 [SMILES: *C1CC=CCC1] | |
| 2-81 | $CH_3$ | 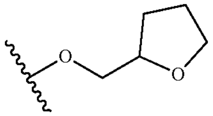 [SMILES: *OCC1CCCO1] | $SO_2CH_3$ | $CH_3CH_2$ | H | 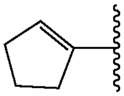 | |
| 2-82 | $CH_3$ | 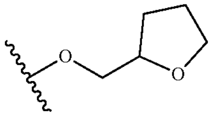 [SMILES: *OCC1CCCO1] | $SO_2CH_3$ | $CH_3CH_2$ | H | 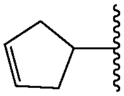 | |
| 2-83 | $CH_3$ | 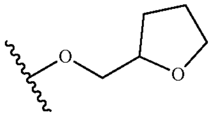 [SMILES: *OCC1CCCO1] | $SO_2CH_3$ | $CH_3CH_2$ | H | 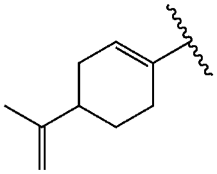 [SMILES: *C1=CCC(C(=C)C)CC1] | |
| 2-84 | $CH_3$ | 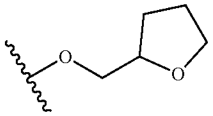 [SMILES: *OCC1CCCO1] | $SO_2CH_3$ | $CH_3CH_2$ | H | 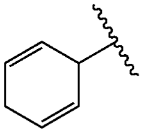 [SMILES: *C1C=CCC=C1] | |
| 2-85 | $CH_3$ | 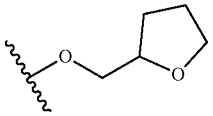 [SMILES: *OCC1CCCO1] | $SO_2CH_3$ | $CH_3$ | H | 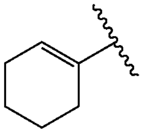 | |

TABLE 2-continued
Structures and Physical Properties of Part of Compounds of Formula I
| Compound | $X_1$ | $X_2$ | $X_3$ | $Z_1$ | $Z_2$ | Q | Appearance (Melting Point ° C.) |
|---|---|---|---|---|---|---|---|
| 2-86 | $CH_3$ | 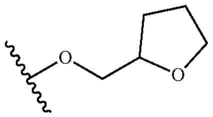 [SMILES: *OCC1CCCO1] | $SO_2CH_3$ | $CH_3$ | H | 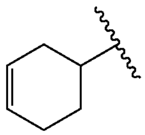 [SMILES: *C1CC=CCC1] | |
| 2-87 | $CH_3$ | 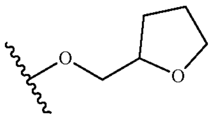 [SMILES: *OCC1CCCO1] | $SO_2CH_3$ | $CH_3$ | H | 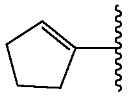 [SMILES: *C1=CCCC1] | |
| 2-88 | $CH_3$ | 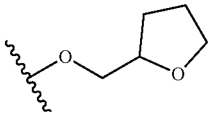 [SMILES: *OCC1CCCO1] | $SO_2CH_3$ | $CH_3$ | H | 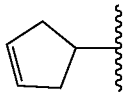 | |
| 2-89 | $CH_3$ | 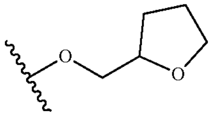 [SMILES: *OCC1CCCO1] | $SO_2CH_3$ | $CH_3$ | H | 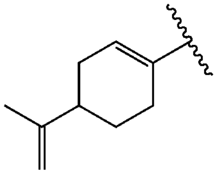 [SMILES: *C1=CCC(C(=C)C)CC1] | |
| 2-90 | $CH_3$ | 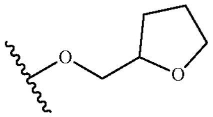 | $SO_2CH_3$ | $CH_3$ | H | 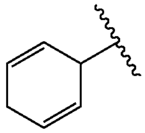 [SMILES: *C1C=CCC=C1] | |
| 2-91 | $CH_3$ | 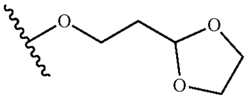 | $SO_2CH_3$ | $CH_3$ | $CH_3$ | 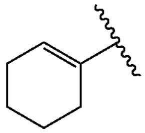 [SMILES: *C1=CCCCC1] | |
| 2-92 | $CH_3$ | 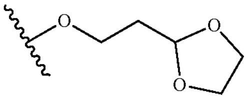 [SMILES: *OCCC1OCCO1] | $SO_2CH_3$ | $CH_3$ | $CH_3$ | 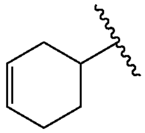 [SMILES: *C1CC=CCC1] | |
| 2-93 | $CH_3$ | 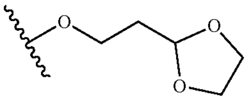 [SMILES: *OCCC1OCCO1] | $SO_2CH_3$ | $CH_3$ | $CH_3$ | 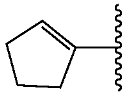 [SMILES: *C1=CCCC1] | |
| 2-94 | $CH_3$ | 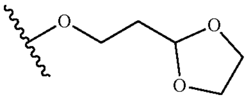 [SMILES: *OCCC1OCCO1] | $SO_2CH_3$ | $CH_3$ | $CH_3$ | 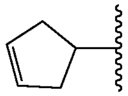 | |
| 2-95 | $CH_3$ | 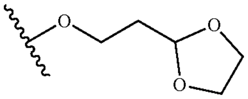 [SMILES: *OCCC1OCCO1] | $SO_2CH_3$ | $CH_3$ | $CH_3$ | 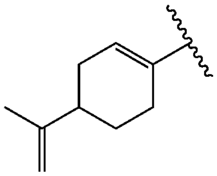 [SMILES: *C1=CCC(C(=C)C)CC1] | |

TABLE 2-continued
Structures and Physical Properties of Part of Compounds of Formula I
| Compound | $X_1$ | $X_2$ | $X_3$ | $Z_1$ | $Z_2$ | Q | Appearance (Melting Point ° C.) |
|---|---|---|---|---|---|---|---|
| 2-96 | $CH_3$ | 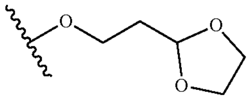 [SMILES: *OCCC1OCCO1] | $SO_2CH_3$ | $CH_3$ | $CH_3$ | 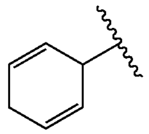 [SMILES: *C1C=CCC=C1] | |
| 2-97 | $CH_3$ | 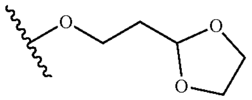 [SMILES: *OCCC1OCCO1] | $SO_2CH_3$ | $CH_3CH_2$ | H | 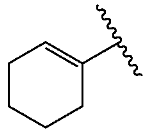 [SMILES: *C1=CCCCC1] | |
| 2-98 | $CH_3$ | 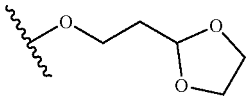 [SMILES: *OCCC1OCCO1] | $SO_2CH_3$ | $CH_3CH_2$ | H | 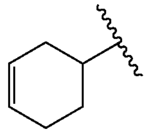 [SMILES: *C1CC=CCC1] | |
| 2-99 | $CH_3$ | 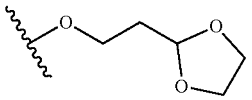 [SMILES: *OCCC1OCCO1] | $SO_2CH_3$ | $CH_3CH_2$ | H | 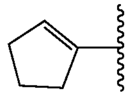 [SMILES: *C1=CCCC1] | |
| 2-100 | $CH_3$ | 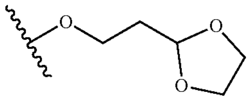 [SMILES: *OCCC1OCCO1] | $SO_2CH_3$ | $CH_3CH_2$ | H | 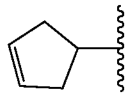 [SMILES: *C1CC=CC1] | |
| 2-101 | $CH_3$ | 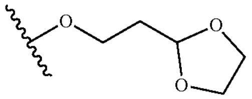 [SMILES: *OCCC1OCCO1] | $SO_2CH_3$ | $CH_3CH_2$ | H | 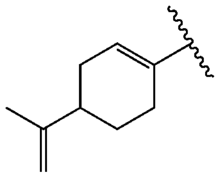 [SMILES: *C1=CCC(C(=C)C)CC1] | |
| 2-102 | $CH_3$ | 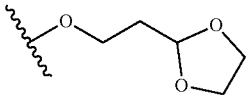 [SMILES: *OCCC1OCCO1] | $SO_2CH_3$ | $CH_3CH_2$ | H | 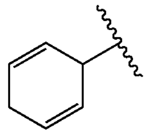 [SMILES: *C1C=CCC=C1] | |
| 2-103 | $CH_3$ | 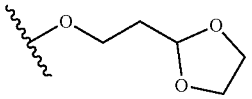 | $SO_2CH_3$ | $CH_3$ | H | 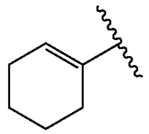 [SMILES: *C1=CCCCC1] | |
| 2-104 | $CH_3$ | 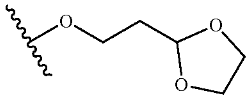 [SMILES: *OCCC1OCCO1] | $SO_2CH_3$ | $CH_3$ | H | 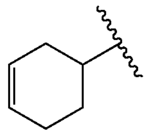 [SMILES: *C1CC=CCC1] | |
| 2-105 | $CH_3$ | 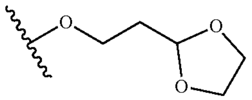 [SMILES: *OCCC1OCCO1] | $SO_2CH_3$ | $CH_3$ | H | 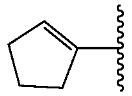 [SMILES: *C1=CCCC1] | |

TABLE 2-continued
Structures and Physical Properties of Part of Compounds of Formula I
| Compound | $X_1$ | $X_2$ | $X_3$ | $Z_1$ | $Z_2$ | Q | Appearance (Melting Point ° C.) |
|---|---|---|---|---|---|---|---|
| 2-106 | $CH_3$ | 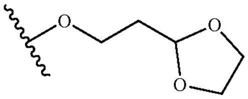 [SMILES: *OCCC1OCCO1] | $SO_2CH_3$ | $CH_3$ | H | 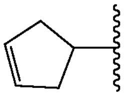 | |
| 2-107 | $CH_3$ | 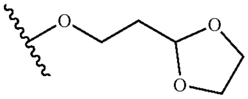 [SMILES: *OCCC1OCCO1] | $SO_2CH_3$ | $CH_3$ | H | 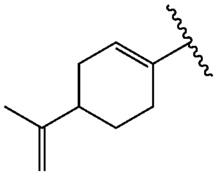 [SMILES: *C1=CCC(C(=C)C)CC1] | |
| 2-108 | $CH_3$ | 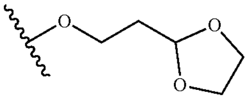 | $SO_2CH_3$ | $CH_3$ | H | 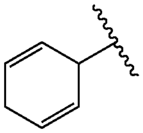 [SMILES: *C1C=CCC=C1] | |
| 2-109 | $CH_3$ | 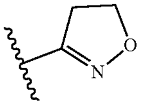 [SMILES: *C1=NOCC1] | $SO_2CH_3$ | $CH_3$ | $CH_3$ | 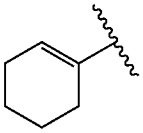 | |
| 2-110 | $CH_3$ | 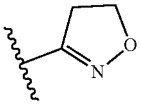 [SMILES: *C1=NOCC1] | $SO_2CH_3$ | $CH_3$ | $CH_3$ | 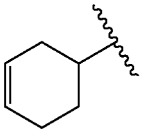 [SMILES: *C1CC=CCC1] | |
| 2-111 | $CH_3$ | 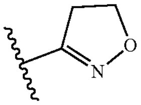 [SMILES: *C1=NOCC1] | $SO_2CH_3$ | $CH_3$ | $CH_3$ | 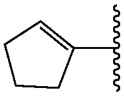 | |
| 2-112 | $CH_3$ | 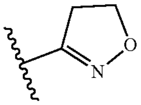 [SMILES: *C1=NOCC1] | $SO_2CH_3$ | $CH_3$ | $CH_3$ | 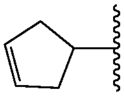 | |
| 2-113 | $CH_3$ | 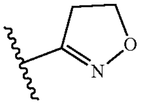 [SMILES: *C1=NOCC1] | $SO_2CH_3$ | $CH_3$ | $CH_3$ | 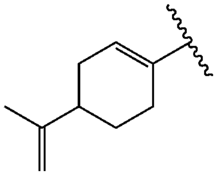 [SMILES: *C1=CCC(C(=C)C)CC1] | |
| 2-114 | $CH_3$ | 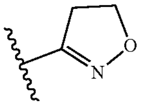 [SMILES: *C1=NOCC1] | $SO_2CH_3$ | $CH_3$ | $CH_3$ | 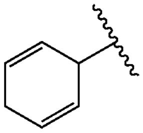 | |
| 2-115 | $CH_3$ | 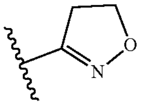 | $SO_2CH_3$ | $CH_3CH_2$ | H | 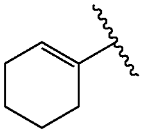 [SMILES: *C1=CCCCC1] | |

TABLE 2-continued

| Structures and Physical Properties of Part of Compounds of Formula I | | | | | | | |
|---|---|---|---|---|---|---|---|
| Compound | $X_1$ | $X_2$ | $X_3$ | $Z_1$ | $Z_2$ | Q | Appearance (Melting Point ° C.) |
| 2-116 | $CH_3$ | 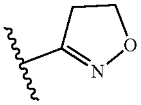 [SMILES: *C1=NOCC1] | $SO_2CH_3$ | $CH_3CH_2$ | H | 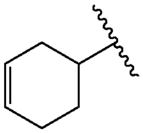 | |
| 2-117 | $CH_3$ | 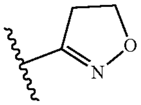 [SMILES: *C1=NOCC1] | $SO_2CH_3$ | $CH_3CH_2$ | H | 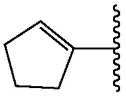 [SMILES: *C1=CCCC1] | |
| 2-118 | $CH_3$ | 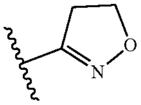 [SMILES: *C1=NOCC1] | $SO_2CH_3$ | $CH_3CH_2$ | H | 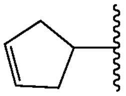 | |
| 2-119 | $CH_3$ | 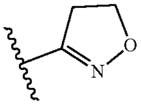 [SMILES: *C1=NOCC1] | $SO_2CH_3$ | $CH_3CH_2$ | H | 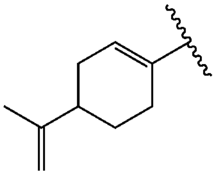 [SMILES: *C1=CCC(C(=C)C)CC1] | |
| 2-120 | $CH_3$ | 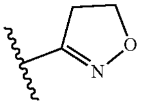 [SMILES: *C1=NOCC1] | $SO_2CH_3$ | $CH_3CH_2$ | H | 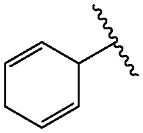 [SMILES: *C1C=CCC=C1] | |
| 2-121 | $CH_3$ | 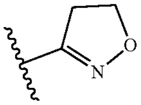 [SMILES: *C1=NOCC1] | $SO_2CH_3$ | $CH_3$ | H | 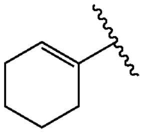 | white solid (209-210) |
| 2-122 | $CH_3$ | 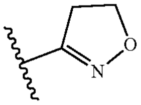 [SMILES: *C1=NOCC1] | $SO_2CH_3$ | $CH_3$ | H | 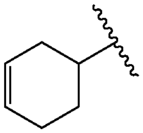 [SMILES: *C1CC=CCC1] | |
| 2-123 | $CH_3$ | 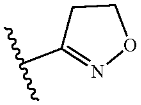 [SMILES: *C1=NOCC1] | $SO_2CH_3$ | $CH_3$ | H | 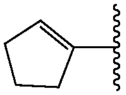 [SMILES: *C1=CCCC1] | white solid (199-200) |
| 2-124 | $CH_3$ | 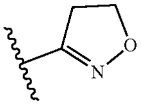 [SMILES: *C1=NOCC1] | $SO_2CH_3$ | $CH_3$ | H | 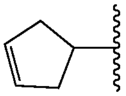 | |
| 2-125 | $CH_3$ | 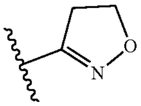 [SMILES: *C1=NOCC1] | $SO_2CH_3$ | $CH_3$ | H | 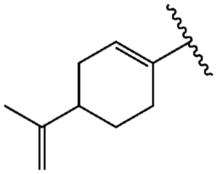 [SMILES: *C1=CCC(C(=C)C)CC1] | |

TABLE 2-continued

Structures and Physical Properties of Part of Compounds of Formula I

| Compound | $X_1$ | $X_2$ | $X_3$ | $Z_1$ | $Z_2$ | Q | Appearance (Melting Point ° C.) |
| --- | --- | --- | --- | --- | --- | --- | --- |
| 2-126 | $CH_3$ | 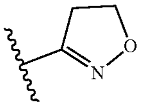 [SMILES: *C1=NOCC1] | $SO_2CH_3$ | $CH_3$ | H | 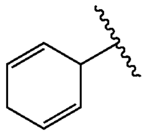 [SMILES: *C1C=CCC=C1] | |
| 2-127 | $CH_3$ | $CH_3$ | $SO_2CH_3$ | $CH_3$ | $CH_3$ | 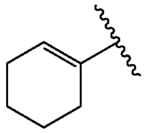 | white solid (186-188) |
| 2-128 | $CH_3$ | $CH_3$ | $SO_2CH_3$ | $CH_3$ | $CH_3$ | 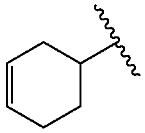 [SMILES: *C1CC=CCC1] | |
| 2-129 | $CH_3$ | $CH_3$ | $SO_2CH_3$ | $CH_3$ | $CH_3$ | 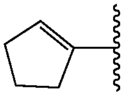 | |
| 2-130 | $CH_3$ | $CH_3$ | $SO_2CH_3$ | $CH_3$ | $CH_3$ | 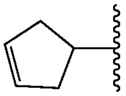 [SMILES: *C1CC=CC1] | |
| 2-131 | $CH_3$ | $CH_3$ | $SO_2CH_3$ | $CH_3$ | $CH_3$ | 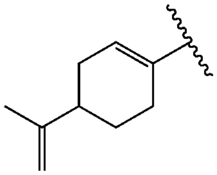 [SMILES: *C1=CCC(C(=C)C)CC1] | |
| 2-132 | $CH_3$ | $CH_3$ | $SO_2CH_3$ | $CH_3$ | $CH_3$ | 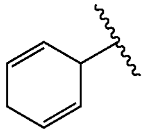 [SMILES: *C1C=CCC=C1] | |
| 2-133 | $CH_3$ | $CH_3$ | $SO_2CH_3$ | $CH_3CH_2$ | H | 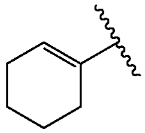 [SMILES: *C1=CCCCC1] | |
| 2-134 | $CH_3$ | $CH_3$ | $SO_2CH_3$ | $CH_3CH_2$ | H | 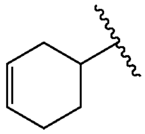 | |
| 2-135 | $CH_3$ | $CH_3$ | $SO_2CH_3$ | $CH_3CH_2$ | H | 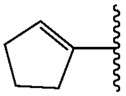 [SMILES: *C1=CCCC1] | |
| 2-136 | $CH_3$ | $CH_3$ | $SO_2CH_3$ | $CH_3CH_2$ | H | 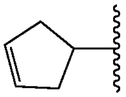 [SMILES: *C1CC=CC1] | |

TABLE 2-continued

Structures and Physical Properties of Part of Compounds of Formula I

| Compound | $X_1$ | $X_2$ | $X_3$ | $Z_1$ | $Z_2$ | Q | Appearance (Melting Point ° C.) |
|---|---|---|---|---|---|---|---|
| 2-137 | $CH_3$ | $CH_3$ | $SO_2CH_3$ | $CH_3CH_2$ | H | 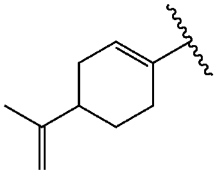 [SMILES: *C1=CCC(C(=C)C)CC1] | |
| 2-138 | $CH_3$ | $CH_3$ | $SO_2CH_3$ | $CH_3CH_2$ | H | 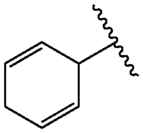 [SMILES: *C1C=CCC=C1] | |
| 2-139 | $CH_3$ | $CH_3$ | $SO_2CH_3$ | $CH_3$ | H | 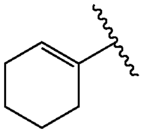 [SMILES: *C1=CCCCC1] | |
| 2-140 | $CH_3$ | $CH_3$ | $SO_2CH_3$ | $CH_3$ | H | 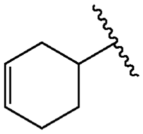 | |
| 2-141 | $CH_3$ | $CH_3$ | $SO_2CH_3$ | $CH_3$ | H | 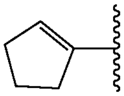 [SMILES: *C1=CCCC1] | |
| 2-142 | $CH_3$ | $CH_3$ | $SO_2CH_3$ | $CH_3$ | H | 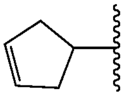 [SMILES: *C1CC=CC1] | |
| 2-143 | $CH_3$ | $CH_3$ | $SO_2CH_3$ | $CH_3$ | H | 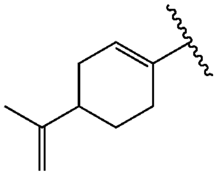 [SMILES: *C1=CCC(C(=C)C)CC1] | |
| 2-144 | $CH_3$ | $CH_3$ | $SO_2CH_3$ | $CH_3$ | H | 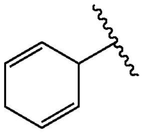 [SMILES: *C1C=CCC=C1] | |
| 2-145 | $CH_3$ | 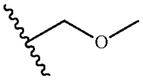 [SMILES: *COC] | $SO_2CH_3$ | $CH_3$ | $CH_3$ | 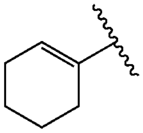 | white solid (116-118) |
| 2-146 | $CH_3$ | 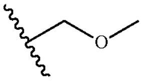 [SMILES: *COC] | $SO_2CH_3$ | $CH_3$ | $CH_3$ | 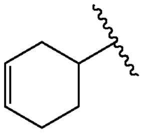 [SMILES: *C1CC=CCC1] | |

TABLE 2-continued
| Structures and Physical Properties of Part of Compounds of Formula I | | | | | | | |
|---|---|---|---|---|---|---|---|
| Compound | $X_1$ | $X_2$ | $X_3$ | $Z_1$ | $Z_2$ | Q | Appearance (Melting Point ° C.) |
| 2-147 | $CH_3$ | 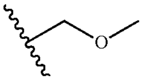 [SMILES: *COC] | $SO_2CH_3$ | $CH_3$ | $CH_3$ | 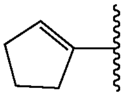 | |
| 2-148 | $CH_3$ | 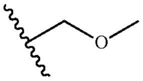 | $SO_2CH_3$ | $CH_3$ | $CH_3$ | 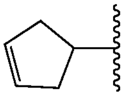 [SMILES: *C1CC=CC1] | |
| 2-149 | $CH_3$ | 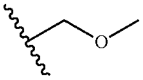 [SMILES: *COC] | $SO_2CH_3$ | $CH_3$ | $CH_3$ | 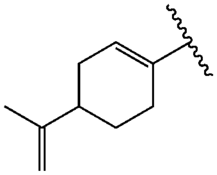 [SMILES: *C1=CCC(C(=C)C)CC1] | |
| 2-150 | $CH_3$ | 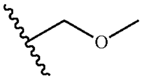 [SMILES: *COC] | $SO_2CH_3$ | $CH_3$ | $CH_3$ | 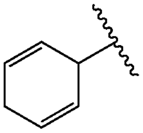 [SMILES: *C1C=CCC=C1] | |
| 2-151 | $CH_3$ | 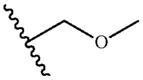 [SMILES: *COC] | $SO_2CH_3$ | $CH_2CH_3$ | H | 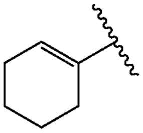 | |
| 2-152 | $CH_3$ | 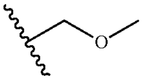 [SMILES: *COC] | $SO_2CH_3$ | $CH_2CH_3$ | H | 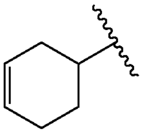 [SMILES: *C1CC=CCC1] | |
| 2-153 | $CH_3$ | 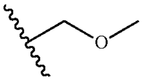 | $SO_2CH_3$ | $CH_2CH_3$ | H | 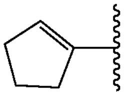 | |
| 2-154 | $CH_3$ | 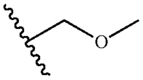 [SMILES: *COC] | $SO_2CH_3$ | $CH_2CH_3$ | H | 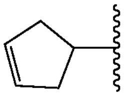 [SMILES: *C1CC=CC1] | |
| 2-155 | $CH_3$ | 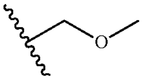 [SMILES: *COC] | $SO_2CH_3$ | $CH_2CH_3$ | H | 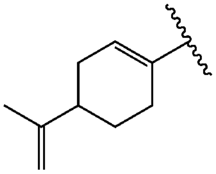 [SMILES: *C1=CCC(C(=C)C)CC1] | |
| 2-156 | $CH_3$ | 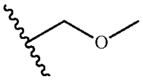 [SMILES: *COC] | $SO_2CH_3$ | $CH_2CH_3$ | H | 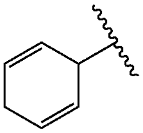 [SMILES: *C1C=CCC=C1] | |

TABLE 2-continued
Structures and Physical Properties of Part of Compounds of Formula I
| Compound | $X_1$ | $X_2$ | $X_3$ | $Z_1$ | $Z_2$ | Q | Appearance (Melting Point ° C.) |
|---|---|---|---|---|---|---|---|
| 2-157 | $CH_3$ | 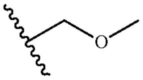 [SMILES: *COC] | $SO_2CH_3$ | $CH_3$ | H | 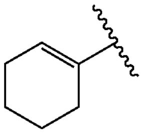 [SMILES: *C1=CCCCC1] | |
| 2-158 | $CH_3$ | 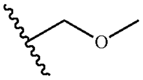 [SMILES: *COC] | $SO_2CH_3$ | $CH_3$ | H | 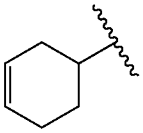 | |
| 2-159 | $CH_3$ | 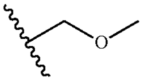 [SMILES: *COC] | $SO_2CH_3$ | $CH_3$ | H | 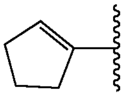 [SMILES: *C1=CCCC1] | |
| 2-160 | $CH_3$ | 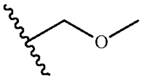 [SMILES: *COC] | $SO_2CH_3$ | $CH_3$ | H | 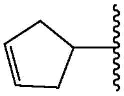 [SMILES: *C1CC=CC1] | |
| 2-161 | $CH_3$ | 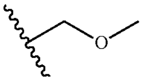 [SMILES: *COC] | $SO_2CH_3$ | $CH_3$ | H | 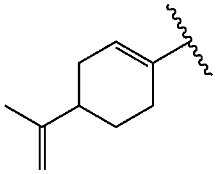 [SMILES: *C1=CCC(C(=C)C)CC1] | |
| 2-162 | $CH_3$ | 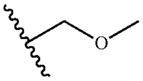 | $SO_2CH_3$ | $CH_3$ | H | 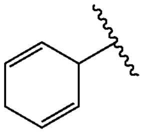 [SMILES: *C1C=CCC=C1] | |
| 2-163 | Cl | 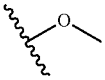 [SMILES: *OC] | $SO_2CH_3$ | $CH_3$ | $CH_3$ | 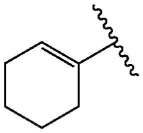 [SMILES: *C1=CCCCC1] | |
| 2-164 | Cl | 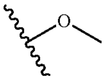 | $SO_2CH_3$ | $CH_3$ | $CH_3$ | 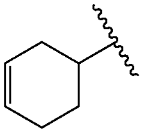 | |
| 2-165 | Cl | 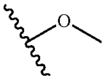 [SMILES: *OC] | $SO_2CH_3$ | $CH_3$ | $CH_3$ | 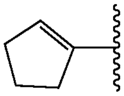 [SMILES: *C1=CCCC1] | |
| 2-166 | Cl | 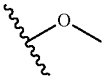 [SMILES: *OC] | $SO_2CH_3$ | $CH_3$ | $CH_3$ | 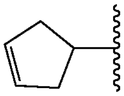 | |

TABLE 2-continued
Structures and Physical Properties of Part of Compounds of Formula I
| Compound | $X_1$ | $X_2$ | $X_3$ | $Z_1$ | $Z_2$ | Q | Appearance (Melting Point ° C.) |
|---|---|---|---|---|---|---|---|
| 2-167 | Cl | 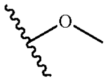 [SMILES: *OC] | $SO_2CH_3$ | $CH_3$ | $CH_3$ | 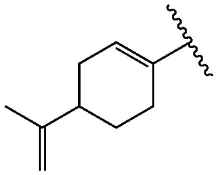 [SMILES: *C1=CCC(C(=C)C)CC1] | |
| 2-168 | Cl | 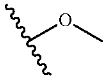 [SMILES: *OC] | $SO_2CH_3$ | $CH_3$ | $CH_3$ | 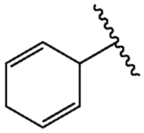 [SMILES: *C1C=CCC=C1] | |
| 2-169 | Cl | 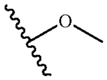 [SMILES: *OC] | $SO_2CH_3$ | $CH_2CH_3$ | H | 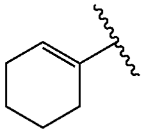 | |
| 2-170 | Cl | 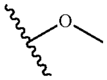 [SMILES: *OC] | $SO_2CH_3$ | $CH_2CH_3$ | H | 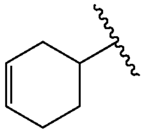 | |
| 2-171 | Cl | 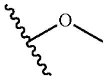 [SMILES: *OC] | $SO_2CH_3$ | $CH_2CH_3$ | H | 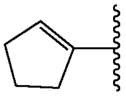 [SMILES: *C1=CCCC1] | |
| 2-172 | Cl | 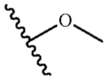 [SMILES: *OC] | $SO_2CH_3$ | $CH_2CH_3$ | H | 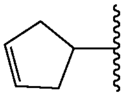 [SMILES: *C1CC=CC1] | |
| 2-173 | Cl | 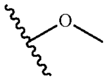 [SMILES: *OC] | $SO_2CH_3$ | $CH_2CH_3$ | H | 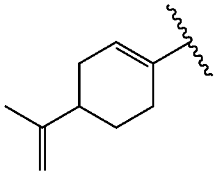 [SMILES: *C1=CCC(C(=C)C)CC1] | |
| 2-174 | Cl | 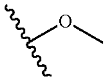 | $SO_2CH_3$ | $CH_2CH_3$ | H | 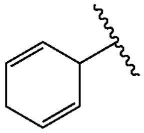 [SMILES: *C1C=CCC=C1] | |
| 2-175 | Cl | 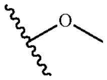 [SMILES: *OC] | $SO_2CH_3$ | $CH_3$ | H | 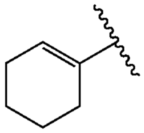 [SMILES: *C1=CCCCC1] | |
| 2-176 | Cl | 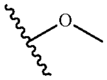 [SMILES: *OC] | $SO_2CH_3$ | $CH_3$ | H | 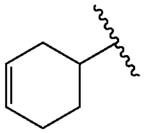 [SMILES: *C1CC=CCC1] | |

TABLE 2-continued
Structures and Physical Properties of Part of Compounds of Formula I
| Compound | $X_1$ | $X_2$ | $X_3$ | $Z_1$ | $Z_2$ | Q | Appearance (Melting Point ° C.) |
|---|---|---|---|---|---|---|---|
| 2-177 | Cl | 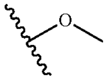 [SMILES: *OC] | $SO_2CH_3$ | $CH_3$ | H | 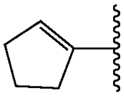 [SMILES: *C1=CCCC1] | |
| 2-178 | Cl | 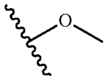 [SMILES: *OC] | $SO_2CH_3$ | $CH_3$ | H | 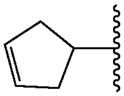 [SMILES: *C1CC=CC1] | |
| 2-179 | Cl | 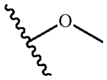 [SMILES: *OC] | $SO_2CH_3$ | $CH_3$ | H | 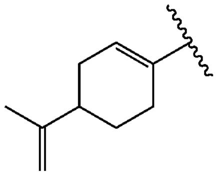 [SMILES: *C1=CCC(C(=C)C)CC1] | |
| 2-180 | Cl | 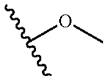 | $SO_2CH_3$ | $CH_3$ | H | 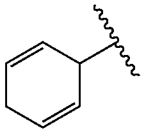 [SMILES: *C1C=CCC=C1] | |
| 2-181 | Cl | 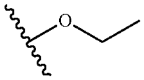 [SMILES: *OCC] | $SO_2CH_3$ | $CH_3$ | $CH_3$ | 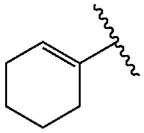 | |
| 2-182 | Cl | 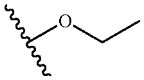 | $SO_2CH_3$ | $CH_3$ | $CH_3$ | 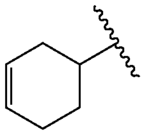 [SMILES: *C1CC=CCC1] | |
| 2-183 | Cl | 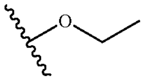 [SMILES: *OCC] | $SO_2CH_3$ | $CH_3$ | $CH_3$ | 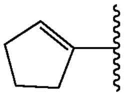 [SMILES: *C1=CCCC1] | |
| 2-184 | Cl | 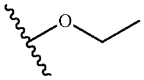 [SMILES: *OCC] | $SO_2CH_3$ | $CH_3$ | $CH_3$ | 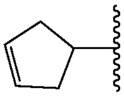 [SMILES: *C1CC=CC1] | |
| 2-185 | Cl | 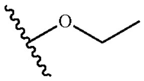 [SMILES: *OCC] | $SO_2CH_3$ | $CH_3$ | $CH_3$ | 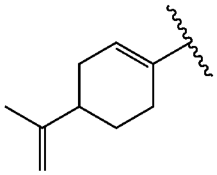 [SMILES: *C1=CCC(C(=C)C)CC1] | |
| 2-186 | Cl | 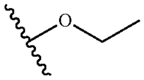 [SMILES: *OCC] | $SO_2CH_3$ | $CH_3$ | $CH_3$ | 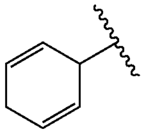 [SMILES: *C1C=CCC=C1] | |

TABLE 2-continued
Structures and Physical Properties of Part of Compounds of Formula I
| Compound | $X_1$ | $X_2$ | $X_3$ | $Z_1$ | $Z_2$ | Q | Appearance (Melting Point ° C.) |
| --- | --- | --- | --- | --- | --- | --- | --- |
| 2-187 | Cl | 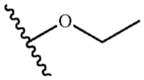 | $SO_2CH_3$ | $CH_2CH_3$ | H | 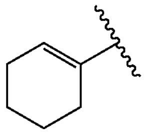 [SMILES: *C1=CCCCC1] | |
| 2-188 | Cl | 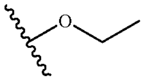 [SMILES: *OCC] | $SO_2CH_3$ | $CH_2CH_3$ | H | 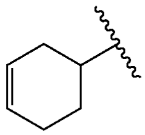 | |
| 2-189 | Cl | 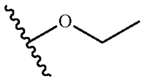 [SMILES: *OCC] | $SO_2CH_3$ | $CH_2CH_3$ | H | 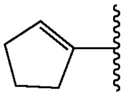 [SMILES: *C1=CCCC1] | |
| 2-190 | Cl | 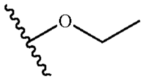 | $SO_2CH_3$ | $CH_2CH_3$ | H | 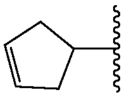 [SMILES: *C1CC=CC1] | |
| 2-191 | Cl | 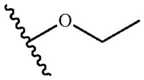 [SMILES: *OCC] | $SO_2CH_3$ | $CH_2CH_3$ | H | 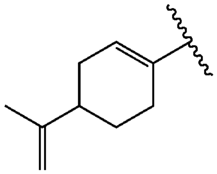 [SMILES: *C1=CCC(C(=C)C)CC1] | |
| 2-192 | Cl | 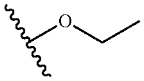 | $SO_2CH_3$ | $CH_2CH_3$ | H | 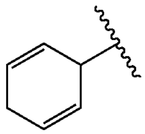 [SMILES: *C1C=CCC=C1] | |
| 2-193 | Cl | 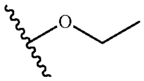 | $SO_2CH_3$ | $CH_3$ | H | 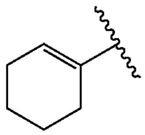 | |
| 2-194 | Cl | 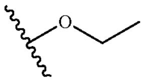 [SMILES: *OCC] | $SO_2CH_3$ | $CH_3$ | H | 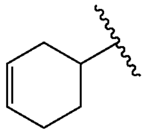 | |
| 2-195 | Cl | 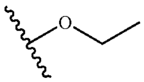 [SMILES: *OCC] | $SO_2CH_3$ | $CH_3$ | H | 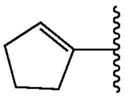 [SMILES: *C1=CCCC1] | |
| 2-196 | Cl | 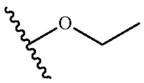 [SMILES: *OCC] | $SO_2CH_3$ | $CH_3$ | H | 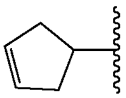 [SMILES: *C1CC=CC1] | |

TABLE 2-continued
Structures and Physical Properties of Part of Compounds of Formula I
| Compound | $X_1$ | $X_2$ | $X_3$ | $Z_1$ | $Z_2$ | Q | Appearance (Melting Point ° C.) |
|---|---|---|---|---|---|---|---|
| 2-197 | Cl | 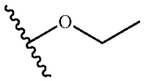 [SMILES: *OCC] | $SO_2CH_3$ | $CH_3$ | H | 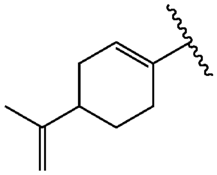 [SMILES: *C1=CCC(C(=C)C)CC1] | |
| 2-198 | Cl | 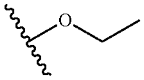 [SMILES: *OCC] | $SO_2CH_3$ | $CH_3$ | H | 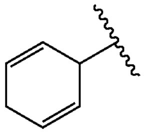 [SMILES: *C1C=CCC=C1] | |
| 2-199 | Cl | 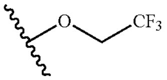 | $SO_2CH_3$ | $CH_3$ | $CH_3$ | 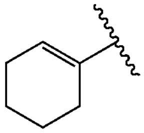 | |
| 2-200 | Cl | 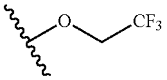 | $SO_2CH_3$ | $CH_3$ | $CH_3$ | 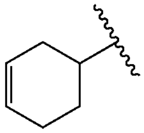 | |
| 2-201 | Cl | 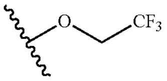 [SMILES: *OCC(F)(F)F] | $SO_2CH_3$ | $CH_3$ | $CH_3$ | 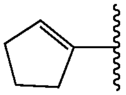 [SMILES: *C1=CCCC1] | |
| 2-202 | Cl | 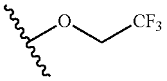 [SMILES: *OCC(F)(F)F] | $SO_2CH_3$ | $CH_3$ | $CH_3$ | 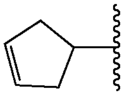 | |
| 2-203 | Cl | 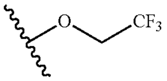 | $SO_2CH_3$ | $CH_3$ | $CH_3$ | 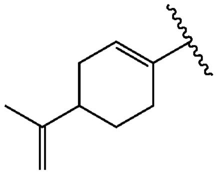 [SMILES: *C1=CCC(C(=C)C)CC1] | |
| 2-204 | Cl | 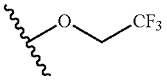 | $SO_2CH_3$ | $CH_3$ | $CH_3$ | 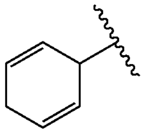 [SMILES: *C1C=CCC=C1] | |
| 2-205 | Cl | 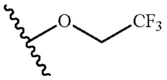 [SMILES: *OCC(F)(F)F] | $SO_2CH_3$ | $CH_2CH_3$ | H | 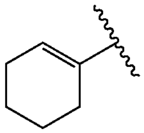 [SMILES: *C1=CCCCC1] | |
| 2-206 | Cl | 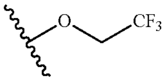 [SMILES: *OCC(F)(F)F] | $SO_2CH_3$ | $CH_2CH_3$ | H | 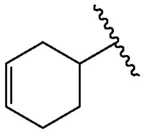 [SMILES: *C1CC=CCC1] | |

TABLE 2-continued
Structures and Physical Properties of Part of Compounds of Formula I
| Compound | $X_1$ | $X_2$ | $X_3$ | $Z_1$ | $Z_2$ | Q | Appearance (Melting Point ° C.) |
|---|---|---|---|---|---|---|---|
| 2-207 | Cl | 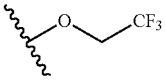 | $SO_2CH_3$ | $CH_2CH_3$ | H | 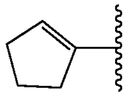 [SMILES: *C1=CCCC1] | |
| 2-208 | Cl | 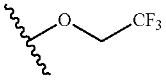 [SMILES: *OCC(F)(F)F] | $SO_2CH_3$ | $CH_2CH_3$ | H | 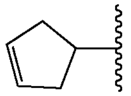 [SMILES: *C1CC=CC1] | |
| 2-209 | Cl | 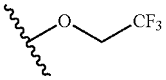 | $SO_2CH_3$ | $CH_2CH_3$ | H | 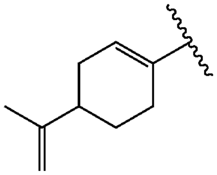 [SMILES: *C1=CCC(C(=C)C)CC1] | |
| 2-210 | Cl | 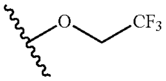 [SMILES: *OCC(F)(F)F] | $SO_2CH_3$ | $CH_2CH_3$ | H | 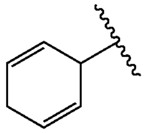 [SMILES: *C1C=CCC=C1] | |
| 2-211 | Cl | 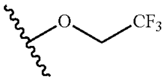 [SMILES: *OCC(F)(F)F] | $SO_2CH_3$ | $CH_3$ | H | 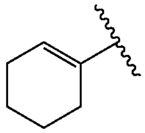 [SMILES: *C1=CCCCC1] | |
| 2-212 | Cl | 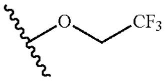 | $SO_2CH_3$ | $CH_3$ | H | 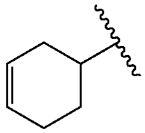 [SMILES: *C1CC=CCC1] | |
| 2-213 | Cl | 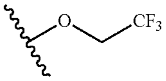 [SMILES: *OCC(F)(F)F] | $SO_2CH_3$ | $CH_3$ | H | 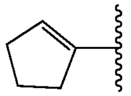 [SMILES: *C1=CCCC1] | |
| 2-214 | Cl | 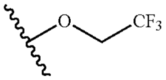 | $SO_2CH_3$ | $CH_3$ | H | 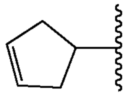 [SMILES: *C1CC=CC1] | |
| 2-215 | Cl | 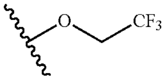 [SMILES: *OCC(F)(F)F] | $SO_2CH_3$ | $CH_3$ | H | 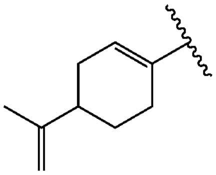 [SMILES: *C1=CCC(C(=C)C)CC1] | |
| 2-216 | Cl | 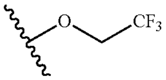 [SMILES: *OCC(F)(F)F] | $SO_2CH_3$ | $CH_3$ | H | 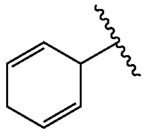 [SMILES: *C1C=CCC=C1] | |

TABLE 2-continued
Structures and Physical Properties of Part of Compounds of Formula I
| Com-pound | $X_1$ | $X_2$ | $X_3$ | $Z_1$ | $Z_2$ | Q | Appearance (Melting Point ° C.) |
|---|---|---|---|---|---|---|---|
| 2-217 | Cl | 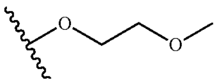 [SMILES: *OCCOC] | $SO_2CH_3$ | $CH_3$ | $CH_3$ | 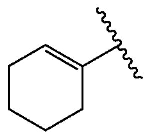 | |
| 2-218 | Cl | 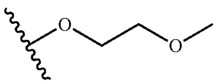 [SMILES: *OCCOC] | $SO_2CH_3$ | $CH_3$ | $CH_3$ | 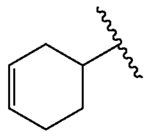 [SMILES: *C1CC=CCC1] | |
| 2-219 | Cl | 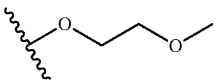 [SMILES: *OCCOC] | $SO_2CH_3$ | $CH_3$ | $CH_3$ | 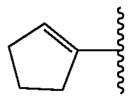 [SMILES: *C1=CCCC1] | |
| 2-220 | Cl | 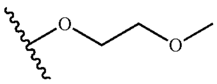 [SMILES: *OCCOC] | $SO_2CH_3$ | $CH_3$ | $CH_3$ | 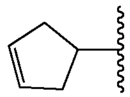 [SMILES: *C1CC=CC1] | |
| 2-221 | Cl | 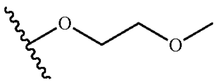 [SMILES: *OCCOC] | $SO_2CH_3$ | $CH_3$ | $CH_3$ | 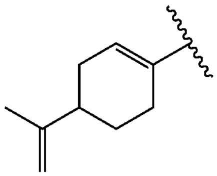 [SMILES: *C1=CCC(C(=C)C)CC1] | |
| 2-222 | Cl | 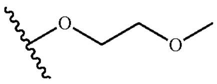 [SMILES: *OCCOC] | $SO_2CH_3$ | $CH_3$ | $CH_3$ | 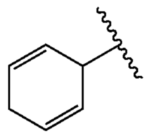 [SMILES: *C1C=CCC=C1] | |
| 2-223 | Cl | 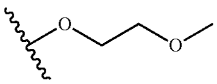 [SMILES: *OCCOC] | $SO_2CH_3$ | $CH_2CH_3$ | H | 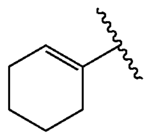 [SMILES: *C1=CCCCC1] | |
| 2-224 | Cl | 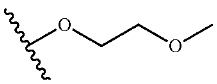 [SMILES: *OCCOC] | $SO_2CH_3$ | $CH_2CH_3$ | H | 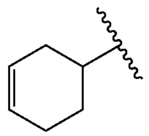 | |
| 2-225 | Cl | 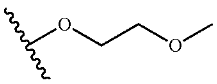 [SMILES: *OCCOC] | $SO_2CH_3$ | $CH_2CH_3$ | H | 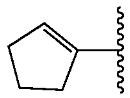 [SMILES: *C1=CCCC1] | |
| 2-226 | Cl | 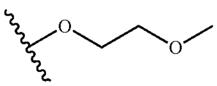 [SMILES: *OCCOC] | $SO_2CH_3$ | $CH_2CH_3$ | H | 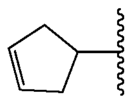 [SMILES: *C1CC=CC1] | |

TABLE 2-continued
Structures and Physical Properties of Part of Compounds of Formula I
| Compound | $X_1$ | $X_2$ | $X_3$ | $Z_1$ | $Z_2$ | Q | Appearance (Melting Point ° C.) |
|---|---|---|---|---|---|---|---|
| 2-227 | Cl | 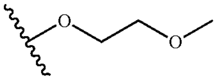 [SMILES: *OCCOC] | $SO_2CH_3$ | $CH_2CH_3$ | H | 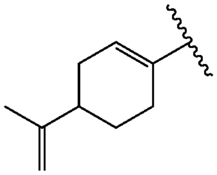 [SMILES: *C1=CCC(C(=C)C)CC1] | |
| 2-228 | Cl | 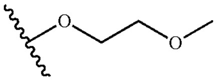 [SMILES: *OCCOC] | $SO_2CH_3$ | $CH_2CH_3$ | H | 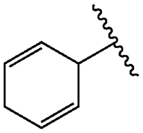 [SMILES: *C1C=CCC=C1] | |
| 2-229 | Cl | 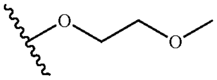 [SMILES: *OCCOC] | $SO_2CH_3$ | $CH_3$ | H | 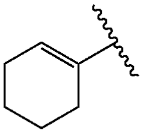 [SMILES: *C1=CCCCC1] | |
| 2-230 | Cl | 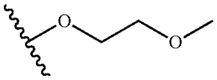 [SMILES: *OCCOC] | $SO_2CH_3$ | $CH_3$ | H | 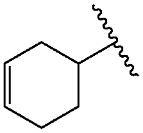 [SMILES: *C1CC=CCC1] | |
| 2-231 | Cl | 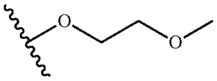 [SMILES: *OCCOC] | $SO_2CH_3$ | $CH_3$ | H | 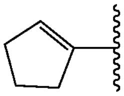 | |
| 2-232 | Cl | 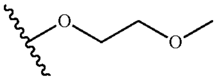 [SMILES: *OCCOC] | $SO_2CH_3$ | $CH_3$ | H | 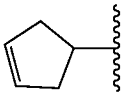 | |
| 2-233 | Cl | 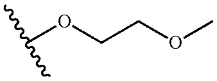 [SMILES: *OCCOC] | $SO_2CH_3$ | $CH_3$ | H | 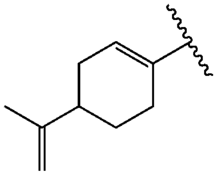 [SMILES: *C1=CCC(C(=C)C)CC1] | |
| 2-234 | Cl | 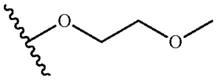 [SMILES: *OCCOC] | $SO_2CH_3$ | $CH_3$ | H | 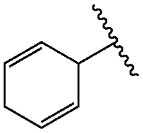 [SMILES: *C1C=CCC=C1] | |
| 2-235 | Cl | 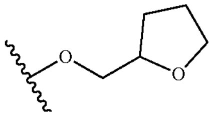 | $SO_2CH_3$ | $CH_3$ | $CH_3$ | 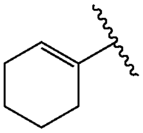 [SMILES: *C1=CCCCC1] | |
| 2-236 | Cl | 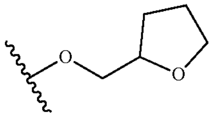 [SMILES: *OCC1CCCO1] | $SO_2CH_3$ | $CH_3$ | $CH_3$ | 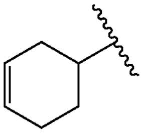 | |

TABLE 2-continued
Structures and Physical Properties of Part of Compounds of Formula I
| Compound | $X_1$ | $X_2$ | $X_3$ | $Z_1$ | $Z_2$ | Q | Appearance (Melting Point ° C.) |
|---|---|---|---|---|---|---|---|
| 2-237 | Cl | 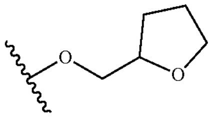 [SMILES: *OCC1CCCO1] | $SO_2CH_3$ | $CH_3$ | $CH_3$ | 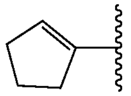 [SMILES: *C1=CCCC1] | |
| 2-238 | Cl | 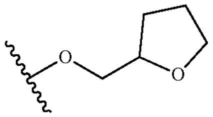 | $SO_2CH_3$ | $CH_3$ | $CH_3$ | 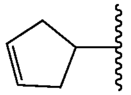 [SMILES: *C1CC=CC1] | |
| 2-239 | Cl | 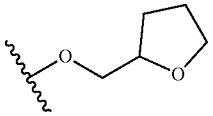 [SMILES: *OCC1CCCO1] | $SO_2CH_3$ | $CH_3$ | $CH_3$ | 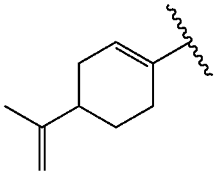 [SMILES: *C1=CCC(C(=C)C)CC1] | |
| 2-240 | Cl | 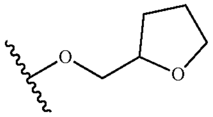 [SMILES: *OCC1CCCO1] | $SO_2CH_3$ | $CH_3$ | $CH_3$ | 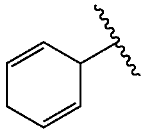 [SMILES: *C1C=CCC=C1] | |
| 2-241 | Cl | 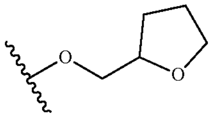 | $SO_2CH_3$ | $CH_2CH_3$ | H | 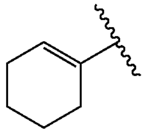 | |
| 2-242 | Cl | 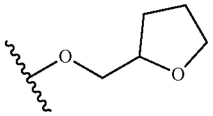 [SMILES: *OCC1CCCO1] | $SO_2CH_3$ | $CH_2CH_3$ | H | 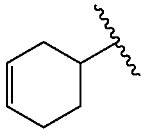 [SMILES: *C1CC=CCC1] | |
| 2-243 | Cl | 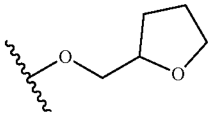 [SMILES: *OCC1CCCO1] | $SO_2CH_3$ | $CH_2CH_3$ | H | 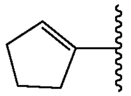 [SMILES: *C1=CCCC1] | |
| 2-244 | Cl | 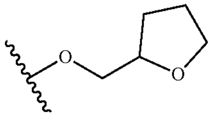 [SMILES: *OCC1CCCO1] | $SO_2CH_3$ | $CH_2CH_3$ | H | 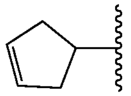 | |
| 2-245 | Cl | 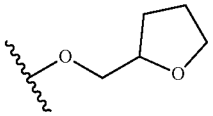 [SMILES: *OCC1CCCO1] | $SO_2CH_3$ | $CH_2CH_3$ | H | 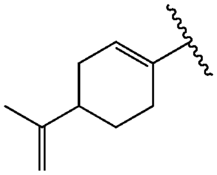 [SMILES: *C1=CCC(C(=C)C)CC1] | |
| 2-246 | Cl | 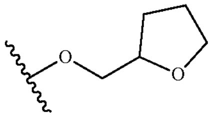 [SMILES: *OCC1CCCO1] | $SO_2CH_3$ | $CH_2CH_3$ | H | 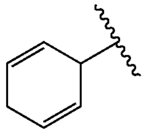 [SMILES: *C1C=CCC=C1] | |

TABLE 2-continued
Structures and Physical Properties of Part of Compounds of Formula I
| Compound | $X_1$ | $X_2$ | $X_3$ | $Z_1$ | $Z_2$ | Q | Appearance (Melting Point ° C.) |
|---|---|---|---|---|---|---|---|
| 2-247 | Cl | 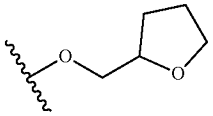 [SMILES: *OCC1CCCO1] | $SO_2CH_3$ | $CH_3$ | H | 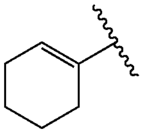 [SMILES: *C1=CCCCC1] | |
| 2-248 | Cl | 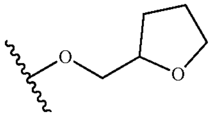 [SMILES: *OCC1CCCO1] | $SO_2CH_3$ | $CH_3$ | H | 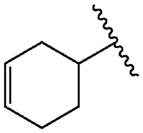 [SMILES: *C1CC=CCC1] | |
| 2-249 | Cl | 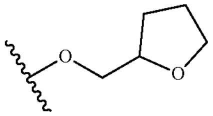 [SMILES: *OCC1CCCO1] | $SO_2CH_3$ | $CH_3$ | H | 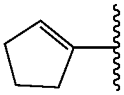 [SMILES: *C1=CCCC1] | |
| 2-250 | Cl | 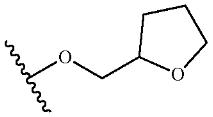 [SMILES: *OCC1CCCO1] | $SO_2CH_3$ | $CH_3$ | H | 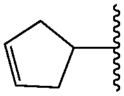 | |
| 2-251 | Cl | 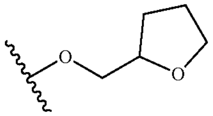 [SMILES: *OCC1CCCO1] | $SO_2CH_3$ | $CH_3$ | H | 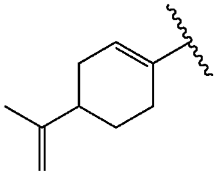 [SMILES: *C1=CCC(C(=C)C)CC1] | |
| 2-252 | Cl | 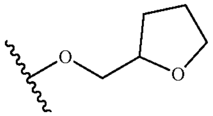 [SMILES: *OCC1CCCO1] | $SO_2CH_3$ | $CH_3$ | H | 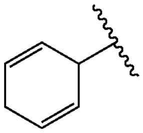 | |
| 2-253 | Cl | 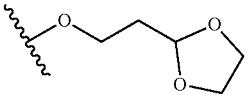 [SMILES: *OCCC1OCCO1] | $SO_2CH_3$ | $CH_3$ | $CH_3$ | 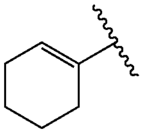 [SMILES: *C1=CCCCC1] | |
| 2-254 | Cl | 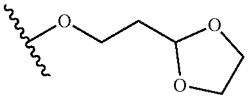 [SMILES: *OCCC1OCCO1] | $SO_2CH_3$ | $CH_3$ | $CH_3$ | 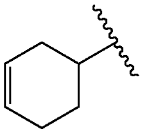 [SMILES: *C1CC=CCC1] | |
| 2-255 | Cl | 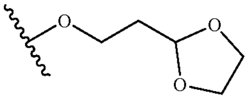 [SMILES: *OCCC1OCCO1] | $SO_2CH_3$ | $CH_3$ | $CH_3$ | 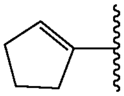 | |
| 2-256 | Cl | 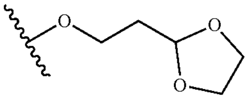 [SMILES: *OCCC1OCCO1] | $SO_2CH_3$ | $CH_3$ | $CH_3$ | 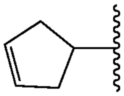 | |

TABLE 2-continued
Structures and Physical Properties of Part of Compounds of Formula I
| Compound | $X_1$ | $X_2$ | $X_3$ | $Z_1$ | $Z_2$ | Q | Appearance (Melting Point ° C.) |
|---|---|---|---|---|---|---|---|
| 2-257 | Cl | 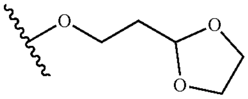 [SMILES: *OCCC1OCCO1] | $SO_2CH_3$ | $CH_3$ | $CH_3$ | 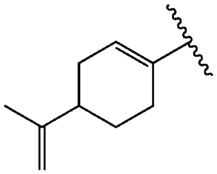 [SMILES: *C1=CCC(C(=C)C)CC1] | |
| 2-258 | Cl | 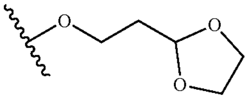 [SMILES: *OCCC1OCCO1] | $SO_2CH_3$ | $CH_3$ | $CH_3$ | 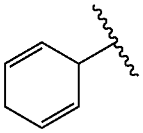 [SMILES: *C1C=CCC=C1] | |
| 2-259 | Cl | 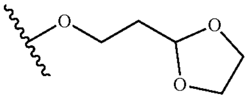 [SMILES: *OCCC1OCCO1] | $SO_2CH_3$ | $CH_2CH_3$ | H | 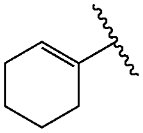 | |
| 2-260 | Cl | 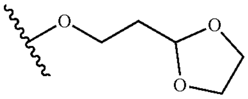 [SMILES: *OCCC1OCCO1] | $SO_2CH_3$ | $CH_2CH_3$ | H | 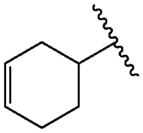 | |
| 2-261 | Cl | 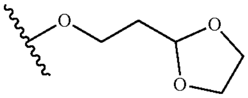 [SMILES: *OCCC1OCCO1] | $SO_2CH_3$ | $CH_2CH_3$ | H | 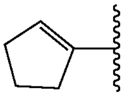 [SMILES: *C1=CCCC1] | |
| 2-262 | Cl | 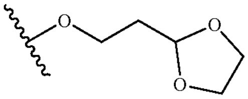 [SMILES: *OCCC1OCCO1] | $SO_2CH_3$ | $CH_2CH_3$ | H | 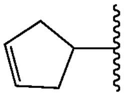 | |
| 2-263 | Cl | 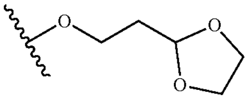 | $SO_2CH_3$ | $CH_2CH_3$ | H | 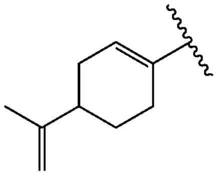 [SMILES: *C1=CCC(C(=C)C)CC1] | |
| 2-264 | Cl | 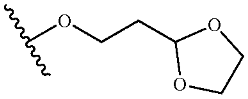 [SMILES: *OCCC1OCCO1] | $SO_2CH_3$ | $CH_2CH_3$ | H | 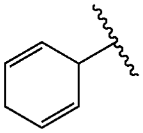 [SMILES: *C1C=CCC=C1] | |
| 2-265 | Cl | 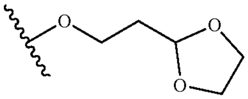 | $SO_2CH_3$ | $CH_3$ | H | 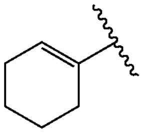 [SMILES: *C1=CCCCC1] | |
| 2-266 | Cl | 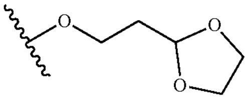 [SMILES: *OCCC1OCCO1] | $SO_2CH_3$ | $CH_3$ | H | 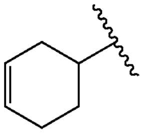 | |

TABLE 2-continued
| Structures and Physical Properties of Part of Compounds of Formula I | | | | | | | |
|---|---|---|---|---|---|---|---|
| Compound | $X_1$ | $X_2$ | $X_3$ | $Z_1$ | $Z_2$ | Q | Appearance (Melting Point ° C.) |
| 2-267 | Cl | 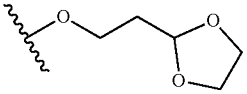 [SMILES: *OCCC1OCCO1] | $SO_2CH_3$ | $CH_3$ | H | 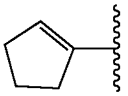 [SMILES: *C1=CCCC1] | |
| 2-268 | Cl | 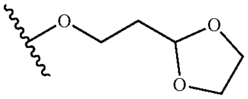 [SMILES: *OCCC1OCCO1] | $SO_2CH_3$ | $CH_3$ | H | 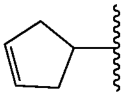 | |
| 2-269 | Cl | 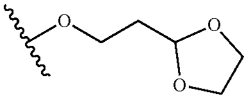 [SMILES: *OCCC1OCCO1] | $SO_2CH_3$ | $CH_3$ | H | 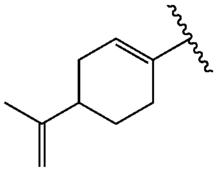 [SMILES: *C1=CCC(C(=C)C)CC1] | |
| 2-270 | Cl | 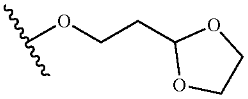 [SMILES: *OCCC1OCCO1] | $SO_2CH_3$ | $CH_3$ | H | 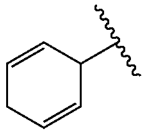 [SMILES: *C1C=CCC=C1] | |
| 2-271 | Cl | 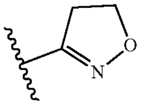 [SMILES: *C1=NOCC1] | $SO_2CH_3$ | $CH_3$ | $CH_3$ | 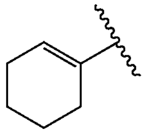 [SMILES: *C1=CCCCC1] | |
| 2-272 | Cl | 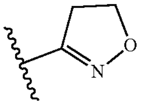 [SMILES: *C1=NOCC1] | $SO_2CH_3$ | $CH_3$ | $CH_3$ | 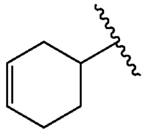 | |
| 2-273 | Cl | 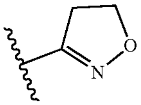 [SMILES: *C1=NOCC1] | $SO_2CH_3$ | $CH_3$ | $CH_3$ | 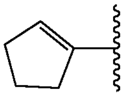 [SMILES: *C1=CCCC1] | |
| 2-274 | Cl | 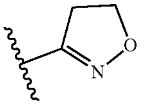 [SMILES: *C1=NOCC1] | $SO_2CH_3$ | $CH_3$ | $CH_3$ | 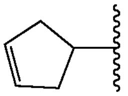 | |
| 2-275 | Cl | 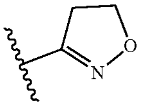 [SMILES: *C1=NOCC1] | $SO_2CH_3$ | $CH_3$ | $CH_3$ | 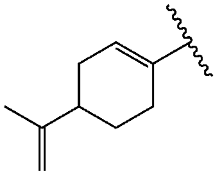 [SMILES: *C1=CCC(C(=C)C)CC1] | |
| 2-276 | Cl | 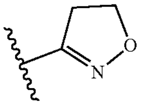 [SMILES: *C1=NOCC1] | $SO_2CH_3$ | $CH_3$ | $CH_3$ | 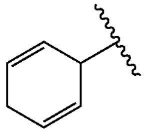 [SMILES: *C1C=CCC=C1] | |

TABLE 2-continued
| Structures and Physical Properties of Part of Compounds of Formula I | | | | | | | |
|---|---|---|---|---|---|---|---|
| Compound | $X_1$ | $X_2$ | $X_3$ | $Z_1$ | $Z_2$ | Q | Appearance (Melting Point ° C.) |
| 2-277 | Cl | 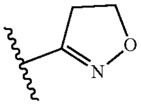 [SMILES: *C1=NOCC1] | $SO_2CH_3$ | $CH_2CH_3$ | H | 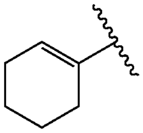 | |
| 2-278 | Cl | 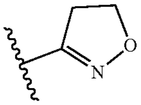 [SMILES: *C1=NOCC1] | $SO_2CH_3$ | $CH_2CH_3$ | H | 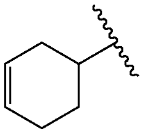 | |
| 2-279 | Cl | 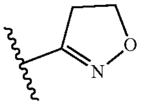 [SMILES: *C1=NOCC1] | $SO_2CH_3$ | $CH_2CH_3$ | H | 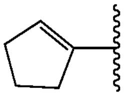 [SMILES: *C1=CCCC1] | |
| 2-280 | Cl | 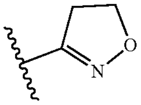 [SMILES: *C1=NOCC1] | $SO_2CH_3$ | $CH_2CH_3$ | H | 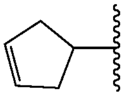 [SMILES: *C1CC=CC1] | |
| 2-281 | Cl | 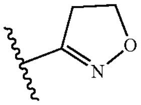 [SMILES: *C1=NOCC1] | $SO_2CH_3$ | $CH_2CH_3$ | H | 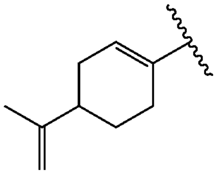 [SMILES: *C1=CCC(C(=C)C)CC1] | |
| 2-282 | Cl | 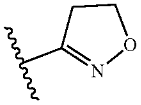 [SMILES: *C1=NOCC1] | $SO_2CH_3$ | $CH_2CH_3$ | H | 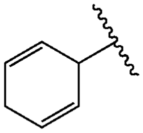 [SMILES: *C1C=CCC=C1] | |
| 2-283 | Cl | 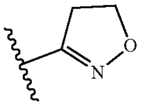 [SMILES: *C1=NOCC1] | $SO_2CH_3$ | $CH_3$ | H | 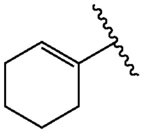 | |
| 2-284 | Cl | 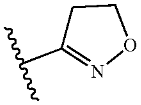 [SMILES: *C1=NOCC1] | $SO_2CH_3$ | $CH_3$ | H | 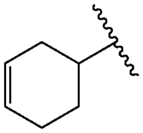 [SMILES: *C1CC=CCC1] | |
| 2-285 | Cl | 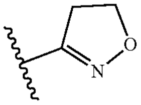 [SMILES: *C1=NOCC1] | $SO_2CH_3$ | $CH_3$ | H | 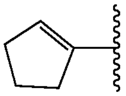 | |
| 2-286 | Cl | 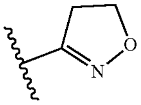 [SMILES: *C1=NOCC1] | $SO_2CH_3$ | $CH_3$ | H | 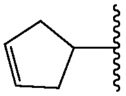 [SMILES: *C1CC=CC1] | |

TABLE 2-continued

Structures and Physical Properties of Part of Compounds of Formula I

| Compound | $X_1$ | $X_2$ | $X_3$ | $Z_1$ | $Z_2$ | Q | Appearance (Melting Point ° C.) |
|---|---|---|---|---|---|---|---|
| 2-287 | Cl | 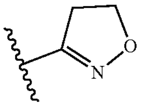 [SMILES: *C1=NOCC1] | $SO_2CH_3$ | $CH_3$ | H | 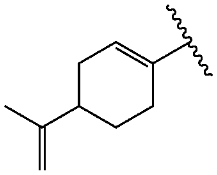 [SMILES: *C1=CCC(C(=C)C)CC1] | |
| 2-288 | Cl | 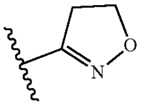 [SMILES: *C1=NOCC1] | $SO_2CH_3$ | $CH_3$ | H | 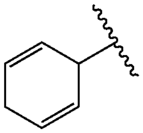 [SMILES: *C1C=CCC=C1] | |
| 2-289 | Cl | $CH_3$ | $SO_2CH_3$ | $CH_3$ | $CH_3$ | 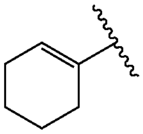 | white solid (172-174) |
| 2-290 | Cl | $CH_3$ | $SO_2CH_3$ | $CH_3$ | $CH_3$ | 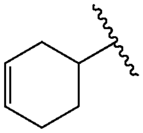 | |
| 2-291 | Cl | $CH_3$ | $SO_2CH_3$ | $CH_3$ | $CH_3$ | 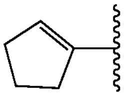 [SMILES: *C1=CCCC1] | white solid (137-139) |
| 2-292 | Cl | $CH_3$ | $SO_2CH_3$ | $CH_3$ | $CH_3$ | 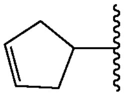 | |
| 2-293 | Cl | $CH_3$ | $SO_2CH_3$ | $CH_3$ | $CH_3$ | 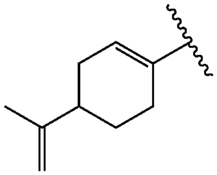 [SMILES: *C1=CCC(C(=C)C)CC1] | |
| 2-294 | Cl | $CH_3$ | $SO_2CH_3$ | $CH_3$ | $CH_3$ | 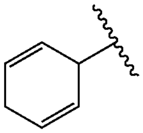 | |
| 2-295 | Cl | $CH_3$ | $SO_2CH_3$ | $CH_2CH_3$ | H | 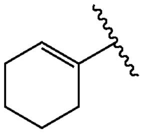 [SMILES: *C1=CCCCC1] | |
| 2-296 | Cl | $CH_3$ | $SO_2CH_3$ | $CH_2CH_3$ | H | 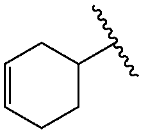 | |

TABLE 2-continued
| Structures and Physical Properties of Part of Compounds of Formula I | | | | | | | |
|---|---|---|---|---|---|---|---|
| Compound | $X_1$ | $X_2$ | $X_3$ | $Z_1$ | $Z_2$ | Q | Appearance (Melting Point ° C.) |
| 2-297 | Cl | $CH_3$ | $SO_2CH_3$ | $CH_2CH_3$ | H | 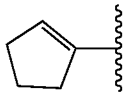 [SMILES: *C1=CCCC1] | |
| 2-298 | Cl | $CH_3$ | $SO_2CH_3$ | $CH_2CH_3$ | H | 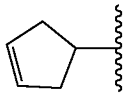 [SMILES: *C1CC=CC1] | |
| 2-299 | Cl | $CH_3$ | $SO_2CH_3$ | $CH_2CH_3$ | H | 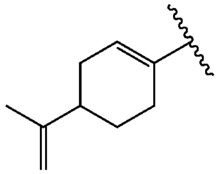 [SMILES: *C1=CCC(C(=C)C)CC1] | |
| 2-300 | Cl | $CH_3$ | $SO_2CH_3$ | $CH_2CH_3$ | H | 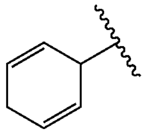 [SMILES: *C1C=CCC=C1] | |
| 2-301 | Cl | $CH_3$ | $SO_2CH_3$ | $CH_3$ | H | 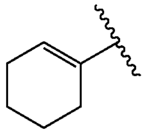 [SMILES: *C1=CCCCC1] | |
| 2-302 | Cl | $CH_3$ | $SO_2CH_3$ | $CH_3$ | H | 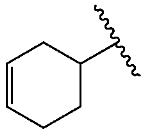 [SMILES: *C1CC=CCC1] | |
| 2-303 | Cl | $CH_3$ | $SO_2CH_3$ | $CH_3$ | H | 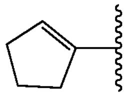 | |
| 2-304 | Cl | $CH_3$ | $SO_2CH_3$ | $CH_3$ | H | 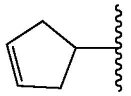 [SMILES: *C1CC=CC1] | |
| 2-305 | Cl | $CH_3$ | $SO_2CH_3$ | $CH_3$ | H | 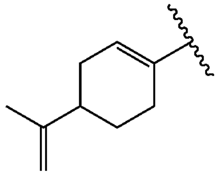 [SMILES: *C1=CCC(C(=C)C)CC1] | |
| 2-306 | Cl | $CH_3$ | $SO_2CH_3$ | $CH_3$ | H | 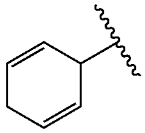 [SMILES: *C1C=CCC=C1] | |

TABLE 2-continued
| Structures and Physical Properties of Part of Compounds of Formula I | | | | | | | |
|---|---|---|---|---|---|---|---|
| Compound | $X_1$ | $X_2$ | $X_3$ | $Z_1$ | $Z_2$ | Q | Appearance (Melting Point ° C.) |
| 2-307 | Cl | 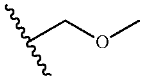 [SMILES: *COC] | $SO_2CH_3$ | $CH_3$ | $CH_3$ | 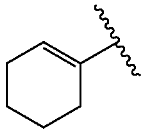 | white solid (181-183) |
| 2-308 | Cl | 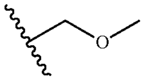 [SMILES: *COC] | $SO_2CH_3$ | $CH_3$ | $CH_3$ | 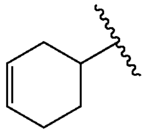 | |
| 2-309 | Cl | 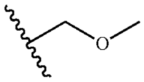 | $SO_2CH_3$ | $CH_3$ | $CH_3$ | 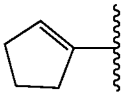 [SMILES: *C1=CCCC1] | yellow solid (128-130) |
| 2-310 | Cl | 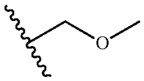 [SMILES: *COC] | $SO_2CH_3$ | $CH_3$ | $CH_3$ | 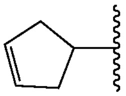 | |
| 2-311 | Cl | 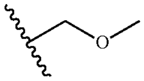 [SMILES: *COC] | $SO_2CH_3$ | $CH_3$ | $CH_3$ | 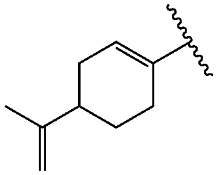 [SMILES: *C1=CCC(C(=C)C)CC1] | |
| 2-312 | Cl | 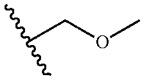 [SMILES: *COC] | $SO_2CH_3$ | $CH_3$ | $CH_3$ | 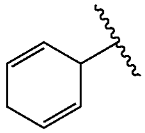 [SMILES: *C1C=CCC=C1] | |
| 2-313 | Cl | 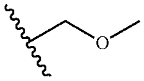 [SMILES: *COC] | $SO_2CH_3$ | $CH_2CH_3$ | H | 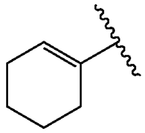 [SMILES: *C1=CCCCC1] | |
| 2-314 | Cl | 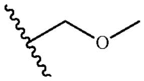 [SMILES: *COC] | $SO_2CH_3$ | $CH_2CH_3$ | H | 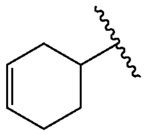 [SMILES: *C1CC=CCC1] | |
| 2-315 | Cl | 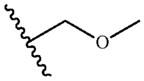 [SMILES: *COC] | $SO_2CH_3$ | $CH_2CH_3$ | H | 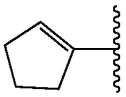 | |
| 2-316 | Cl | 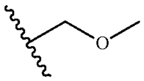 [SMILES: *COC] | $SO_2CH_3$ | $CH_2CH_3$ | H | 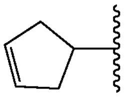 | |

TABLE 2-continued
Structures and Physical Properties of Part of Compounds of Formula I
| Compound | $X_1$ | $X_2$ | $X_3$ | $Z_1$ | $Z_2$ | Q | Appearance (Melting Point ° C.) |
|---|---|---|---|---|---|---|---|
| 2-317 | Cl | 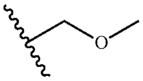 [SMILES: *COC] | $SO_2CH_3$ | $CH_2CH_3$ | H | 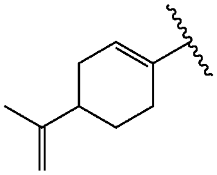 [SMILES: *C1=CCC(C(=C)C)CC1] | |
| 2-318 | Cl | 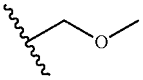 [SMILES: *COC] | $SO_2CH_3$ | $CH_2CH_3$ | H | 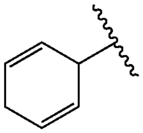 [SMILES: *C1C=CCC=C1] | |
| 2-319 | Cl | 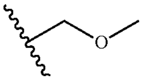 [SMILES: *COC] | $SO_2CH_3$ | $CH_3$ | H | 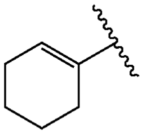 | |
| 2-320 | Cl | 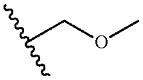 [SMILES: *COC] | $SO_2CH_3$ | $CH_3$ | H | 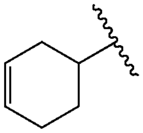 | |
| 2-321 | Cl | 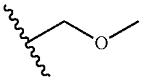 [SMILES: *COC] | $SO_2CH_3$ | $CH_3$ | H | 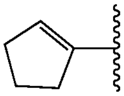 [SMILES: *C1=CCCC1] | |
| 2-322 | Cl | 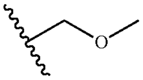 [SMILES: *COC] | $SO_2CH_3$ | $CH_3$ | H | 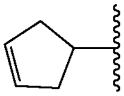 | |
| 2-323 | Cl | 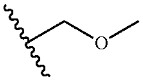 | $SO_2CH_3$ | $CH_3$ | H | 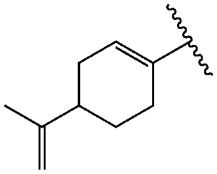 | |
| 2-324 | Cl | 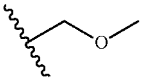 [SMILES: *COC] | $SO_2CH_3$ | $CH_3$ | H | 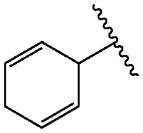 [SMILES: *C1C=CCC=C1] | |
| 2-325 | Cl | 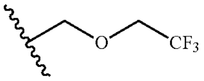 [SMILES: *COCC(F)(F)F] | $SO_2CH_3$ | $CH_3$ | $CH_3$ | 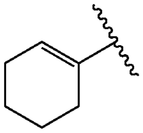 | |
| 2-326 | Cl | 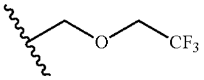 [SMILES: *COCC(F)(F)F] | $SO_2CH_3$ | $CH_3$ | $CH_3$ | 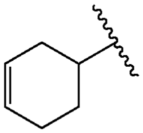 [SMILES: *C1CC=CCC1] | |

TABLE 2-continued
Structures and Physical Properties of Part of Compounds of Formula I
| Compound | $X_1$ | $X_2$ | $X_3$ | $Z_1$ | $Z_2$ | Q | Appearance (Melting Point ° C.) |
|---|---|---|---|---|---|---|---|
| 2-327 | Cl | 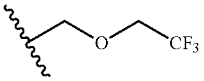 | $SO_2CH_3$ | $CH_3$ | $CH_3$ | 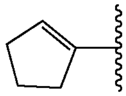 [SMILES: *C1=CCCC1] | |
| 2-328 | Cl | 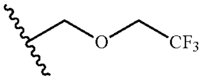 [SMILES: *COCC(F)(F)F] | $SO_2CH_3$ | $CH_3$ | $CH_3$ | 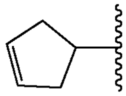 [SMILES: *C1CC=CC1] | |
| 2-329 | Cl | 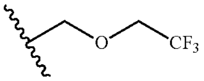 | $SO_2CH_3$ | $CH_3$ | $CH_3$ | 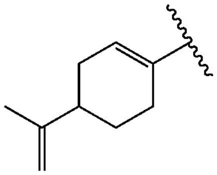 [SMILES: *C1=CCC(C(=C)C)CC1] | |
| 2-330 | Cl | 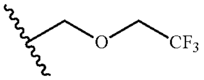 [SMILES: *COCC(F)(F)F] | $SO_2CH_3$ | $CH_3$ | $CH_3$ | 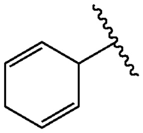 [SMILES: *C1C=CCC=C1] | |
| 2-331 | Cl | 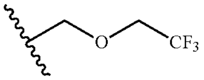 [SMILES: *COCC(F)(F)F] | $SO_2CH_3$ | $CH_3$ | $CH_3$ | 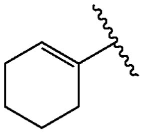 [SMILES: *C1=CCCCC1] | |
| 2-332 | Cl | 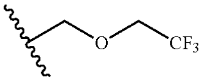 | $SO_2CH_3$ | $CH_3$ | $CH_3$ | 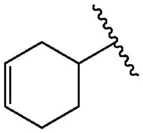 | |
| 2-333 | Cl | 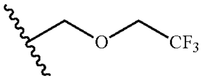 [SMILES: *COCC(F)(F)F] | $SO_2CH_3$ | $CH_3$ | $CH_3$ | 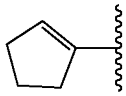 [SMILES: *C1=CCCC1] | |
| 2-334 | Cl | 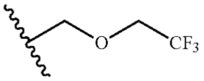 [SMILES: *COCC(F)(F)F] | $SO_2CH_3$ | $CH_3$ | $CH_3$ | 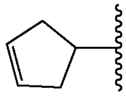 | |
| 2-335 | Cl | 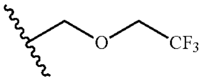 [SMILES: *COCC(F)(F)F] | $SO_2CH_3$ | $CH_3$ | $CH_3$ | 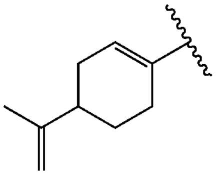 [SMILES: *C1=CCC(C(=C)C)CC1] | |
| 2-336 | Cl | 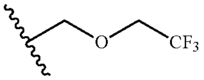 [SMILES: *COCC(F)(F)F] | $SO_2CH_3$ | $CH_3$ | $CH_3$ | 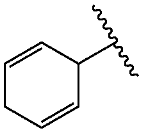 [SMILES: *C1C=CCC=C1] | |

TABLE 2-continued
Structures and Physical Properties of Part of Compounds of Formula I
| Compound | $X_1$ | $X_2$ | $X_3$ | $Z_1$ | $Z_2$ | Q | Appearance (Melting Point ° C.) |
|---|---|---|---|---|---|---|---|
| 2-337 | Cl | 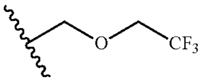 | $SO_2CH_3$ | $CH_3$ | $CH_3$ | 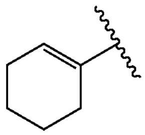 | |
| 2-338 | Cl | 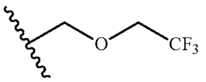 [SMILES: *COCC(F)(F)F] | $SO_2CH_3$ | $CH_3$ | $CH_3$ | 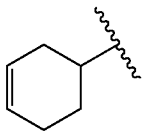 | |
| 2-339 | Cl | 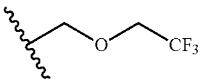 [SMILES: *COCC(F)(F)F] | $SO_2CH_3$ | $CH_3$ | $CH_3$ | 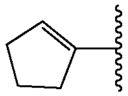 [SMILES: *C1=CCCC1] | |
| 2-340 | Cl | 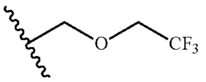 | $SO_2CH_3$ | $CH_3$ | $CH_3$ | 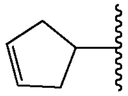 | |
| 2-341 | Cl | 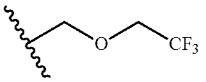 [SMILES: *COCC(F)(F)F] | $SO_2CH_3$ | $CH_3$ | $CH_3$ | 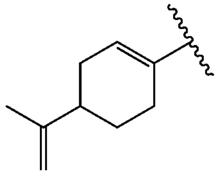 [SMILES: *C1=CCC(C(=C)C)CC1] | |
| 2-342 | Cl | 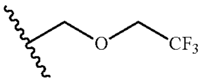 | $SO_2CH_3$ | $CH_3$ | $CH_3$ | 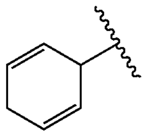 [SMILES: *C1C=CCC=C1] | |
| 2-343 | $SO_2CH_3$ | H | Cl | $CH_3$ | $CH_3$ | 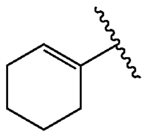 | white solid (170-171) |
| 2-344 | $SO_2CH_3$ | H | Cl | $CH_3$ | $CH_3$ | 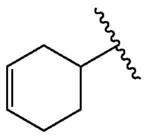 [SMILES: *C1CC=CCC1] | |
| 2-345 | $SO_2CH_3$ | H | Cl | $CH_3$ | $CH_3$ | 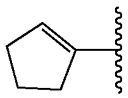 [SMILES: *C1=CCCC1] | |
| 2-346 | $SO_2CH_3$ | H | Cl | $CH_3$ | $CH_3$ | 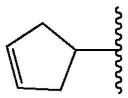 [SMILES: *C1CC=CC1] | |

TABLE 2-continued
Structures and Physical Properties of Part of Compounds of Formula I
| Compound | $X_1$ | $X_2$ | $X_3$ | $Z_1$ | $Z_2$ | Q | Appearance (Melting Point ° C.) |
|---|---|---|---|---|---|---|---|
| 2-347 | $SO_2CH_3$ | H | Cl | $CH_3$ | $CH_3$ | 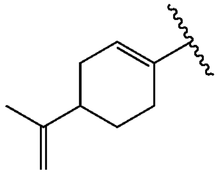 [SMILES: *C1=CCC(C(=C)C)CC1] | |
| 2-348 | $SO_2CH_3$ | H | Cl | $CH_3$ | $CH_3$ | 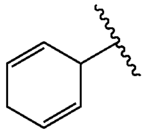 [SMILES: *C1C=CCC=C1] | |
| 2-349 | $SO_2CH_3$ | H | Cl | $CH_2CH_3$ | H | 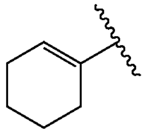 | |
| 2-350 | $SO_2CH_3$ | H | Cl | $CH_2CH_3$ | H | 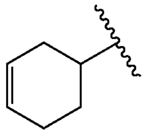 | |
| 2-351 | $SO_2CH_3$ | H | Cl | $CH_2CH_3$ | H | 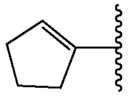 [SMILES: *C1=CCCC1] | |
| 2-352 | $SO_2CH_3$ | H | Cl | $CH_2CH_3$ | H | 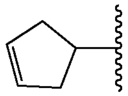 | |
| 2-353 | $SO_2CH_3$ | H | Cl | $CH_2CH_3$ | H | 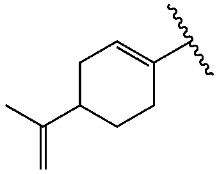 [SMILES: *C1=CCC(C(=C)C)CC1] | |
| 2-354 | $SO_2CH_3$ | H | Cl | $CH_2CH_3$ | H | 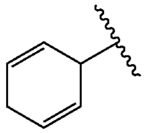 [SMILES: *C1C=CCC=C1] | |
| 2-355 | $SO_2CH_3$ | H | Cl | $CH_3$ | H | 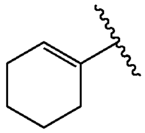 | |
| 2-356 | $SO_2CH_3$ | H | Cl | $CH_3$ | H | 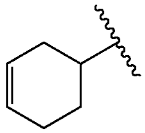 [SMILES: *C1CC=CCC1] | |

TABLE 2-continued
Structures and Physical Properties of Part of Compounds of Formula I
| Compound | $X_1$ | $X_2$ | $X_3$ | $Z_1$ | $Z_2$ | Q | Appearance (Melting Point ° C.) |
|---|---|---|---|---|---|---|---|
| 2-357 | $SO_2CH_3$ | H | Cl | $CH_3$ | H | 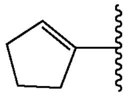 [SMILES: *C1=CCCC1] | |
| 2-358 | $SO_2CH_3$ | H | Cl | $CH_3$ | H | 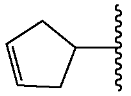 [SMILES: *C1CC=CC1] | |
| 2-359 | $SO_2CH_3$ | H | Cl | $CH_3$ | H | 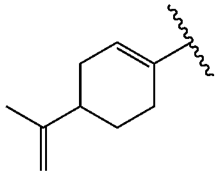 [SMILES: *C1=CCC(C(=C)C)CC1] | |
| 2-360 | $SO_2CH_3$ | H | Cl | $CH_3$ | H | 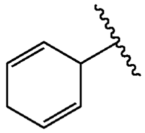 [SMILES: *C1C=CCC=C1] | |
| 2-361 | Cl | Cl | $SO_2CH_3$ | $CH_3$ | $CH_3$ | 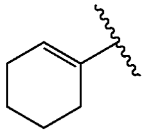 [SMILES: *C1=CCCCC1] | |
| 2-362 | Cl | Cl | $SO_2CH_3$ | $CH_3$ | $CH_3$ | 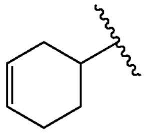 | |
| 2-363 | Cl | Cl | $SO_2CH_3$ | $CH_3$ | $CH_3$ | 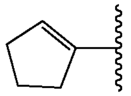 [SMILES: *C1=CCCC1] | |
| 2-364 | Cl | Cl | $SO_2CH_3$ | $CH_3$ | $CH_3$ | 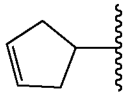 | |
| 2-365 | Cl | Cl | $SO_2CH_3$ | $CH_3$ | $CH_3$ | 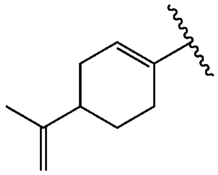 [SMILES: *C1=CCC(C(=C)C)CC1] | |
| 2-366 | Cl | Cl | $SO_2CH_3$ | $CH_3$ | $CH_3$ | 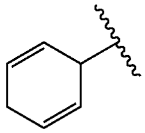 [SMILES: *C1C=CCC=C1] | |

TABLE 2-continued
| Structures and Physical Properties of Part of Compounds of Formula I | | | | | | | |
|---|---|---|---|---|---|---|---|
| Compound | $X_1$ | $X_2$ | $X_3$ | $Z_1$ | $Z_2$ | Q | Appearance (Melting Point ° C.) |
| 2-367 | Cl | Cl | $SO_2CH_3$ | $CH_2CH_3$ | H | 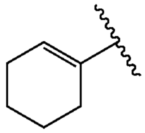 | |
| 2-368 | Cl | Cl | $SO_2CH_3$ | $CH_2CH_3$ | H | 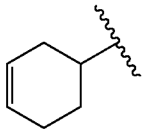 | |
| 2-369 | Cl | Cl | $SO_2CH_3$ | $CH_2CH_3$ | H | 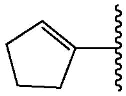 [SMILES: *C1=CCCC1] | |
| 2-370 | Cl | Cl | $SO_2CH_3$ | $CH_2CH_3$ | H | 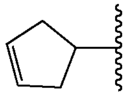 | |
| 2-371 | Cl | Cl | $SO_2CH_3$ | $CH_2CH_3$ | H | 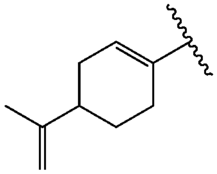 [SMILES: *C1=CCC(C(=C)C)CC1] | |
| 2-372 | Cl | Cl | $SO_2CH_3$ | $CH_2CH_3$ | H | 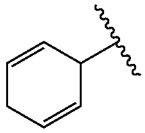 [SMILES: *C1C=CCC=C1] | |
| 2-373 | Cl | Cl | $SO_2CH_3$ | $CH_3$ | H | 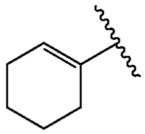 | |
| 2-374 | Cl | Cl | $SO_2CH_3$ | $CH_3$ | H | 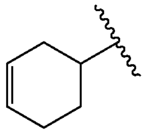 [SMILES: *C1CC=CCC1] | |
| 2-375 | Cl | Cl | $SO_2CH_3$ | $CH_3$ | H | 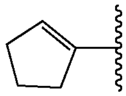 [SMILES: *C1=CCCC1] | |
| 2-376 | Cl | Cl | $SO_2CH_3$ | $CH_3$ | H | 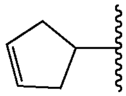 [SMILES: *C1CC=CC1] | |

TABLE 2-continued

Structures and Physical Properties of Part of Compounds of Formula I

| Compound | $X_1$ | $X_2$ | $X_3$ | $Z_1$ | $Z_2$ | Q | Appearance (Melting Point ° C.) |
|---|---|---|---|---|---|---|---|
| 2-377 | Cl | Cl | $SO_2CH_3$ | $CH_3$ | H | 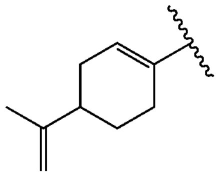 [SMILES: *C1=CCC(C(=C)C)CC1] | |
| 2-378 | Cl | Cl | $SO_2CH_3$ | $CH_3$ | H | 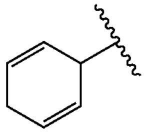 | |
| 2-379 | $SO_2CH_3$ | H | $CF_3$ | $CH_3$ | $CH_3$ | 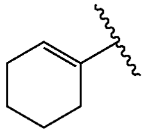 | while solid (129-131) |
| 2-380 | $SO_2CH_3$ | H | $CF_3$ | $CH_3$ | $CH_3$ | 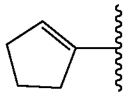 | pale pink solid (124-126) |
| 2-381 | Cl | 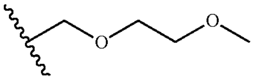 [SMILES: *COCCOC] | $SO_2CH_3$ | $CH_3$ | $CH_3$ | 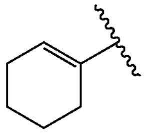 [SMILES: *C1=CCCCC1] | yellow oil |
| 2-382 | Cl | 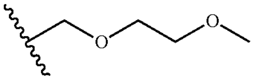 [SMILES: *COCCOC] | $SO_2CH_3$ | $CH_3$ | $CH_3$ | 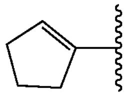 | yellow oil |
| 2-383 | Cl | H | $SO_2CH_3$ | $CH_3$ | $CH_3$ | 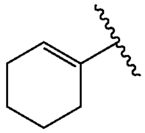 [SMILES: *C1=CCCCC1] | yellow solid (168-170) |
| 2-384 | Cl | H | $SO_2CH_3$ | $CH_3$ | $CH_3$ | 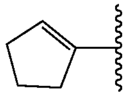 [SMILES: *C1=CCCC1] | pale yellow solid (136-138) |
| 2-385 | Cl | H | Cl | $CH_3$ | $CH_3$ | 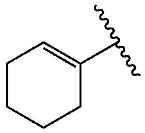 [SMILES: *C1=CCCCC1] | pink solid (133-135) |
| 2-386 | Cl | H | Cl | $CH_3$ | $CH_3$ | 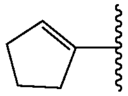 [SMILES: *C1=CCCC1] | while solid (112-114) |
| 2-387 | $NO_2$ | H | $SO_2CH_3$ | $CH_3$ | $CH_3$ | 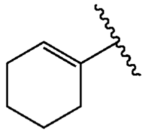 | pale yellow solid (144-146) |

TABLE 2-continued

| Structures and Physical Properties of Part of Compounds of Formula I | | | | | | | |
|---|---|---|---|---|---|---|---|
| Compound | $X_1$ | $X_2$ | $X_3$ | $Z_1$ | $Z_2$ | Q | Appearance (Melting Point ° C.) |
| 2-388 | $NO_2$ | H | $SO_2CH_3$ | $CH_3$ | $CH_3$ | 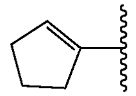 [SMILES: *C1=CCCC1] | orange solid (150-152) |
| 2-389 | Cl | H | $NO_2$ | $CH_3$ | $CH_3$ | 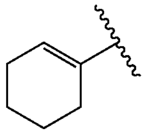 [SMILES: *C1=CCCCC1] | yellow oil |
| 2-390 | Cl | H | $NO_2$ | $CH_3$ | $CH_3$ | 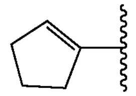 [SMILES: *C1=CCCC1] | yellow solid (115-117) |
| 2-391 | $NO_2$ | H | Cl | $CH_3$ | $CH_3$ | 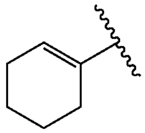 [SMILES: *C1=CCCCC1] | pale yellow solid (128-130) |
| 2-392 | $NO_2$ | H | Cl | $CH_3$ | $CH_3$ | 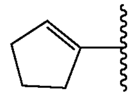 [SMILES: *C1=CCCC1] | pale yellow solid (134-136) |
| 2-393 | Cl | 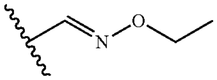 [SMILES: */C=N/OCC] | $SO_2CH_3$ | $CH_3$ | $CH_3$ | 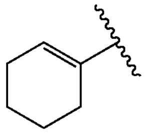 | |
| 2-394 | Cl | 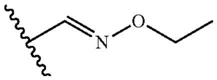 [SMILES: */C=N/OCC] | $SO_2CH_3$ | $CH_3$ | $CH_3$ | 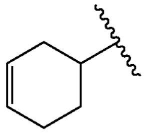 [SMILES: *C1CC=CCC1] | |
| 2-395 | Cl | 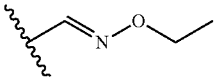 | $SO_2CH_3$ | $CH_3$ | $CH_3$ | 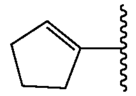 [SMILES: *C1=CCCC1] | |
| 2-396 | Cl | 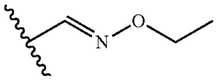 [SMILES: */C=N/OCC] | $SO_2CH_3$ | $CH_3$ | $CH_3$ | 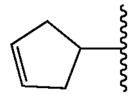 [SMILES: *C1CC=CC1] | |
| 2-397 | Cl | 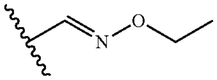 [SMILES: */C=N/OCC] | $SO_2CH_3$ | $CH_3$ | $CH_3$ | 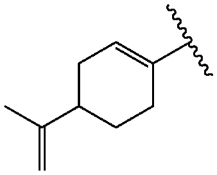 [SMILES: *C1=CCC(C(=C)C)CC1] | |
| 2-398 | Cl | 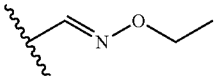 [SMILES: */C=N/OCC] | $SO_2CH_3$ | $CH_3$ | $CH_3$ | 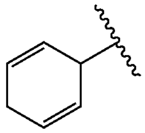 [SMILES: *C1C=CCC=C1] | |

TABLE 2-continued
Structures and Physical Properties of Part of Compounds of Formula I
| Compound | $X_1$ | $X_2$ | $X_3$ | $Z_1$ | $Z_2$ | Q | Appearance (Melting Point ° C.) |
|---|---|---|---|---|---|---|---|
| 2-399 | Cl | 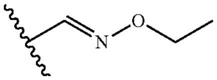 | $SO_2CH_3$ | $CH_2CH_3$ | H | 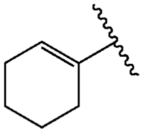 | |
| 2-400 | Cl | 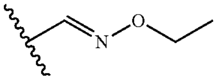 | $SO_2CH_3$ | $CH_2CH_3$ | H | 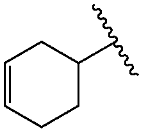 | |
| 2-401 | Cl | 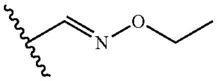 [SMILES: */C=N/OCC] | $SO_2CH_3$ | $CH_2CH_3$ | H | 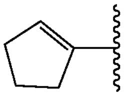 | |
| 2-402 | Cl | 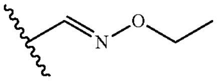 [SMILES: */C=N/OCC] | $SO_2CH_3$ | $CH_2CH_3$ | H | 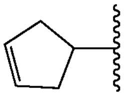 [SMILES: *C1CC=CC1] | |
| 2-403 | Cl | 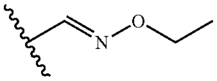 [SMILES: */C=N/OCC] | $SO_2CH_3$ | $CH_2CH_3$ | H | 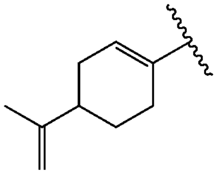 [SMILES: *C1=CCC(C(=C)C)CC1] | |
| 2-404 | Cl | 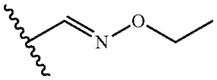 | $SO_2CH_3$ | $CH_2CH_3$ | H | 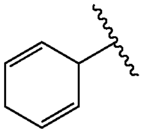 [SMILES: *C1C=CCC=C1] | |
| 2-405 | Cl | 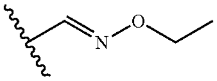 [SMILES: */C=N/OCC] | $SO_2CH_3$ | $CH_3$ | H | 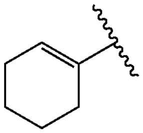 [SMILES: *C1=CCCCC1] | |
| 2-406 | Cl | 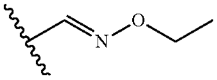 [SMILES: */C=N/OCC] | $SO_2CH_3$ | $CH_3$ | H | 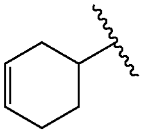 [SMILES: *C1CC=CCC1] | |
| 2-407 | Cl | 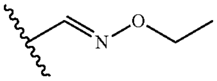 [SMILES: */C=N/OCC] | $SO_2CH_3$ | $CH_3$ | H | 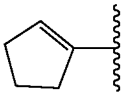 [SMILES: *C1=CCCC1] | |
| 2-408 | Cl | 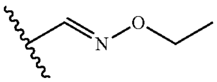 | $SO_2CH_3$ | $CH_3$ | H | 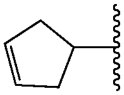 [SMILES: *C1CC=CC1] | |

TABLE 2-continued

Structures and Physical Properties of Part of Compounds of Formula I

| Compound | $X_1$ | $X_2$ | $X_3$ | $Z_1$ | $Z_2$ | Q | Appearance (Melting Point ° C.) |
|---|---|---|---|---|---|---|---|
| 2-409 | Cl | 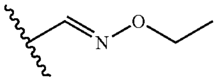 [SMILES: */C=N/OCC] | $SO_2CH_3$ | $CH_3$ | H | 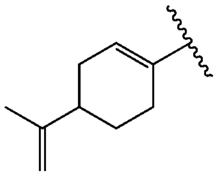 [SMILES: *C1=CCC(C(=C)C)CC1] | |
| 2-410 | Cl | 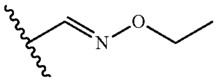 | $SO_2CH_3$ | $CH_3$ | H | 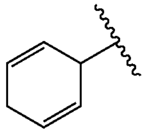 | |
| 2-411 | Cl | $CH_3SO_2CH_2$ | $SO_2CH_3$ | $CH_3$ | $CH_3$ | 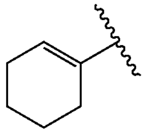 | |
| 2-412 | Cl | $CH_3SO_2CH_2$ | $SO_2CH_3$ | $CH_2CH_3$ | H | 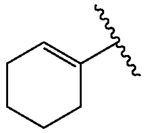 [SMILES: *C1=CCCCC1] | |
| 2-413 | Cl | $CH_3SO_2CH_2$ | $SO_2CH_3$ | $CH_3$ | H | 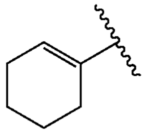 | |
| 2-414 | $CH_3$ | 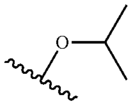 [SMILES: *OC(C)C] | $SO_2CH_3$ | $CH_3$ | $CH_3$ | 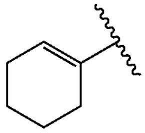 | yellow solid (147-149) |
| 2-415 | $CH_3$ | 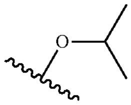 [SMILES: *OC(C)C] | $SO_2CH_3$ | $CH_3$ | $CH_3$ | 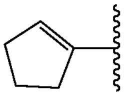 | yellow solid (167-169) |
| 2-416 | $CH_3$ | 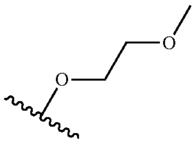 [SMILES: *OCCOC] | $SO_2CH_3$ | $CH_3$ | 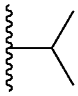 [SMILES: *C(C)C] | 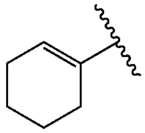 | yellow oil |
| 2-417 | $CH_3$ | 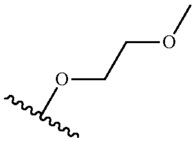 [SMILES: *OCCOC] | $SO_2CH_3$ | $CH_3$ | 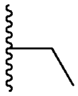 [SMILES: *CC] | 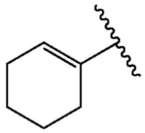 [SMILES: *C1=CCCCC1] | yellow solid (110-111) |
| 2-418 | $CH_3$ | 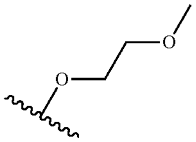 [SMILES: *OCCOC] | $SO_2CH_3$ | $CH_3$ | 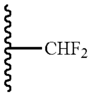 | 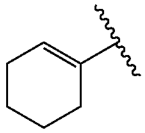 [SMILES: *C1=CCCCC1] | yellow solid (101-103) |

TABLE 2-continued

| Structures and Physical Properties of Part of Compounds of Formula I | | | | | | | |
|---|---|---|---|---|---|---|---|
| Compound | $X_1$ | $X_2$ | $X_3$ | $Z_1$ | $Z_2$ | Q | Appearance (Melting Point ° C.) |
| 2-419 | $CH_3$ | 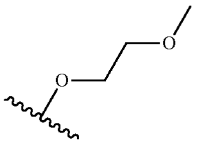 [SMILES: *OCCOC] | $SO_2CH_3$ | $CH_3$ | 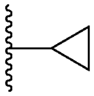 [SMILES: *C1CC1] | 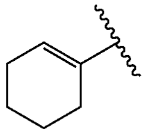 [SMILES: *C1=CCCCC1] | yellow oil |
| 2-420 | $CH_3$ | 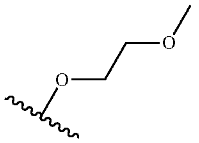 [SMILES: *OCCOC] | $SO_2CH_3$ | $CH_2CH_3$ | $CH_3$ | 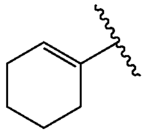 [SMILES: *C1=CCCCC1] | yellow solid (105-106) |
| 2-421 | Cl | 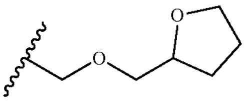 [SMILES: *COCC1CCCO1] | $SO_2CH_3$ | $CH_3$ | $CH_3$ | 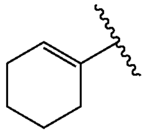 | pink oil |

In the compound of the formula I, W is N and the stereo configuration is trans.

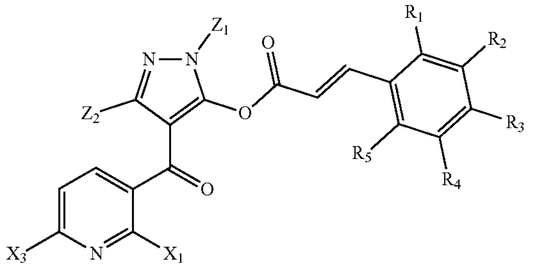

TABLE 3

| Structures and Physical Properties of Part of Compounds of Formula I | | | | | | | | | | |
|---|---|---|---|---|---|---|---|---|---|---|
| Compound | $X_1$ | $X_3$ | $Z_1$ | $Z_2$ | $R_1$ | $R_2$ | $R_3$ | $R_4$ | $R_5$ | Appearance (Melting Point ° C.) |
| 3-1 | $SO_2CH_3$ | $CF_3$ | $CH_3$ | $CH_3$ | H | H | H | H | H | |
| 3-2 | $SO_2CH_3$ | $CF_3$ | 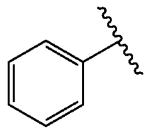 [SMILES: *c1ccccc1] | $CH_3$ | H | H | H | H | H | |
| 3-3 | $SO_2CH_3$ | $CF_3$ | $CH_3$ | 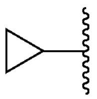 [SMILES: *C1CC1] | H | H | H | H | H | |
| 3-4 | $SO_2CH_3$ | $CF_3$ | $CH_3$ | $CH_3$ | Cl | H | Cl | H | H | |

TABLE 3-continued

Structures and Physical Properties of Part of Compounds of Formula I

| Compound | $X_1$ | $X_3$ | $Z_1$ | $Z_2$ | $R_1$ | $R_2$ | $R_3$ | $R_4$ | $R_5$ | Appearance (Melting Point ° C.) |
|---|---|---|---|---|---|---|---|---|---|---|
| 3-5 | $SO_2CH_3$ | $CF_3$ | 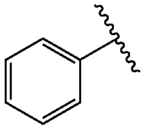 [SMILES: *c1ccccc1] | $CH_3$ | Cl | H | Cl | H | H | |
| 3-6 | $SO_2CH_3$ | $CF_3$ | $CH_3$ | 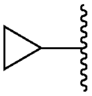 [SMILES: *C1CC1] | Cl | H | Cl | H | H | |
| 3-7 | $SO_2CH_3$ | $CF_3$ | $CH_3$ | $CH_3$ | H | H | $OCH_3$ | H | H | |
| 3-8 | $SO_2CH_3$ | $CF_3$ | 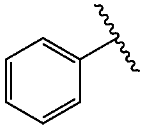 [SMILES: *c1ccccc1] | $CH_3$ | H | H | $OCH_3$ | H | H | |
| 3-9 | $SO_2CH_3$ | $CF_3$ | $CH_3$ | 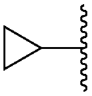 [SMILES: *C1CC1] | H | H | $OCH_3$ | H | H | |
| 3-10 | $SO_2CH_3$ | $CF_3$ | $CH_3$ | $CH_3$ | H | H | $NO_2$ | H | H | |
| 3-11 | $SO_2CH_3$ | $CF_3$ | 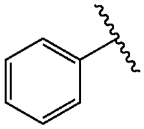 [SMILES: *c1ccccc1] | $CH_3$ | H | H | $NO_2$ | H | H | |
| 3-12 | $SO_2CH_3$ | $CF_3$ | $CH_3$ | 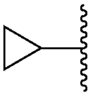 [SMILES: *C1CC1] | H | H | $NO_2$ | H | H | |
| 3-13 | $SO_2CH_3$ | $CF_3$ | $CH_3$ | $CH_3$ | H | H | $CF_3$ | H | H | |
| 3-14 | $SO_2CH_3$ | $CF_3$ | 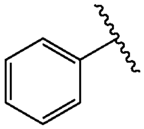 [SMILES: *c1ccccc1] | $CH_3$ | H | H | $CF_3$ | H | H | |
| 3-15 | $SO_2CH_3$ | $CF_3$ | $CH_3$ | 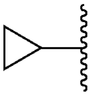 [SMILES: *C1CC1] | H | H | $CF_3$ | H | H | |
| 3-16 | $SO_2CH_3$ | $CF_3$ | $CH_3$ | $CH_3$ | H | $OCF_3$ | H | H | H | |
| 3-17 | $SO_2CH_3$ | $CF_3$ | 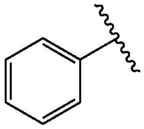 [SMILES: *c1ccccc1] | $CH_3$ | H | $OCF_3$ | H | H | H | |
| 3-18 | $SO_2CH_3$ | $CF_3$ | $CH_3$ | 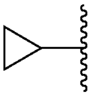 [SMILES: *C1CC1] | H | $OCF_3$ | H | H | H | |

TABLE 3-continued
Structures and Physical Properties of Part of Compounds of Formula I
| Compound | $X_1$ | $X_3$ | $Z_1$ | $Z_2$ | $R_1$ | $R_2$ | $R_3$ | $R_4$ | $R_5$ | Appearance (Melting Point ° C.) |
|---|---|---|---|---|---|---|---|---|---|---|
| 3-19 | $SO_2CH_3$ | $CF_3$ | $CH_3$ | $CH_3$ | H | H | 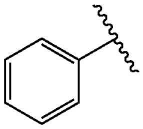 [SMILES: *c1ccccc1] | H | H | |
| 3-20 | $SO_2CH_3$ | $CF_3$ | 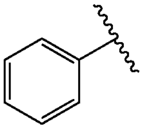 [SMILES: *c1ccccc1] | $CH_3$ | H | H | 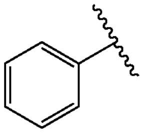 [SMILES: *c1ccccc1] | H | H | |
| 3-21 | $SO_2CH_3$ | $CF_3$ | $CH_3$ | 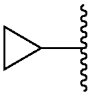 [SMILES: *C1CC1] | H | H | 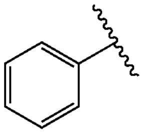 [SMILES: *c1ccccc1] | H | H | |
| 3-22 | $SO_2CH_3$ | $CF_3$ | $CH_3$ | $CH_3$ | H | | 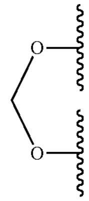 [SMILES: *OCO*] | H | H | |
| 3-23 | $SO_2CH_3$ | $CF_3$ | 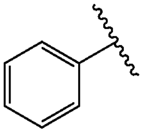 [SMILES: *c1ccccc1] | $CH_3$ | H | | 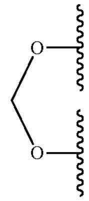 [SMILES: *OCO*] | H | H | |
| 3-24 | $SO_2CH_3$ | $CF_3$ | $CH_3$ | 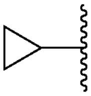 [SMILES: *C1CC1] | H | | 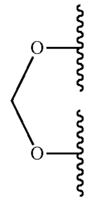 [SMILES: *OCO*] | H | H | |
| 3-25 | $SO_2CH_3$ | $CF_3$ | $CH_3$ | $CH_3$ | H | | 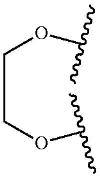 [SMILES: *OCCO*] | H | H | |
| 3-26 | $SO_2CH_3$ | $CF_3$ | 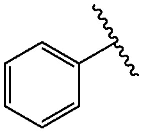 [SMILES: *c1ccccc1] | $CH_3$ | H | | 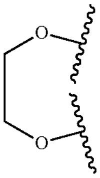 [SMILES: *OCCO*] | H | H | |

TABLE 3-continued
Structures and Physical Properties of Part of Compounds of Formula I
| Compound | $X_1$ | $X_3$ | $Z_1$ | $Z_2$ | $R_1$ | $R_2$ | $R_3$ | $R_4$ | $R_5$ | Appearance (Melting Point ° C.) |
|---|---|---|---|---|---|---|---|---|---|---|
| 3-27 | $SO_2CH_3$ | $CF_3$ | $CH_3$ | 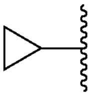 [SMILES: *C1CC1] | H | 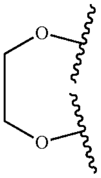 [SMILES: *OCCO*] | | H | H | |
| 3-28 | $SO_2CH_3$ | $CF_3$ | $CH_3$ | $CH_3$ | H | 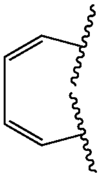 [SMILES: */C=C\C=C/*] | | H | H | |
| 3-29 | $SO_2CH_3$ | $CF_3$ | 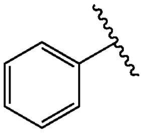 [SMILES: *c1ccccc1] | $CH_3$ | H | 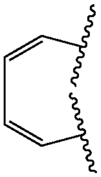 | | H | H | |
| 3-30 | $SO_2CH_3$ | $CF_3$ | $CH_3$ | 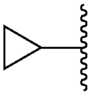 [SMILES: *C1CC1] | H | 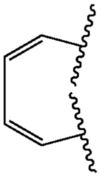 [SMILES: */C=C\C=C/*] | | H | H | |
| 3-31 | $SO_2CH_3$ | $CF_3$ | $CH_3$ | $CH_3$ | 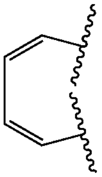 [SMILES: */C=C\C=C/*] | | H | H | H | |
| 3-32 | $SO_2CH_3$ | $CF_3$ | 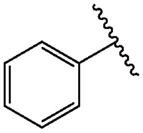 [SMILES: *c1ccccc1] | $CH_3$ | 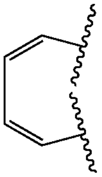 [SMILES: */C=C\C=C/*] | | H | H | H | |
| 3-33 | $SO_2CH_3$ | $CF_3$ | $CH_3$ | 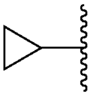 [SMILES: *C1CC1] | 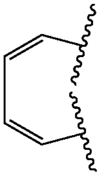 [SMILES: */C=C\C=C/*] | | H | H | H | |
| 3-34 | $NO_2$ | $SO_2CH_3$ | $CH_3$ | $CH_3$ | H | H | H | H | H | |

TABLE 3-continued

Structures and Physical Properties of Part of Compounds of Formula I

| Compound | $X_1$ | $X_3$ | $Z_1$ | $Z_2$ | $R_1$ | $R_2$ | $R_3$ | $R_4$ | $R_5$ | Appearance (Melting Point ° C.) |
|---|---|---|---|---|---|---|---|---|---|---|
| 3-35 | $NO_2$ | $SO_2CH_3$ | 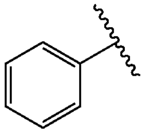 [SMILES: *c1ccccc1] | $CH_3$ | H | H | H | H | H | |
| 3-36 | $NO_2$ | $SO_2CH_3$ | $CH_3$ | 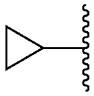 [SMILES: *C1CC1] | H | H | H | H | H | |
| 3-37 | $NO_2$ | $SO_2CH_3$ | $CH_3$ | $CH_3$ | H | | 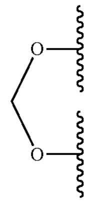 [SMILES: *OCO*] | H | H | |
| 3-38 | $NO_2$ | $SO_2CH_3$ | 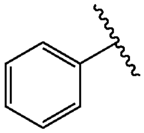 [SMILES: *c1ccccc1] | $CH_3$ | H | | 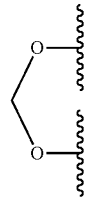 [SMILES: *OCO*] | H | H | |
| 3-39 | $NO_2$ | $SO_2CH_3$ | $CH_3$ | 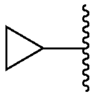 [SMILES: *C1CC1] | H | | 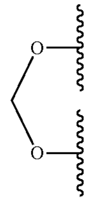 [SMILES: *OCO*] | H | H | |
| 3-40 | $NO_2$ | Cl | $CH_3$ | $CH_3$ | H | H | H | H | H | |
| 3-41 | $NO_2$ | Cl | 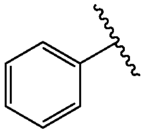 [SMILES: *c1ccccc1] | $CH_3$ | H | H | H | H | H | |
| 3-42 | $NO_2$ | Cl | $CH_3$ | 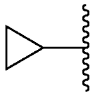 [SMILES: *C1CC1] | H | H | H | H | H | |
| 3-43 | Cl | Cl | $CH_3$ | $CH_3$ | H | H | H | H | H | |
| 3-44 | Cl | Cl | 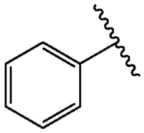 [SMILES: *c1ccccc1] | $CH_3$ | H | H | H | H | H | |
| 3-45 | Cl | Cl | $CH_3$ | 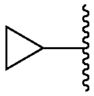 [SMILES: *C1CC1] | H | H | H | H | H | |

TABLE 3-continued
Structures and Physical Properties of Part of Compounds of Formula I
| Compound | $X_1$ | $X_3$ | $Z_1$ | $Z_2$ | $R_1$ | $R_2$ | $R_3$ | $R_4$ | $R_5$ | Appearance (Melting Point ° C.) |
|---|---|---|---|---|---|---|---|---|---|---|
| 3-46 | Cl | Cl | $CH_3$ | $CH_3$ | H | | 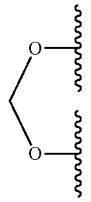 [SMILES: *OCO*] | H | H | |
| 3-47 | Cl | Cl | 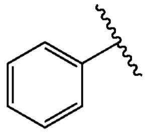 [SMILES: *c1ccccc1] | $CH_3$ | H | | 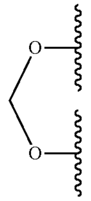 [SMILES: *OCO*] | H | H | |
| 3-48 | Cl | Cl | $CH_3$ | 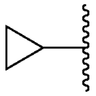 [SMILES: *C1CC1] | H | | 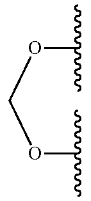 [SMILES: *OCO*] | H | H | |
| 3-49 | Cl | $SO_2CH_3$ | $CH_3$ | $CH_3$ | H | H | H | H | H | |
| 3-50 | Cl | $SO_2CH_3$ | 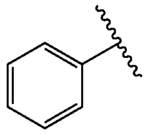 [SMILES: *c1ccccc1] | $CH_3$ | H | H | H | H | H | |
| 3-51 | Cl | $SO_2CH_3$ | $CH_3$ | 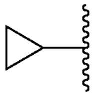 [SMILES: *C1CC1] | H | H | H | H | H | |
| 3-52 | Cl | $SO_2CH_3$ | $CH_3$ | $CH_3$ | H | | 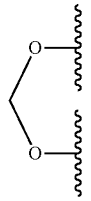 [SMILES: *OCO*] | H | H | |
| 3-53 | Cl | $SO_2CH_3$ | 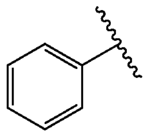 [SMILES: *c1ccccc1] | $CH_3$ | H | | 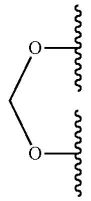 [SMILES: *OCO*] | H | H | |

TABLE 3-continued

Structures and Physical Properties of Part of Compounds of Formula I

| Compound | $X_1$ | $X_3$ | $Z_1$ | $Z_2$ | $R_1$ | $R_2$ | $R_3$ | $R_4$ | $R_5$ | Appearance (Melting Point ° C.) |
|---|---|---|---|---|---|---|---|---|---|---|
| 3-54 | Cl | $SO_2CH_3$ | $CH_3$ | 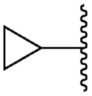 [SMILES: *C1CC1] | H | | 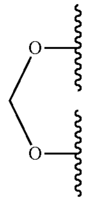 [SMILES: *OCO*] | H | H | |
| 3-55 | $CH_3$ | | $CH_3$ | $CH_3$ | H | H | H | H | H | |
| 3-56 | $CH_3$ | $SO_2CH_3$ | 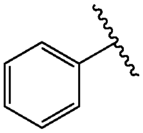 [SMILES: *c1ccccc1] | $CH_3$ | H | H | H | H | H | |
| 3-57 | $CH_3$ | $SO_2CH_3$ | $CH_3$ | 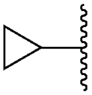 [SMILES: *C1CC1] | H | H | H | H | H | |
| 3-58 | CN | $SO_2CH_3$ | $CH_3$ | $CH_3$ | H | H | H | H | H | |
| 3-59 | CN | $SO_2CH_3$ | 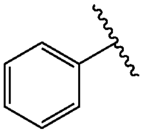 [SMILES: *c1ccccc1] | $CH_3$ | H | H | H | H | H | |
| 3-60 | CN | $SO_2CH_3$ | $CH_3$ | 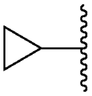 | H | H | H | H | H | |
| 3-61 | $CF_3$ | $SO_2CH_3$ | $CH_3$ | $CH_3$ | H | H | H | H | H | |
| 3-62 | $CF_3$ | $SO_2CH_3$ | 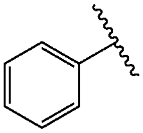 [SMILES: *c1ccccc1] | $CH_3$ | H | H | H | H | H | |
| 3-63 | $CF_3$ | $SO_2CH_3$ | $CH_3$ | 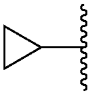 [SMILES: *C1CC1] | H | H | H | H | H | |
| 3-64 | 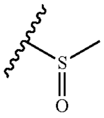 [SMILES: *S(C)=O] | $SO_2CH_3$ | $CH_3$ | $CH_3$ | H | H | H | H | H | |
| 3-65 | 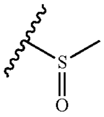 [SMILES: *S(C)=O] | $SO_2CH_3$ | 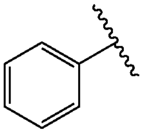 [SMILES: *c1ccccc1] | $CH_3$ | H | H | H | H | H | |

TABLE 3-continued

Structures and Physical Properties of Part of Compounds of Formula I

| Compound | $X_1$ | $X_3$ | $Z_1$ | $Z_2$ | $R_1$ | $R_2$ | $R_3$ | $R_4$ | $R_5$ | Appearance (Melting Point ° C.) |
|---|---|---|---|---|---|---|---|---|---|---|
| 3-66 | 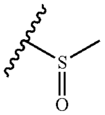 [SMILES: *S(C)=O] | $SO_2CH_3$ | $CH_3$ | 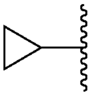 [SMILES: *C1CC1] | H | H | H | H | H | |
| 3-67 | 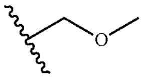 [SMILES: *COC] | $SO_2CH_3$ | $CH_3$ | $CH_3$ | H | H | H | H | H | |
| 3-68 | 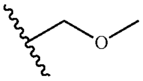 [SMILES: *COC] | $SO_2CH_3$ | 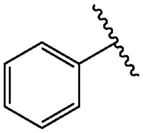 [SMILES: *c1ccccc1] | $CH_3$ | H | H | H | H | H | |
| 3-69 | 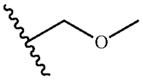 [SMILES: *COC] | $SO_2CH_3$ | $CH_3$ | 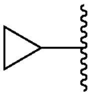 | H | H | H | H | H | |
| 3-70 | 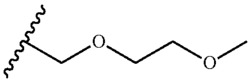 [SMILES: *COCCOC] | $SO_2CH_3$ | $CH_3$ | $CH_3$ | H | H | H | H | H | |
| 3-71 | 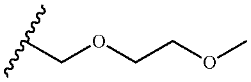 [SMILES: *COCCOC] | $SO_2CH_3$ | 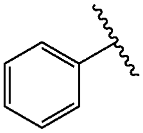 [SMILES: *c1ccccc1] | $CH_3$ | H | H | H | H | H | |
| 3-72 | 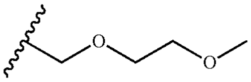 [SMILES: *COCCOC] | $SO_2CH_3$ | $CH_3$ | 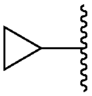 [SMILES: *C1CC1] | H | H | H | H | H | |
| 3-73 | 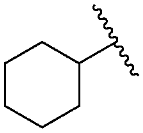 [SMILES: *C1CCCCC1] | $SO_2CH_3$ | $CH_3$ | $CH_3$ | H | H | H | H | H | |
| 3-74 | 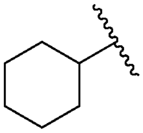 [SMILES: *C1CCCCC1] | $SO_2CH_3$ | 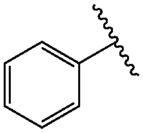 [SMILES: *c1ccccc1] | $CH_3$ | H | H | H | H | H | |
| 3-75 | 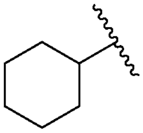 [SMILES: *C1CCCCC1] | $SO_2CH_3$ | $CH_3$ | 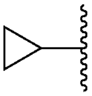 [SMILES: *C1CC1] | H | H | H | H | H | |
| 3-76 | 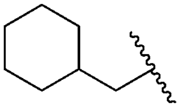 [SMILES: *CC1CCCCC1] | $SO_2CH_3$ | $CH_3$ | $CH_3$ | H | H | H | H | H | |

TABLE 3-continued

| Structures and Physical Properties of Part of Compounds of Formula I | | | | | | | | | | |
|---|---|---|---|---|---|---|---|---|---|---|
| Compound | $X_1$ | $X_3$ | $Z_1$ | $Z_2$ | $R_1$ | $R_2$ | $R_3$ | $R_4$ | $R_5$ | Appearance (Melting Point ° C.) |
| 3-77 | 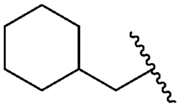 [SMILES: *CC1CCCCC1] | $SO_2CH_3$ | 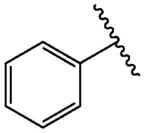 [SMILES: *c1ccccc1] | $CH_3$ | H | H | H | H | H | |
| 3-78 | 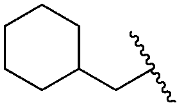 [SMILES: *CC1CCCCC1] | $SO_2CH_3$ | $CH_3$ | 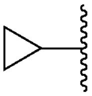 [SMILES: *C1CC1] | H | H | H | H | H | |
| 3-79 | 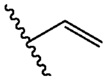 | $SO_2CH_3$ | $CH_3$ | $CH_3$ | H | H | H | H | H | |
| 3-80 | 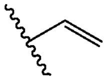 [SMILES: *C=C] | $SO_2CH_3$ | 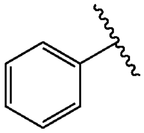 [SMILES: *c1ccccc1] | $CH_3$ | H | H | H | H | H | |
| 3-81 | 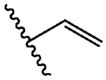 | $SO_2CH_3$ | $CH_3$ | 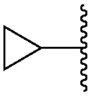 [SMILES: *C1CC1] | H | H | H | H | H | |
| 3-82 | 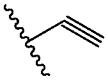 | $SO_2CH_3$ | $CH_3$ | $CH_3$ | H | H | H | H | H | |
| 3-83 | 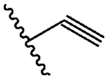 | $SO_2CH_3$ | 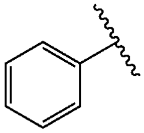 [SMILES: *c1ccccc1] | $CH_3$ | H | H | H | H | H | |
| 3-84 | 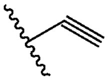 | $SO_2CH_3$ | $CH_3$ | 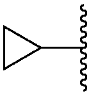 [SMILES: *C1CC1] | H | H | H | H | H | |
| 3-85 | $SO2CH{=}CH_2$ | $SO_2CH_3$ | $CH_3$ | $CH_3$ | H | H | H | H | H | |
| 3-86 | $SO2CH{=}CH_2$ | $SO_2CH_3$ | 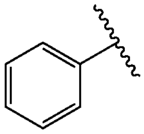 [SMILES: *c1ccccc1] | $CH_3$ | H | H | H | H | H | |
| 3-87 | $SO2CH{=}CH_2$ | $SO_2CH_3$ | $CH_3$ | 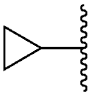 [SMILES: *C1CC1] | H | H | H | H | H | |
| 3-88 | 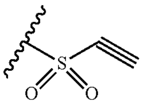 [SMILES: *S(=O)(=O)C#C] | $SO_2CH_3$ | $CH_3$ | $CH_3$ | H | H | H | H | H | |

TABLE 3-continued
Structures and Physical Properties of Part of Compounds of Formula I
| Compound | $X_1$ | $X_3$ | $Z_1$ | $Z_2$ | $R_1$ | $R_2$ | $R_3$ | $R_4$ | $R_5$ | Appearance (Melting Point ° C.) |
|---|---|---|---|---|---|---|---|---|---|---|
| 3-89 | 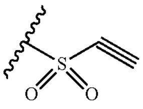 [SMILES: *S(=O)(=O)C#C] | $SO_2CH_3$ | 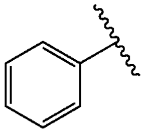 [SMILES: *c1ccccc1] | $CH_3$ | H | H | H | H | H | |
| 3-90 | 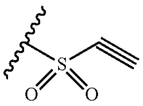 [SMILES: *S(=O)(=O)C#C] | $SO_2CH$ | $CH_3$ | 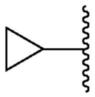 [SMILES: *C1CC1] | H | H | H | H | H | |
| 3-91 | 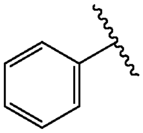 [SMILES: *c1ccccc1] | $SO_2CH_3$ | $CH_3$ | $CH_3$ | H | H | H | H | H | |
| 3-92 | 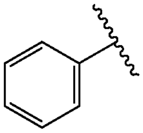 [SMILES: *c1ccccc1] | $SO_2CH_3$ | 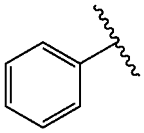 [SMILES: *c1ccccc1] | $CH_3$ | H | H | H | H | H | |
| 3-93 | 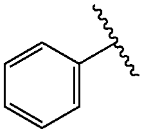 [SMILES: *c1ccccc1] | $SO_2CH_3$ | $CH_3$ | 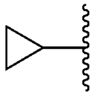 [SMILES: *C1CC1] | H | H | H | H | H | |
| 3-94 | 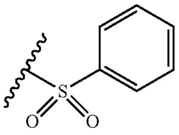 | $SO_2CH_3$ | $CH_3$ | $CH_3$ | H | H | H | H | H | |
| 3-95 | 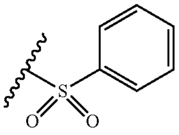 [SMILES: *S(=O)(=O)c1ccccc1] | $SO_2CH_3$ | 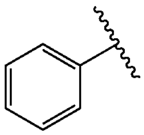 [SMILES: *c1ccccc1] | $CH_3$ | H | H | H | H | H | |
| 3-96 | 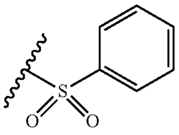 [SMILES: *S(=O)(=O)c1ccccc1] | $SO_2CH$ | $CH_3$ | 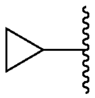 [SMILES: *C1CC1] | H | H | H | H | H | |
| 3-97 | 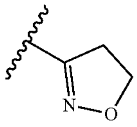 [SMILES: *C1=NOCC1] | $SO_2CH_3$ | $CH_3$ | $CH_3$ | H | H | H | H | H | |
| 3-98 | 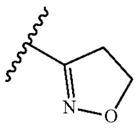 [SMILES: *C1=NOCC1] | $SO_2CH_3$ | 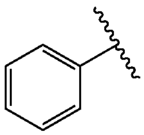 [SMILES: *c1ccccc1] | $CH_3$ | H | H | H | H | H | |

TABLE 3-continued
Structures and Physical Properties of Part of Compounds of Formula I
| Compound | $X_1$ | $X_3$ | $Z_1$ | $Z_2$ | $R_1$ | $R_2$ | $R_3$ | $R_4$ | $R_5$ | Appearance (Melting Point ° C.) |
|---|---|---|---|---|---|---|---|---|---|---|
| 3-99 | 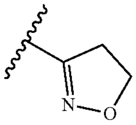 [SMILES: *C1=NOCC1] | $SO_2CH_3$ | $CH_3$ | 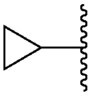 [SMILES: *C1CC1] | H | H | H | H | H | |
| 3-100 | 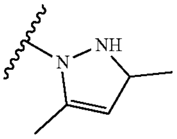 [SMILES: *N1NC(C)C=C1C] | $SO_2CH_3$ | $CH_3$ | $CH_3$ | H | H | H | H | H | |
| 3-101 | 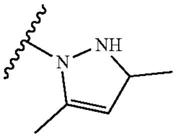 [SMILES: *N1NC(C)C=C1C] | $SO_2CH_3$ | 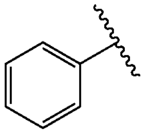 [SMILES: *c1ccccc1] | $CH_3$ | H | H | H | H | H | |
| 3-102 | 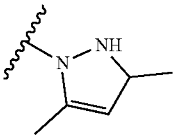 [SMILES: *N1NC(C)C=C1C] | $SO_2CH_3$ | $CH_3$ | 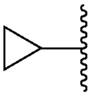 [SMILES: *C1CC1] | H | H | H | H | H | |
| 3-103 | 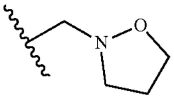 [SMILES: *CN1CCCO1] | $SO_2CH_3$ | $CH_3$ | $CH_3$ | H | H | H | H | H | |
| 3-104 | 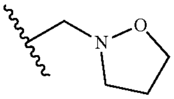 [SMILES: *CN1CCCO1] | $SO_2CH_3$ | 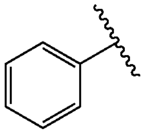 [SMILES: *c1ccccc1] | $CH_3$ | H | H | H | H | H | |
| 3-105 | 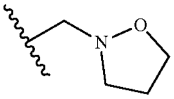 [SMILES: *CN1CCCO1] | $SO_2CH_3$ | $CH_3$ | 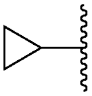 [SMILES: *C1CC1] | H | H | H | H | H | |
| 3-106 | 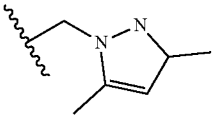 | $SO_2CH_3$ | $CH_3$ | $CH_3$ | H | H | H | H | H | |
| 3-107 | 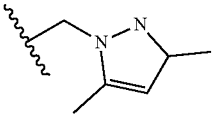 [SMILES: *CN1NC(C)C=C1C] | $SO_2CH_3$ | 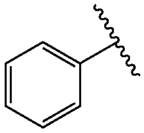 [SMILES: *c1ccccc1] | $CH_3$ | H | H | H | H | H | |
| 3-108 | 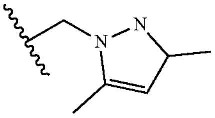 [SMILES: *CN1NC(C)C=C1C] | $SO_2CH_3$ | $CH_3$ | 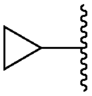 [SMILES: *C1CC1] | H | H | H | H | H | |

TABLE 3-continued

| Structures and Physical Properties of Part of Compounds of Formula I | | | | | | | | | | |
|---|---|---|---|---|---|---|---|---|---|---|
| Compound | $X_1$ | $X_3$ | $Z_1$ | $Z_2$ | $R_1$ | $R_2$ | $R_3$ | $R_4$ | $R_5$ | Appearance (Melting Point ° C.) |
| 3-109 | H | Cl | $CH_3$ | $CH_3$ | H | H | H | H | H | white solid (115-120) |

In the compound of the formula I, W is N.

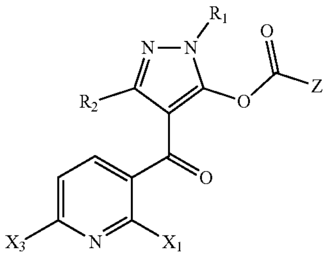

TABLE 4

| Structures and Physical Properties of Part of Compounds of Formula I | | | | | | |
|---|---|---|---|---|---|---|
| Compound | $X_1$ | $X_3$ | $R_1$ | $R_2$ | Z | Appearance (Melting Point ° C.) |
| 4-1 | $SO_2CH_3$ | $CF_3$ | $CH_3$ | $CH_3$ | 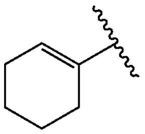 [SMILES: *C1=CCCCC1] | |
| 4-2 | $SO_2CH_3$ | $CF_3$ | 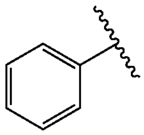 [SMILES: *c1ccccc1] | $CH_3$ | 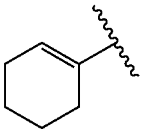 [SMILES: *C1=CCCCC1] | |
| 4-3 | $SO_2CH_3$ | $CF_3$ | $CH_3$ | 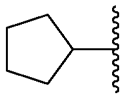 [SMILES: *C1CCCC1] | 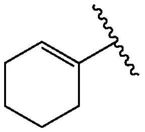 [SMILES: *C1=CCCCC1] | |
| 4-4 | $SO_2CH_3$ | $CF_3$ | $CH_3$ | $CH_3$ | 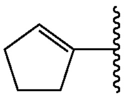 [SMILES: *C1=CCCC1] | |
| 4-5 | $SO_2CH_3$ | $CF_3$ | 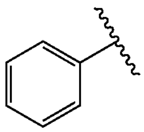 [SMILES: *c1ccccc1] | $CH_3$ | 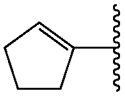 [SMILES: *C1=CCCC1] | |

TABLE 4-continued
Structures and Physical Properties of Part of Compounds of Formula I
| Compound | $X_1$ | $X_3$ | $R_1$ | $R_2$ | Z | Appearance (Melting Point ° C.) |
|---|---|---|---|---|---|---|
| 4-6 | $SO_2CH_3$ | $CF_3$ | $CH_3$ | 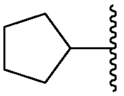 [SMILES: *C1CCCC1] | 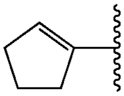 | |
| 4-7 | $SO_2CH_3$ | $CF_3$ | $CH_3$ | $CH_3$ | 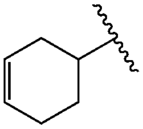 | |
| 4-8 | $SO_2CH_3$ | $CF_3$ | 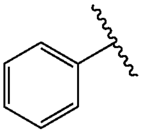 [SMILES: *c1ccccc1] | $CH_3$ | 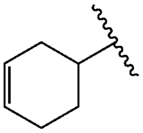 [SMILES: *C1CC=CCC1] | |
| 4-9 | $SO_2CH_3$ | $CF_3$ | $CH_3$ | 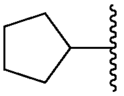 [SMILES: *C1CCCC1] | 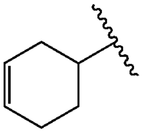 [SMILES: *C1CC=CCC1] | |
| 4-10 | $SO_2CH_3$ | $CF_3$ | $CH_3$ | $CH_3$ | 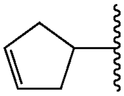 [SMILES: *C1CC=CC1] | |
| 4-11 | $SO_2CH_3$ | $CF_3$ | 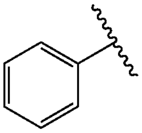 [SMILES: *c1ccccc1] | $CH_3$ | 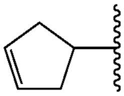 [SMILES: *C1CC=CC1] | |
| 4-12 | $SO_2CH_3$ | $CF_3$ | $CH_3$ | 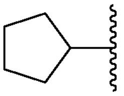 [SMILES: *C1CCCC1] | 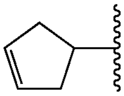 [SMILES: *C1CC=CC1] | |
| 4-13 | $SO_2CH_3$ | $CF_3$ | $CH_3$ | $CH_3$ | 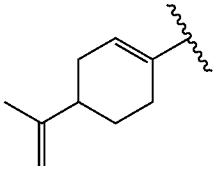 [SMILES: *C1=CCC(C(=C)C)CC1] | |
| 4-14 | $SO_2CH_3$ | $CF_3$ | 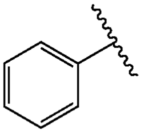 [SMILES: *c1ccccc1] | $CH_3$ | 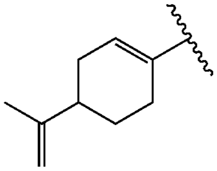 [SMILES: *C1=CCC(C(=C)C)CC1] | |
| 4-15 | $SO_2CH_3$ | $CF_3$ | $CH_3$ | 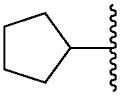 [SMILES: *C1CCCC1] | 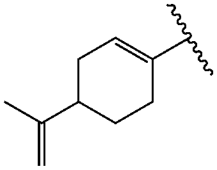 [SMILES: *C1=CCC(C(=C)C)CC1] | |

TABLE 4-continued
Structures and Physical Properties of Part of Compounds of Formula I
| Compound | $X_1$ | $X_3$ | $R_1$ | $R_2$ | Z | Appearance (Melting Point ° C.) |
|---|---|---|---|---|---|---|
| 4-16 | $SO_2CH_3$ | $CF_3$ | $CH_3$ | $CH_3$ | 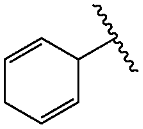 [SMILES: *C1C=CCC=C1] | |
| 4-17 | $SO_2CH_3$ | $CF_3$ | 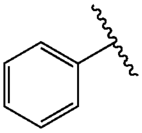 [SMILES: *c1ccccc1] | $CH_3$ | 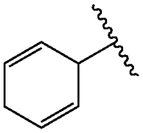 [SMILES: *C1C=CCC=C1] | |
| 4-18 | $SO_2CH_3$ | $CF_3$ | $CH_3$ | 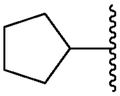 [SMILES: *C1CCCC1] | 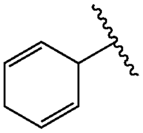 [SMILES: *C1C=CCC=C1] | |
| 4-19 | $SO_2CH_3$ | $CF_3$ | $CH_3$ | $CH_3$ | 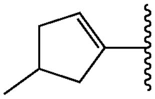 [SMILES: *C1=CCC(C)C1] | |
| 4-20 | $SO_2CH_3$ | $CF_3$ | 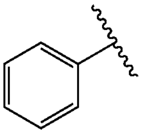 [SMILES: *c1ccccc1] | $CH_3$ | 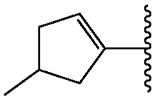 [SMILES: *C1=CCC(C)C1] | |
| 4-21 | $SO_2CH_3$ | $CF_3$ | $CH_3$ | 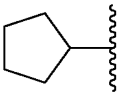 [SMILES: *C1CCCC1] | 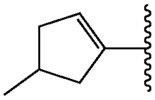 [SMILES: *C1=CCC(C)C1] | |
| 4-22 | $SO_2CH_3$ | $CF_3$ | $CH_3$ | $CH_3$ | 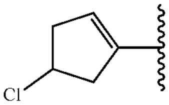 [SMILES: *C1=CCC(Cl)C1] | |
| 4-23 | $SO_2CH_3$ | $CF_3$ | 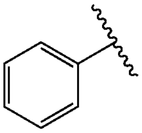 [SMILES: *c1ccccc1] | $CH_3$ | 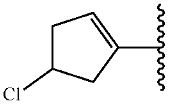 [SMILES: *C1=CCC(Cl)C1] | |
| 4-24 | $SO_2CH_3$ | $CF_3$ | $CH_3$ | 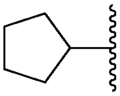 [SMILES: *C1CCCC1] | 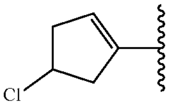 [SMILES: *C1=CCC(Cl)C1] | |
| 4-25 | $SO_2CH_3$ | $CF_3$ | $CH_3$ | $CH_3$ | 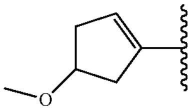 [SMILES: *C1=CCC(OC)C1] | |
| 4-26 | $SO_2CH_3$ | $CF_3$ | 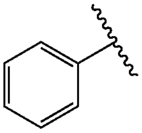 [SMILES: *c1ccccc1] | $CH_3$ | 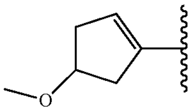 [SMILES: *C1=CCC(OC)C1] | |

TABLE 4-continued
Structures and Physical Properties of Part of Compounds of Formula I
| Compound | $X_1$ | $X_3$ | $R_1$ | $R_2$ | Z | Appearance (Melting Point ° C.) |
|---|---|---|---|---|---|---|
| 4-27 | $SO_2CH_3$ | $CF_3$ | $CH_3$ | 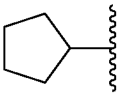 [SMILES: *C1CCCC1] | 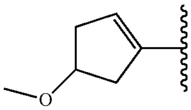 [SMILES: *C1=CCC(OC)C1] | |
| 4-28 | $SO_2CH_3$ | $CF_3$ | $CH_3$ | $CH_3$ | 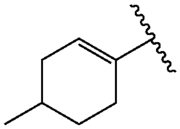 [SMILES: *C1=CCC(C)CC1] | |
| 4-29 | $SO_2CH_3$ | $CF_3$ | 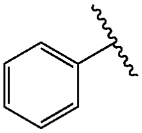 [SMILES: *c1ccccc1] | $CH_3$ | 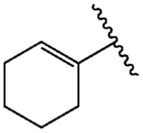 [SMILES: *C1=CCCCC1] | |
| 4-30 | $SO_2CH_3$ | $CF_3$ | $CH_3$ | 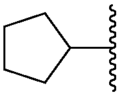 [SMILES: *C1CCCC1] | 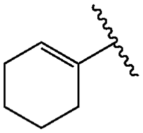 [SMILES: *C1=CCCCC1] | |
| 4-31 | $SO_2CH_3$ | $CF_3$ | $CH_3$ | $CH_3$ | 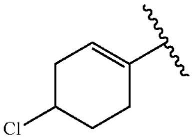 [SMILES: *C1=CCC(Cl)CC1] | |
| 4-32 | $SO_2CH_3$ | $CF_3$ | 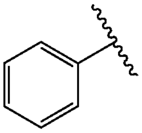 [SMILES: *c1ccccc1] | $CH_3$ | 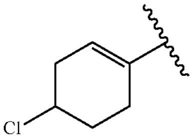 [SMILES: *C1=CCC(Cl)CC1] | |
| 4-33 | $SO_2CH_3$ | $CF_3$ | $CH_3$ | 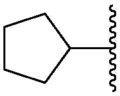 [SMILES: *C1CCCC1] | 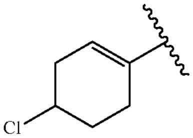 [SMILES: *C1=CCC(Cl)CC1] | |
| 4-34 | $NO_2$ | $SO_2CH_3$ | $CH_3$ | $CH_3$ | 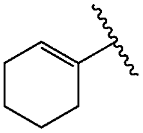 [SMILES: *C1=CCCCC1] | |
| 4-35 | $NO_2$ | $SO_2CH_3$ | 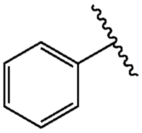 [SMILES: *c1ccccc1] | $CH_3$ | 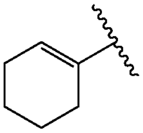 [SMILES: *C1=CCCCC1] | |
| 4-36 | $NO_2$ | $SO_2CH_3$ | $CH_3$ | 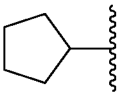 [SMILES: *C1CCCC1] | 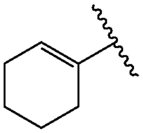 [SMILES: *C1=CCCCC1] | |

TABLE 4-continued
Structures and Physical Properties of Part of Compounds of Formula I
| Compound | $X_1$ | $X_3$ | $R_1$ | $R_2$ | Z | Appearance (Melting Point ° C.) |
|---|---|---|---|---|---|---|
| 4-37 | $NO_2$ | $SO_2CH_3$ | $CH_3$ | $CH_3$ | 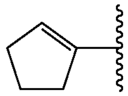 [SMILES: *C1=CCCC1] | |
| 4-38 | $NO_2$ | $SO_2CH_3$ | 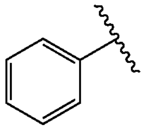 [SMILES: *c1ccccc1] | $CH_3$ | 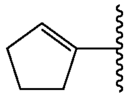 | |
| 4-39 | $NO_2$ | $SO_2CH_3$ | $CH_3$ | 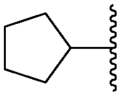 [SMILES: *C1CCCC1] | 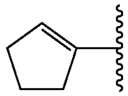 [SMILES: *C1=CCCC1] | |
| 4-40 | $NO_2$ | Cl | $CH_3$ | $CH_3$ | 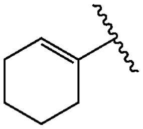 [SMILES: *C1=CCCCC1] | |
| 4-41 | $NO_2$ | Cl | 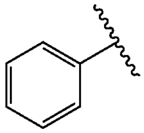 [SMILES: *c1ccccc1] | $CH_3$ | 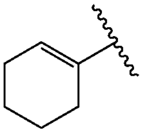 [SMILES: *C1=CCCCC1] | |
| 4-42 | $NO_2$ | Cl | $CH_3$ | 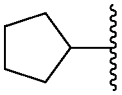 [SMILES: *C1CCCC1] | 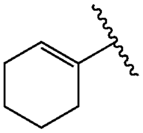 [SMILES: *C1=CCCCC1] | |
| 4-43 | Cl | Cl | $CH_3$ | $CH_3$ | 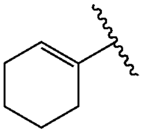 [SMILES: *C1=CCCCC1] | |
| 4-44 | Cl | Cl | 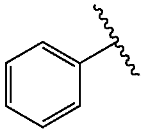 | $CH_3$ | 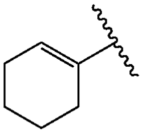 [SMILES: *C1=CCCCC1] | |
| 4-45 | Cl | Cl | $CH_3$ | 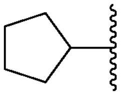 [SMILES: *C1CCCC1] | 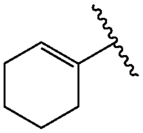 [SMILES: *C1=CCCCC1] | |
| 4-46 | Cl | Cl | $CH_3$ | $CH_3$ | 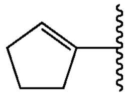 | |
| 4-47 | Cl | Cl | 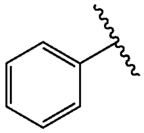 [SMILES: *c1ccccc1] | $CH_3$ | 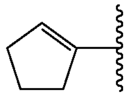 [SMILES: *C1=CCCC1] | |

TABLE 4-continued
Structures and Physical Properties of Part of Compounds of Formula I
| Compound | $X_1$ | $X_3$ | $R_1$ | $R_2$ | Z | Appearance (Melting Point ° C.) |
| --- | --- | --- | --- | --- | --- | --- |
| 4-48 | Cl | Cl | $CH_3$ | 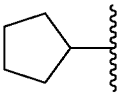 [SMILES: *C1CCCC1] | 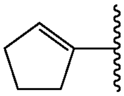 [SMILES: *C1=CCCC1] | |
| 4-49 | Cl | $SO_2CH_3$ | $CH_3$ | $CH_3$ | 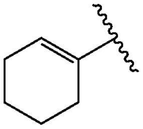 [SMILES: *C1=CCCCC1] | |
| 4-50 | Cl | $SO_2CH_3$ | 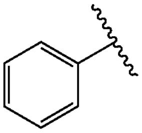 [SMILES: *c1ccccc1] | $CH_3$ | 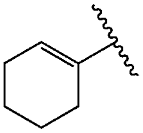 [SMILES: *C1=CCCCC1] | |
| 4-51 | Cl | $SO_2CH_3$ | $CH_3$ | 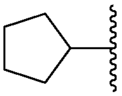 [SMILES: *C1CCCC1] | 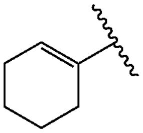 [SMILES: *C1=CCCCC1] | |
| 4-52 | Cl | $SO_2CH_3$ | $CH_3$ | $CH_3$ | 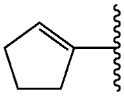 [SMILES: *C1=CCCC1] | |
| 4-53 | Cl | $SO_2CH_3$ | 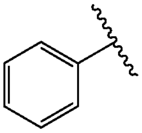 [SMILES: *c1ccccc1] | $CH_3$ | 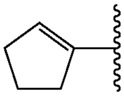 [SMILES: *C1=CCCC1] | |
| 4-54 | Cl | $SO_2CH_3$ | $CH_3$ | 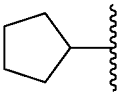 [SMILES: *C1CCCC1] | 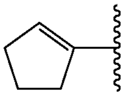 [SMILES: *C1=CCCC1] | |
| 4-55 | $CH_3$ | $SO_2CH_3$ | $CH_3$ | $CH_3$ | 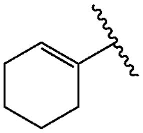 [SMILES: *C1=CCCCC1] | |
| 4-56 | $CH_3$ | $SO_2CH_3$ | 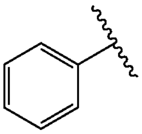 [SMILES: *c1ccccc1] | $CH_3$ | 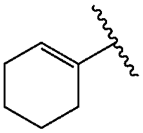 [SMILES: *C1=CCCCC1] | |
| 4-57 | $CH_3$ | $SO_2CH_3$ | $CH_3$ | 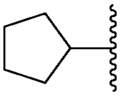 [SMILES: *C1CCCC1] | 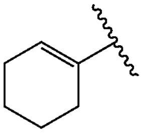 [SMILES: *C1=CCCCC1] | |
| 4-58 | CN | $SO_2CH_3$ | $CH_3$ | $CH_3$ | 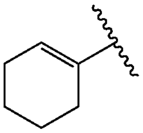 [SMILES: *C1=CCCCC1] | |

TABLE 4-continued
Structures and Physical Properties of Part of Compounds of Formula I
| Compound | $X_1$ | $X_3$ | $R_1$ | $R_2$ | Z | Appearance (Melting Point ° C.) |
|---|---|---|---|---|---|---|
| 4-59 | CN | $SO_2CH_3$ | 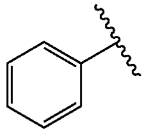 [SMILES: *c1ccccc1] | $CH_3$ | 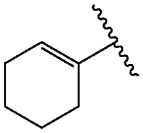 [SMILES: *C1=CCCCC1] | |
| 4-60 | CN | $SO_2CH_3$ | $CH_3$ | 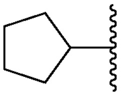 [SMILES: *C1CCCC1] | 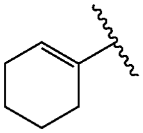 [SMILES: *C1=CCCCC1] | |
| 4-61 | $CF_3$ | $SO_2CH_3$ | $CH_3$ | $CH_3$ | 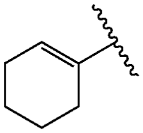 [SMILES: *C1=CCCCC1] | |
| 4-62 | $CF_3$ | $SO_2CH_3$ | 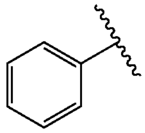 [SMILES: *c1ccccc1] | $CH_3$ | 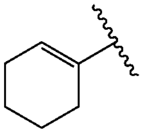 [SMILES: *C1=CCCCC1] | |
| 4-63 | $CF_3$ | $SO_2CH_3$ | $CH_3$ | 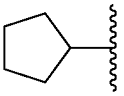 [SMILES: *C1CCCC1] | 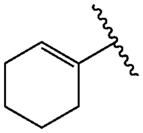 [SMILES: *C1=CCCCC1] | |
| 4-64 | 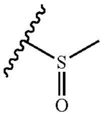 [SMILES: *S(C)=O] | $SO_2CH_3$ | $CH_3$ | $CH_3$ | 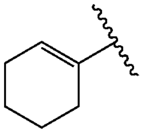 [SMILES: *C1=CCCCC1] | |
| 4-65 | 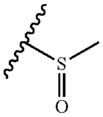 | $SO_2CH_3$ | 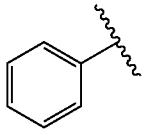 [SMILES: *c1ccccc1] | $CH_3$ | 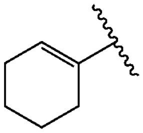 [SMILES: *C1=CCCCC1] | |
| 4-66 | 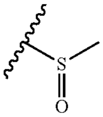 [SMILES: *S(C)=O] | $SO_2CH_3$ | $CH_3$ | 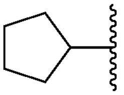 [SMILES: *C1CCCC1] | 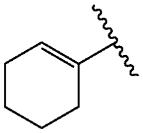 [SMILES: *C1=CCCCC1] | |
| 4-67 | 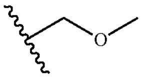 [SMILES: *COC] | $SO_2CH_3$ | $CH_3$ | $CH_3$ | 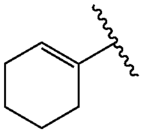 [SMILES: *C1=CCCCC1] | |
| 4-68 | 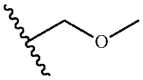 [SMILES: *COC] | $SO_2CH_3$ | 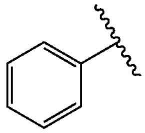 [SMILES: *c1ccccc1] | $CH_3$ | 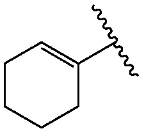 [SMILES: *C1=CCCCC1] | |

TABLE 4-continued
Structures and Physical Properties of Part of Compounds of Formula I
| Compound | $X_1$ | $X_3$ | $R_1$ | $R_2$ | Z | Appearance (Melting Point ° C.) |
|---|---|---|---|---|---|---|
| 4-69 | 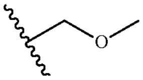 | $SO_2CH_3$ | $CH_3$ | 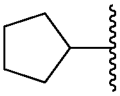 [SMILES: *C1CCCC1] | 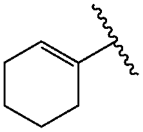 [SMILES: *C1=CCCCC1] | |
| 4-70 | 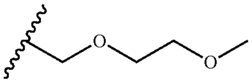 [SMILES: *COCCOC] | $SO_2CH_3$ | $CH_3$ | $CH_3$ | 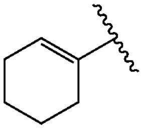 [SMILES: *C1=CCCCC1] | |
| 4-71 | 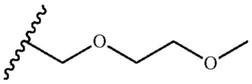 [SMILES: *COCCOC] | $SO_2CH_3$ | 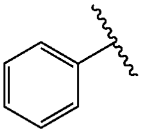 [SMILES: *c1ccccc1] | $CH_3$ | 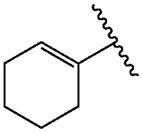 [SMILES: *C1=CCCCC1] | |
| 4-72 | 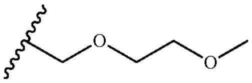 [SMILES: *COCCOC] | $SO_2CH_3$ | $CH_3$ | 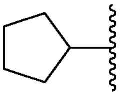 [SMILES: *C1CCCC1] | 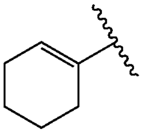 [SMILES: *C1=CCCCC1] | |
| 4-73 | 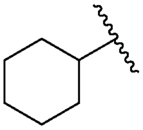 [SMILES: *C1CCCCC1] | $SO_2CH_3$ | $CH_3$ | $CH_3$ | 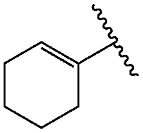 [SMILES: *C1=CCCCC1] | |
| 4-74 | 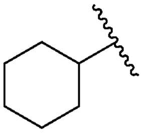 [SMILES: *C1CCCCC1] | $SO_2CH_3$ | 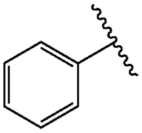 [SMILES: *c1ccccc1] | $CH_3$ | 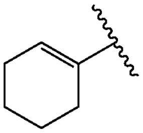 [SMILES: *C1=CCCCC1] | |
| 4-75 | 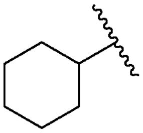 [SMILES: *C1CCCCC1] | $SO_2CH_3$ | $CH_3$ | 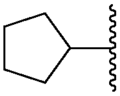 [SMILES: *C1CCCC1] | 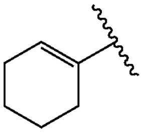 [SMILES: *C1=CCCCC1] | |
| 4-76 | 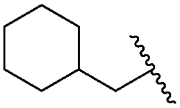 [SMILES: *CC1CCCCC1] | $SO_2CH_3$ | $CH_3$ | $CH_3$ | 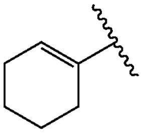 [SMILES: *C1=CCCCC1] | |
| 4-77 | 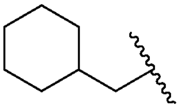 [SMILES: *CC1CCCCC1] | $SO_2CH_3$ | 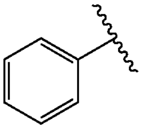 [SMILES: *c1ccccc1] | $CH_3$ | 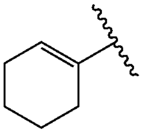 [SMILES: *C1=CCCCC1] | |
| 4-78 | 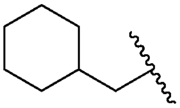 [SMILES: *CC1CCCCC1] | $SO_2CH_3$ | $CH_3$ | 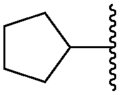 [SMILES: *C1CCCC1] | 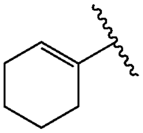 [SMILES: *C1=CCCCC1] | |

TABLE 4-continued
Structures and Physical Properties of Part of Compounds of Formula I
| Compound | $X_1$ | $X_3$ | $R_1$ | $R_2$ | Z | Appearance (Melting Point ° C.) |
|---|---|---|---|---|---|---|
| 4-79 | 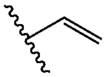 [SMILES: *C=C] | $SO_2CH_3$ | $CH_3$ | $CH_3$ | 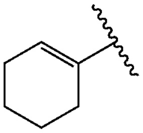 [SMILES: *C1=CCCCC1] | |
| 4-80 | 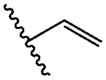 [SMILES: *C=C] | $SO_2CH_3$ | 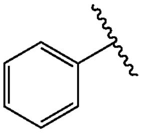 [SMILES: *c1ccccc1] | $CH_3$ | 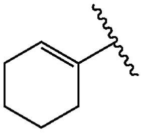 [SMILES: *C1=CCCCC1] | |
| 4-81 | 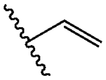 [SMILES: *C=C] | $SO_2CH_3$ | $CH_3$ | 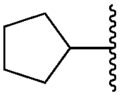 [SMILES: *C1CCCC1] | 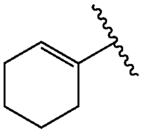 [SMILES: *C1=CCCCC1] | |
| 4-82 | 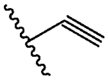 [SMILES: *C#C] | $SO_2CH_3$ | $CH_3$ | $CH_3$ | 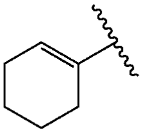 [SMILES: *C1=CCCCC1] | |
| 4-83 | 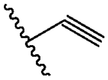 [SMILES: *C#C] | $SO_2CH_3$ | 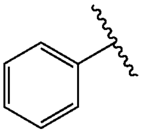 [SMILES: *c1ccccc1] | $CH_3$ | 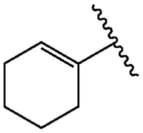 [SMILES: *C1=CCCCC1] | |
| 4-84 | 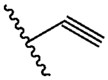 | $SO_2CH_3$ | $CH_3$ | 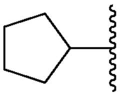 [SMILES: *C1CCCC1] | 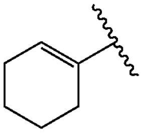 [SMILES: *C1=CCCCC1] | |
| 4-85 | $SO_2CH{=}CH_2$ | $SO_2CH_3$ | $CH_3$ | $CH_3$ | 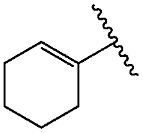 [SMILES: *C1=CCCCC1] | |
| 4-86 | $SO_2CH{=}CH_2$ | $SO_2CH_3$ | 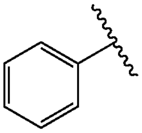 [SMILES: *c1ccccc1] | $CH_3$ | 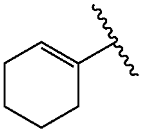 [SMILES: *C1=CCCCC1] | |
| 4-87 | $SO_2CH{=}CH_2$ | $SO_2CH_3$ | $CH_3$ | 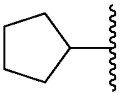 [SMILES: *C1CCCC1] | 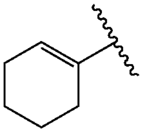 [SMILES: *C1=CCCCC1] | |
| 4-88 | 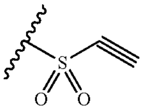 [SMILES: *S(=O)(=O)C#C] | $SO_2CH_3$ | $CH_3$ | $CH_3$ | 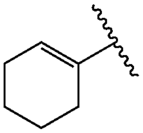 [SMILES: *C1=CCCCC1] | |

TABLE 4-continued
Structures and Physical Properties of Part of Compounds of Formula I
| Compound | $X_1$ | $X_3$ | $R_1$ | $R_2$ | Z | Appearance (Melting Point ° C.) |
|---|---|---|---|---|---|---|
| 4-89 | 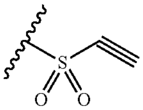 [SMILES: *S(=O)(=O)C#C] | $SO_2CH_3$ | 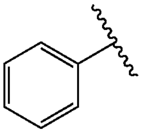 [SMILES: *c1ccccc1] | $CH_3$ | 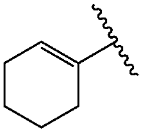 [SMILES: *C1=CCCCC1] | |
| 4-90 | 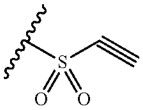 [SMILES: *S(=O)(=O)C#C] | $SO_2CH_3$ | $CH_3$ | 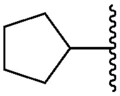 [SMILES: *C1CCCC1] | 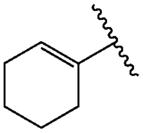 [SMILES: *C1=CCCCC1] | |
| 4-91 | 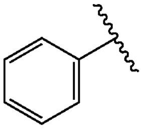 [SMILES: *c1ccccc1] | $SO_2CH_3$ | $CH_3$ | $CH_3$ | 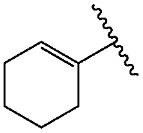 [SMILES: *C1=CCCCC1] | |
| 4-92 | 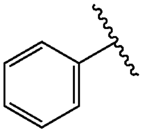 [SMILES: *c1ccccc1] | $SO_2CH_3$ | 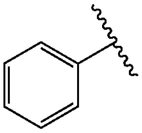 [SMILES: *c1ccccc1] | $CH_3$ | 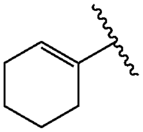 [SMILES: *C1=CCCCC1] | |
| 4-93 | 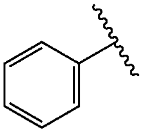 [SMILES: *c1ccccc1] | $SO_2CH_3$ | $CH_3$ | 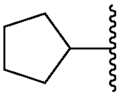 [SMILES: *C1CCCC1] | 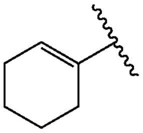 [SMILES: *C1=CCCCC1] | |
| 4-94 | 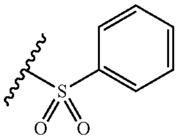 [SMILES: *S(=O)(=O)c1ccccc1] | $SO_2CH_3$ | $CH_3$ | $CH_3$ | 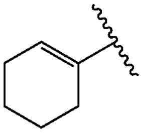 [SMILES: *C1=CCCCC1] | |
| 4-95 | 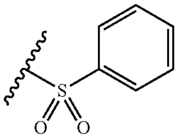 [SMILES: *S(=O)(=O)c1ccccc1] | $SO_2CH_3$ | 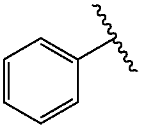 [SMILES: *c1ccccc1] | $CH_3$ | 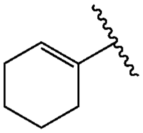 [SMILES: *C1=CCCCC1] | |
| 4-96 | 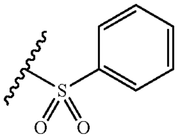 [SMILES: *S(=O)(=O)c1ccccc1] | $SO_2CH_3$ | $CH_3$ | 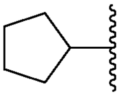 [SMILES: *C1CCCC1] | 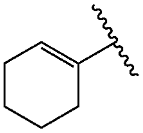 [SMILES: *C1=CCCCC1] | |
| 4-97 | 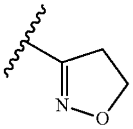 [SMILES: *C1=NOCC1] | $SO_2CH_3$ | $CH_3$ | $CH_3$ | 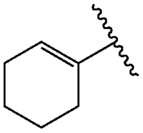 [SMILES: *C1=CCCCC1] | |
| 4-98 | 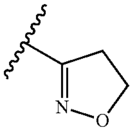 [SMILES: *C1=NOCC1] | $SO_2CH_3$ | 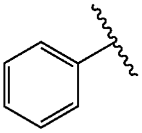 [SMILES: *c1ccccc1] | $CH_3$ | 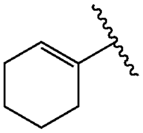 [SMILES: *C1=CCCCC1] | |

TABLE 4-continued
Structures and Physical Properties of Part of Compounds of Formula I
| Compound | $X_1$ | $X_3$ | $R_1$ | $R_2$ | Z | Appearance (Melting Point ° C.) |
|---|---|---|---|---|---|---|
| 4-99 | 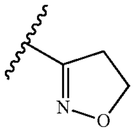 [SMILES: *C1=NOCC1] | $SO_2CH_3$ | $CH_3$ | 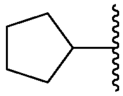 [SMILES: *C1CCCC1] | 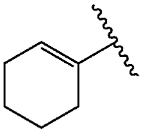 [SMILES: *C1=CCCCC1] | |
| 4-100 | 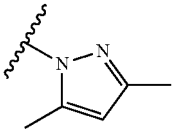 [SMILES: *n1nc(C)cc1C] | $SO_2CH_3$ | $CH_3$ | $CH_3$ | 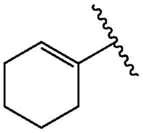 [SMILES: *C1=CCCCC1] | |
| 4-101 | 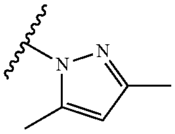 [SMILES: *n1nc(C)cc1C] | $SO_2CH_3$ | 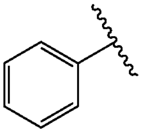 [SMILES: *c1ccccc1] | $CH_3$ | 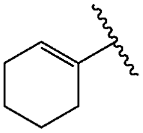 [SMILES: *C1=CCCCC1] | |
| 4-102 | 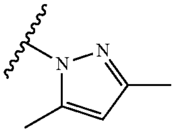 [SMILES: *n1nc(C)cc1C] | $SO_2CH_3$ | $CH_3$ | 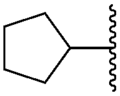 [SMILES: *C1CCCC1] | 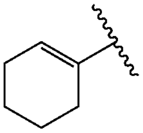 [SMILES: *C1=CCCCC1] | |
| 4-103 | 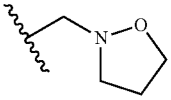 [SMILES: *CN1CCCO1] | $SO_2CH_3$ | $CH_3$ | $CH_3$ | 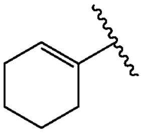 [SMILES: *C1=CCCCC1] | |
| 4-104 | 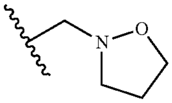 [SMILES: *CN1CCCO1] | $SO_2CH_3$ | 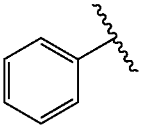 [SMILES: *c1ccccc1] | $CH_3$ | 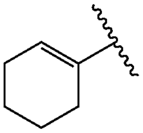 [SMILES: *C1=CCCCC1] | |
| 4-105 | 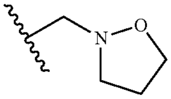 [SMILES: *CN1CCCO1] | $SO_2CH_3$ | $CH_3$ | 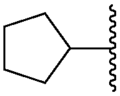 [SMILES: *C1CCCC1] | 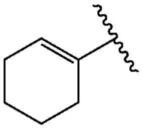 [SMILES: *C1=CCCCC1] | |
| 4-106 | 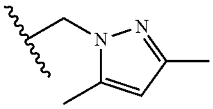 [SMILES: *Cn1nc(C)cc1C] | $SO_2CH_3$ | $CH_3$ | $CH_3$ | 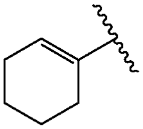 [SMILES: *C1=CCCCC1] | |
| 4-107 | 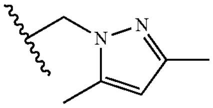 [SMILES: *Cn1nc(C)cc1C] | $SO_2CH_3$ | 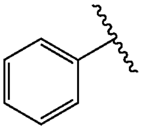 | $CH_3$ | 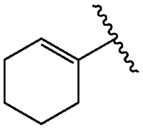 [SMILES: *C1=CCCCC1] | |
| 4-108 | 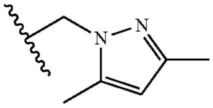 [SMILES: *Cn1nc(C)cc1C] | $SO_2CH_3$ | $CH_3$ | 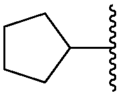 [SMILES: *C1CCCC1] | 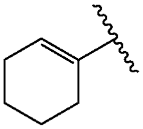 [SMILES: *C1=CCCCC1] | |

TABLE 4-continued
Structures and Physical Properties of Part of Compounds of Formula I
| Compound | $X_1$ | $X_3$ | $R_1$ | $R_2$ | Z | Appearance (Melting Point ° C.) |
| --- | --- | --- | --- | --- | --- | --- |
| 4-109 | 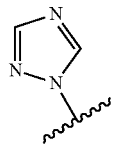 [SMILES: *n1cncn1] | $CF_3$ | $CH_3$ | $CH_3$ | 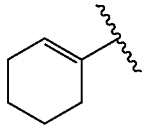 [SMILES: *C1=CCCCC1] | |
| 4-110 | 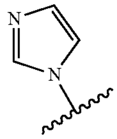 | $CF_3$ | $CH_3$ | $CH_3$ | 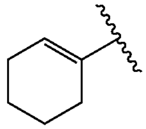 [SMILES: *C1=CCCCC1] | |
| 4-111 | 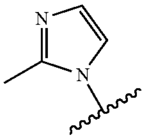 [SMILES: *n1ccnc1C] | $CF_3$ | $CH_3$ | $CH_3$ | 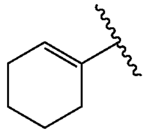 [SMILES: *C1=CCCCC1] | |
| 4-112 | 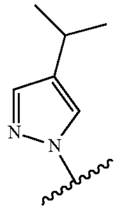 [SMILES: *n1cc(C(C)C)cn1] | $CF_3$ | $CH_3$ | $CH_3$ | 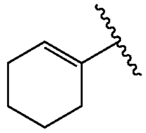 [SMILES: *C1=CCCCC1] | |
| 4-113 | 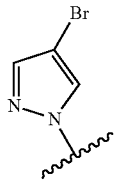 [SMILES: *n1cc(Br)cn1] | $CF_3$ | $CH_3$ | $CH_3$ | 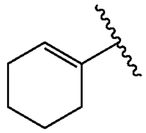 [SMILES: *C1=CCCCC1] | |
| 4-114 | 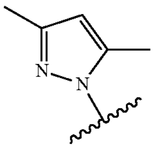 | $CF_3$ | $CH_3$ | $CH_3$ | 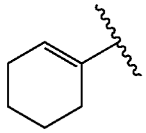 [SMILES: *C1=CCCCC1] | |
| 4-115 | 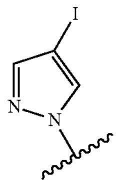 [SMILES: *n1cc(I)cn1] | $CF_3$ | $CH_3$ | $CH_3$ | 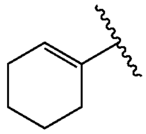 [SMILES: *C1=CCCCC1] | |
| 4-116 | 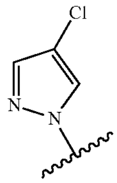 [SMILES: *n1cc(Cl)cn1] | $CF_3$ | $CH_3$ | $CH_3$ | 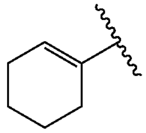 [SMILES: *C1=CCCCC1] | |

TABLE 4-continued
Structures and Physical Properties of Part of Compounds of Formula I
| Compound | $X_1$ | $X_3$ | $R_1$ | $R_2$ | Z | Appearance (Melting Point ° C.) |
|---|---|---|---|---|---|---|
| 4-117 | 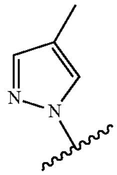 [SMILES: *n1cc(C)cn1] | $CF_3$ | $CH_3$ | $CH_3$ | 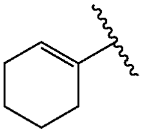 [SMILES: *C1=CCCCC1] | |
| 4-118 | 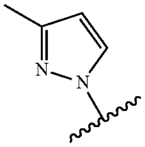 [SMILES: *n1ccc(C)n1] | $CF_3$ | $CH_3$ | $CH_3$ | 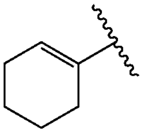 [SMILES: *C1=CCCCC1] | |
| 4-119 | 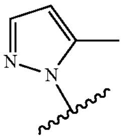 [SMILES: *n1nccc1C] | $CF_3$ | $CH_3$ | $CH_3$ | 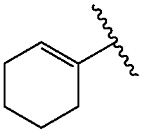 [SMILES: *C1=CCCCC1] | |
| 4-120 | 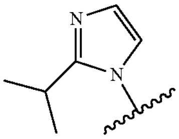 [SMILES: *n1ccnc1C(C)C] | $CF_3$ | $CH_3$ | $CH_3$ | 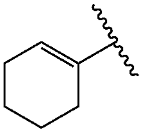 [SMILES: *C1=CCCCC1] | |
| 4-121 | 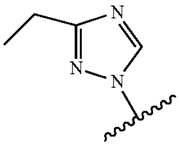 [SMILES: *n1cnc(CC)n1] | $CF_3$ | $CH_3$ | $CH_3$ | 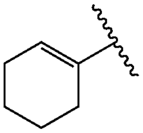 [SMILES: *C1=CCCCC1] | |
| 4-122 | 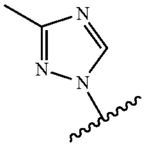 [SMILES: *n1cnc(C)n1] | $CF_3$ | $CH_3$ | $CH_3$ | 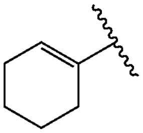 [SMILES: *C1=CCCCC1] | |
| 4-123 | 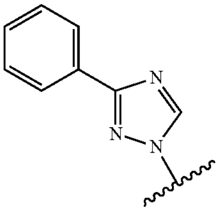 [SMILES: *n1cnc(-c2ccccc2)n1] | $CF_3$ | $CH_3$ | $CH_3$ | 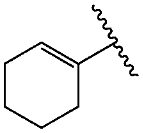 [SMILES: *C1=CCCCC1] | |
| 4-124 | 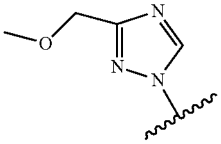 [SMILES: *n1cnc(COC)n1] | $CF_3$ | $CH_3$ | $CH_3$ | 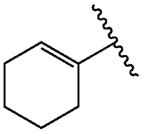 [SMILES: *C1=CCCCC1] | |
| 4-125 | 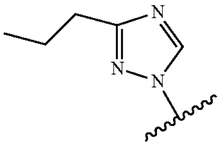 [SMILES: *n1cnc(CCC)n1] | $CF_3$ | $CH_3$ | $CH_3$ | 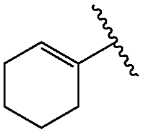 [SMILES: *C1=CCCCC1] | |

TABLE 4-continued
| Structures and Physical Properties of Part of Compounds of Formula I | | | | | | |
|---|---|---|---|---|---|---|
| Compound | $X_1$ | $X_3$ | $R_1$ | $R_2$ | Z | Appearance (Melting Point ° C.) |
| 4-126 | 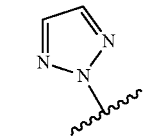 [SMILES: *n1nccn1] | $CF_3$ | $CH_3$ | $CH_3$ | 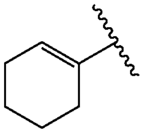 [SMILES: *C1=CCCCC1] | |
| 4-127 | 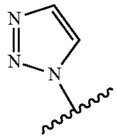 [SMILES: *n1ccnn1] | $CF_3$ | $CH_3$ | $CH_3$ | 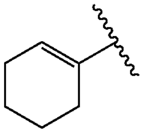 [SMILES: *C1=CCCCC1] | |
| 4-128 | 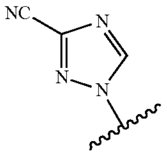 [SMILES: *n1cnc(C#N)n1] | $CF_3$ | $CH_3$ | $CH_3$ | 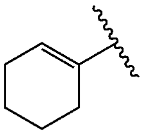 [SMILES: *C1=CCCCC1] | |
| 4-129 | 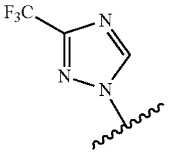 | $CF_3$ | $CH_3$ | $CH_3$ | 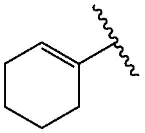 [SMILES: *C1=CCCCC1] | |
| 4-130 | 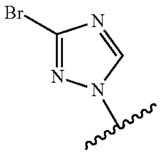 [SMILES: *n1cnc(Br)n1] | $CF_3$ | $CH_3$ | $CH_3$ | 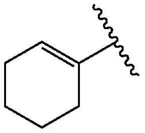 [SMILES: *C1=CCCCC1] | |
| 4-131 | 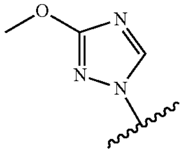 [SMILES: *n1cnc(OC)n1] | $CF_3$ | $CH_3$ | $CH_3$ | 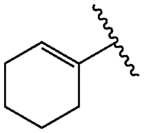 [SMILES: *C1=CCCCC1] | |
| 4-132 | 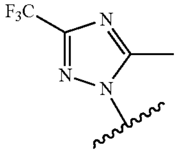 [SMILES: *n1nc(C(F)(F)F)nc1C] | $CF_3$ | $CH_3$ | $CH_3$ | 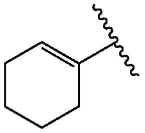 [SMILES: *C1=CCCCC1] | |
| 4-133 | 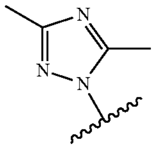 | $CF_3$ | $CH_3$ | $CH_3$ | 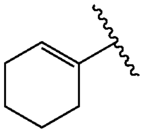 [SMILES: *C1=CCCCC1] | |
| 4-134 | 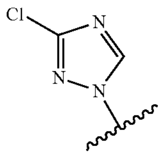 [SMILES: *n1cnc(Cl)n1] | $CF_3$ | $CH_3$ | $CH_3$ | 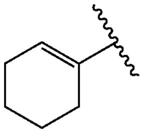 [SMILES: *C1=CCCCC1] | |

TABLE 4-continued

Structures and Physical Properties of Part of Compounds of Formula I

| Compound | $X_1$ | $X_3$ | $R_1$ | $R_2$ | Z | Appearance (Melting Point ° C.) |
|---|---|---|---|---|---|---|
| 4-135 | 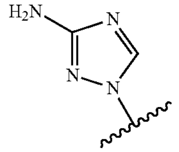 [SMILES: *n1cnc(N)n1] | $CF_3$ | $CH_3$ | $CH_3$ | 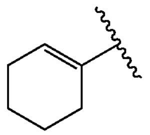 [SMILES: *C1=CCCCC1] | |
| 4-136 | 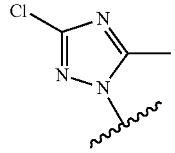 [SMILES: *n1nc(Cl)nc1C] | $CF_3$ | $CH_3$ | $CH_3$ | 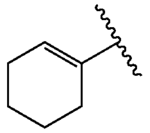 [SMILES: *C1=CCCCC1] | |
| 4-137 | 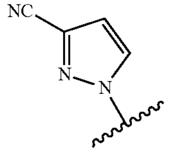 [SMILES: *n1ccc(C#N)n1] | $CF_3$ | $CH_3$ | $CH_3$ | 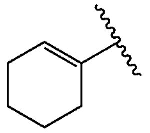 [SMILES: *C1=CCCCC1] | |
| 4-138 | 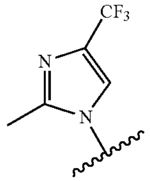 [SMILES: *n1cc(C(F)(F)F)nc1C] | $CF_3$ | $CH_3$ | $CH_3$ | 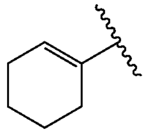 [SMILES: *C1=CCCCC1] | |
| 4-139 | 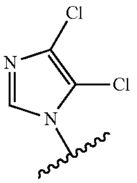 [SMILES: *n1cnc(Cl)c1Cl] | $CF_3$ | $CH_3$ | $CH_3$ | 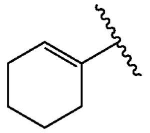 [SMILES: *C1=CCCCC1] | |
| 4-140 | H | Cl | $CH_3$ | $CH_3$ | 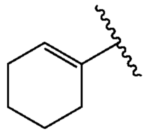 [SMILES: *C1=CCCCC1] | white solid (122-126) |
| 4-141 | H | Cl | $CH_3$ | $CH_3$ | 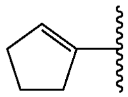 [SMILES: *C1=CCCC1] | yellow solid (105-109) |

$^1H$ NMR data of part of compounds is as follows:

Compound 1-1 (600 MHz, DMSO-$d_6$): 8.11 (s, 2H), 7.63-7.67 (m, 3H), 7.42-7.51 (m, 4H), 6.28 (d, 1H), 3.57 (s, 3H), 3.34 (s, 3H), 2.33 (s, 3H).

Compound 1-7 (600 MHz, $CDCl_3$): 8.18 (s, 1H), 7.81 (d, 1H), 7.45 (d, 1H), 7.37 (d, 1H), 6.96 (dd, 1H), 6.90 (s, 1H), 6.82 (d, 1H), 6.03 (s, 2H), 5.76 (d, 1H), 3.57 (s, 3H), 3.26 (s, 3H), 2.42 (s, 3H).

Compound 1-16 (600 MHz, $CDCl_3$): 8.03 (d, 1H), 7.59 (d, 1H), 7.37-7.48 (m, 6H), 6.09 (d, 1H), 4.98 (s, 2H), 3.61 (s, 3H), 3.47 (s, 3H), 2.81 (s, 3H), 2.47 (s, 3H).

Compound 1-18 (600 MHz, DMSO-$d_6$): 7.98 (d, 1H), 7.56-7.65 (m, 4H), 6.98 (d, 2H), 6.15 (d, 1H), 4.86 (s, 2H), 3.82 (s, 3H), 3.57 (s, 3H), 3.34 (s, 3H), 2.94 (s, 3H), 2.35 (s, 3H).

Compound 1-20 (600 MHz, DMSO-$d_6$): 7.98 (d, 1H), 7.90 (d, 2H), 7.78 (d, 2H), 7.70 (d, 1H), 7.60 (d, 1H), 6.50 (d, 1H), 4.84 (s, 2H), 3.60 (s, 3H), 3.32 (s, 3H), 3.01 (s, 3H), 2.34 (s, 3H).

Compound 1-21 (600 MHz, DMSO-$d_6$): 8.00 (d, 1H), 7.74-7.79 (m, 6H), 7.68 (d, 1H), 7.61 (d, 1H), 7.50 (t, 2H), 7.42 (t, 1H), 6.38 (d, 1H), 4.86 (s, 2H), 3.60 (s, 3H), 3.34 (s, 3H), 2.97 (s, 3H), 2.34 (s, 3H).

Compound 1-22 (600 MHz, DMSO-$d_6$): 7.98 (d, 1H), 7.58 (d, 1H), 7.52 (d, 1H), 7.33 (s, 1H), 7.19 (d, 1H), 6.97 (d, 1H), 6.18 (d, 1H), 6.11 (s, 2H), 4.86 (s, 2H), 3.57 (s, 3H), 3.35 (s, 3H), 2.99 (s, 3H), 2.34 (s, 3H).

Compound 1-31 (600 MHz, $CDCl_3$): 8.01 (d, 1H), 7.63 (d, 1H), 7.44-7.49 (m, 5H), 7.28 (d, 1H), 6.03 (d, 1H), 3.62 (s, 3H), 2.84 (s, 3H), 2.67 (s, 3H), 2.45 (s, 3H).

Compound 1-37 (600 MHz, DMSO-$d_6$): 7.92 (d, 1H), 7.55 (d, 1H), 7.42 (d, 11H), 7.37 (s, 1H), 7.22 (d, 1H), 6.98 (d, 1H), 6.21 (d, 1H), 6.11 (s, 2H), 3.56 (s, 3H), 2.99 (s, 3H), 2.59 (s, 3H), 2.33 (s, 3H).

Compound 1-42 (600 MHz, $CDCl_3$): 8.05 (d, 1H), 7.71 (t, 2H), 7.35 (d, 1H), 7.06 (s, 1H), 7.05 (s, 1H), 6.86 (d, 1H), 6.18 (d, 1H), 6.06 (s, 2H), 3.74 (s, 3H), 3.03 (s, 3H), 2.76 (s, 3H).

Compound 1-76 (600 MHz, DMSO-$d_6$): 7.99 (d, 1H), 7.60-7.70 (m, 4H), 7.43-7.51 (m, 3H), 6.34 (d, 1H), 4.95 (s, 2H), 3.65 (t, 2H), 3.60 (s, 3H), 3.47 (t, 2H), 3.23 (s, 3H), 2.99 (s, 3H), 2.34 (s, 3H).

Compound 1-81 (600 MHz, $CDCl_3$): 8.07 (d, 1H), 7.65-7.67 (m, 3H), 7.62 (d, 2H), 7.58 (d, 2H), 7.46-7.48 (m, 2H), 7.39-7.41 (m, 2H), 6.10 (d, J=15.6 Hz, 1H), 5.10 (s, 2H), 3.76-3.78 (m, 2H), 3.62 (s, 3H), 3.58-3.59 (m, 2H), 3.34 (s, 3H), 2.99 (s, 3H), 2.46 (s, 3H).

Compound 1-82 (600 MHz, $CDCl_3$): 8.04 (d, 1H), 7.48 (d, 1H), 7.37 (d, 1H), 6.99-7.00 (m, 2H), 6.83 (d, 1H), 6.04 (s, 2H), 5.86 (d, 1H), 5.10 (s, 2H), 3.76-3.78 (m, 2H), 3.60 (s, 3H), 3.58-3.59 (m, 2H), 3.35 (s, 3H), 3.03 (s, 3H), 2.46 (s, 3H).

Compound 1-115 (600 MHz, $CDCl_3$): 7.85 (d, 1H), 7.62 (d, 1H), 7.40-7.50 (m, 5H), 7.18 (d, 1H), 6.09 (d, 1H), 4.00 (s, 3H), 3.62 (s, 3H), 2.83 (s, 3H), 2.44 (s, 3H).

Compound 1-223 (600 MHz, DMSO-$d_6$): 7.97 (d, 2H), 7.65-7.71 (m, 4H), 7.44-7.48 (m, 31H), 6.40 (d, 1H), 3.60 (s, 3H), 2.93 (s, 3H), 2.32 (s, 3H).

Compound 1-226 (600 MHz, DMSO-$d_6$): 8.01 (s, 1H), 7.90 (d, 1H), 7.62 (d, 1H), 7.55 (d, 1H), 7.37 (s, 1H), 7.21 (d, 1H), 6.97 (d, 1H), 6.24 (d, 1H), 6.11 (s, 2H), 3.58 (s, 3H), 2.99 (s, 3H), 2.33 (s, 3H).

Compound 1-229 (600 MHz, DMSO-$d_6$): 7.73 (d, 2H), 7.60 (d, 1H), 7.56 (d, 1H), 7.46-7.52 (m, 3H), 7.43 (dd, 1H), 7.36 (d, 1H), 6.39 (d, 1H), 3.59 (s, 3H), 2.33 (s, 3H).

Compound 1-232 (600 MHz, DMSO-$d_6$): 7.59 (s, 1H), 7.46 (d, 1H), 7.40-7.43 (m, 2H), 7.34 (d, 1H), 7.22 (d, 1H), 7.00 (d, 1H), 6.23 (d, 1H), 6.12 (s, 2H), 3.57 (s, 3H), 2.32 (s, 3H).

Compound 1-235 (600 MHz, DMSO-$d_6$): 8.58 (s, 1H), 8.36 (d, 1H), 7.84 (d, 1H), 7.69 (d, 2H), 7.62 (d, 1H), 7.44-7.51 (m, 3H), 6.37 (d, 1H), 3.58 (s, 3H), 3.01 (s, 3H), 2.35 (s, 3H).

Compound 1-238 (600 MHz, DMSO-$d_6$): 8.58 (s, 1H), 8.34 (d, 1H), 7.82 (d, 1H), 7.51 (d, 1H), 7.36 (s, 1H), 7.20 (d, 1H), 6.98 (d, 1H), 6.20 (d, 1H), 6.12 (s, 2H), 3.55 (s, 3H), 3.07 (s, 3H), 2.36 (s, 3H).

Compound 1-259 (600 MHz, DMSO-$d_6$): 7.68-7.70 (m, 3H), 7.62 (d, 1H), 7.48 (t, 1H), 7.42-7.44 (m, 2H), 7.23 (d, 1H), 6.40 (d, 1H), 4.01 (t, 2H), 3.62 (t, 2H), 3.59 (s, 3H), 3.30 (s, 3H), 2.88 (s, 3H), 2.34 (s, 3H), 2.17 (s, 3H).

Compound 1-262 (600 MHz, $CDCl_3$): 7.78 (d, 1H), 7.44 (d, 1H), 7.13 (d, 1H), 6.93-6.96 (m, 2H), 6.81 (d, 1H), 6.01 (s, 2H), 5.83 (d, 1H), 4.09 (t, 2H), 3.69 (t, 2H), 3.58 (s, 3H), 3.40 (s, 3H), 2.96 (s, 3H), 2.39 (s, 3H), 2.26 (s, 3H).

Compound 1-265 (600 MHz, $CDCl_3$): 7.82 (d, 1H), 7.58 (d, 1H), 7.41-7.49 (m, 5H), 7.17 (d, 1H), 6.07 (d, 1H), 3.85 (s, 3H), 3.63 (s, 3H), 2.84 (s, 3H), 2.44 (s, 3H), 2.28 (s, 3H).

Compound 1-268 (600 MHz, $CDCl_3$): 7.95 (d, 1H), 7.59 (d, 1H), 7.41-7.48 (m, 5H), 7.22 (d, 1H), 5.98 (d, 1H), 3.61 (s, 3H), 2.81 (s, 3H), 2.52 (s, 3H), 2.42 (s, 3H), 2.23 (s, 3H).

Compound 1-280 (600 MHz, $CDCl_3$): 7.78 (d, 1H), 7.55 (d, 1H), 7.39-7.47 (m, 5H), 7.12 (d, 1H), 6.04 (d, 1H), 3.97 (q, 2H), 3.61 (s, 3H), 2.83 (s, 3H), 2.42 (s, 3H), 2.24 (s, 3H), 1.37 (t, 3H).

Compound 1-292 (600 MHz, $CDCl_3$): 8.00 (d, 1H), 7.79 (d, 1H), 7.75 (s, 1H), 7.53-7.56 (m, 3H), 7.41-7.47 (m, 3H), 6.40 (d, 1H), 4.54 (t, 2H), 3.75 (s, 3H), 3.29 (brs, 2H), 2.92 (s, 3H), 2.28 (s, 3H).

Compound 1-346 (600 MHz, $CDCl_3$): 7.85 (d, 1H), 7.57 (d, 1H), 7.43-7.50 (m, 5H), 7.27 (d, 1H), 6.05 (d, 1H), 4.34 (q, 2H), 3.63 (s, 3H), 2.80 (s, 3H), 2.47 (s, 3H), 2.31 (s, 3H).

Compound 1-349 (600 MHz, $CDCl_3$): 7.83 (d, 1H), 7.58 (d, 1H), 7.41-7.49 (m, 5H), 7.17 (d, 1H), 6.05 (d, 1H), 4.27-4.31 (m, 1H), 3.81-3.39 (m, 4H), 3.63 (s, 3H), 2.91 (s, 3H), 2.44 (s, 3H), 2.30 (s, 3H), 1.94-1.99 (m, 1H), 1.84-1.91 (m, 2H), 1.49-1.55 (m, 1H).

Compound 1-367 (600 MHz, $CDCl_3$): 8.04 (s, 1H), 7.46-7.60 (m, 7H), 7.33 (d, 1H), 6.06 (d, 1H), 3.58 (s, 3H), 2.47 (s, 3H).

Compound 1-370 (600 MHz, $CDCl_3$): 7.82 (d, 1H), 7.52 (d, 1H), 7.43 (d, 2H), 7.17 (d, 1H), 6.92 (d, 2H), 5.88 (d, 1H), 4.10 (t, 2H), 3.86 (s, 3H), 3.69 (t, 2H), 3.61 (s, 3H), 3.42 (s, 3H), 2.91 (s, 3H), 2.44 (s, 3H), 2.29 (s, 3H).

Compound 1-371 (600 MHz, $CDCl_3$): 7.93 (d, 1H), 7.50-7.56 (m, 4H), 7.42-7.49 (m, 3H), 7.29 (d, 1H), 6.10 (d, 1H), 3.61 (s, 3H), 3.26 (s, 3H), 2.40 (s, 3H).

Compound 1-372 (600 MHz, $CDCl_3$): 7.86 (d, 1H), 7.81 (d, 1H), 7.70 (s, 1H), 7.55-7.57 (m, 2H), 7.41-7.46 (m, 3H), 7.26 (d, 1H), 6.44 (d, 1H), 4.17 (t, 2H), 4.03-4.07 (m, 2H), 3.75 (t, 2H), 3.44 (s, 3H), 3.10 (s, 3H), 2.33 (s, 3H), 1.46 (t, 3H).

Compound 1-373 (600 MHz, $CDCl_3$): 7.87 (d, 1H), 7.65 (d, 1H), 7.41-7.51 (m, 5H), 7.19 (d, 1H), 6.11 (d, 1H), 4.32 (t, 2H), 3.79 (t, 2H), 3.62 (s, 3H), 3.57 (q, 2H), 2.89 (s, 3H), 2.43 (s, 3H), 1.22 (t, 3H).

Compound 1-374 (600 MHz, $CDCl_3$): 7.87 (d, 1H), 7.64 (d, 1H), 7.41-7.51 (m, 5H), 7.18 (d, 1H), 6.10 (d, 1H), 4.24 (t, 2H), 3.62 (s, 3H), 3.55 (t, 2H), 3.34 (s, 3H), 2.87 (s, 3H), 2.44 (s, 3H), 2.09-2.10 (m, 2H).

Compound 1-375 (600 MHz, $CDCl_3$): 7.84 (d, 1H), 7.59 (d, 1H), 7.39-7.49 (m, 5H), 7.15 (d, 1H), 6.07 (d, 1H), 4.15 (t, 2H), 3.60 (s, 3H), 3.41 (t, 2H), 3.32 (s, 3H), 2.82 (s, 3H), 2.43 (s, 3H), 1.88-1.89 (m, 2H), 1.69-1.70 (m, 2H).

Compound 1-376 (600 MHz, $CDCl_3$): 7.85 (d, 1H), 7.62 (d, 1H), 7.40-7.50 (m, 5H), 7.15 (d, 1H), 6.08 (d, 1H), 4.10 (td, 2H), 3.61 (s, 3H), 2.84 (s, 3H), 2.44 (s, 3H), 1.84 (p, 2H), 0.99 (t, 3H).

Compound 1-377 (600 MHz, $CDCl_3$): 7.89 (d, 1H), 7.66 (d, 1H), 7.40-7.51 (m, 5H), 7.11 (d, 1H), 6.12 (d, 1H), 5.21-5.27 (m, 1H), 3.62 (s, 3H), 2.83 (s, 3H), 2.40 (s, 3H), 1.35 (d, 6H).

Compound 2-1 (600 MHz, $CDCl_3$): 7.79 (d, 1H), 7.11 (d, 1H), 6.82-6.84 (m, 1H), 3.91 (s, 3H), 3.57 (s, 3H), 3.21 (s, 3H), 2.47 (s, 3H), 2.23 (s, 3H), 2.21 (q, 2H), 2.00-2.02 (m, 2H), 1.57-1.64 (m, 4H).

Compound 2-19 (600 MHz, $CDCl_3$): 7.80 (d, 1H), 7.10 (d, 1H), 6.81-6.83 (m, 1H), 4.07 (q, 2H), 3.56 (s, 3H), 3.22 (s, 3H), 2.47 (s, 3H), 2.21 (s, 3H), 2.19-2.22 (m, 2H), 1.99-2.02 (m, 2H), 1.58-1.63 (m, 4H), 1.48 (t, 3H).

Compound 2-37 (600 MHz, $CDCl_3$): 7.84 (d, 1H), 7.22 (d, 1H), 6.85-6.87 (m, 1H), 4.46 (q, 2H), 3.57 (s, 3H), 3.24 (s, 3H), 2.46 (s, 3H), 2.25 (s, 3H), 2.20 (q, 2H), 1.98-2.01 (m, 2H), 1.57-1.64 (m, 4H).

Compound 2-55 (600 MHz, $CDCl_3$): 7.80 (d, 1H), 7.12 (d, 1H), 6.85 (t, 1H), 4.18 (t, 2H), 3.80 (t, 2H), 3.57 (s, 3H), 3.47 (s, 3H), 3.26 (s, 3H), 2.45 (s, 3H), 2.26 (s, 3H), 2.19-2.21 (m, 2H), 2.00-2.01 (m, 2H), 1.57-1.63 (m, 4H).

Compound 2-57 (600 MHz, $CDCl_3$): 7.78 (d, 1H), 7.09 (d, 1H), 6.68 (t, 1H), 4.15 (t, 2H), 3.78 (t, 2H), 3.56 (s, 3H), 3.45 (s, 3H), 3.24 (s, 3H), 2.50-2.52 (m, 2H), 2.43 (s, 3H), 2.32-2.34 (m, 2H), 2.24 (s, 3H), 1.93-1.95 (m, 2H).

Compound 2-61 (600 MHz, $CDCl_3$): 7.84 (d, 1H), 7.72 (s, 1H), 7.22 (d, 1H), 7.12-7.13 (m, 1H), 4.21 (t, 2H), 3.97-4.00 (m, 2H), 3.79 (t, 2H), 3.46 (s, 3H), 3.27 (s, 3H), 2.30 (s, 3H), 2.20-2.21 (m, 2H), 2.19-2.20 (m, 2H), 1.65-1.70 (m, 2H), 1.62-1.64 (m, 2H), 1.43 (t, 3H).

Compound 2-63 (600 MHz, $CDCl_3$): 7.82-7.84 (m, 1H), 7.72 (s, 1H), 7.22 (d, 1H), 6.70 (d, 1H), 4.20 (d, 2H), 3.97-4.01 (m, 2H), 3.79 (d, 2H), 3.45 (s, 3H), 3.27 (s, 3H), 2.53-2.60 (m, 4H), 2.32 (s, 3H), 2.00-2.03 (m, 2H), 1.42 (t, 3H).

Compound 2-67 (600 MHz, $CDCl_3$): 7.85 (d, 1H), 7.73 (s, 1H), 7.22 (d, 1H), 7.12-7.13 (m, 1H), 4.20 (t, 2H), 3.80 (t, 2H), 3.70 (s, 3H), 3.47 (s, 3H), 3.28 (s, 3H), 2.31 (s, 3H), 2.25-2.28 (m, 2H), 2.20-2.22 (m, 2H), 1.67-1.70 (m, 2H), 1.62-1.65 (m, 2H).

Compound 2-73 (600 MHz, CDCb3): 7.81 (d, 1H), 7.11 (d, 1H), 6.82-6.84 (m, 1H), 4.35-4.39 (m, 1H), 4.01 (d, 2H), 3.85-3.97 (m, 2H), 3.56 (s, 3H), 3.26 (s, 3H), 2.45 (s, 3H), 2.26 (s, 3H), 2.19-2.20 (m, 2H), 1.95-2.00 (m, 4H), 1.57-1.63 (m, 6H).

Compound 2-121 (600 MHz, $CDCl_3$): 8.01 (d, 1H), 7.75 (s, 1H), 7.50 (d, 1H), 7.10-7.12 (m, 1H), 4.57 (t, 2H), 3.69 (s, 3H), 3.36-3.32 (m, 2H), 3.18 (s, 3H), 2.25-2.28 (m, 5H), 2.09-2.10 (m, 2H), 1.67-1.69 (m, 2H), 1.62-1.63 (m, 2H).

Compound 2-123 (600 MHz, $CDCl_3$): 8.01 (d, 1H), 7.76 (s, 1H), 7.51 (d, 1H), 6.95-6.98 (m, 1H), 4.58 (t, 2H), 3.71 (s, 3H), 3.32-3.37 (m, 2H), 3.19 (s, 3H), 2.58-2.62 (m, 2H), 2.52-2.54 (m, 2H), 2.26 (s, 3H), 2.01-2.04 (m, 2H).

Compound 2-127 (600 MHz, $CDCl_3$): 7.92 (d, 1H), 7.15 (d, 1H), 6.68-6.69 (m, 1H), 3.55 (s, 3H), 3.05 (s, 3H), 2.61 (s, 3H), 2.49 (s, 3H), 2.19 (s, 3H), 2.16-2.17 (m, 2H), 1.94-1.95 (m, 2H), 1.55-1.65 (m, 4H).

Compound 2-145 (600 MHz, $CDCl_3$): 7.95 (d, 1H), 7.26 (d, 1H), 6.69-6.70 (m, 1H), 4.87 (s, 2H), 3.54 (s, 3H), 3.47 (s, 3H), 3.15 (s, 3H), 2.47 (s, 3H), 2.31 (s, 3H), 2.15-2.16 (m, 2H), 1.94-1.95 (m, 2H), 1.56-1.60 (m, 4H).

Compound 2-289 (600 MHz, $CDCl_3$): 7.98 (d, 1H), 7.20 (d, 1H), 6.72 (s, 1H), 3.54 (s, 3H), 3.07 (s, 3H), 2.74 (s, 3H), 2.49 (s, 3H), 2.16-2.17 (m, 2H), 1.96-1.97 (m, 2H), 1.55-1.60 (m, 4H).

Compound 2-291 (600 MHz, $CDCl_3$): 7.97 (d, 1H), 7.21 (d, 1H), 6.59 (s, 1H), 3.55 (s, 3H), 3.07 (s, 3H), 2.73 (s, 3H), 2.50-2.52 (m, 5H), 2.30-2.32 (m, 2H), 1.91-1.96 (m, 2H).

Compound 2-307 (600 MHz, $CDCl_3$): 8.01 (d, 1H), 7.31 (d, 1H), 6.71 (s, 1H), 5.01 (s, 2H), 3.52 (s, 3H), 3.46 (s, 3H), 3.19 (s, 3H), 2.46 (s, 3H), 2.13-2.14 (m, 2H), 1.94-1.95 (m, 2H), 1.54-1.56 (m, 4H).

Compound 2-309 (600 MHz, $CDCl_3$): 8.03 (d, 1H), 7.33 (d, 1H), 6.60 (s, 1H), 5.03 (s, 2H), 3.56 (s, 3H), 3.48 (s, 3H), 3.22 (s, 3H), 2.49-2.52 (m, 5H), 2.30-2.33 (m, 2H), 1.91-1.96 (m, 2H).

Compound 2-343 (600 MHz, $CDCl_3$): 8.01 (d, 1H), 7.54 (q, 1H), 7.23 (d, 1H), 6.77-6.78 (m, 1H), 3.55 (s, 3H), 3.26 (s, 3H), 2.45 (s, 3H), 2.17 (q, 2H), 2.00-2.01 (m, 2H), 1.56-1.63 (m, 4H).

Compound 2-379 (600 MHz, DMSO-$d_6$): 8.22 (s, 1H), 8.16 (d, 1H), 7.61 (d, 1H), 6.58 (s, 1H), 3.51 (s, 3H), 3.32 (s, 3H), 2.36 (s, 3H), 2.02-2.04 (m, 2H), 1.85-1.87 (m, 2H), 1.40-1.50 (m, 4H).

Compound 2-380 (600 MHz, DMSO-$d_6$): 8.21 (s, 1H), 8.17 (d, 1H), 7.61 (d, 1H), 6.49 (s, 1H), 3.52 (s, 3H), 3.32 (s, 3H), 2.34-2.36 (m, 5H), 2.20-2.21 (m, 2H), 1.76-1.82 (m, 2H).

Compound 2-381 (600 MHz, $CDCl_3$): 8.05 (d, 1H), 7.34 (d, 1H), 6.74 (s, 1H), 5.16 (s, 2H), 3.77 (t, 2H), 3.56 (t, 2H), 3.55 (s, 3H), 3.34 (s, 3H), 3.29 (s, 3H), 2.50 (s, 3H), 2.16-2.17 (m, 2H), 1.98-1.99 (m, 2H), 1.57-1.61 (m, 4H).

Compound 2-382 (600 MHz, $CDCl_3$): 8.04 (d, 1H), 7.34 (d, 1H), 6.61 (s, 1H), 5.15 (s, 2H), 3.77 (t, 2H), 3.56-3.58 (m, 5H), 3.34 (s, 3H), 3.29 (s, 3H), 2.50-2.53 (m, 5H), 2.31-2.33 (m, 2H), 1.92-1.97 (m, 2H).

Compound 2-383 (600 MHz, CDCh3): 7.91 (s, 1H), 7.79 (d, 1H), 7.37 (d, 1H), 6.77 (s, 1H), 3.54 (s, 3H), 3.03 (s, 3H), 2.47 (s, 3H), 2.15-2.16 (m, 2H), 1.97-1.98 (m, 2H), 1.55-1.58 (m, 4H).

Compound 2-384 (600 MHz, $CDCl_3$): 7.93 (s, 1H), 7.81 (d, 1H), 7.40 (d, 1H), 6.67 (s, 1H), 3.58 (s, 3H), 3.07 (s, 3H), 2.49-2.52 (m, 5H), 2.33-2.34 (m, 2H), 1.93-1.96 (m, 2H).

Compound 2-385 (600 MHz, $CDCl_3$): 7.36 (s, 1H), 7.22 (d, 1H), 7.15 (d, 1H), 6.87 (s, 1H), 3.57 (s, 3H), 2.47 (s, 3H), 2.20-2.22 (m, 2H), 2.04-2.06 (m, 2H), 1.61-1.63 (m, 4H).

Compound 2-386 (600 MHz, $CDCl_3$): 7.36 (d, 1H), 7.24 (dd, 1H), 7.15 (d, 1H), 6.73 (s, 1H), 3.59 (s, 3H), 2.52-2.54 (m, 2H), 2.46 (s, 3H), 2.38-2.42 (m, 2H), 1.94-1.99 (m, 2H).

Compound 2-387 (600 MHz, $CDCl_3$): 8.66 (s, 1H), 8.19 (d, 1H), 7.55 (d, 1H), 6.75 (s, 1H), 3.52 (s, 3H), 3.11 (s, 3H), 2.52 (s, 3H), 2.18-2.21 (m, 2H), 1.92-1.93 (m, 2H), 1.57-1.64 (m, 4H).

Compound 2-388 (600 MHz, $CDCl_3$): 8.64 (s, 1H), 7.19 (d, 1H), 7.54 (d, 1H), 6.63 (s, 1H), 3.52 (s, 3H), 3.11 (s, 3H), 2.51-2.54 (m, 5H), 2.26-2.28 (m, 2H), 1.92-1.94 (m, 2H).

Compound 2-389 (600 MHz, $CDCl_3$): 8.21 (d, 1H), 8.10 (dd, 1H), 7.37 (d, 1H), 6.82 (t, 1H), 3.56 (s, 3H), 2.47 (s, 3H), 2.06-2.08 (m, 2H), 1.98-1.99 (m, 2H), 1.44-1.53 (m, 4H).

Compound 2-390 (600 MHz, $CDCl_3$): 8.20 (d, 1H), 8.09 (dd, 1H), 7.38 (d, 1H), 6.69 (s, 1H), 3.57 (s, 3H), 2.44 (s, 3H), 2.38-2.41 (m, 2H), 2.34-2.36 (m, 2H), 1.82-1.88 (m, 2H).

Compound 2-391 (600 MHz, $CDCl_3$): 8.09 (s, 1H), 7.63 (d, 1H), 7.28 (d, 1H), 6.83 (s, 1H), 3.52 (s, 3H), 2.51 (s, 3H), 2.20-2.21 (m, 2H), 1.98-1.99 (m, 2H), 1.62-1.64 (m, 4H).

Compound 2-392 (600 MHz, $CDCl_3$): 8.08 (s, 1H), 7.63 (d, 1H), 7.29 (d, 1H), 6.71 (s, 1H), 3.54 (s, 3H), 2.53-2.55 (m, 2H), 2.50 (s, 3H), 2.34-2.36 (m, 2H), 1.96-1.99 (m, 2H).

Compound 2-414 (600 MHz, $CDCl_3$): 7.83 (d, 1H), 7.07 (d, 1H), 6.90-6.91 (m, 1H), 4.77-4.81 (m, 1H), 3.57 (s, 3H), 3.19 (s, 3H), 2.36 (s, 3H), 2.23 (s, 3H), 2.17-2.20 (m, 2H), 2.05-2.07 (m, 2H), 1.57-1.63 (m, 4H), 1.34 (d, 6H).

Compound 2-415 (600 MHz, $CDCl_3$): 7.83 (d, 1H), 7.08 (d, 1H), 6.76-6.77 (m, 1H), 4.76-4.81 (m, 1H), 3.59 (s, 3H), 3.20 (s, 3H), 2.50-2.54 (m, 2H), 2.40-2.43 (m, 2H), 2.37 (s, 3H), 2.24 (s, 3H), 1.93-1.98 (m, 2H), 1.35 (d, 6H).

Compound 2-416 (600 MHz, $CDCl_3$): 7.79 (d, 1H), 7.11 (d, 1H), 6.76-6.78 (m, 1H), 4.16 (t, 2H), 3.79 (t, 2H), 3.55-3.59 (m, 4H), 3.47 (s, 3H), 3.24 (s, 3H), 2.24 (s, 3H), 2.17-2.19 (m, 2H), 1.96-1.97 (m, 2H), 1.59-1.63 (m, 4H), 1.32 (d, 6H).

Compound 2-417 (600 MHz, $CDCl_3$): 7.79 (d, 1H), 7.11 (d, 1H), 6.79-6.81 (m, 1H), 4.17 (t, 2H), 3.79 (t, 2H), 3.56 (s, 3H), 3.47 (s, 3H), 3.25 (s, 3H), 2.91 (q, 2H), 2.25 (s, 3H), 2.18-2.20 (m, 2H), 1.97-1.99 (m, 2H), 1.59-1.64 (m, 4H), 1.28 (t, 3H).

Compound 2-418 (600 MHz, $CDCl_3$): 7.81 (d, 1H), 7.16 (d, 1H), 7.09 (t, 1H), 6.86-6.87 (m, 1H), 4.17 (t, 2H), 3.79

(t, 2H), 3.69 (s, 3H), 3.47 (s, 3H), 3.26 (s, 3H), 2.27 (s, 3H), 2.18-2.20 (m, 2H), 1.98-2.00 (m, 2H), 1.59-1.63 (m, 4H).

Compound 2-419 (600 MHz, $CDCl_3$): 7.80 (d, 1H), 7.15 (d, 1H), 6.86-6.87 (m, 1H), 4.17 (t, 2H), 3.79 (t, 2H), 3.52 (s, 3H), 3.47 (s, 3H), 3.25 (s, 3H), 2.34-2.39 (m, 1H), 2.28 (s, 3H), 2.18-2.21 (m, 2H), 2.02-2.04 (m, 2H), 1.58-1.64 (m, 4H), 0.89-0.98 (m, 4H).

Compound 2-420 (600 MHz, $CDCl_3$): 7.80 (d, 1H), 7.12 (d, 1H), 6.85-6.87 (m, 1H), 4.17 (t, 2H), 3.85 (q, 2H), 3.79 (t, 2H), 3.47 (s, 3H), 3.25 (s, 3H), 2.44 (s, 3H), 2.26 (s, 3H), 2.19-2.21 (m, 2H), 2.02-2.04 (m, 2H), 1.57-1.62 (m, 4H), 1.38 (t, 3H).

Compound 2-421 (600 MHz, $CDCl_3$): 8.02 (d, 1H), 7.31 (d, 1H), 6.72-6.73 (m, 1H), 5.14 (s, 2H), 4.04-4.05 (m, 1H), 3.79-3.80 (m, 1H), 3.72-3.73 (m, 1H), 3.62-3.65 (m, 2H), 3.53 (s, 3H), 3.27 (s, 3H), 2.48 (s, 3H), 2.15-2.17 (m, 2H), 1.97-2.00 (m, 2H), 1.91-1.92 (m, 1H), 1.84-1.87 (m, 2H), 1.57-1.60 (m, 5H).

Compound 3-109 (600 MHz, $CDCl_3$): 8.64 (d, 1H), 7.88-7.92 (m, 1H), 7.63 (d, 1H), 7.51 (d, 2H), 7.39-7.47 (m, 3H), 7.33 (d, 1H), 6.22 (d, 1H), 3.67 (s, 3H), 2.40 (s, 3H).

Compound 4-140 (600 MHz, $CDCl_3$): 8.54 (d, 1H), 7.81-7.85 (m, 1H), 7.35 (d, 1H), 6.91-6.97 (m, 1H), 3.62 (s, 3H), 2.42 (s, 3H), 2.18-2.24 (m, 2H), 2.01-2.06 (m, 2H), 1.55-1.64 (m, 4H).

Compound 4-141 (600 MHz, $CDCl_3$): 8.56 (d, 1H), 7.83-7.87 (m, 1H), 7.35 (d, 1H), 6.80-6.85 (m, 1H), 3.62 (s, 3H), 2.50-2.55 (m, 2H), 2.38-2.43 (m, 5H), 1.89-2.00 (m, 2H).

Biometric Test Examples

Embodiment 4 Determination of Herbicidal Activity

Seeds of broadleaf weeds (zinnia and piemarker) or grassy weeds (green bristlegrass and barnyard grass) were respectively sown in a paper cup having a diameter of 7 cm and containing nutrient soil; after sowing, the seeds were covered with 1 cm of soil, the soil was pressed and watered, and then the seeds were cultivated in a greenhouse according to a conventional method; and stems and leaves were sprayed after 2-3 leaf stage of the weeds.

After the original medicinal acetone was dissolved, the test requires to use 1‰ of Tween 80 to stand in running water to prepare the solution to be tested with a required concentration. According to the design dose of the test, spray treatment was carried out on a track-type crop sprayer (designed and produced by British Engineer Research Ltd.) (spray pressure is 1.95 kg/$cm^2$, spray volume is 500 L/$hm^2$ and track speed is 1.48 km/h). The test was repeated for three times. The test material was treated and then placed in an operation hall. The medicinal liquid was naturally dried in the shade, and then was placed in a greenhouse and managed according to the conventional method. The response of the weeds to the drug was observed and recorded. After treatment, the control effects of the test drug on the weeds were visually inspected regularly, expressed by 0-100%. "0" represents no control effect and "100%4" represents complete killing.

The test results show that the compounds of the formula I generally have high control effects on various weeds. Part of the test compounds, such as compounds 1-1, 1-7, 1-18, 1-20, 1-42, 1-76, 1-81, 1-82, 1-226, 1-259, 1-262, 1-265, 1-280, 1-292, 1-346, 1-349, 1-367, 1-370, 1-371, 2-1, 2-19, 2-37, 2-55, 2-67, 2-73, 2-121, 2-123, 2-289, 2-291, 2-307, 2-309, 2-379, 2-380, 2-383, 2-386, 2-391, 2416, 2417, 2-418, 2-419 and 2420, have good control effects on zinnia, piemarker, green bristlegrass or barnyard grass at the application dose of 600 g a.i./$hm^2$, and the control effects are greater than or equal to 90%.

According to the above test method, part of the compounds of the formula I and $KC_1$ are selected for activity test of controlling the zinnia. The results are shown in Table 5.

TABLE 5

Zinnia Control Activity of Part of Compounds of Formula 1 and Reference Compound $KC_1$ (after emergence, control effect %)

| | dose g a.i./$hm^2$ | | |
|---|---|---|---|
| Compound | 600 | 150 | 37.5 |
| 1-42 | 100 | 100 | 100 |
| 1-81 | 100 | 95 | 90 |
| $KC_1$ | 0 | 0 | 0 |

According to the above test method, part of the compounds of the formula and $KC_1$ are selected for activity test of controlling the piemarker. The results are shown in Table 6.

TABLE 6

Piemarker Control Activity of Part of Compounds of Formula 1 and Reference Compound $KC_1$ (after emergence, control effect %)

| | dose g a.i./$hm^2$ | | |
|---|---|---|---|
| Compound | 600 | 150 | 37.5 |
| 1-1 | 100 | 95 | 90 |
| 1-42 | 100 | 95 | 90 |
| 1-259 | / | 100 | 100 |
| 1-292 | 95 | 90 | 90 |
| $KC_1$ | 100 | 70 | 20 |

"/" in the table indicates no test.

According to the above test method, part of the compounds of the formula I and $KC_1$ or $KC_2$ are selected for activity test of controlling the green bristlegrass. The results are shown in Table 7.

TABLE 7

Green Bristlegrass Control Activity of Part of Compounds of Formula 1 and Reference Compounds $KC_1$ or $KC_2$ (after emergence, control effect %)

| | dose g a.i./$hm^2$ | | |
|---|---|---|---|
| Compound | 600 | 150 | 37.5 |
| 1-259 | / | 100 | 100 |
| 1-280 | 100 | 90 | 80 |
| 1-292 | 95 | 90 | 90 |
| $KC_1$ | 10 | 10 | 10 |
| 2-121 | 98 | 90 | 80 |
| 2-123 | 100 | 100 | 90 |
| $KC_2$ | / | 60 | 30 |

"/" in the table indicates no test.

According to the above test method, part of the compounds of the formula I and $KC_1$ or $KC_2$ are selected for activity test of controlling the barnyard grass. The results are shown in Table 8.

TABLE 8

Barnyard Grass Control Activity of Part of Compounds of Formula 1 and Reference Compounds $KC_1$ or $KC_2$ (after emergence, control effect %)

| | dose g a.i./$hm^2$ | | |
|---|---|---|---|
| Compound | 600 | 150 | 37.5 |
| 1-42 | 100 | 95 | 80 |
| 1-81 | 95 | 90 | 80 |
| 1-82 | 100 | 95 | 90 |
| 1-259 | / | 100 | 100 |
| 1-280 | 100 | 95 | 85 |
| 1-292 | 100 | 95 | 90 |
| $KC_1$ | 0 | 0 | 0 |
| 2-37 | 100 | 100 | 95 |
| 2-67 | 100 | 100 | 90 |
| 2-73 | 100 | 100 | 95 |
| 2-123 | 100 | 100 | 100 |
| $KC_2$ | / | 90 | 60 |

"/" in the table indicates no test.

To sum up, the alkene-containing carboxylic ester compound of the present invention has excellent herbicidal activity, also has high herbicidal activity at a lower dosage, and can be used for agriculturally controlling various weeds.

The invention claimed is:

1. An alkene-containing carboxylic ester compound of formula 1, a stereoisomer thereof, or an agriculturally acceptable salt thereof,

I

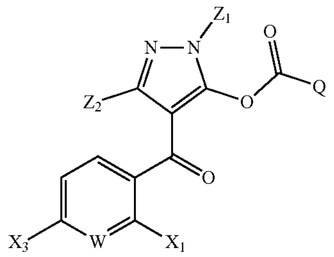

wherein:

$X_1$ is selected from halogen, $C_1$-$C_6$ alkylsulfonyl, $C_1$-$C_6$ alkyl, and $C_1$-$C_6$ haloalkyl;

W is selected from $CX_2$;

$X_2$ is selected from $Y_1$ oxy, $Y_1$ sulfonyl, $Y_1$ oxy $C_1$-$C_6$ alkyl, $Y_1$ sulfonyl $C_1$-$C_6$ alkyl, 5-7 membered alicyclic heterocycle containing 1-4 heteroatoms, 5-7 membered aromatic heterocycle containing 1-4 heteroatoms, 5-7 membered aliphatic heterocyclic $C_1$-$C_6$ alkyl containing 1-4 heteroatoms, and 5-7 membered aromatic heterocyclic $C_1$-$C_6$ alkyl containing 1-4 heteroatoms; wherein at least one hydrogen on the aliphatic heterocycle or the aromatic heterocycle is optionally substituted by a substituent selected from nitro, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, $C_3$-$C_6$ cycloalkoxy, $C_2$-$C_6$ alkenyl, $C_2$-$C_6$ alkynyl, phenyl, and halophenyl;

$Y_1$ is selected from $C_1$-$C_6$ alkyl, $C_1$-$C_6$ haloalkyl, $C_3$-$C_6$ cycloalkyl, $C_3$-$C_6$ cycloalkyl $C_1$-$C_6$ alkyl, $C_1$-$C_6$ alkoxy $C_1$-$C_6$ alkyl, $C_2$-$C_6$ alkenyl, $C_2$-$C_6$ alkynyl, phenyl, 5-7 membered aliphatic heterocycle containing 1-4 heteroatoms, 5-7 membered aromatic heterocycle containing 1-4 heteroatoms, 5-7 membered aliphatic heterocyclic $C_1$-$C_6$ alkyl containing 1-4 heteroatoms, and 5-7 membered aromatic heterocyclic $C_1$-$C_6$ alkyl containing 1-4 heteroatoms; wherein at least one hydrogen on the phenyl, the aliphatic heterocycle, or the aromatic heterocycle is substituted by a substituent selected from nitro, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, $C_3$-$C_6$ cycloalkoxy, $C_2$-$C_6$ alkenyl, $C_2$-$C_6$ alkynyl, phenyl, and halophenyl;

$X_3$ is selected from halogen, $C_1$-$C_6$ alkylsulfonyl, $C_1$-$C_6$ alkyl, and $C_1$-$C_6$ haloalkyl;

wherein, when $X_1$ is chlorine and $X_3$ is methylsulfonyl, $X_2$ is not 2-thiazolyl;

$Z_1$ is selected from $C_1$-$C_6$ alkyl, $C_3$-$C_6$ cycloalkyl, $C_3$-$C_6$ cycloalkyl $C_1$-$C_6$ alkyl, $C_3$-$C_6$ alkenyl, $C_3$-$C_6$ alkynyl, $C_1$-$C_6$ alkylsulfonyl $C_1$-$C_6$ alkyl, and phenyl;

$Z_2$ is selected from H, $C_1$-$C_6$ alkyl, $C_4$-$C_6$ cycloalkyl, $C_1$-$C_6$ haloalkyl, and phenyl, wherein at least one hydrogen on the phenyl ring is optionally substituted by a substitute selected from halogen, cyano, nitro, $C_1$-$C_6$ alkyl, $C_3$-$C_6$ cycloalkyl, and $C_1$-$C_6$haloalkyl; and Q is $Q_2$, and $Q_2$ is a $C_3$-$C_8$ cycloalkenyl in which at least one hydrogen on the ring thereof is optionally substituted by a substituent selected from nitro, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, and $C_3$-$C_6$ cycloalkyl.

2. The compound according to claim 1, wherein, in formula I:

$X_1$ is selected from halogen and $C_1$-$C_6$ alkyl;

W is selected from $CX_2$;

$X_2$ is selected from $Y_1$ oxy;

$Y_1$ is selected from $C_1$-$C_6$ alkyl, $C_1$-$C_6$ haloalkyl, $C_3$-$C_6$ cycloalkyl, $C_3$-$C_6$ cycloalkyl $C_1$-$C_6$ alkyl, $C_1$-$C_6$ alkoxy $C_1$-$C_6$ alkyl, phenyl, a 5-7 membered aliphatic heterocycle containing 1-4 heteroatoms, a 5-7 membered aromatic heterocycle containing 1-4 heteroatoms, a 5-7 membered aliphatic heterocyclic $C_1$-$C_6$ alkyl containing 1-4 heteroatoms, and a 5-7 membered aromatic heterocyclic $C_1$-$C_6$ alkyl containing 1-4 heteroatoms; wherein at least one hydrogen on the phenyl; the aliphatic heterocycle, or the aromatic heterocycle is substituted by one or more substituents selected from nitro, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, and $C_3$-$C_6$ cycloalkoxy;

$X_3$ is selected from $C_1$-$C_6$ alkylsulfonyl;

$Z_1$ is selected from $C_1$-$C_6$ alkyl, $C_3$-$C_6$ cycloalkyl, $C_3$-$C_6$ cycloalkyl $C_1$-$C_6$ alkyl, $C_3$-$C_6$ alkenyl, $C_3$-$C_6$ alkynyl, and phenyl; and $Z_2$ is selected from H, $C_1$-$C_6$ alkyl, $C_1$-$C_6$ haloalkyl, and phenyl, wherein at least one hydrogen on the phenyl ring is optionally substituted by a substituent selected from halogen, cyano, nitro, $C_1$-$C_6$ alkyl, $C_3$-$C_6$ cycloalkyl, and $C_1$-$C_6$ haloalkyl.

3. The compound according to claim 2, wherein, in formula I:

$X_1$ is selected from halogen or $C_1$-$C_3$ alkyl;

W is selected from $CX_2$;

$X_2$ is selected from $Y_1$ oxy;

$Y_1$ is selected from $C_1$-$C_6$ alkyl, $C_1$-$C_6$ haloalkyl, $C_3$-$C_6$ cycloalkyl, $C_3$-$C_6$ cycloalkyl $C_1$-$C_6$ alkyl, $C_1$-$C_6$ alkoxy $C_1$-$C_6$ alkyl, a 5-7 membered aliphatic heterocycle containing 1-4 heteroatoms, a 5-7 membered aromatic heterocycle containing 1-4 heteroatoms, a 5-7 membered aliphatic heterocyclic $C_1$-$C_6$ alkyl containing 1-4 heteroatoms, and a 5-7 membered aromatic heterocyclic $C_1$-$C_6$ alkyl containing 1-4 heteroatoms; wherein at least one hydrogen on the aliphatic heterocycle or the aromatic heterocycle is substituted by one or more substituents selected from nitro, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, and $C_3$-$C_6$ cycloalkoxy;

$X_3$ is selected from $C_1$-$C_3$ alkylsulfonyl;

$Z_1$ is selected from $C_1$-$C_6$ alkyl and $C_3$-$C_6$ cycloalkyl;

$Z_2$ is selected from H and $C_1$-$C_6$ alkyl; and $Q_2$ is a $C_3$-$C_8$ cycloalkenyl in which at least one hydrogen on the ring thereof is optionally substituted by a substutuent selected from $C_1$-$C_6$ alkyl, $C_1$-$C_6$ alkoxy, and $C_1$-$C_6$ alkenyl.

4. The compound according to claim 3, wherein, in formula I:

$X_1$ is selected from halogen or $C_1$-$C_3$ alkyl;

W is selected from $CX_2$;

$X_2$ is selected from $Y_1$ oxy;

$Y_1$ is selected from $C_1$-$C_6$ alkyl, $C_1$-$C_6$ haloalkyl, $C_3$-$C_6$ cycloalkyl, $C_3$-$C_6$ cycloalkyl $C_1$-$C_6$ alkyl, $C_1$-$C_6$ alkoxy $C_1$-$C_6$ alkyl, a 5-7 membered aliphatic heterocycle containing 1-4 heteroatoms, a 5-7 membered aromatic heterocycle containing 1-4 heteroatoms, a 5-7 membered aliphatic heterocyclic $C_1$-$C_6$ alkyl containing 1-4 heteroatoms, and a 5-7 membered aromatic heterocyclic $C_1$-$C_6$ alkyl containing 1-4 heteroatoms, wherein at least one hydrogen on the aliphatic heterocycle or the aromatic heterocycle is optionally substituted by a substituent selected from nitro, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, and $C_3$-$C_6$ cycloalkoxy;

$X_3$ is selected from $C_1$-$C_3$ alkylsulfonyl;

$Z_1$ is selected from $C_1$-$C_3$ alkyl;

$Z_2$ is selected from H and $C_1$-$C_3$ alkyl; and $Q_2$ is selected from G1, G2, G3, G4, G5, and G6 group:

$G_1$

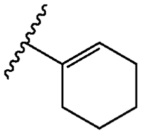

-continued $G_2$

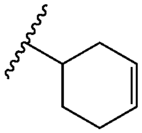

$G_3$

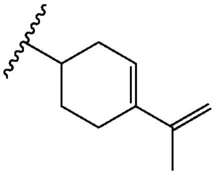

$G_4$

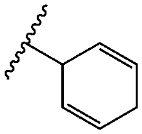

$G_5$

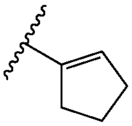

$G_6$

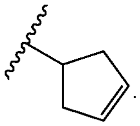

5. A herbicidal composition, comprising an active ingredient and an agriculturally acceptable carrier, wherein the active ingredient is the compound of formula I, a stereoisomer thereof, or an agriculturally acceptable salt thereof according to claim 1; and the weight percentage of the active ingredient in the composition is 1-99%.

6. A method for controlling weeds comprising applying a herbicidally effective dose of the herbicidal composition of claim 5 to a weed or a growth medium or site of the weed.

* * * * *